(12) United States Patent
Rudolf et al.

(10) Patent No.: US 7,595,312 B2
(45) Date of Patent: Sep. 29, 2009

(54) SELECTED CGRP ANTAGONISTS, PROCESSES FOR PREPARING THEM AND THEIR USE AS PHARMACEUTICAL COMPOSITIONS

(75) Inventors: Klaus Rudolf, Warthausen (DE); Stephan Georg Mueller, Warthausen (DE); Dirk Stenkamp, Biberach (DE); Philipp Lustenberger, Warthausen (DE); Alexander Dreyer, Ochsenhausen (DE); Eckhart Bauer, Biberach (DE); Marcus Schindler, Biberach (DE); Kirsten Arndt, Biberach (DE); Henri Doods, Warthausen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 203 days.

(21) Appl. No.: 10/687,262

(22) Filed: Oct. 16, 2003

(65) Prior Publication Data

US 2006/0079504 A1   Apr. 13, 2006

Related U.S. Application Data

(60) Provisional application No. 60/426,168, filed on Nov. 14, 2002.

(30) Foreign Application Priority Data

Oct. 25, 2002   (DE)   ................. 102 50 080

(51) Int. Cl.
*A61K 31/551* (2006.01)
*C07D 401/14* (2006.01)

(52) U.S. Cl. .............. 514/217.04; 514/227.8; 514/235.2; 514/253.11; 514/326; 540/500; 544/60; 544/124; 544/360; 546/187; 546/189; 546/191; 546/207

(58) Field of Classification Search ............... 546/220, 546/187, 190, 191, 189, 207; 514/211.05, 514/252.17, 316, 217.04, 227.8, 253.11, 514/235.2, 326; 540/500, 504; 544/284, 544/60, 124, 360
See application file for complete search history.

(56) References Cited

U.S. PATENT DOCUMENTS

| 5,442,044 | A | 8/1995 | Hoover et al. |
|---|---|---|---|
| 5,798,337 | A | 8/1998 | Somers et al. |
| 6,025,372 | A | 2/2000 | Yang et al. |
| 6,194,437 | B1 | 2/2001 | Horwell et al. |
| 6,300,501 | B1 | 10/2001 | Dobrusin et al. |
| 6,313,097 | B1 | 11/2001 | Eberlein et al. |
| 6,344,449 | B1 * | 2/2002 | Rudolf et al. .......... 514/211.05 |
| 6,521,609 | B1 | 2/2003 | Doods et al. |
| 6,653,478 | B2 | 11/2003 | Urbanski et al. |
| 7,026,312 | B2 | 4/2006 | Hurnaus et al. |
| 7,205,294 | B2 | 4/2007 | Lustenberger et al. |
| 7,230,001 | B1 | 6/2007 | Rudolf et al. |
| 2004/0076587 | A1 | 4/2004 | Kruss et al. |
| 2004/0132716 | A1 | 7/2004 | Rudolf et al. |
| 2004/0192729 | A1 | 9/2004 | Rudolf et al. |
| 2004/0204397 | A1 | 10/2004 | Chaturvedula et al. |
| 2004/0214819 | A1 | 10/2004 | Rudolf et al. |
| 2005/0147568 | A1 | 7/2005 | Trunk et al. |
| 2005/0227968 | A1 | 10/2005 | Lustenberger et al. |
| 2005/0234054 | A1 | 10/2005 | Mueller et al. |
| 2005/0234067 | A1 | 10/2005 | Mueller et al. |
| 2005/0250763 | A1 | 11/2005 | Mueller et al. |
| 2005/0256099 | A1 | 11/2005 | Mueller et al. |
| 2005/0282857 | A1 | 12/2005 | Rudolf et al. |
| 2006/0142273 | A1 | 6/2006 | Rudolf et al. |
| 2006/0142274 | A1 * | 6/2006 | Rudolf et al. ............... 514/221 |
| 2006/0154921 | A1 * | 7/2006 | Rudolf et al. ............... 514/221 |
| 2006/0252750 | A1 | 11/2006 | Mueller et al. |
| 2006/0252931 | A1 | 11/2006 | Mueller et al. |
| 2007/0049581 | A1 | 3/2007 | Mueller et al. |
| 2007/0072847 | A1 | 3/2007 | Mueller et al. |
| 2007/0099903 | A1 | 5/2007 | Mueller et al. |

FOREIGN PATENT DOCUMENTS

| CA | 2361939 A1 | 9/2000 |
|---|---|---|
| CA | 2378428 A1 | 2/2001 |
| CA | 2387613 A1 | 5/2001 |
| CA | 2476711 A1 | 8/2003 |
| CA | 2476031 A1 | 9/2003 |

(Continued)

OTHER PUBLICATIONS

Brittain, "Polymorphism in Pharmaceutical Solids", 1999, pp. 5-8.*

(Continued)

*Primary Examiner*—Celia Chang
(74) *Attorney, Agent, or Firm*—Michael P. Morris; Mary-Ellen M. Devlin; Alan R. Stempel

(57) ABSTRACT

The present invention relates to CGRP antagonists of general formula

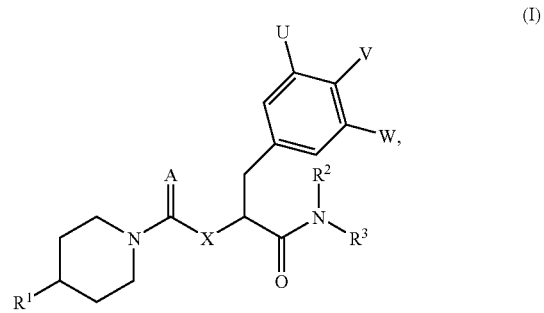

(I)

wherein A, U, V, W, X and $R^1$ to $R^3$ are defined as in claim 1, the tautomers, diastereomers, enantiomers, hydrates, mixtures thereof and the salts thereof as well as the hydrates of the salts, particularly the physiologically acceptable salts thereof with inorganic or organic acids, pharmaceutical compositions containing these compounds, the use thereof and processes for preparing them.

66 Claims, No Drawings

FOREIGN PATENT DOCUMENTS

| | | |
|---|---|---|
| CA | 2487716 A1 | 12/2003 |
| CA | 2503455 A1 | 5/2004 |
| CA | 2503462 A1 | 5/2004 |
| CA | 2513132 A1 | 7/2004 |
| CA | 2558889 A1 | 10/2005 |
| CA | 2562526 A1 | 10/2005 |
| CA | 2565219 A1 | 11/2005 |
| DE | 19911039 A1 | 9/2000 |
| DE | 102 27 294 A1 | 1/2004 |
| EP | 0438233 A2 | 7/1991 |
| WO | 9325574 A1 | 12/1993 |
| WO | 9615148 A2 | 5/1996 |
| WO | 9744350 A1 | 11/1997 |
| WO | 9807718 A1 | 2/1998 |
| WO | WO 98/11128 | 3/1998 |
| WO | WO 00/18764 | 4/2000 |
| WO | WO 01/10425 A2 | 2/2001 |
| WO | 0132649 A1 | 5/2001 |
| WO | 03070753 A1 | 8/2003 |
| WO | 03076432 A1 | 9/2003 |
| WO | 03104236 A1 | 12/2003 |
| WO | 2004000289 A2 | 12/2003 |
| WO | 2004037810 A1 | 5/2004 |
| WO | 2004037811 A1 | 5/2004 |
| WO | 2004063171 A1 | 7/2004 |
| WO | 2005084672 A1 | 9/2005 |
| WO | 2005092880 A1 | 10/2005 |
| WO | 2005095383 A1 | 10/2005 |
| WO | 2005100343 A1 | 10/2005 |
| WO | 2005100352 A1 | 10/2005 |
| WO | 2005103037 A2 | 11/2005 |
| WO | 2006069754 A1 | 7/2006 |
| WO | 2006072413 A1 | 7/2006 |
| WO | 2006072415 A1 | 7/2006 |
| WO | 2006100009 A1 | 9/2006 |

OTHER PUBLICATIONS

Rudolf et al. "Preparation of modified amino acids . . . " CA 128:257695 (1998).*

Mallee et al. "Receptor activity modifying . . . " CA 137:304712 (2002).*

Seddon "Pseudopolymorph: a polemic" Crystal growth & design 4(6)1087 (2004).*

Evans "An introduction to crystal chemistry" p. 284-285 (1964).*

Braga et al. "Making crystal from crystals . . . " Chem. Commun. p. 3635-3645 (2005).*

Rudolf et al. "preparation of modified amino acids . . . " CA 128:257695 (1998).*

John J. Mallee et al; Receptor Activity-modifying Protein 1 Determines the Species Selectivity of Non-peptide CGRP Receptor Antagonists; The Journal of Biological Chemistry (Apr. 19, 2002) vol. 277 No. 16 p. 14294-14928; The American Society for Biochemistry and Molecular Biology, Inc.

Klaus Rudolf et al, U.S. Appl. No. 11/168,123, "Selected CGRP-antagonists, process for preparing them and their use as pharmaceutical compositions" filed Mar. 19, 2007.

Bachem Bioscience, Inc., Datalog US Jun. 1993; E-1160 and E-1170, p. 13, 1993.

Edvinsson Funct. Neural. 15 Suppl. 3 (2000) 50-60 (Medline abstract only).

Fang, et al; Clin. Exp. Allergy 28 (1998) 228-232 (Medline abstract only).

Hamiliton, et al; A Quantitative Analysis of the Binding of N-Acyl Derivatives of alpha- Aminoamides by alpha-Chymotrypsin, Proc. Nat. Acad. Sci. (1966), 55(3), pp. 664-669.

Doods, Henri et al; Pharmacological profile of BIBN4096BS, the first selective small molecule CGRP antagonist; British Journal of Pharmacology (2000) vol. 129 p. 420-423; Macmillan Publishers Ltd.

Onuoha, et al; Eur. J. Clin. Invest 31 (2001) 253-257 (Medline abstract only).

Pasternak, A. et al; "Potent Orally Bioavailable Somatostatin Agonists: Good Absorption Achieved by Urea Backbone Cyclization"; Bioorganic & Medicinal Chemistry Letters, Bd. 9, Nr. 3, Feb. 8,1999, pp. 491-496.

Powell, et al; Br. J. Pharmacol. 131 (2000) 875-884 (Medline abstract only).

Thurieau et al; "Preparation of imidazolyl derivatives as agonists or antagonists of somatostatin receptors" CAPLUS 132:35701 (1999).

U.S. Appl. No. 11/757,743, filed Jun. 4, 2007, applicant Klaus Rudolf.

* cited by examiner

SELECTED CGRP ANTAGONISTS, PROCESSES FOR PREPARING THEM AND THEIR USE AS PHARMACEUTICAL COMPOSITIONS

RELATED APPLICATIONS

Benefit of U.S. Provisional Application Ser. No. 60/426,168, filed on Nov. 14, 2002 is hereby claimed.

FIELD OF THE INVENTION

The present invention relates to CGRP antagonists of general formula

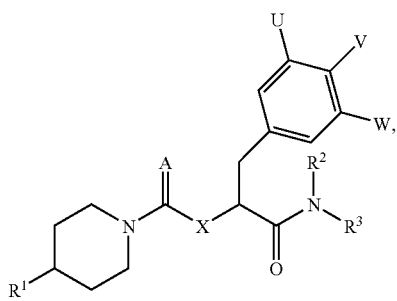

(I)

the tautomers, diastereomers, enantiomers, hydrates, mixtures thereof and the salts thereof as well as the hydrates of the salts, particularly the physiologically acceptable salts thereof with inorganic or organic acids, pharmaceutical compositions containing these compounds, the use thereof and processes for the preparation thereof.

In the above general formula (I) in a first embodiment

A denotes an oxygen or sulphur atom, a phenylsulphonylimino or cyanimino group,

X denotes an oxygen or sulphur atom, an imino group optionally substituted by a $C_{1-6}$-alkyl group or a methylene group optionally substituted by a $C_{1-6}$-alkyl group, U denotes a $C_{1-6}$-alkyl, $C_{2-6}$-alkenyl or $C_{2-6}$-alkynyl group wherein each methylene group may be substituted by up to 2 fluorine atoms and each methyl group may be substituted by up to 3 fluorine atoms, V denotes a chlorine or bromine atom, an amino, methylamino or hydroxy group, W denotes a hydrogen, fluorine, chlorine, bromine or iodine atom, a difluoro- or trifluoromethyl group, $R^1$ denotes a saturated, mono- or diunsaturated 5- to 7-membered aza, diaza, triaza, oxaza, thiaza, thiadiaza or S,S-dioxido-thiadiaza heterocyclic group, in which the abovementioned heterocycles are linked via a carbon or nitrogen atom, contain one or two carbonyl or thiocarbonyl groups adjacent to a nitrogen atom, may be substituted at one of the nitrogen atoms by an alkyl group, may be substituted at one or at two carbon atoms by an alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, while the substituents may be identical or different, and while an olefinic double bond of one of the abovementioned unsaturated heterocycles may be fused to a phenyl, naphthyl, pyridine, diazine, 1,3-oxazole, thienyl, furan, thiazole, pyrrole, N-methylpyrrole or quinoline ring, to a 1H-quinolin-2-one ring optionally substituted at the nitrogen atom by an alkyl group or to an imidazole or N-methylimidazole ring or also two olefinic double bonds of one of the abovementioned unsaturated heterocycles may each be fused to a phenyl ring, while the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in $R^1$ as well as benzo-, thieno-, pyrido- and diazino-fused heterocycles in the carbon skeleton may additionally be mono-, di- or trisubstituted by fluorine, chlorine, bromine or iodine atoms, by alkyl, alkoxy, nitro, alkylthio, alkylsulphinyl, alkylsulphonyl, alkylsulphonylamino, phenyl, difluoromethyl, trifluoromethyl, alkoxycarbonyl, carboxy, hydroxy, amino, alkylamino, dialkylamino, acetyl, acetylamino, propionylamino, aminocarbonyl, alkylaminocarbonyl, dialkylaminocarbonyl, (4-morpholinyl)carbonyl, (1-pyrro-lidinyl)carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, difluoromethoxy, trifluoromethoxy, trifluoromethylthio, trifluoromethylsulphinyl or trifluoromethylsulphonyl groups, while the substituents may be identical or different, $R^2$ denotes the hydrogen atom, a phenylmethyl group or a $C_{2-7}$-alkyl group which may be substituted in the (ω position by a cyclohexyl, phenyl, pyridinyl, diazinyl, hydroxy, amino, alkylamino, dialkylamino, carboxy, alkoxycarbonyl, aminocarbonyl, aminocarbonylamino, acetylamino, 1-pyrrolidinyl, 1-piperidinyl, 4-(1-piperidinyl)-1-piperidinyl, 4-morpholinyl, hexahydro-1H-1-azepinyl, [bis-(2-hydroxyethyl)]amino, 4-alkyl-1-piperazinyl or 4-(ω-hydroxy-$C_{2-7}$-alkyl)-1-piperazinyl group, a phenyl or pyridinyl group, while the abovementioned heterocyclic groups and phenyl groups may additionally be mono- di- or trisubstituted in the carbon skeleton by fluorine, chlorine, bromine or iodine atoms, by methyl, alkoxy, difluoromethyl, trifluoromethyl, hydroxy, amino, $C_{1-3}$-alkylamino, di-($C_{1-3}$-alkyl)-amino, acetylamino, aminocarbonyl, cyano, methylsulphonyloxy, difluoromethoxy, trifluoromethoxy, trifluoromethylthio, trifluoromethylsulphinyl, trifluoromethylsulphonyl, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group optionally substituted by a phenyl or pyridinyl group, while the $C_{1-3}$-alkyl group may be linked to an alkyl group present in $R^2$ or a phenyl or pyridyl ring present in $R^2$ and the nitrogen atom to which they are bound, forming a ring, or $R^2$ and $R^3$ together with the enclosed nitrogen atom denote a group of general formula

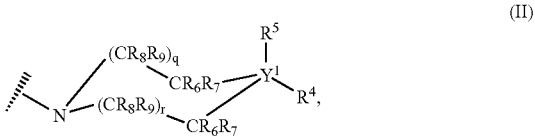

(II)

wherein
$Y^1$ denotes the carbon atom or, if $R^5$ is a pair of free electrons, it may also denote the nitrogen atom, q and r, if $Y^1$ denotes the carbon atom, represent the numbers 0, 1 or 2, or q and r, if $Y^1$ denotes the nitrogen atom, represent the numbers 1 or 2, $R^4$ denotes the hydrogen atom, an amino, alkylamino, cycloalkylamino, dialkyl-amino, N-(cycloalkyl)-alkylamino, dicycloalkylamino, hydroxy, alkyl, cycloalkyl, amino-$C_{2-7}$-alkyl, alkylamino-$C_{2-7}$-alkyl, dialkylamino-$C_{2-7}$-alkyl, amino-iminomethyl, alkylcarbonyl, alkylsulphonyl, alkylcarbonylamino, alkylsulphonylamino, N-alkylcarbonyl-N-alkylamino, N-alkylsulphonyl-N-alkylamino, amino-carbonylamino, alkylaminocarbonylamino, dialkylaminocarbonylamino, cycloalkylaminocarbonylamino, dicycloalkylaminocarbonylamino, phenylamino-carbonylamino, aminocarbonylalkyl, alkylaminocarbonylalkyl, dialkylamino-carbonylalkyl, aminocarbonylaminoalkyl, alkoxycarbonyl, alkoxycarbonylalkyl or carboxyalkyl group, or, if $Y^1$ does not denote the nitrogen atom, the carboxy, aminomethyl, alkylaminomethyl or dialkylaminomethyl group, a phenyl, phenyl-$C_{1-3}$-alkyl, pyridinyl, diazinyl, 1-naphthyl, 2-naphthyl, pyridinylcarbonyl or phenylcarbonyl group which may each be mono-, di- or trisubstituted in the carbon skeleton by fluorine, chlorine, bromine or iodine atoms, by alkyl, alkoxy, methylsulphonyloxy, difluoromethyl, trifluoromethyl, hydroxy, amino, acetylamino, aminocarbonyl, aminocarbonylamino, aminocarbonylaminomethyl, cyano, carboxy, alkoxycarbonyl, carboxyalkyl, alkoxycarbonylalkyl, alkanoyl, ω-(dialkylamino)alkanoyl, ω-(dialkylamino)alkyl, ω-(dialkylamino)hydroxyalkyl, ω-(carboxy)alkanoyl, difluoromethoxy, trifluoromethoxy, trifluoromethylthio, trifluoromethylsulphinyl or trifluoromethylsulphonyl groups, while the substituents may be identical or different, a saturated or mono- or polyunsaturated 4- to 10-membered azacycloalkyl group, a 5- to 10-membered oxaza-, thiaza, diaza- or triazacycloalkyl group, a 6- to 10-membered azabicyclo- or diazabicycloalkyl group, a 1-alkyl-4-piperidinylcarbonyl or 4-alkyl-1-piperazinylcarbonyl, a 1-alkyl-4-piperidinylamino, 1-alkyl-4-piperidinylaminocarbonyl or 1-alkyl-4-piperidinylaminosulphonyl group, while the abovementioned mono- and bicyclic heterocycles are bound via a nitrogen or carbon atom, a methylene group in the abovementioned mono- and bicyclic heterocycles may be replaced by a carbonyl or sulphonyl group, in the abovementioned mono- and bicyclic heterocycles any methylene group not directly bound to a nitrogen, oxygen or sulphur atom may be substituted by one or two fluorine atoms, the abovementioned mono- and bicyclic heterocycles as well as the 1-alkyl-4-piperidinylcarbonyl- and 4-alkyl-1-piperazinylcarbonyl group in the ring may be mono- or polysubstituted by a $C_{1-7}$-alkyl group and/or monosubstituted by a benzyl, alkanoyl, dialkylamino, phenylcarbonyl, pyridinylcarbonyl, carboxy, carboxyalkanoyl, carboxyalkyl, alkoxycarbonylalkyl, alkoxycarbonyl, aminocarbonyl, alkylaminocarbonyl, alkylsulphonyl, cycloalkyl or cycloalkylalkyl group, or substituted by a cycloalkylcarbonyl, azacycloalkylcarbonyl, diazacycloalkylcarbonyl or oxazacycloalkylcarbonyl group optionally alkyl-substituted in the ring, while the alicyclic moieties contained in these substituents each comprise 3 to 10 ring members and the heteroalicyclic moieties each comprise 4 to 10 ring members and the phenyl and pyridinyl groups contained in the abovementioned groups may in turn be mono-, di- or trisubstituted by fluorine, chlorine, bromine or iodine atoms, by alkyl, alkoxy, methylsulphonyloxy, difluoromethyl, trifluoromethyl, hydroxy, amino, acetylamino, aminocarbonyl, aminocarbonylamino, aminocarbonylaminomethyl, cyano, carboxy, alkoxycarbonyl, carboxyalkyl, alkoxycarbonylalkyl, alkanoyl, ω-(dialkylamino)alkanoyl, ω-(carboxy)alkanoyl, difluoromethoxy, trifluoromethoxy, trifluoromethylthio, trifluoromethylsulphinyl or trifluoromethylsulphonyl groups, while the substituents may be identical or different, $R^5$ denotes a hydrogen atom, a $C_{1-4}$-alkyl group, while an unbranched alkyl group may be substituted in the ω position by a phenyl, pyridinyl, diazinyl, amino, alkylamino, dialkylamino, 1-pyrrolidinyl, 1-piperidinyl, 4-methyl-1-piperazinyl, 4-morpholinyl or hexahydro-1H-1-azepinyl group, an alkoxycarbonyl, the cyano or aminocarbonyl group or also, if $Y^1$ denotes a nitrogen atom, a pair of free electrons, or, if $Y^1$ does not denote a nitrogen atom, also the fluorine atom, or $R^4$ and $R^5$ together, if $Y^1$ denotes the carbon atom, denote a 4- to 7-membered cycloaliphatic ring in which one or two methylene groups may be replaced by an —NH— or —N(alkyl)-group and one or two additional methylene groups may be replaced by carbonyl groups, while a hydrogen atom bound to a nitrogen atom within the abovementioned group $R^4$ may be replaced by a protecting group, $R^6$ and $R^7$, which may be identical or different, in each case denote a hydrogen atom, a $C_{1-3}$-alkyl or dialkylamino group or also, if $Y^1$ does not denote a nitrogen atom, the fluorine atom and $R^8$ and $R^9$, which may be identical or different, each denote a hydrogen atom or a $C_{1-3}$-alkyl, carboxy or $C_{1-3}$-alkoxycarbonyl group, while, unless otherwise stated, all the abovementioned alkyl and alkoxy groups as well as the alkyl groups present within the other groups specified comprise 1 to 7 carbon atoms and may be straight-chain or branched, while each methylene group may be substituted by up to 2 fluorine atoms and each methyl group may be substituted by up to 3 fluorine atoms, all the abovementioned cycloalkyl groups as well as the cycloalkyl groups present within the other groups specified, unless otherwise stated, may comprise 3 to 10 carbon atoms, while each methylene group may be substituted by up to 2 fluorine atoms, all the abovementioned aromatic and heteroaromatic groups may additionally be mono- di- or trisubstituted by fluorine, chlorine or bromine atoms, by cyano or hydroxy groups and the substituents may be identical or different and by the protective groups mentioned in the foregoing and subsequent definitions are meant the protective groups familiar from peptide chemistry, particularly a phenylalkoxycarbonyl group with 1 to 3 carbon atoms in the alkoxy moiety optionally substituted in the phenyl nucleus by a halogen atom, by a nitro or phenyl group or by one or two methoxy groups, for example the benzyloxycarbonyl, 2-nitro-benzyloxycarbonyl, 4-nitro-benzyl-oxycarbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α,α-dimethyl-benzyloxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, isopropoxycarbonyl, n-butoxycarbonyl, 1-methylpropoxycarbonyl, 2-methyl-propoxy-carbonyl or tert.butyloxycarbonyl group, the allyloxycarbonyl, 2,2,2-trichloro-(1,1-dimethylethoxy)carbonyl or 9-fluorenyl-methoxycarbonyl group or the formyl, acetyl or trifluoroacetyl group.

A second embodiment of the present invention comprises the compounds of the above general formula (I), wherein A, U, V, W, X, $R^2$ and $R^3$ are defined as mentioned in the first embodiment hereinbefore and $R^1$ denotes a mono- or diunsaturated 5- to 7-membered aza, diaza, triaza or thiaza heterocyclic group, in which the abovementioned heterocycles are linked via a carbon or nitrogen atom, contain one or two carbonyl groups adjacent to a nitrogen atom, may be substituted at a carbon atom by a phenyl, pyridinyl, diazinyl, thienyl, pyrrolyl, 1,3-thiazolyl, isoxazolyl, pyrazolyl or 1-methylpyrazolyl group and an olefinic double bond of one of the abovementioned unsaturated heterocycles may be fused to a phenyl, naphthyl, pyridine, diazine, thienyl or quinoline ring or to a 1H-quinolin-2-one ring optionally substituted at the nitrogen atom by a methyl group, while the phenyl, pyridinyl, diazinyl, thienyl, pyrrolyl, 1,3-thiazolyl, isoxazolyl, pyrazolyl or 1-methylpyrazolyl groups contained in $R^1$ as well as the benzo-, pyrido- and diazino-fused heterocycles in the carbon skeleton may additionally be mono-, di- or trisubstituted by fluorine, chlorine, bromine or iodine atoms, by alkyl, alkoxy, nitro, difluoromethyl, trifluoromethyl, hydroxy, amino, alkylamino, dialkylamino, acetylamino, acetyl, cyano, difluoromethoxy or trifluoromethoxy groups, while the substituents may be identical or different, while the abovementioned alkyl groups or the alkyl groups contained in the abovementioned groups, unless otherwise stated, contain 1 to 7 carbon atoms and may be branched or unbranched, while each methylene group may be substituted by up to 2 fluorine atoms and each methyl group may be substituted by up to 3 fluorine atoms, and the abovementioned aromatic and heteroaromatic groups may additionally be mono-, di- or trisubstituted by fluorine, chlorine or bromine atoms or by cyano or hydroxy groups and the substituents may be identical or different.

A third embodiment of the present invention comprises the compounds of the above general formula (I), wherein A, U, V, W, X, $R^2$ and $R^3$ are defined as mentioned in the first embodiment and $R^1$ denotes a monounsaturated 5- to 7-membered diaza or triaza heterocyclic group, while the abovementioned heterocycles are linked via a nitrogen atom, contain a carbonyl group adjacent to a nitrogen atom and may additionally be substituted at a carbon atom by a phenyl group, and while an olefinic double bond of one of the abovementioned unsaturated heterocycles may be fused to a phenyl, thienyl or quinoline ring, while the phenyl groups contained in $R^1$ as well as benzo-fused heterocycles in the carbon skeleton may additionally be mono-, di- or trisubstituted by fluorine, chlorine, bromine or iodine atoms, by methyl, methoxy, nitro, difluoromethyl, trifluoromethyl, hydroxy, amino, alkylamino, dialkylamino, acetylamino, acetyl, cyano, difluoromethoxy or trifluoromethoxy groups, while the substituents may be identical or different, but are preferably unsubstituted, or monosubstituted by a fluorine, chlorine or bromine atom or by a methyl or methoxy group, while, unless otherwise stated, all the abovementioned alkyl groups as well as the alkyl groups present within the other groups comprise 1 to 7 carbon atoms and may be straight-chain or branched and the abovementioned aromatic and heteroaromatic groups may additionally be mono- di- or trisubstituted by fluorine, chlorine or bromine atoms or by cyano or hydroxy groups and the substituents may be identical or different.

A fourth embodiment of the present invention comprises the compounds of the above general formula (I), wherein A, U, V, W, X, $R^2$ and $R^3$ are defined as mentioned in the first embodiment and $R^1$ denotes a 4-(2-oxo-1,2,4,5-tetrahydro-1,3-benzodiazepin-3-yl)-piperidin-1-yl, 4-(2-oxo-1,4-dihydro-2H-quinazolin-3-yl)-piperidin-1-yl, 4-(5-oxo-3-phenyl-4,5-dihydro-1,2,4-triazol-1-yl)-piperidin-1-yl, 4-(2-oxo-1,2-dihydro-imidazo[4,5-c]quinolin-3-yl)-piperidin-1-yl, 4-(2-oxo-1,2-dihydro-4H-thieno[3,4-d]pyrimidin-3-yl)-piperidin-1-yl, 4-(2-oxo-1,4-dihydro-2H-thieno[3,2-d]pyrimidin-3-yl)-piperidin-1-yl, 4-(5-oxo-4,5,7,8-tetrahydro-2-thia-4,6-diaza-azulen-6-yl)-piperidin-1-yl, 4-(2-oxo-1,2,4,5-tetrahydro-thieno[3,2-d]-1,3-diazepin-3-yl)-piperidin-1-yl, 4-(2-oxo-1,2,4,5-tetrahydro-thieno[2,3-d]-1,3-diazepin-3-yl)-piperidin-1-yl or 4-(2-oxo-1,4-dihydro-2H-thieno[2,3-d]pyrimidin-3-yl)-piperidin-1-yl group, while the abovementioned mono- and bicyclic heterocycles in the carbon skeleton may additionally be monosubstituted by a methoxy group, while the abovementioned aromatic and heteroaromatic groups by fluorine, chlorine or bromine atoms, by cyano or hydroxy groups may additionally be mono- di- or trisubstituted and the substituents may be identical or different.

A fifth embodiment of the present invention comprises the compounds of the above general formula (I), wherein A, U, V, W, X and $R^1$ are defined as mentioned in the first embodiment and $R^2$ denotes the hydrogen atom or a phenylmethyl group or a $C_{2-7}$-alkyl group which may be substituted in the ω position by a phenyl, pyridinyl, hydroxy, amino, alkylamino, dialkylamino, carboxy, alkoxycarbonyl, aminocarbonyl, aminocarbonylamino, acetylamino, 1-pyrrolidinyl, 1-piperidinyl, 4-morpholinyl, [bis-(2-hydroxyethyl)]amino group while the abovementioned heterocyclic groups and phenyl groups may additionally be mono-, di- or trisubstituted in the carbon skeleton by fluorine, chlorine, bromine or iodine atoms, by methyl, alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group, while the $C_{1-3}$-alkyl group may be linked to an alkyl group present in $R^2$ or a phenyl or pyridyl ring present in $R^2$ and the nitrogen atom to which they are bound, forming a 5- to 7-membered ring, or $R^2$ and $R^3$ together with the enclosed nitrogen atom denote a group of general formula

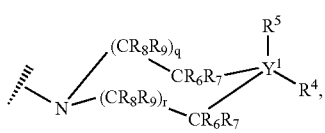

(II)

wherein $Y^1$ denotes the carbon atom or, if $R^5$ denotes a pair of free electrons, it may also denote the nitrogen atom, q and r, if $Y^1$ denotes the carbon atom, represent the numbers 0 or 1 or q and r, if $Y^1$ denotes the nitrogen atom, represent the numbers 1 or 2, $R^4$ denotes the hydrogen atom, a hydroxy, amino, alkylamino, $C_{3-6}$-cycloalkylamino, N—($C_{3-6}$-cycloalkyl)-alkylamino or dialkylamino, an alkyl, trifluoromethyl, $C_{3-6}$-cycloalkyl, dialkylamino-$C_{2-7}$-alkyl, carboxyalkyl, alkoxycarbonylalkyl, alkylsulphonyl, alkylsulphonylamino or N-(alkylsulphonyl)-alkylamino group, or, if $Y^1$ does not denote the nitrogen atom, it denotes the carboxy or dialkylaminomethyl group, a phenyl, phenyl-$C_{1-3}$-alkyl, pyridinyl or diazinyl group each of which may be substituted by a fluorine, chlorine or bromine atom or by a trifluoromethylcarbonyl, methyl or methoxy group, a saturated or mono- or polyunsaturated 4- to 7-membered azacycloalkyl group, a 5- to 7-membered oxaza-, diaza or triazacycloalkyl group, a 7- to 9-membered azabicyclo or diazabicycloalkyl group, a 1-alkyl-4-piperidinylamino or 1-alkyl-4-piperidinylaminosulphonyl group, while the abovementioned mono- and bicyclic heterocycles are bound via a nitrogen or carbon atom, a methylene group of the abovementioned mono- and bicyclic heterocycles may be replaced by a carbonyl or sulphonyl group, in the abovementioned mono- and bicyclic heterocycles any methylene group not directly bound to a nitrogen, oxygen or sulphur atom may be substituted by one or two fluorine atoms, the abovementioned mono- and bicyclic heterocycles may be substituted by one or two $C_{1-3}$-alkyl groups wherein each methylene group may be substituted by up to 2 fluorine atoms and each methyl group may be substituted by up to 3 fluorine atoms, and/or by a $C_{3-6}$-cycloalkyl-$C_{1-3}$-alkyl, benzyl, $C_{1-4}$-alkanoyl, di-($C_{1-3}$-alkyl)-amino or $C_{1-3}$-alkylsulphonyl, by an alkoxycarbonyl, benzyloxycarbonyl, alkoxycarbonylalkyl, carboxy or carboxyalkyl group, $R^5$ denotes a hydrogen atom, a $C_{1-3}$-alkyl or alkoxycarbonyl group or, if $Y^1$ denotes a nitrogen atom, it may also denote a pair of free electrons, or $R^4$ and $R^5$ together, if $Y^1$ denotes the carbon atom, represent a 5- to 6-membered cycloaliphatic ring in which one or two methylene groups may be replaced by a —NH or —N(methyl) group and one or two further methylene groups may be replaced by carbonyl groups, $R^6$ and $R^7$, which may be identical or different, in each case denote a hydrogen atom or a $C_{1-3}$-alkyl or di-($C_{1-3}$-alkyl)-amino group and $R^8$ and $R^9$, which may be identical or different, in each case denote a hydrogen atom or a $C_{1-3}$-alkyl, carboxy or $C_{1-3}$-alkoxycarbonyl group, while, unless otherwise stated, all the abovementioned alkyl groups as well as the alkyl groups present within the other groups comprise 1 to 7 carbon atoms and may be straight-chain or branched and the abovementioned aromatic and heteroaromatic groups may additionally be mono-, di- or trisubstituted by fluorine, chlorine or bromine atoms or by cyano or hydroxy groups and the substituents may be identical or different.

A sixth embodiment of the present invention comprises the compounds of the above general formula (I), wherein A, U, V, W, X and $R^1$ are defined as mentioned in the first embodiment and $R^2$ denotes a phenylmethyl group or a $C_{2-7}$-alkyl group which may be substituted in the ω position by a phenyl, amino, alkylamino or dialkylamino group, while the abovementioned phenyl group may be substituted by an amino-$C_{1-3}$-alkyl, $C_{1-3}$-alkylamino-$C_{1-3}$ alkyl or di-($C_{1-3}$-alkyl)-amino-$C_{1-3}$-alkyl group, or $R^3$ denotes the hydrogen atom or a $C_{1-3}$-alkyl group, $R^2$ and $R^3$ together with the nitrogen atom to which they are bound denote a 7-dimethylaminomethyl-1,2,4,5-tetrahydro-3-benzazepin-3-yl or 2-amino-4,5,7,8-tetrahydrothiazolo[4,5-d]azepin-6-yl-group or $R^2$ and $R^3$ together with the enclosed nitrogen atom denote a group of general formula

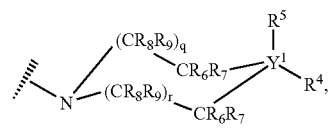

(II)

wherein $Y^1$ denotes the carbon atom or, if $R^5$ denotes a pair of free electrons, it may also denote the nitrogen atom, q and r, if $Y^1$ denotes the carbon atom, represent the numbers 0 or 1 or q and r, if $Y^1$ denotes the nitrogen atom, represent the numbers 1 or 2, $R^4$ denotes the hydrogen atom, a phenyl, benzyl or pyridinyl group which may be substituted in each case by a fluorine, chlorine or bromine atom, by a trifluoromethylcarbonyl, methyl or methoxy group, a hydroxy, carboxy, methyl, trifluoromethyl, n-propyl, phenyl, p-tolyl, p-trifluoromethylcarbonyl-phenyl, p-(3-dimethylaminopropyl)-phenyl, amino, benzyl, tert-butylamino, dimethylamino, diethylamino, diethylaminomethyl, 2-dimethylaminoethyl, 2-diethylaminoethyl, 5-aminopentyl, methoxycarbonyl, methoxycarbonylmethyl, perhydro-azepin-1-yl, 4-methyl-perhydro-1,4-diazepin-1-yl, 1-methyl-1-piperidinyl-4-yl, 4-piperazin-1-yl, 4-acetyl-piperazin-1-yl, 4-cyclopropylmethyl-piperazin-1-yl, pyrrolidin-1-yl, 4-ethyl-piperazin-1-yl, 4-isopropyl-piperazin-1-yl, piperidin-1-yl, piperidin-4-yl, morpholin-4-yl, 4,4-difluoro-1-piperidin-1-yl, 1-methyl-1-aza-bicyclo[3.2.1]oct-4-yl or 4-methyl-piperazin-1-yl, 4-ethylpiperazin-1-yl, 1-methyl-piperidin-1-yl, 4-carboxymethyl-piperazin-1-yl, 1-carboxymethyl-piperidin-4-yl, 4-benzyloxycarbonyl-piperazin-1-yl, 1-ethoxycarbonylmethyl-piperidin-4-yl, azetidin-1-yl, 5-methyl-2,5-diaza-bicyclo[2.2.1]hept-2-yl, 1-benzyl-piperidin-4-yl, 4-benzyl-piperazin-1-yl, 4-dimethylaminomethyl-1-phenyl, 2,2,2-trifluoroethyl-piperazin-1-yl, 1-methyl-sulphonyl-piperidin-4-yl, piperidin-1-yl-methyl, 1-methyl-piperidin-4-yl-amino, methylsulphonylamino, N-methylsulphonyl-N-methylamino, N-(cyclopentyl)-methylamino, 1,1-dioxo-$\lambda^6$-isothiazolidin-2-yl, 2-oxo-perhydro-1,3-oxazin-3-yl, cyclohexyl, 2-oxo-imidazolidin-1-yl, 2-methyl-imidazol-1-yl, 4-methyl-imidazol-1-yl, 4-thiazol-2-yl, 2,4-dimethyl-imidazol-1-yl, 4-imidazol-1-yl, 1,2,4-triazol-1-yl, 1-aza-bicyclo[2.2.2]oct-3-yl, 1-methyl-piperidin-4-yl-methylsulphonyl, 1H-imidazol-4-yl, 4-ethoxycarbonylmethyl-piperazin-1-yl, 1-ethoxycarbonyl-piperidin-4-yl, 4-tert-butoxycarbonylmethyl-piperazin-1-yl, 1-(2,2,2-trifluoroethyl)-piperidin-4-yl, 4-methylsulphonyl-piperazin-1-yl, 2-carboxy-4-methyl-piperazin-1-yl, 3-carboxy-4-methyl-piperazin-1-yl, 2-ethoxycarbonyl-4-methyl-piperazin-1-yl, 3-ethoxycarbonyl-4-methyl-piperazin-1-yl or 4-(2,2,2-trifluoroethyl)-piperazin-1-yl-group, $R^5$ denotes a hydrogen atom, a methyl group or, if $Y^1$ denotes a nitrogen atom, it may also denote a pair of free electrons, or $R^4$ and $R^5$ together, if $Y^1$ denotes the carbon atom, denote a 1-methyl-piperidin-4-ylidene, cyclohexylidene or imidazolidin-2,4-dion-5-ylidene group, $R^6$ and $R^7$ in each case denote a hydrogen atom or a dimethylamino group and $R^8$ and $R^9$ in each case denote the hydrogen atom, a carboxy or ethoxycarbonyl group, while, unless otherwise stated, all the abovementioned alkyl groups as well as the alkyl groups present within the other groups comprise 1 to 7 carbon atoms and may be straight-chain or branched and the abovementioned aromatic and heteroaromatic groups may additionally be mono-, di- or trisubstituted by fluorine, chlorine or bromine atoms, by cyano or hydroxy groups and the substituents may be identical or different, while in all the embodiments mentioned above those compounds wherein (i) A denotes an oxygen atom, a cyanoimino or phenylsulphonylimino group,
X denotes an oxygen atom, an imino or methylene group,
U denotes an unbranched $C_{1-6}$-alkyl, $C_{2-4}$-alkenyl or $C_{2-4}$-alkynyl group wherein each methylene group may be substituted by up to 2 fluorine atoms and the methyl group may be substituted by up to 3 fluorine atoms,
V denotes an amino or hydroxy group and
W denotes a hydrogen, chlorine or bromine atom or a trifluoromethyl group, are of exceptional importance, those compounds wherein
(ii) A denotes an oxygen atom,
X denotes an oxygen atom, an imino or methylene group,
U denotes a methyl, ethyl, $C_{2-4}$-alkenyl or $C_{2-4}$-alkynyl group wherein the methylene group may be substituted by up to 2 fluorine atoms and the methyl group may be substituted by up to 3 fluorine atoms,
V denotes an amino or hydroxy group and
W denotes a hydrogen, chlorine or bromine atom or a trifluoromethyl group, are of particularly outstanding importance and those compounds wherein
(iii) A denotes an oxygen atom,
X denotes an oxygen atom, an imino or methylene group,
U denotes a trifluoromethyl or pentafluoroethyl group,
V denotes an amino or hydroxy group and
W denotes a hydrogen, chlorine or bromine atom or a trifluoromethyl group, are of most particularly outstanding importance.

A seventh embodiment of the present invention comprises the compounds of the above general formula (I) wherein A denotes an oxygen atom, a cyanoimino or phenylsulphonylimino group,
X denotes an oxygen atom, an imino or methylene group,
U denotes an unbranched $C_{1-6}$-alkyl, $C_{2-6}$-alkenyl or $C_{2-6}$-alkynyl group wherein each methylene group may be substituted by up to 2 fluorine atoms and the methyl group may be substituted by up to 3 fluorine atoms,
V denotes an amino or hydroxy group,
W denotes a hydrogen, chlorine or bromine atom or a trifluoromethyl group,
$R^1$ denotes a monounsaturated 5- to 7-membered diaza or triaza heterocyclic group,
while the abovementioned heterocycles are linked via a nitrogen atom,
contain a carbonyl group adjacent to a nitrogen atom,
may additionally be substituted at a carbon atom by a phenyl group and
an olefinic double bond of one of the abovementioned unsaturated heterocycles may be fused to a phenyl, thienyl or quinoline ring,
while the phenyl groups contained in $R^1$ as well as benzo-fused heterocycles in the carbon skeleton may additionally be mono-, di- or trisubstituted by fluorine, chlorine, bromine or iodine atoms, by methyl, methoxy, nitro, difluoromethyl, trifluoromethyl, hydroxy, amino, alkylamino, dialkylamino, acetylamino, acetyl, cyano, difluoromethoxy or trifluoromethoxy groups, while the substituents may be identical or different, but are preferably unsubstituted or are monosubstituted by a fluorine, chlorine or bromine atom or by a methyl or methoxy group, $R^2$ denotes the hydrogen atom or a phenylmethyl group or a $C_{2-7}$-alkyl group which may be substituted in the ω position by a phenyl, pyridinyl, hydroxy, amino, alkylamino, dialkylamino, alkoxycarbonyl, carboxy, aminocarbonyl, aminocarbonylamino, acetylamino, 1-pyrrolidinyl, 1-piperidinyl, 4-morpholinyl or [bis-(2-hydroxyethyl)]amino group, while the abovementioned heterocyclic groups and phenyl groups may additionally be mono-, di- or trisubstituted in the carbon skeleton by fluorine, chlorine, bromine or iodine atoms, by methyl, alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group, while the $C_{1-3}$-alkyl group may be linked to an alkyl group present in $R^2$ or a phenyl or pyridyl ring present in $R^2$ and the nitrogen atom to which they are bound, forming a 5- to 7-membered ring, or $R^2$ and $R^3$ together with the enclosed nitrogen atom denote a group of general formula

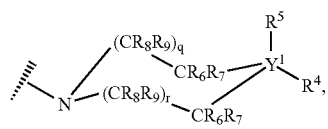

(II)

wherein $Y^1$ denotes the carbon atom or, if $R^5$ denotes a pair of free electrons, it may also denote the nitrogen atom, q and r, if $Y^1$ denotes the carbon atom, represent the numbers 0 or 1 or q and r, if $Y^1$ denotes the nitrogen atom, represent the numbers 1 or 2, $R^4$ denotes the hydrogen atom, a hydroxy, amino, alkylamino, $C_{3-6}$-cycloalkylamino, N—($C_{3-6}$-cycloalkyl)-alkylamino or dialkylamino, an alkyl, trifluoromethyl, $C_{3-6}$-cycloalkyl, dialkylamino-$C_{2-7}$-alkyl, carboxyalkyl, alkoxycarbonylalkyl, alkylsulphonyl, alkylsulphonylamino or N-(alkylsulphonyl)-alkylamino group, or, if $Y^1$ does not denote the nitrogen atom, it denotes the carboxy or dialkyl-aminomethyl group, a phenyl, phenyl-$C_{1-3}$-alkyl, pyridinyl or diazinyl group which may be substituted in each case by a fluorine, chlorine or bromine atom, by a trifluoromethylcarbonyl, methyl or methoxy group, a saturated or mono- or polyunsaturated 4- to 7-membered azacycloalkyl group, a 5- to 7-membered oxaza-, diaza- or triazacycloalkyl group, a 7- to 9-membered azabicyclo- or diazabicycloalkyl group, a 1-alkyl-4-piperidinylamino or 1-alkyl-4-piperidinylaminosulphonyl group, while the abovementioned mono- and bicyclic heterocycles are bound via a nitrogen or carbon atom, a methylene group of the abovementioned mono- and bicyclic heterocycles may be replaced by a carbonyl or sulphonyl group, in the abovementioned mono- and bicyclic heterocycles any methylene group not directly bound to a nitrogen, oxygen or sulphur atom may be substituted by one or two fluorine atoms, the abovementioned mono- and bicyclic heterocycles may be substituted by one or two $C_{1-3}$-alkyl groups, wherein each methylene group may be substituted by up to 2 fluorine atoms and each methyl group may be substituted by up to 3 fluorine atoms, and/or may be substituted by a $C_{3-6}$-cycloalkyl-$C_{1-3}$-alkyl, benzyl, $C_{1-4}$-alkanoyl, di-($C_{1-3}$-alkyl)-amino or $C_3$alkylsulphonyl, by an alkoxycarbonyl, benzyloxycarbonyl, alkoxycarbonylalkyl, carboxy or carboxyalkyl group, $R^5$ denotes a hydrogen atom, a $C_{1-3}$-alkyl or alkoxycarbonyl group or, if $Y^1$ denotes a nitrogen atom, it may also denote a pair of free electrons, or $R^4$ and $R^5$ together, if $Y^1$ denotes the carbon atom, denote a 5- to 6-membered cycloaliphatic ring wherein one or two methylene groups may be replaced by a —NH or —N(methyl) group and one or two further methylene groups may be replaced by one or two carbonyl groups, $R^6$ and $R^7$, which may be identical or different, in each case denote the hydrogen atom or a $C_{1-3}$-alkyl or di-($C_{1-3}$-alkyl)-amino group and $R^8$ and $R^9$, which may be identical or different, in each case denote the hydrogen atom or a $C_{1-3}$-alkyl, carboxy or $C_{1-3}$-alkoxycarbonyl group, while, unless otherwise stated, the abovementioned alkyl groups or the alkyl groups contained in the abovementioned groups contain 1 to 7 carbon atoms and may be branched or unbranched and the abovementioned aromatic and heteroaromatic groups may additionally be mono-, di- or trisubstituted by fluorine, chlorine or bromine atoms, by cyano or hydroxy groups and the substituents may be identical or different.

An eighth embodiment of the present invention comprises the compounds of the above general formula (I), wherein A denotes an oxygen atom, X denotes an oxygen atom, an imino or methylene group, U denotes a methyl, ethyl, $C_{2-4}$-alkenyl or $C_{2-4}$-alkynyl group wherein the methylene group may be substituted by up to 2 fluorine atoms and the methyl group may be substituted by up to 3 fluorine atoms, V denotes an amino or hydroxy group, W denotes a hydrogen, chlorine or bromine atom or a trifluoromethyl group, $R^1$ denotes a 4-(2-oxo-1,2,4,5-tetrahydro-1,3-benzodiazepin-3-yl)-piperidin-1-yl, 4-(2-oxo-1,4-dihydro-2H-quinazolin-3-yl)-piperidin-1-yl, 4-(5-oxo-3-phenyl-4,5-dihydro-1,2,4-triazol-1-yl)-piperidin-1-yl, 4-(2-oxo-1,2-dihydro-imidazo[4,5-c]quinolin-3-yl)-piperidin-1-yl, 4-(2-oxo-1,2-dihydro-4H-thieno[3,4-d]pyrimidin-3-yl)-piperidin-1-yl, 4-(2-oxo-1,4-dihydro-2H-thieno[3,2-d]pyrimidin-3-yl)-piperidin-1-yl, 4-(5-oxo-4,5,7,8-tetrahydro-2-thia-4,6-diaza-azulen-6-yl)-piperidin-1-yl, 4-(2-oxo-1,2,4,5-tetrahydro-thieno[3,2-d]-1,3-diazepin-3-yl)-piperidin-1-yl, 4-(2-oxo-1,2,4,5-tetrahydro-thieno[2,3-d]-1,3-diazepin-3-yl)-piperidin-1-yl or 4-(2-oxo-1,4-dihydro-2H-thieno[2,3-d]pyrimidin-3-yl)-piperidin-1-yl group, while the abovementioned mono- and bicyclic heterocycles in the carbon skeleton may additionally be monosubstituted by a methoxy group, $R^2$ denotes a phenylmethyl group or a $C_{2-7}$-alkyl group which may be substituted in the 0) position by a phenyl, amino, alkylamino or dialkylamino group, while the abovementioned phenyl group may be substituted by an amino-$C_{1-3}$-alkyl, $C_{1-3}$-alkylamino-$C_{1-3}$-alkyl or di-($C_{1-3}$-alkyl)-amino-$C_{1-3}$-alkyl group, or $R^3$ denotes the hydrogen atom or a $C_{1-3}$-alkyl group, $R^2$ and $R^3$ together with the nitrogen atom to which they are bound denote a 7-dimethylaminomethyl-1,2,4,5-tetrahydro-3-benzazepin-3-yl or 2-amino-4,5,7,8-tetrahydro-thiazolo[4,5-d]azepin-6-yl-group or R² and R³ together with the enclosed nitrogen atom denote a group of general formula

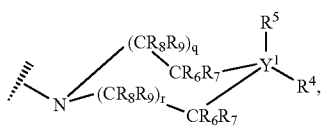

wherein

Y¹ represents the carbon atom or, if R⁵ denotes a pair of free electrons, it may also denote the nitrogen atom, q and r, if Y¹ denotes the carbon atom, represent the numbers 0 or 1 or q and r, if Y¹ denotes the nitrogen atom, represent the numbers 1 or 2, R⁴ denotes the hydrogen atom, a phenyl, benzyl or pyridinyl group which may be substituted in each case by a fluorine, chlorine or bromine atom, by a trifluoromethylcarbonyl, methyl or methoxy group, a hydroxy, carboxy, methyl, trifluoromethyl, n-propyl, phenyl, p-tolyl, p-trifluoromethylcarbonyl-phenyl, p-(3-dimethylaminopropyl)-phenyl, amino, benzyl, tert-butylamino, dimethylamino, diethylamino, diethylaminomethyl, 2-dimethylaminoethyl, 2-diethylaminoethyl, 5-aminopentyl, methoxycarbonyl, methoxycarbonylmethyl, perhydro-azepin-1-yl, 4-methyl-perhydro-1,4-diazepin-1-yl, 1-methyl-1-piperidinyl-4-yl, 4-piperazin-1-yl, 4-acetyl-piperazin-1-yl, 4-cyclopropylmethyl-piperazin-1-yl, pyrrolidin-1-yl, 4-ethyl-piperazin-1-yl, 4-isopropyl-piperazin-1-yl, piperidin-1-yl, piperidin-4-yl, morpholin-4-yl, 4,4-difluoro-1-piperidin-1-yl, 1-methyl-1-aza-bicyclo[3.2.1]oct-4-yl, 4-methyl-piperazin-1-yl, 4-ethylpiperazin-1-yl, 1-methyl-piperidin-1-yl, 4-carboxymethyl-piperazin-1-yl, 1-carboxymethyl-piperidin-4-yl, 4-benzyloxycarbonyl-piperazin-1-yl, 1-ethoxycarbonylmethyl-piperidin-4-yl, azetidin-1-yl, 5-methyl-2,5-diaza-bicyclo[2.2.1]hept-2-yl, 1-benzyl-piperidin-4-yl, 4-benzyl-piperazin-1-yl, 4-dimethylaminomethyl-1-phenyl, 2,2,2-trifluoroethyl-piperazin-1-yl, 1-methyl-sulphonyl-piperidin-4-yl, piperidin-1-yl-methyl, 1-methyl-piperidin-4-yl-amino, methylsulphonylamino, N-methylsulphonyl-N-methylamino, N-(cyclopentyl)-methylamino, 1,1-dioxo-λ⁶-isothiazolidin-2-yl, 2-oxo-perhydro-1,3-oxazin-3-yl, cyclohexyl, 2-oxo-imidazolidin-1-yl, 2-methyl-imidazol-1-yl, 4-methyl-imidazol-1-yl, 4-thiazol-2-yl, 2,4-dimethyl-imidazol-1-yl, 4-imidazol-1-yl, 1,2,4-triazol-1-yl, 1-aza-bicyclo[2.2.2]oct-3-yl, 1-methyl-piperidin-4-yl-methylsulphonyl, 1H-imidazol-4-yl, 4-ethoxycarbonylmethyl-piperazin-1-yl, 1-ethoxycarbonyl-piperidin-4-yl, 4-tert-butoxycarbonylmethyl-piperazin-1-yl, 1-(2,2,2-trifluoroethyl)-piperidin-4-yl, 4-methylsulphonyl-piperazin-1-yl, 2-carboxy-4-methyl-piperazin-1-yl, 3-carboxy-4-methyl-piperazin-1-yl, 2-ethoxycarbonyl-4-methyl-piperazin-1-yl, 3-ethoxycarbonyl-4-methyl-piperazin-1-yl or 4-(2,2,2-trifluoroethyl)-piperazin-1-yl group, R⁵ denotes a hydrogen atom, a methyl group or, if Y¹ denotes a nitrogen atom, it may also denote a pair of free electrons, or R⁴ and R⁵ together, if Y¹ denotes the carbon atom, denote a 1-methyl-piperidin-4-ylidene, cyclohexylidene or imidazolidin-2,4-dion-5-ylidene group, R⁶ and R⁷ in each case denote a hydrogen atom or a dimethylamino group and R⁸ and R⁹ in each case denote the hydrogen atom, a carboxy or ethoxycarbonyl group, while, unless otherwise stated, all the abovementioned alkyl groups as well as the alkyl groups present within the other groups comprise 1 to 7 carbon atoms and may be straight-chain or branched and the abovementioned aromatic and heteroaromatic groups may additionally be mono-, di- or trisubstituted by fluorine, chlorine or bromine atoms or by cyano or hydroxy groups and the substituents may be identical or different.

The following are mentioned as examples of most particularly preferred compounds of the above general formula (I):

| Structure | | Name |
|---|---|---|
| (1) | 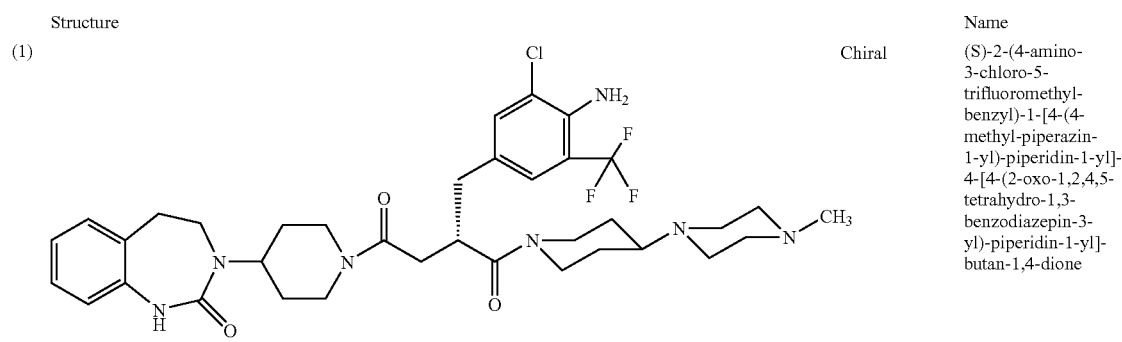 Chiral | (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione |

-continued

| Structure | Name |
|---|---|
| (2) 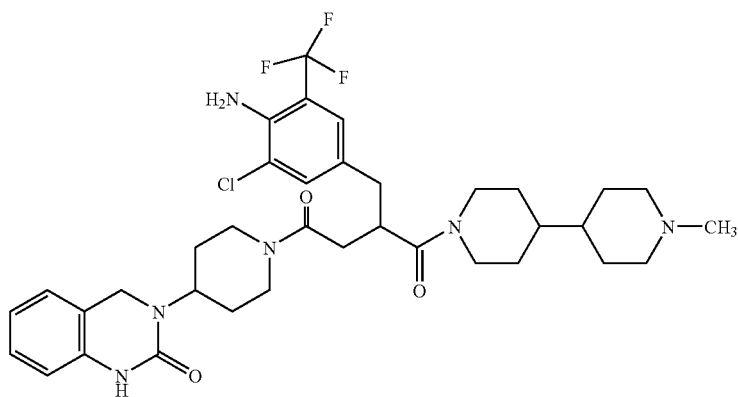 | 2-(4-amino-3-chlorro-5-trifluoromethyl-benzyl)-1-(1'-methyl-[4,4']bipiperi-dinyl-1-yl)-4-[4-(2-oxo-1,4-dihydro-2H-quinazolin-3-yl)-piperidin-1-yl]-butan-1,4-dione |
| (3) 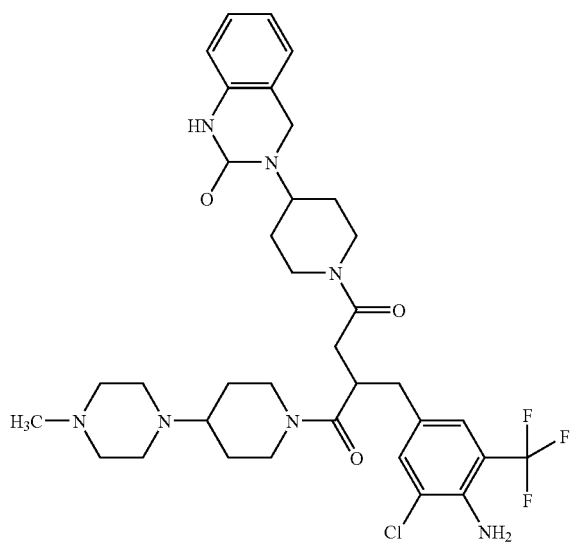 | 2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione |
| (4) 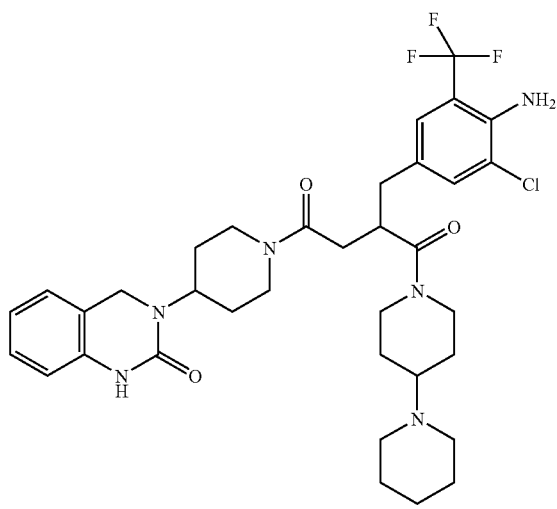 | 2-(4-amino-3-chloro 5-trifluoromethyl-benzyl)-1-[1,4']bipiper-idinyl-1'-yl-4-[4-(2-oxo-1,4-dihydro-2H-quinazolin-3-yl)-piperidin-1-yl]-butan-1,4-dione |

| | Structure | Name |
|---|---|---|
| (5) | 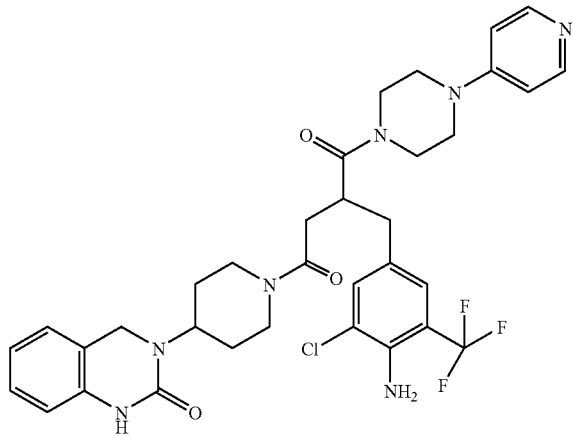 | 2-(4-amino-3-chloro-5-trifluoromethyl-benzyl)-4-[4-(2-oxo-1,4-dihydro-2H-quinazolin-3-yl)-piperidin-1-yl]-1-(4-pyridin-4-yl-piperazin-1-yl)-butan-1,4-dione |
| (6) | 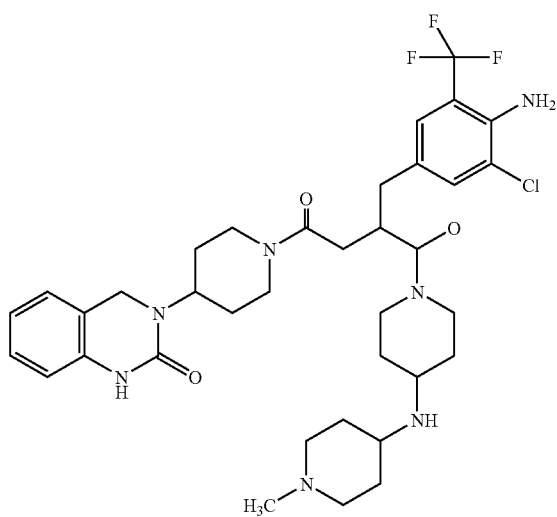 | 2-(4-amino-3-chloro-5-trifluoromethyl-benzyl)-1-[4-(1-methyl-piperidin-4-ylamino)-piperidin-1-yl]-4-[4-(2-oxo-1,4-dihydro-2H-quinazolin-3-yl)-piperidin-1-yl]-butan-1,4-dione |
| (7) | 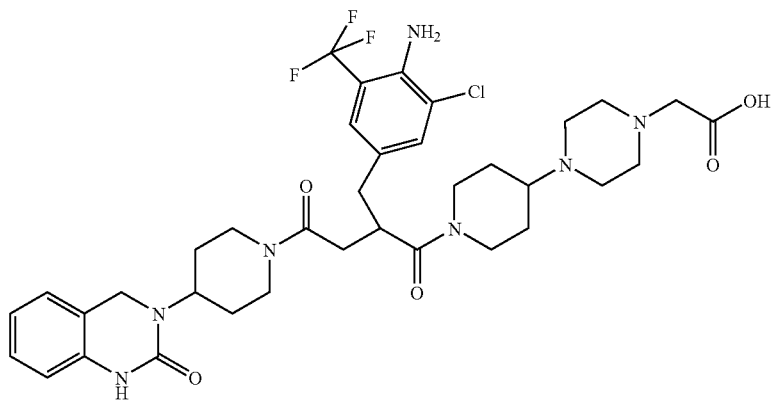 | [4-(1-{2-(4-amino-3-chloro-5-trifluoromethyl-benzyl)-4-oxo-4-[4-(2-oxxo-1,4-dihydro-2H-quinazolin-33-yl)-piperidin-1-yl]-butyryl}-piperidin-4-yl)-piperazin-1-yl]-acetic acid |

| | Structure | Name |
|---|---|---|
| (8) | | methyl (1'-{2-[4-amino-3-chloro-5-trifluoromethyl-benzyl)-4-oxo-4-[4-(2-oxo-1,4-dihydr-2H-quinazolin-3-yl)-piperidin-1-yl]-butyryl}-[4,4']bipiperi-dinyl-1-yl)-acetate |
| (9) | | (1'-{2-(4-amino-3-chloro-5-trifluoromethyl-benzyl)--4-oxo-4-[4-(2-oxo-1,4-dihydro-2H-quinazolin-3-yl)-piperidin-1-yl]-butyryl}-[4,4']bipiperi-dinyl-1-yl)-acetic acid |
| (10) | Chiral | 4-(2-oxo-1,2,4,5-tetrahydro-1,3-benzodiazepin-3-yl)-piperidin-1-carboxylic acid-[(R)-1-(4-amino-3-chloro-5-trifluoro-methyl-benzyl)-2-1,4'-dipiperidinyl-1'-yl-2-oxo-ethyl]-amide |
| (11) | Chiral | 4-(2-oxo-1,2,4,5-tetrahydro-1,3-benzodiazepin-3-yl)-piperidin-1-carboxylic acid-[(R)-1-(4-amino-3-chloro-5-trifluoro-methyl-benzyl)-2-(4-dimethylamino-piperidin-1-yl)-2-oxo-ethyl]-amide |

-continued

| Structure | | Name |
|---|---|---|
| (12) | 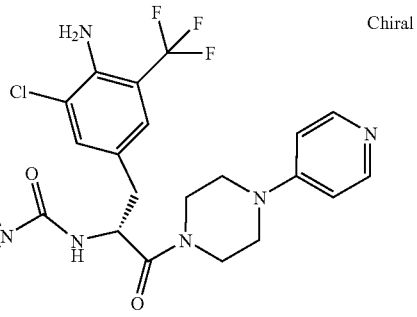 Chiral | 4-(2-oxo-1,2,4,5-tetrahydro-1,3-benzodiazepin-3-yl)-piperidin-1-carboxxylic acid-[(R)-1-(4-amino-3-chloro-5-trifluoro-methyl-benzyl)-2-oxo-2-(4-pyridin-4-yl-piperazin-1-yl)-ethyl]-amide |
| (13) | 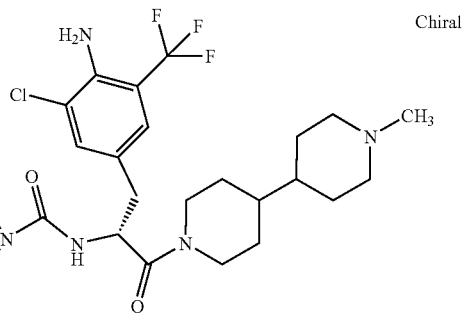 Chiral | 4-(2-oxo-1,2,4,5-tetrahydro-1,3-benzodiazepin-3-yl)-piperidin-1-carboxylic acid-[(R)-1-(4-amino-3-chloro-5-trifluoro-methyl-benzyl)-2-(1'-methyl-4,4'-bipiperi-dinyl-1-yl)-2-oxo-ethyl]-amide |
| (14) | 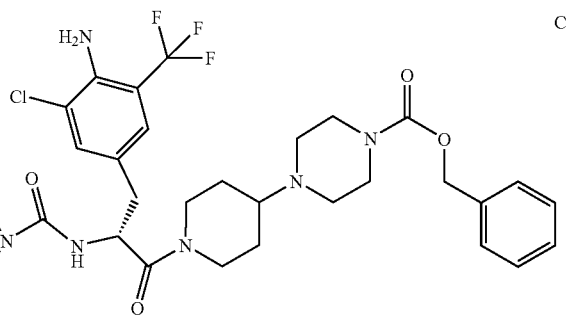 Chiral | benzyl 4-[1-((R)-3-(4-amino-3-chloro-5-trifluoromethyl-phhenyl)-2-{[4-(2-oxo-1,2,4,5-tetrahydro-1,3-benzodi-azepin-3-yl)-piper-idin-1-carbonyl]-amino}-propionyl)-piperidin-4-yl]-piperazin-1-carboxylate |
| (15) | 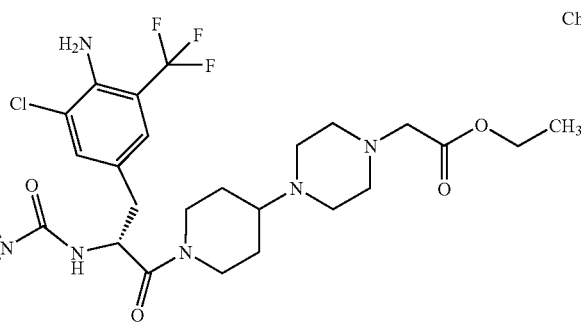 Chiral | ethyl [1'-((R)-3-(4-amino-3-chloro-5-trifluoromethyl-phenyl)-3-‡[4-(2-oxo-1,2,4,5-tetrahydro-1,3-benzodiazepin-3-yl)-piperidin-1-carbonyl]-amino}-propionyl)-4,4'-bipiper-idinyl-1-yl]-acetate |

-continued

| | Structure | Name |
|---|---|---|
| (16) | Chiral | 4-(2-oxo-1,2,4,5-tetrahydro-1,3-benzodiazepin-3-yl)-piperidin-1-carboxylic acid-{(R)-1-(4-amino-3-chlorro-5-trifluoro-methyl-benzyl)-3-[4-(4-methyl-piperazin-1-yl)-piperidin-1-yl]-2-oxo-ethyl}-amide |
| (17) | Chiral | 4-(2-oxo-1,2,4,5-tetrahydro-1,3-benzodiazepin-3-yl)-piperidin-1-carboxylic acid-{(R)-1-(4-amino-3-chloro-55-trifluoro-methyl-benzyl)-2-[4-(1-methyl-piperidin-4-yl)-piperazin-1-yl]-2-oxo-ethyl]}-amide |
| (18) | Chiral | 4-(2-oxo-1,2,4,5-tetrahydro-1,3-benzodiazepin-3-yl)-piperidin-1-carboxylic acid-[(R)-1-(4-amino-3-chloro-55-trifluoro-methyl-benzyl)-2-(4-azetidin-1-yl-piperidin-1-yl)-2-oxo-ethyl]-amide |
| (19) | Chiral | 4-(2-oxo-1,2,4,5-tetrahydro-1,3-benzodiazepin-3-yl)-piperidin-1-carboxylic acid-{(R)-1-(4-amino-3-chloro-5-trifluoro-methyl-benzyl)-2-[4-(5-methyl-2,5-diaza-bicyclo[2.2.1]-hept-2-yl)-piperidin-1-yl]-2-oxo-ethyl}-amide |

| Structure | | Name |
|---|---|---|
| (20) | Chiral | 4-(2-oxo-1,2,4,5-tetrahydro-1,3-benzodiazepin-3-yl)-piperidin-1-carboxylic acid-[(R)-1-(4-amino-3-chloro-5-trifluoro-methyl-benzyl)-2-oxo-2-(4-piperazin-1-yl-piperidin-1-yl)-ethyl]-amide |
| (21) | Chiral | [1'-((R)-3-(4-amino-3-chloro-5-trifluoromethyl-phenyl)-2-‡[4-(2-oxo-1,2,4,5-tetraahydro-1,3-benzodiazepin-3-yl)-piperidin-1-carbonyl]-amino}-propionyl)-4,4'-bipiperidinyl-1-yl]-acetic acid |
| (22) | | 4-(2-oxo-1,2,4,5-tetrahydro-1,3-benzodiazepin-3-yl)-piperidin-1-carboxylic acid-[1-(4-amino-3-chloro-5-trifluoromethyl-benzyl)-2,1,4'-bipiperidinyl-1'-yl-2-oxo-ethy]-amide |
| (23) | Chiral | (S)-2-(4-amino-3-bromo-5-trifluoromethyl-benzyl)-1-[4-(4-methyl-piperazin-1-yl)piperidin-1-yl]-4-[4-(2-oxo-1,2,4,5-tetrahydro-1,3-benzodiazepin-3-yl)-piperidin-1-yl]-butan-1,4-dione |
| (24) | Chiral | (S)-2-(4-amino-3-bromo-5-trifluoromethyl-benzyl)-4-[4-(2-oxo-1,2,4,5-tetrahydro-1,3-benzodiazepin-3-yl)-piperidin-1-yl]-1-(4-pyridin-4-yl-piperazin-1-yl)-butan-1,4-dione |

-continued

| Structure | | Name |
|---|---|---|
| (25) | 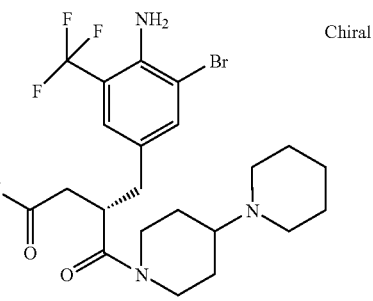 Chiral | (S)-2-(4-amino-3-bromo-5-trifluoromethyl-benzyl)-1-1,4'-bipiperidinyl-1'-yl-0 4-[4-(2-oxo-1,2,4,5-tetrahydro-1,3-benzo-diazepin-3-yl)-piperidin-1-yl]-butan-1,4-dione |
| (26) | 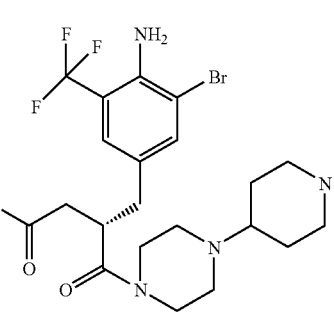 Chiral | (S)-2-(4-amino-3-bromo-5-trifluoromethyl-benzyl)-1-[4-(1-methyl-piperidin-4-yl)-piperazin-1-yl]-4-[4-(2-oxxo-1,2,4,5-tetrahydro-1,3-benzodiazepin-3-yl)-piperidin-1-yl]-butan-1,4-dione |
| (27) | 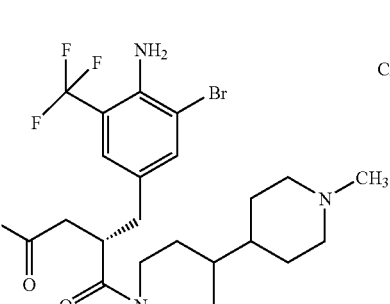 Chiral | (S)-2-(4-amino-3-bromo-5-trifluoromethyl-benzyl)-1-(1'-methyl-4,4'-bipiperidinyl-1-yl)-4-[4-(2-oxo-1,2,4,5-tetrahydro-1,3-benzodiazerpin-3-yl)-piperidin-1-yl]-butan-1,4-dione |
| (28) | 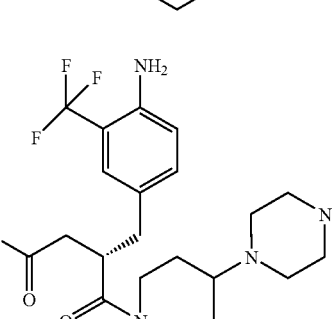 Chiral | (S)-2-(4-amino-3-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione |
| (29) | 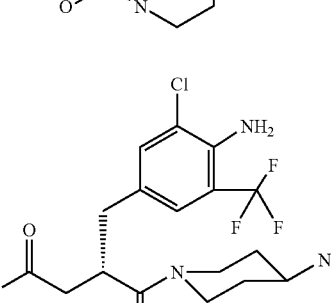 Chiral | (S)-2-(4-amino-3-chloro-5-trifluoromethyl-benzyl)-1-(4-dimethylamino-piperidin-1-yl)-4-[4-(2-oxo-1,2,4,5-tetra-hydro-1,3-benzodiazepin-3-yl)-piperidin-1-yl]-butan-1,4-dione |

| Structure | Name |
|---|---|
| (30) | (S)-2-(4-amino-3-chloro-5-trifluoromethyl-benzyl)-1-(3-dimethylamino-piperidin-1-yl)-4-[4-(2-oxo-1,2,4,5-tetrahydro-1,3-benzodiazepin-3-yl)-piperidin-1-yl]-butan-1,4-dione |
| (31) | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyrrolidin-1-yl-piuperidin-1-yl)-butan-1,4-dione |
| (32) | (S)-2-(4-amino-3-chloro-5-trifluoromethylbenzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione |
| (33) | (S)-2-(4-amino-3-chloro-5-trifluoromethyl-benzyl)-1-[4-(4-cyclopropylmethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione |

-continued

| Structure | Name |
|---|---|
| (34) | (S)-2-(4-amino-3-chloro-5-trifluoromethyl-benzyl)-1-(4-morpholine-4-yl-piperidin-1-yl)-4-[4-(2-oxo-1,2,4,5-tetrahydro-1,3-benzodiazepin-3-yl)-piperidin-1-yl]-butan-1,4-dione |
| (35) | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione |
| (36) | (S)-2-(4-amino-3-chloro-5-trifluoromethyl-benzyl)-1[4-(4-methyl-perhydro-1,4-diazepin-1-yl)-piperidin-1-yl]-4-[4-(2-oxo-1,2,4,5-tetrahydro-1,3-benzo-diazepin-3-yl)-piperidin-1-yl]-butan-1,4-dione |
| (37) | (S)-2-(4-amino-3-chloro-5-trifluoromethyl-benzyl)-1-[4-(4-isopropyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione |

| Structure | Name |
|---|---|
| (38) 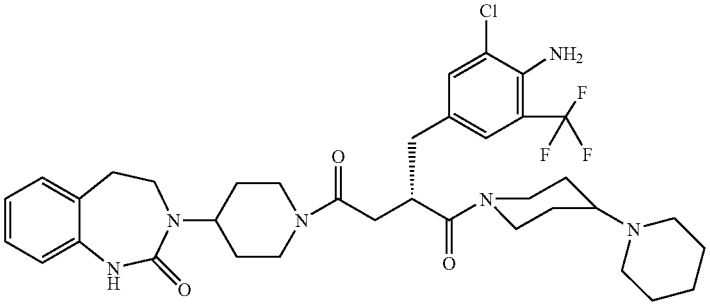 Chiral | (S)-2-(4-amino-3-chloro-5-trifluoromethyl-benzyl)-11-1,4'-bipiperidinyl-1'-yl-4-[2-oxo-1,2,4,5-tetrahydro-1,3-benzodiazepin-3-yl)-piperidin-1-yl]-butan-1,4-dione |
| (39) 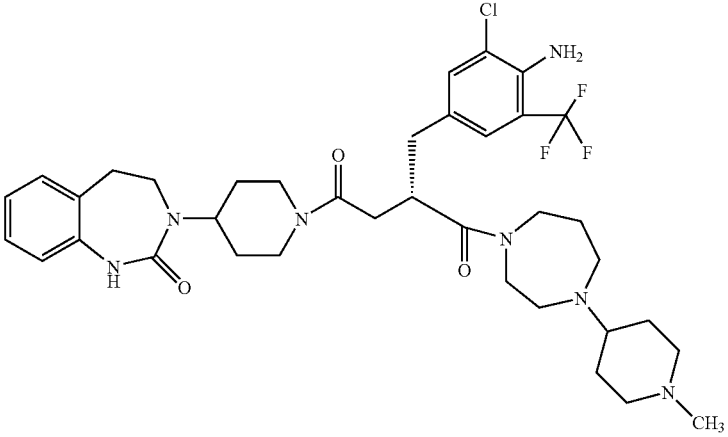 Chiral | (S)-2-(4-amino-3-chloro-5-trifluoromethyl-benzyl)-1-[4-(1-methyl-piperidin-4-yl)-perhydro-1,4-diazepin-1-yl]-4-[4-(2-oxo-1,2,4,5-tetrahydro-1,3-benzo-diazepin-3-yl)-piperidin-1-yl]-butan-1,4-dione |
| (40) 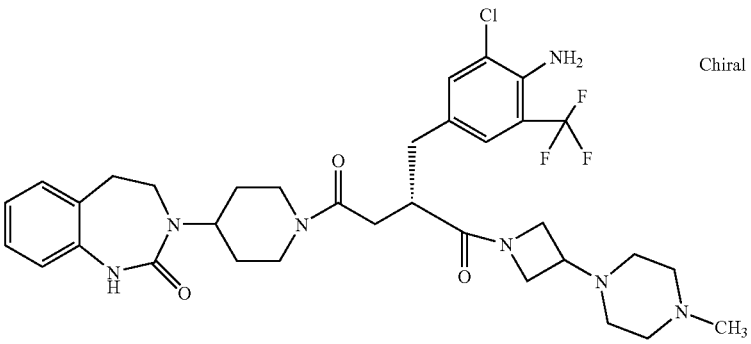 Chiral | (S)-2-(4-amino-3-chloro-5-trifluoromethyl-benzyl)-1-[3-(4-methyl-piperazin-1-yl)-azetidin-1-yl]-4-[4-(2-oxo-1,2,4,5-tetrahydro-1,3-benzodiazepin-3-yl)-piperidin-1-yl]-butan-1,4-dione |
| (41) 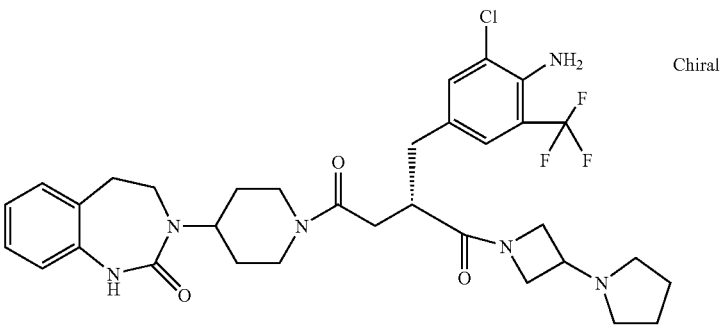 Chiral | (S)-2-(4-amino-3-chloro-5-trifluoromethyl-benzyl)-4-[4-(2-oxxo-1,2,4,5-tetrahydro-1,3-bbenzodiazpin-3-yl)-piperidin-1-yl]-1-(3-pyrrolidin-1-yl-azetidin-1-yl)-butan-1,4-dione |

-continued

| | Structure | Name |
|---|---|---|
| (42) | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3-piperidin-1-yl-azetidin-1-yl)-butan-1,4-dione |
| (43) | Chiral | (S)-2-(4-amino-3-chloro-5-trifluoromethyl-benzyl)-1-(3-diethylamino-azetidin-1-yl)-4-[4-(2-oxo-1,2,4,5-tetrahydro-1,3-benzodiazepin-3-yl)-piperidin-1-yl]-butan-1,4-dione |
| (44) | Chiral | (S)-2-(4-amino-3-chloro-5-trifluoromethyl-benzyl)-1-(4-azetidin-1-yl-piperidin-1-yl)-4-[4-(2-oxo-1,2,4,5-tetrahydro-1,3-benzodiazepin-3-yl)-piperidin-1-yl]-butan-1,4-dione |
| (45) | Chiral | (S)-1-[4-(4-acetyl-piperazin-1-yl)-piperidin-1-yl]-2-(4-amino-3-chloro-5-trifluoromethyl-benzyl)-4-[4-(2-oxo-1,2,4,5-tetrahydro-1,3-benzodiazepin-3-yl)-piperidin-1-yl]-butan-1,4-dione |

| Structure | Name |
|---|---|
| (46) | (S)-2-(4-amino-3-chloro-5-trifluoromethyl-benzyl)-1-(4-diethylaminomethyl-piperidin-1-yl)-[4-(2-oxo-1,2,4,5-tetrahydro-1,3-benzodiazepin-3-yl)-piperidin-1-yl]-butan-1,4-dione |
| (47) | (S)-2-(4-amino-3-chloro-5-trifluoromethyl-benzyl)-1-[4-(4-ethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione |
| (48) | (S)-2-(4-amino-3-chloro-5-trifluoromethyl-benzyl)-1-[4-(1-ethyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione |
| (49) | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3,4,5,6-tetrahydro-2H-4,4'-bipyridinyl-1-yl)-butan-1,4-dione |

-continued

| | Structure | | Name |
|---|---|---|---|
| (50) | 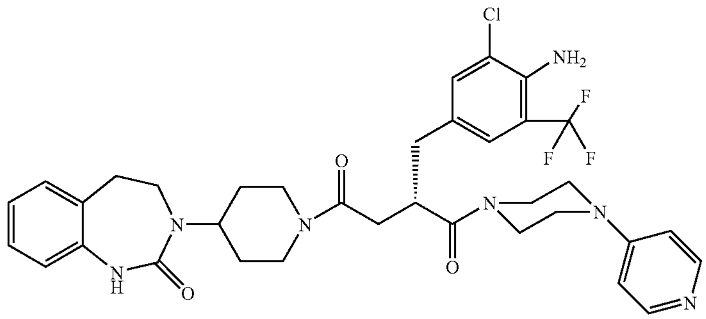 | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyrridin-4-yl-piperazin-1-yl)-butan-1,4-dione |
| (51) | 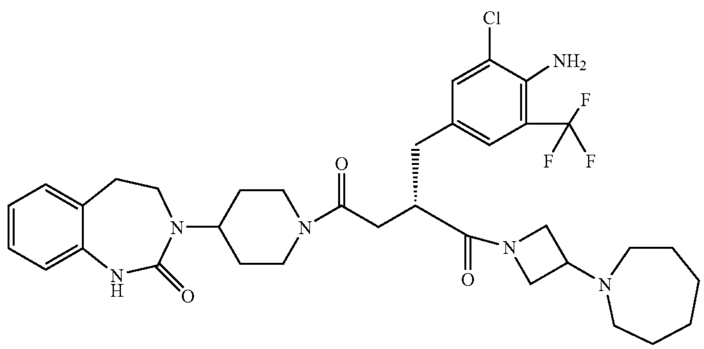 | Chiral | (S)-2-(4-amino-3-chloro-5-trifluorromethyl-benzyl)-4-[4-(2-oxo-1,2,4,5-tetrahydro-1,3-benzodiazepin-3-yl)-piperidin-1-yl]-1-(3-perhydro-azepin-1-yl-azetidin-1-yl)-butan-1,4-dione |
| (52) | 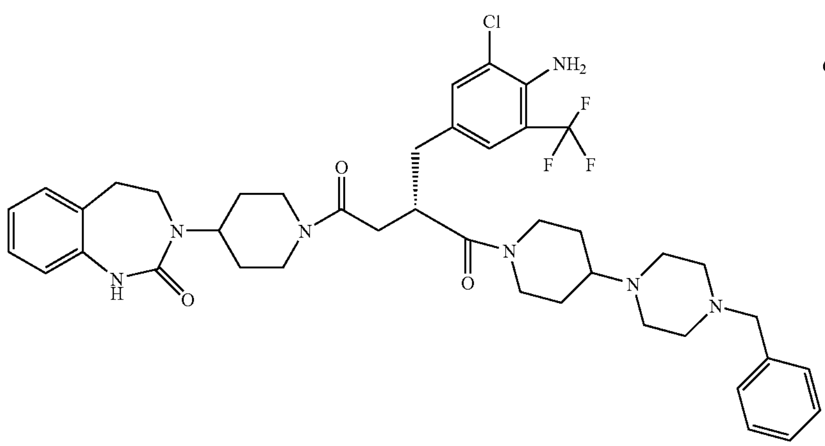 | Chiral | (S)-2-(4-amino-3-chloro-5-trifluoromethyl-benzyl)-1-[4-(1-benzyl-piperidin-44-yl)-piperazin-1-]4-[4-(2-oxo-1,2,4,5-tetra-hydro-1,3-benzodiazepin-3-yl)-piperidin-1-yl]-butan-1,4-dione |
| (53) | 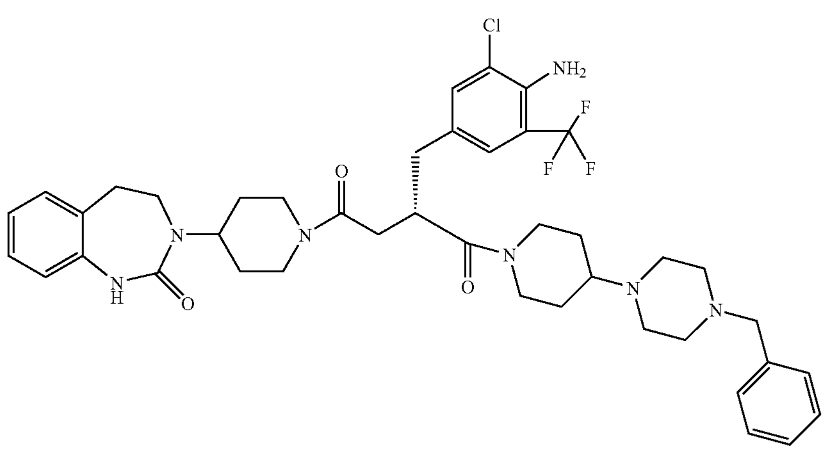 | Chiral | (S)-2-(4-amino-3-chloro-5-trifluoromethyl-benzyl)-1-[4-(4-benzyl-piperazin-1-yl)-piperidin-1-yl]-4-[4-(2-oxo-1,2,4,5-tetrahydro-1,3-benzodiaszepin-3-yl)-piperidin-1-yl]-butan-1,4-dione |

-continued

| | Structure | | Name |
|---|---|---|---|
| (54) | | Chiral | (S)-2-(4-amino-3-chloro-5-trifluoromethyl-benzyl)-1-(7-dimethylamino-methyl-1,2,4,5-tetrahydro-3-benzaze3pin-3-yl)-4-[4-(2-oxo-1,2,4,5-tetrahydro-1,3-benzodiazepin-3-yl)-piperidin-1-yl]-butan-1,4-dione |
| (55) | | Chiral | (S)-2-(4-amino-3-chloro-5-trifluoromethyl-benzyl)-1-[4-(4-dimethylamino-methyl-phenyl)-piperidin-1-yl]-4-[4-(2-oxxo-1,2,4,5-tetrahydro-1,3-benzodiazepin-3-yl)-piperidin-1-yl]-butan-1,4-dione |
| (56) | | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-ethyl)-piperazin-1-yl]-piperidin-1-yl}-butan-1,4-dione |

| Structure | | Name |
|---|---|---|
| (57) | Chiral | (S)-2-(4-amino-3-chloro-5-trifluoromethyl-benzyl)-1-(1'-methanesulphonyl-4,4'-bipieridinyl-1-yl)-4-[4-(2-oxo-1,2,4,5-tetrahydro-1,3-benzodiazepin-3-yl)-piperidin-1-yl]-butan-1,4-dione |
| (58) | Chiral | (S)-2-(4-amino-3-chloro-5-trifluoromethyl-benzyl)-1-(9-methyl-3,9-diaza-spiro[5.5]-undec-3-yl)-4-[44-(2-oxo-1,2,4,5-tetra-hydro-1,3-benzodi-azepin-3-yl)-piper-idin-1-yl]-butan-1,4-dione |
| (59) | Chiral | (S)-2-(4-amino-3-chloro-5-trifluoromethyl-benzyl)-4-[4-(2-oxxo-1,2,4,5-tetrahydro-1,3-benzodiazepin-33-yl)-piperidin-1-yl]-1-(4-piperidin-1-ylmethyl-piperidin-1-yl)-butan-1,4-dione |

-continued

| Structure | | Name |
|---|---|---|
| (60) | Chiral | (S)-2-(4-amino-3-chloro-5-trifluoromethyl-benzyl)-1-[4-(2-dimethylamino-ethyl)-piperidin-1-yl]-4-[4-(2-oxo-1,2,4,5-tetrahydro-1,3-benzodiazepin-3-yl)-piperidin-1-yl]-butan-1,4-dione |
| (61) | Chiral | (S)-2-(4-amino-3-chloro-5-trifluoromethyl-benzyl)-N-methyl-N-[2-(1-methyl-piperidin-4-yl)-ethyl]-4-oxo-4-[4-(2-oxo-1,2,4,5-tetrahydro-1,3-benzodiazepin-3-yl)-piperidin-1-yl]-butyramide |
| (62) | Chiral | (S)-2-(4-amino-3-chloro-5-trifluoromethyl-benzyl)-N-methyl-N-(1-methyl-piperidin-4-ylmethyl)-4-oxo-4-[4-(2-oxo-1,2,4,5-tetrahydro-1,3-benzodiazepin-3-yl)-piperidin-1-yl]-butyramide |

-continued

| Structure | | Name |
|---|---|---|
| (63) | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-piperidin-1-yl-butan-1,4-dione |
| (64) | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-propyl-piperidin-1-yl)-butan-1,4-dione |
| (65) | Chiral | (S)-2-(4-amino-3-chloro-5-trifluoromethyl-benzyl)-1-(4-benzyl-piperidin-1-yl)-4-[4-(2-oxo-1,2,4,5-tetrahydro-1,3-benzo-diazepin-3-yl)-piperidin-1-yl]-butan-1,4-dione |

| Structure | | Name |
|---|---|---|
| (66) | Chiral | (S)-2-(4-amino-3-chloro-5-trifluoromethyl-benzyl)-1-[4-(2-diethylamino-ethyl)-piperidin-1-yl]-4-[4-(2-oxo-1,2,4,5-tetrahydro-1,3-benzodiazepin-3-yl)-piperidin-1-yl]-butan-1,4-dione |
| (67) | Chiral | (S)-2-(4-amino-3-chloro-5-trifluoromethyl-benzyl)-1-(3-aza-spiro[5.5]undec-3-yl)-4-[4-(2-oxo-1,2,4,5-tetrahydro-1,3-benzodiazepin-3-yl)-piperidin-1-yl]-butan-1,4-dione |
| (68) | Chiral | N-(1-{(S)-2-(4-amino-3-chloro-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-N-methyl-methanesulphonamide |

-continued

| Structure | | Name |
|---|---|---|
| (69) | Chiral | N-(1-{(S)-2-(4-amino-3-chloro-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-methanesulphonamide |
| (70) | Chiral | (S)-2-(4-amino-3-chloro-5-trifluoromethyl-benzyl)-1-[4-(cyclopentyl-methyl-amino)piperidin-1-yl]-4-[4-(2-oxo-1,2,4,5-tetrahydro-1,3-benzodiazepin-3-yl)-piperidin-1-yl]-butan-1,4-dione |
| (71) | Chiral | (S)-2-(4-amino-3-chloro-5-trifluoromethyl-benzyl)-1-(4-methyl-piperidin-1-yl)-4-[4-(2-oxo-1,2,4,5-tetrahydro-1,3-benzodiazepin-3-yl)-piperidin-1-yl]-butan-1,4-dione |

-continued

| Structure | | Name |
|---|---|---|
| (72) 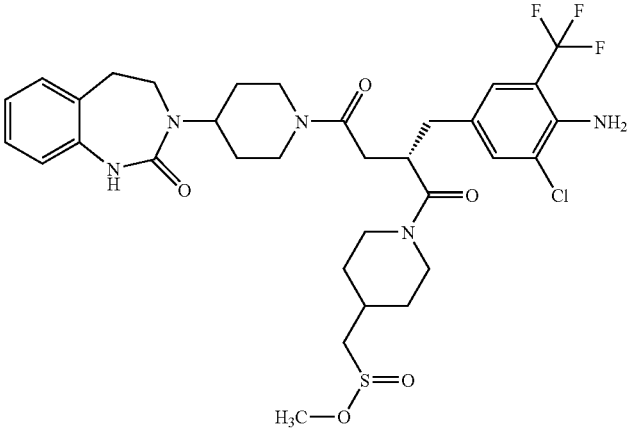 | Chiral | methyl (1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]butyryl}-piperidin-4-yl)-acetate |
| (73) 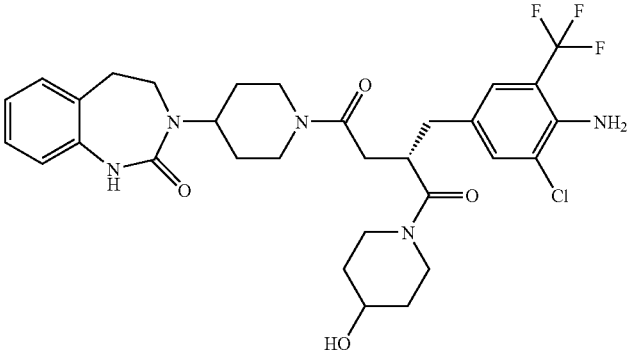 | Chiral | (S)-2-(4-amino-3-chloro-5-trifluoromethyl-benzyl)-1-(4-hydroxy-piperidin-1-yl)-4-[4-(2-oxo-1,2,4,5-tetrahydro-1,3-benzodiazepin-3-yl)-piperidin-1-yl]-butan-1,4-dione |
| (74) 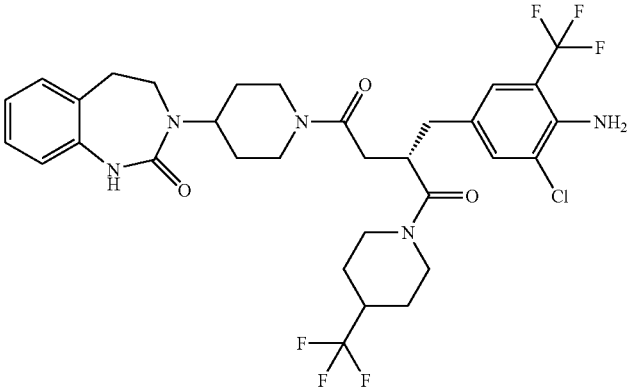 | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-trifluoromethyl-piperidin-1-yl)-butan-1,4-dione |

| | Structure | Chiral | Name |
|---|---|---|---|
| (75) | 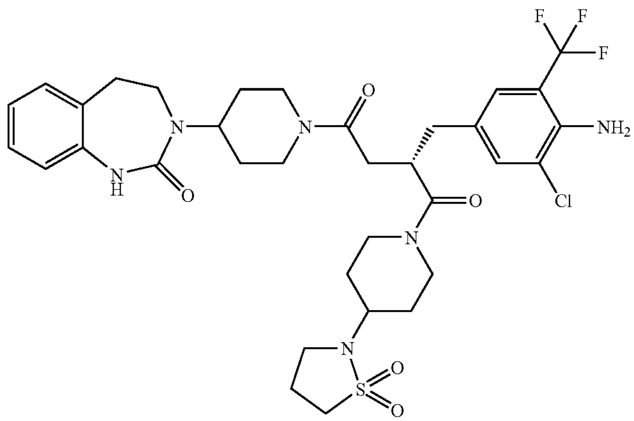 | Chiral | (S)-2-(4-amino-3-chloro-5-trifluoromethyl-benzyl)-1-[4-(1,1-dioxo-λ⁶-isothia-zolidin-2-yl)-piperidin-1-yl]-4-[4-(2-oxo-1,2,4,5-tetrahydro-1,3-benzodiazepin-3-yl)-piperidin-1-yl]-butan-1,4-dione |
| (76) | 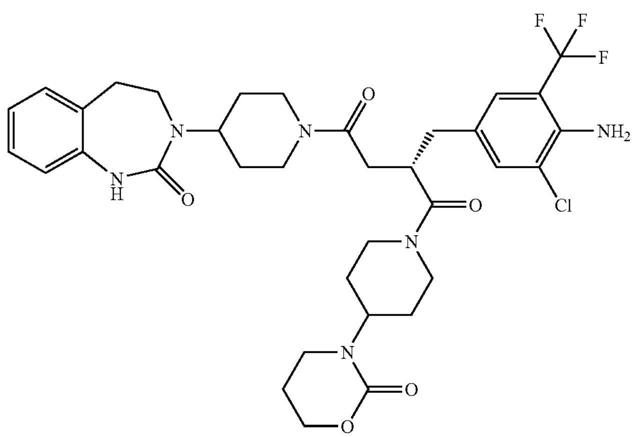 | Chiral | (S)-2-(4-amino-3-chloro-5-trifluoromethyl-benzyl)-1-[4-(2-oxo-perhydro-1,3-oxazin-3-yl)-piperidin-1-yl]-4-[4-(2-oxo-1,2,4,5-tetrahydro-1,3-benzodiazepin-3-yl)-piperidin-1-yl]-butan-1,4-dione |
| (77) | 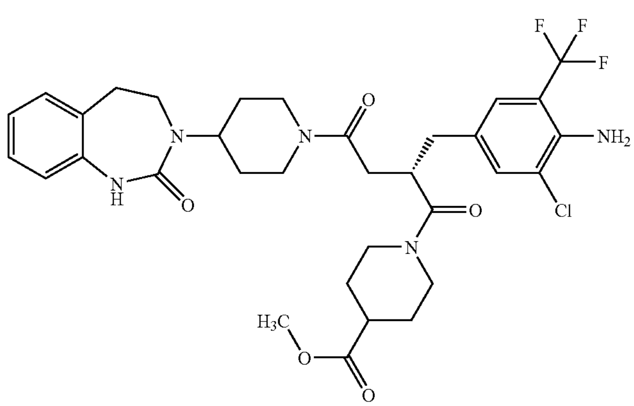 | Chiral | methyl 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-carboxylate |

-continued

| Structure | | Name |
|---|---|---|
| (78) | Chiral | (S)-2-(4-amino-3-chloro-5-trifluoromethyl-benzyl)-1-(4-cyclohexyl-piperidin-1-yl)-4-[4-(2-oxo-1,2,4,5-tetrahydro-1,3-benzodiazepin-3-yl)-piperidin-1-yl]butan-1,4-dione |
| (79) | Chiral | (S)-2-(4-amino-3-chloro-5-trifluoromethyl-benzyl)-1-(4-tert-butylamino-piperidin-1-yl)-4-[4-(2-oxo-1,2,4,5-tetrahydro-1,3-benzodiazepin-3-yl)-piperidin-1-yl]-butan-1,4-dione |
| (80) | Chiral | (S)-2-(4-amino-3-chloro-5-trifluoromethyl-benzyl)-4-[4-(2-oxo-1,2,4,5-tetrahydr-1,3-benzodiazepin-3-yl)-piperidin-1-yl]-1-(4-phenyl-piperidin-1-yl)-butan-1,4-dione |

| Structure | | Name |
|---|---|---|
| (81) | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-p-tolyl-piperidin-1-yl)-butan-1,4-dione |
| 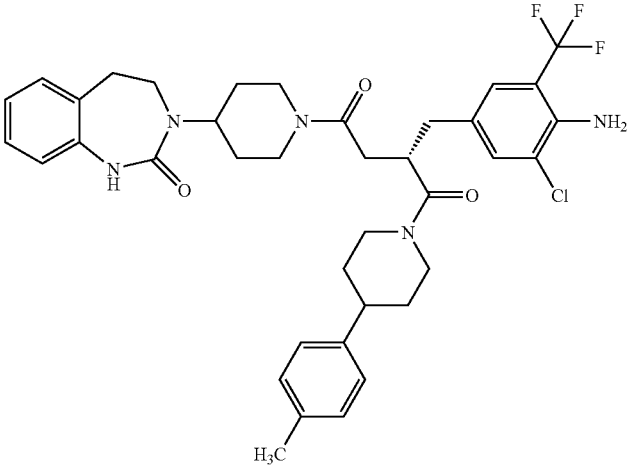 | | |
| (82) | Chiral | 8-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]butyryl}-1,3,8-triaza-spiro-[4.5]decan-2,4-dione |
| 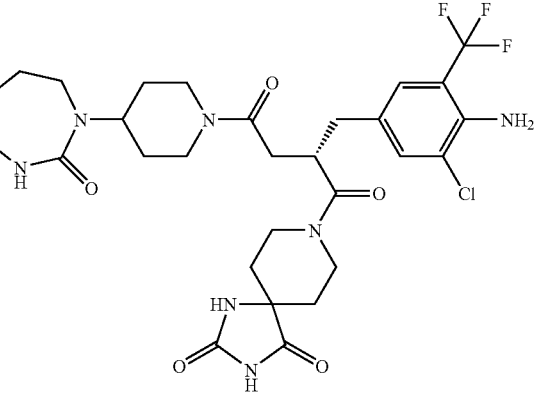 | | |
| (83) | Chiral | (S)-2-(4-amino-3-chloro-5-trifluoromethyl-benzyl)-1-[4-(2-oxo-imidazolin-1-yl)-piperidin-1-yl]-4-[4-(2-oxo-1,2,4,5-tetrahydro-1,3-benzodiazepin-3-yl)-piperidin-1-yl]-butan-1,4-dione |
| 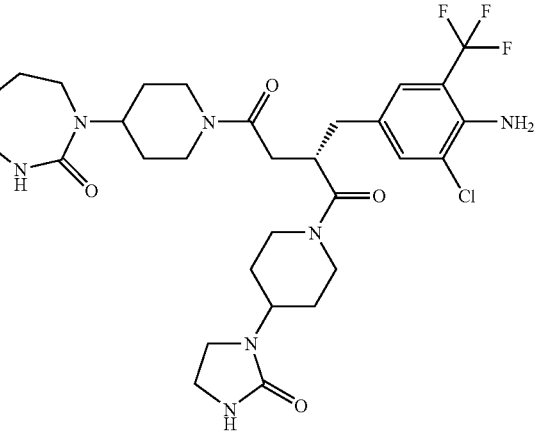 | | |

| Structure | | Name |
|---|---|---|
| (84) | Chiral | (S)-2-(4-amino-3-chloro-5-trifluoromethyl-benzyl)-1-(4-amino-4-methyl-piperidin-1-yl)-4-[4-(2-oxo-1,2,4,5-tetrahydro-1,3-benzodiazepin-3-yl)-piperidin-1-yl]-butan-1,4-dione |
| (85) | Chiral | (S)-2-(4-amino-3-chloro-5-trifluoromethyl-benzyl)-1-[4-(1-methyl-piperidin-4-nl yl)piperazin-1-yl]-4-[4-(2-oxo-1,2,4,5-tetrahydro-1,3-benzodiazepin-3-yl)-piperidin-1-yl]-butan-1,4-dione |
| (86) | Chiral | (S)-2-(4-amino-3-chloro-5-trifluoromethyl-benzyl)-1-(2-amino-4,5,7,8-tetrahydro-thiazolo[4,5-d]azepin-6-yl)-4-[4-(2-oxo-1,2,4,5-tetrahydro-1,3-benzodiazepin-33-yl)-piperidin-1-yl]-butan-1,4-dione |
| (87) | Chiral | (S)-2-(4-amino-3-chloro-5-trifluoromethyl-benzyl)-1-[4-(2-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione |

| Structure | | Name |
|---|---|---|
| (88) | Chiral | (S)-2-(4-amino-3-chloro-5-trifluoromethyl-benzyl)-1-[4-(4-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione |
| (89) | Chiral | (S)-2-(4-amino-3-chloro-5-trifluoromethyl-benzyl-4-[4-(2-oxo-1,2,4,5-tetrahydro-1,3-benzodiazepin-3-yl)-piperidin-10 yl]-1-(4-thiazol-2-yl-piperazin-1-yl)-butan-1,4-dione |
| (90) | Chiral | (S)-2-(4-amino-3-chloro-5-trifluoromethyl-benzyl)-1-[4-(2,4-dimethyl-imidazol-1-yl)-piperidin-1-yl]-4-[4-(2-oxo-1,2,4,5-tetrahydro-1,3-benzodiazerpin-3-yl)-piperidin-1-yl]-butan-1,4-dione |
| (91) | Chiral | (S)-2-(4-amino-3-chloro-5-trifluromethyl-benzyl)-1-(4-imidazol-1-yl-piperidin-1-yl)-4-[4-(2-oxo-1,2,4,5-tetrahydro-1,3-benzodiazepin-3-yl)-piperidin-1-yl]-butan-1,4-dione |

-continued

| | Structure | Name |
|---|---|---|
| (92) | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-1,2,4-triazol-1-yl-piperidin-1-yl)-butan-1,4-dione |
| (93) | Chiral | (S)-2-(4-amino-3-chloro-5-trifluoromethyl-benzyl)-1-[4-(1-aza-bicyclo[2.2.2]oct-3-yl)-piperazin-1q-yl]-4-[4-(2-oxo-1,2,4,5-tetrahydro-1,3-benzodiazepin-3-yl)-piperidin-1-yl]-butan-1,4-dione |
| (94) | Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-piperazin-1-yl-butan-1,4-dione |
| (95) | Chiral | 4-{(S)-2-(4-amino-3-chloro-5-trifluoromethyl-benzyl)-4-oxo-4-[4-(2-oxo-1,2,4,5-tetrahydro-1,3-benzodiaze-pin-3-yl)-piperidin-1-yl]-butyryl}-piperazin-1-sulphonic acid-(1-methyl-piperidin-4-yl)-amide |

-continued

| Structure | | Name |
|---|---|---|
| (96) | 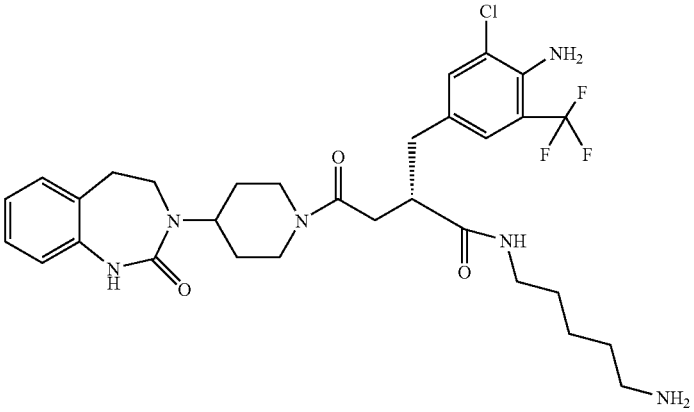 Chiral | (S)-2-(4-amino-3-chloro-5-trifluoromethyl-benzyl)-N-(5-amino-pentyl)-4-oxo-4-[4-(2-oxo-1,2,4,5-tetrahydro-1,3-benzodiazepin-3-yl)-piperidin-1-yl]-butyramide |
| (97) | 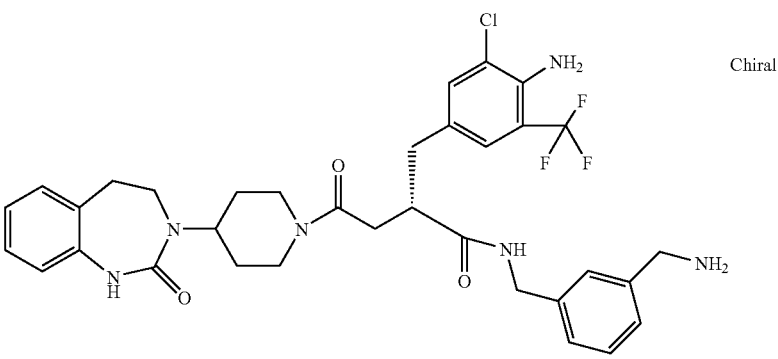 Chiral | (S)-2-(4-amino-3-chloro-5-trifluoromethyl-benzyl)-N-(3-aminomethyl-benzyl)-4-oxo-4-[4-(2-oxo-1,2,4,5-tetrahydro-1,3-benzodiazepin-3-yl)-piperidin-1-yl]-butyramide |
| (98) | 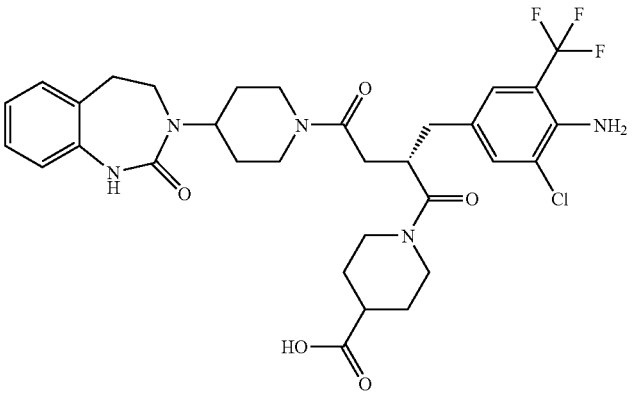 Chiral | 1-{(S)-2-(4-amino-3-chloro-5-trifluorromethyl-benzyl)-4-oxo-4-[4-(2-oxo-1,2,4,5-tetrahydro-1,3-benzodiazepin-3-yl)-piperidin-1-yl]-butyryl}-piperidin2-4-carboxylic acid |
| (99) | 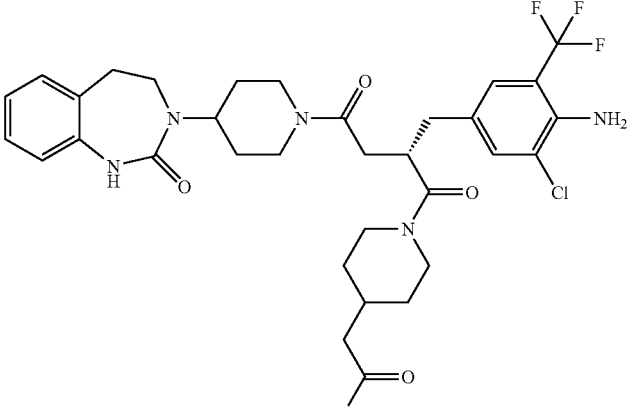 Chiral | (1-{(S)-2-(4-amino-3-chloro-5-trifluoromethyl-benzyl)--4-oxo-4-[4-(2-oxo-1,2,4,5-tetrahydro-1,3-benzodiazepin-3-yl)-piperidin-1-yl]butyryl}-piperidin-4-yl)-acetic acid |

-continued

| Structure | | Name |
|---|---|---|
| (100) | 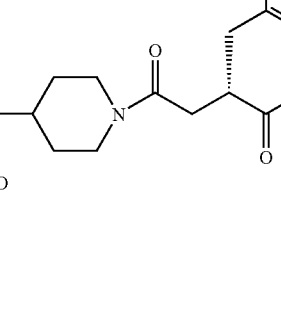 Chiral | (S)-2-(4-amino-3-chloro-5-trifluoromethyl-benzyl)-1-[4-(8-methyl-8-aza-bicyclo[3.2.1]oct-3-yl)-piperazin-1-yl]-4-[4-(2-oxo-1,2,4,5-tetrahydro-1,3-benzodiazepin-3-yl)-piperidin-1-yl]-butan-1,4-dione |
| (101) | 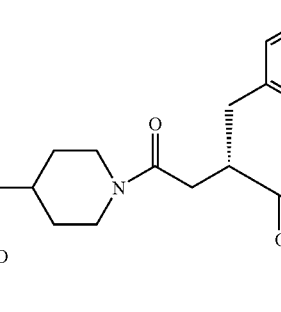 Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazine-1-yl-piperidin-1-yl)-butan-1,4-dione |
| (102) | 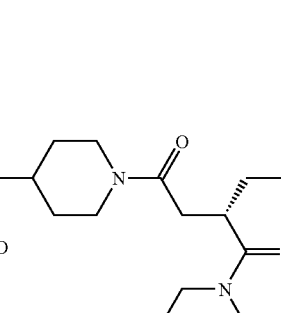 Chiral | (S)-2-(4-amino-3-chloro-5-trifluoromethyl-benzyl)-1-[4-(1H-imidazol-4-yl)-piperidin-1-yl]-4-[4-(2-oxo-1,2,4,5-tetrahydro-1,3-benzodiazepin-3-yl)-piperidin-1-yl]-butan-1,4-dione |
| (103) | 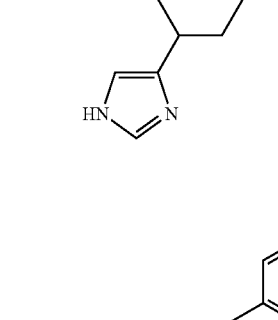 Chiral | (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-acetyl)-phenyl]-piperazin-1-yl}-butan-1,4-dione |

| Structure | Name |
|---|---|
| (104) Chiral | (S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione |
| (105) Chiral | (S)-2-(4-amino-3-chloro-5-trifluoromethyl-benzyl)-1-[4-(4-methyl-piperazin-1-yl)-piperidin-1-yl]-4-[4-(5-oxo-3-phenyl-4,5-dihydro-1,2,4-triazol-1-yl)-piperidin-1-yl]-butan-1,4-dione |
| (106) Chiral | (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-imidazo[4,5-c]quinolin-3-yl)-piperidin-1-yl]-butan-1,4-dione |
| (107) Chiral | (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-4H)-thieno[3,4-d]pyrimidin-3-yl)-piperidin-1-yl]-butan-1,4-dione |

| | Structure | Name |
|---|---|---|
| (108) | 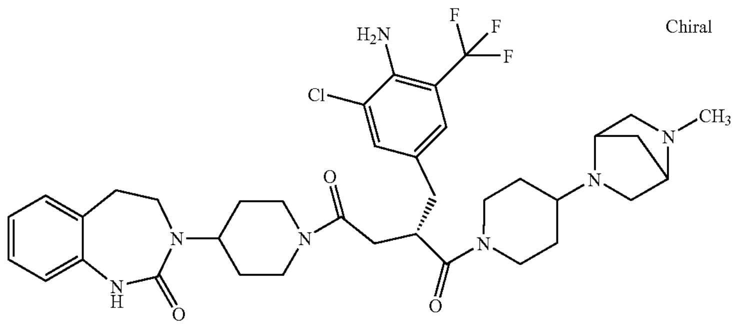 | (S)-2-(4-amino-3-chloro-5-trifluoromethyl-benzyl)-1-[4-(5-methyl-2,5-diaza-bicyclo[2.2.1]hept-2-yl)-piperidin-1-yl]-4-[4-2-oxo-1,2,4,5-tetrahydro-1,3-benzo-diazepin-3-yl]-piperidin-1-yl]-butan-1,4-dione |
| (109) | 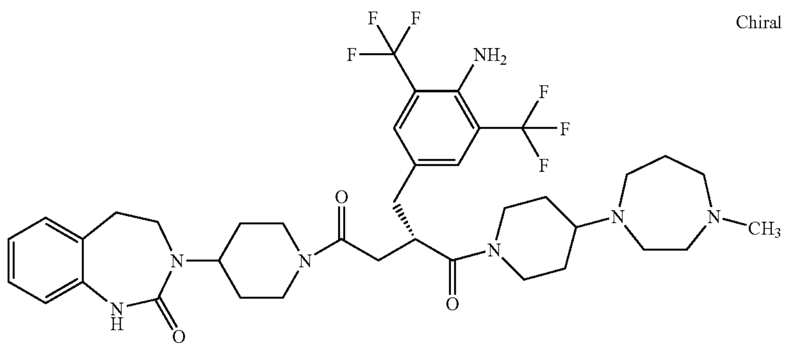 | (SS)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione |
| (110) | 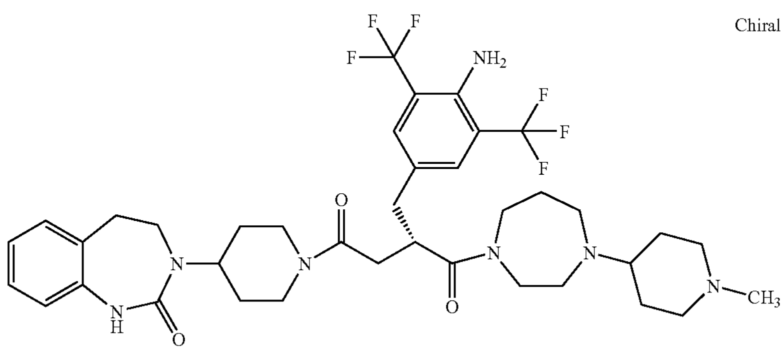 | (S)-2-(4-amino-3,5-bis-trifluoromethyl-benzyl)-1-[4-(1-methyl-piperidin-4-yl)-perhydro-1,4-diazzepin-1-yl]-4-[4-(2-oxo-1,2,4,5-tetrahydro-1,3-benzodiazepin-3-yl)-piperidin-1-yl]-butan-1,4-dione |
| (111) | 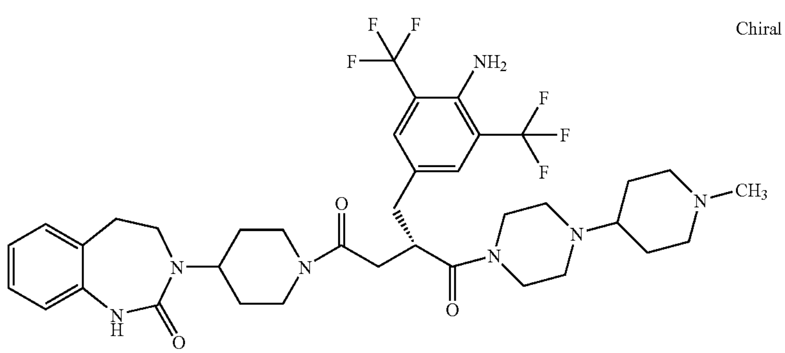 | (S)-2-(4-amino-3,5-bis-trifluoromethyl-benzyl)-1-[4-(1-methyl-piperidin-4-yl)-piperiazin-1-yl]-4-[4-(2-oxo-1,2,4,5-tetrahydro-1,3-benzo-diazepin-3-yl)-piperidin-1-yl]-butan-1,4-dione |

| Structure | | Name |
|---|---|---|
| (112) | Chiral | (S)-2-(4-amino-3,5-bis-trifluoromethyl-benzyl)-1-[4-(1-aza-bicyclo[2.2.2]oct-3-yl)-piperazin-1-yl]-4-[4-(2-oxo-1,2,4,5-tetrahydro-1,3-benzodiazepin-33-yl)-piperidin-1-yl]-butan-1,4-dione |
| (113) | Chiral | (S)-2-(4-amino-3,5-bis-trifluoromethyl-benzyl)-1-[4-(4-methyl-piperazin-1-yl)-piperidin-1-yl]-4-[4-2-(oxo-1,2,4,5-tetrahydro-1,3-benzodiazepin-3-yl)-piperidin-1-yl]-butan-1,4-dione |
| (114) | Chiral | (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione |
| (115) | Chiral | (S)-2-(4-amino-3,5-bis-trifluoromethyl-benzyl)-1,1',4'-bipiperidinyl-1'-yl-4-[4-(2-oxo-1,2,4,5-tetrahydro-1,3-benzodiazepin-3-yl)-piperidin-1-yl]-butan-1,4-dione |

-continued

| | Structure | | Name |
|---|---|---|---|
| (116) | Chiral | | (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione |
| (117) | Chiral | | 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(4-methyl-piperazin-1-yl)-piperidin-1-yl]-2-oxo-ethyl}-amide |
| (118) | Chiral | | 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(1-methyl-piperidin-1-yl)-piperazin-1-yl]-2-oxo-ethyl}-amide |
| (119) | Chiral | | 4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-1,4'-bipiperidinyl-1'-yl-2-oxo-ethyl]-amide |

| | Structure | Name |
|---|---|---|
| (120) | 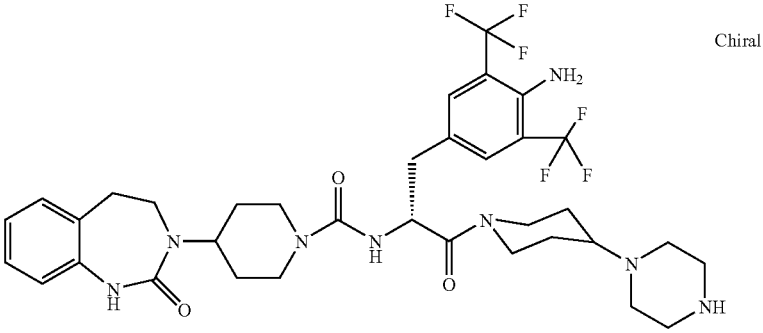 Chiral | 4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-oxo-2-(4-piperazin-1-yl-piperidin-1-yl)-ethyl]-amide |
| (121) | 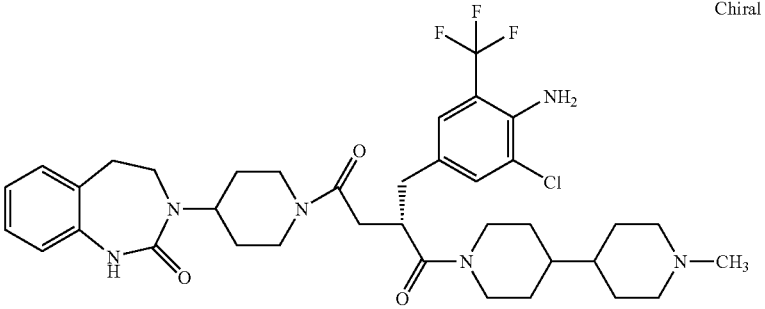 Chiral | 4-(2-oxo-1,2,4,5-tetrahydro-1,3-benzodiazepin-3-yl)-piperidin-1-carboxylic acid-(R)-1-(4-amino-3-chloro-5-trifluoromethyl-benzyl)-2-[4-(4-methyl-piperazin-1-yl)-piperidin-1-yl]-2-oxo-ethyl ester |
| (122) | 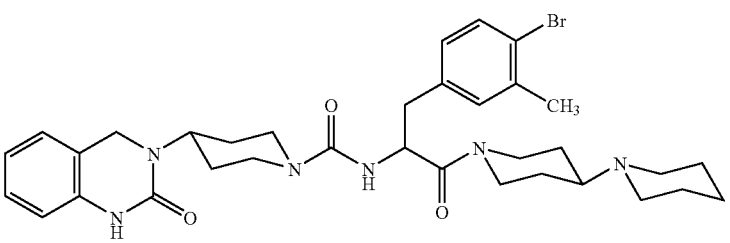 | 4-(2-oxo-1,4-dihydro-2H-quinazolin-3-yl)-piperidin-1-carboxylic acid-[2-[1,4'nipiperidinyl-1'-yl-1-(4-bromo-3-methyl-benzyl)-2-oxo-ethyl]-amide |
| (123) | 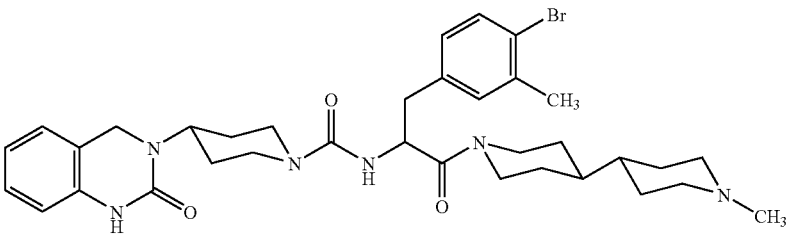 | 4-(2-oxo-1,4-dihydro-2H-quinazolin-3-yl)-piperidin-1-carboxylic acid-[1-(4-bromo-3-methyl-benzyl)-2-(1'-methyl-[4,4'-bipiperidinyl-1-yl)-2-oxo-ethyl]-amide |
| (124) | 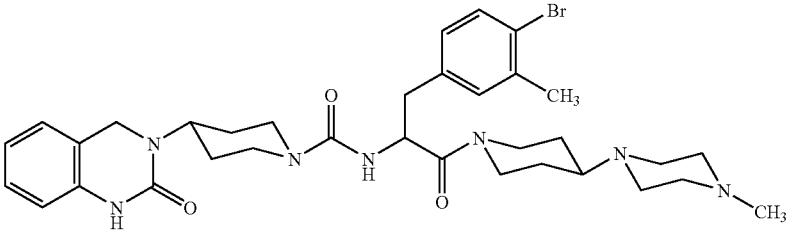 | 4-(2-oxo-1,4-dihydro-2H-quinazolin-3-yl)-piperidin-1-carboxylic acid-{1-(4-bromo-3-methyl-benzyl)-2-[4-(4-methyl-piperazin-1-yl)-piperidin-1-yl]-2-oxo-ethyl}-amide |

| Structure | Name |
|---|---|
| (125) 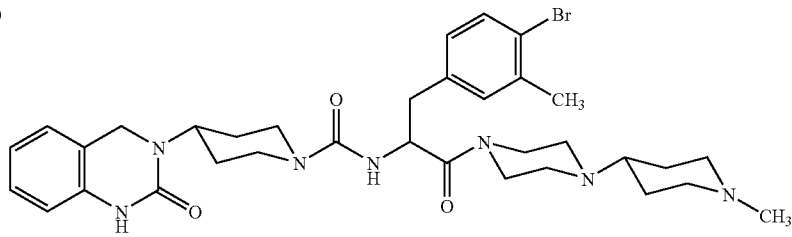 | 4-(2-oxo-1,4-dihydro-2H-quinazolin-3-yl)-piperidin-1-carboxylic acid-{1-(4-bromo-3-methyl-benzyl)-2-[4-(1-methyl-piperidin-4-yl)-piperazin-1-yl]-2-oxo-ethyl}-amide |
| (126) 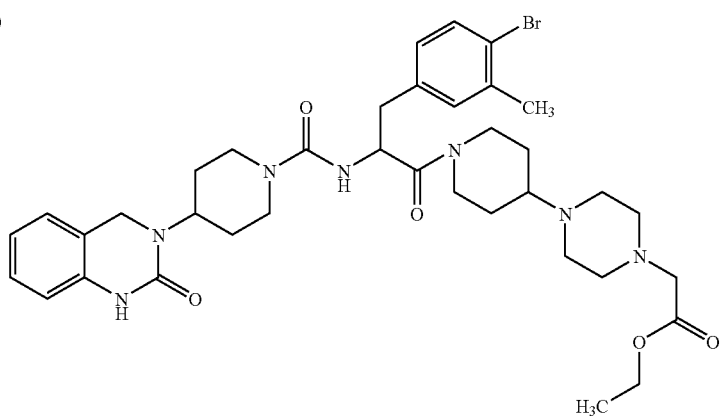 | ethyl {4-[1-(3-(4-bromo-3-methyl-phenyl)-2-{[4-(2-oxo-1,4-dihydro-2H-quinazolin-3-yl)-piperidin-1-carbonyl]-amino}-propionyl)-piperidin-4-yl]-piperazin-1-yl}-acetate |
| (127) 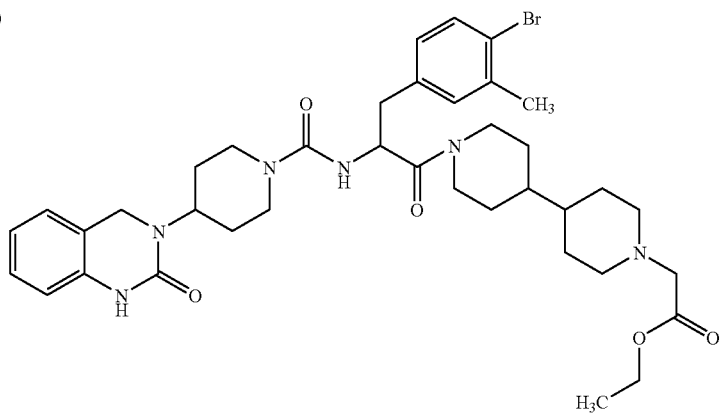 | ethyl [1'-(3-(4-bromo-3-methyl-phenyl)-2-{[4-(2-oxo-1,4-dihydro-2H-quinazolin-3-yl)-piperidin-1-carbonyl]-amino}-propionyl)-[4,4']bipiperidinyl-1-yl]acetate |
| (128) 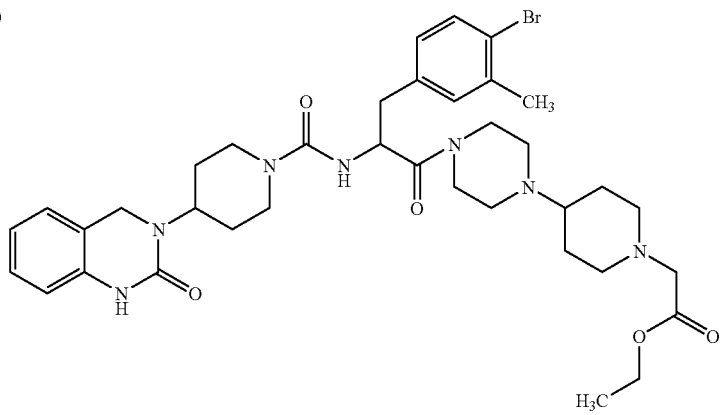 | ethyl {4-[4-(3-(4-bromo-3-methyl-phenyl)-2-{[4-(2-oxo-1,4-dihydro-2H-quinazolin-3-yl)-piperidin-1-carbonyl]-amino}-propionyl)-piperazin-1-yl]-piperidin-1-yl}-acetate |

-continued

| | Structure | Name |
|---|---|---|
| (129) | | {4-[1-(3-(4-bromo-3-methyl-phenyl)-2-{[4-(2-oxo-1,4-dihydro-2H-quinazolin-3-yl)-piperidin-1-carbonyl]-amino}-propionyl)-piperidin-4-yl]-piperazin-1-yl}-acetic acid |
| (130) | | [1'-(3-(4-bromo-3-methyl-phenyl)-2-{[4-(2-oxo-1,4-dihydro-2H-quinazolin-33-yl)-piperidin-1-carbonyl]-amino}-propionyl)-[4,4']-bipiperidinyl-1-yl]-acetic acid |
| (131) | | {4-[4-(3-(4-bromo-3-methyl-phenyl)-2-{[4-(2-oxo-1,4-dihydro-2H-quinazolin-3-yl)-piperidin-1-carbonyl]-amino}-propionyl)-piperazin-1-yl]-piperidin-1-yl}-acetic acid |
| (132) | | 2-(4-bromo-3-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione |

-continued

| | Structure | Name |
|---|---|---|
| (133) | | 2-(4-bromo-3-methyl-benzyl)-1-(1'-methyl-[4,4']bipiperidinyl-1-yl)-4-[4-(2-oxo-11,4-dihydro-2H_quinazolin-3-yl)-piperidin-1-yl]butan-1,4-dione |
| (134) | | 1-[1,4']Bipiperidinyl-1'-yl-2-(4-bromo-3-methyl-benzyl)-4-[4-(2-oxo-1,4-dihydro-2H-quinazolin-3-yl)-piperidin-1-yl]butan-1,4-dione |
| (135) | | 2-(4-bromo-3-methyl-benzyl)-1-{4-[4-(3-dimethylamino-propyl)-phenyl]-piperazin-1-yl}-4-[4-(2-oxo-1,4-dihydro-2H-quinazolin-3-yl)-piperidin-1-yl]-butan-1,4-dione |
| (136) | | [4-(1-{2-(4-bromo-3-methyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid |

-continued

| | Structure | Name |
|---|---|---|
| (137) | | methyl (1'-{2-(4-bromo-3-methyl-benzyl)-4-oxo-4-[4-(2-oxo-1,4-dihydro-2H-quinazolin-3-yl)-piperidin-1-yl]-butyryl}-[4,4'bipiperidinyl-1-yl])-acetate |
| (138) | | (1'-{2-(4-bromo-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid |
| (139) | | 4-(2-oxo-1,4-dihydro-2H-quinazolin-3-yl)-piperidin-1-carboxylic acid {1-(4-chloro-3-methyl-benzyl)-2-0[4-(4-methyl-piperazin-1-yl)-piperidin-1-yl]-2-oxo-ethyl}-amide |
| (140) | | 4-(2-oxo-1,4-dihydro-2H-quinazolin-3-yl)-piperidin-1-carboxylic acid-[2-[1,4']bipiperidinyl-1'-yl-1-(4-chloro-3-methyl-benzyl)-2-oxo-ethyl]-amide |
| (141) | | 4-(2-oxo-1,4-dihydro-2H-quinazolin-3-yl)-piperidin-1-carboxylic acid-{1-(4-chloro-3-methyl-benzyl)-3-[4-(1-methyl-piperidin-4-yl)-piperazin-1-yl]-2-oxo-ethyl}-amide |

| | Structure | Name |
|---|---|---|
| (142) | | 4-(2-oxo-1,4-dihydro-2H-quinazolin-3-yl)-piperidin-1-carboxylic acid-[1-(4-chloro-3-methyl-benzyl)-2-(1'-methyl-[4,4']bipiperidinyl-1-yl)-2-oxo-ethyl]-amide |
| (143) | | ethyl [1'-(3-(4-chloro-3-methyl-phenyl)-2-{[4-(2-oxo-1,4-dihydro-2H-quinazolin-3-yl)-piperidin-1-carbonyl]-amino}-propionyl)-[4,4']bipiperidinyl-1-yl]-acetate |
| (144) | | tert-butyl{4-[1-(3-(4-chloro-3-methyl-phenyl)-2-{[4-(2-oxo-1,4-dihydro-2H-quinazolin-3-yl)-piperidin-1-carbonyl]-amino}-propionyl)-piperidin-4-yl]-piperazin-1-yl}-acetate |
| (145) | | 4-(2-oxo-1,4-dihydro-2H-quinazolin-3-yl)-piperidin-1-carboxylic acid-{1-(4-chloro-3-methyl-benzyl)-2-oxo-2-[1'-(2,2,2-trifluoro-ethyl)-[4,4']bipiperidinyl-1-yl]-ethyl}-amide |

| Structure | Name |
|---|---|
| (146) | 4-(2-oxo-1,4-dihydro-2H-quinazolin-3-yl)-piperidin-1-carboxylic acid-(1-(4-chloro-3-methyl-benzyl)-2-oxo-2-{4-[4-(2,2,2-trifluoro-ethyl)-piperazin-1-yl]-piperidin-1-yl}-ethyl)-amide |
| (147) | [1'-(3-(4-chloro-3-methyl-phenyl)-2-{[4-(2-oxo-1,4-dihydro-2H-quinazolin-3-yl)-piperidin-1-carbonyl]-amino}-propionyl)-[4,4']bipiperidinyl-1-yl]-acetic acid |
| (148) | 2-(4-chloro-3-methyl-benzyl)-1-[4-(4-ethyl-piperazin-1-yl)-piperidin-1-yl]-4-[4-(2-oxo-1,4-dihydro-2H-quinazolin-3-yl)-piperidin-1-yl]-butan-1,4-dione |
| (149) | 2-(4-chloro-3-methyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione |

-continued

| Structure | Name |
|---|---|
| (150) | 1-[1,4']bipiperidinyl-1'-yl-2-(4-chloro-3-methyl-benzyl)-4-[4-(2-oxo-1,4-dihydro-2H-quinazolin-3-yl)-piperidin-1-yl]-butan-1,4-dione |
| (151) | 2-(4-chloro-3-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione |
| (152) | 2-(4-chloro-3-methyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione |
| (153) | 2-(4-chloro-3-methyl-benzyl)-1-[4-(4-methanesulphonyl-piperain-1-yl)-piperidin-1-yl]-4-[4-(2-oxo-1,4-dihydro-2H-quinazolin-3-yl)-piperidin-1-yl]-butan-1,4-dione |
| (154) | 2-(4-chloro-3-methyl-benzyl)-1-[4-(4-isopropyl-piperazin-1-yl)-piperidin-1-yl]-4-[4-(2-oxo-1,4-dihydro-2H-quinazolin-3-yl)-piperidin-1-yl]-butan-1,4-dione |

-continued

| | Structure | Name |
|---|---|---|
| (155) | 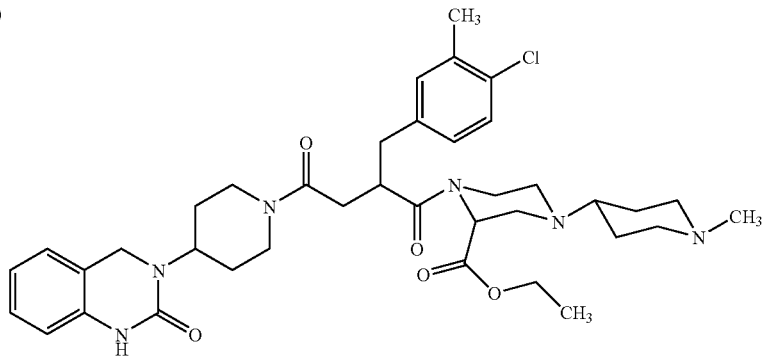 | ethyl 1-{2-(4-chloro-3-methyl-benzyl)-4-oxo-4-[4-(2-oxo-1,4-dihydro-2H-quinazolin-3-yl)-piperidin-1-yl]-butyryl}-4-(1-methyl-piperidin-4-yl)-piperazin-2-carboxylate |
| (156) | 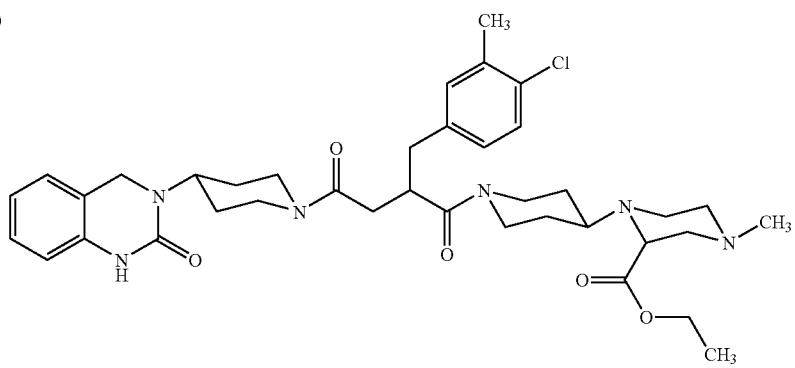 | ethyl 1-(1-{2-(4-chloro-3-methyl-benzyl)-4-oxo-4-[4-(2-oxo-1,4-dihydro-2H-quinazolin-3-yl)-piperidin-1-yl]-butyryl}-piperidin-4-yl)-4-methyl-piperiazin-2-carboxylate |
| (157) | 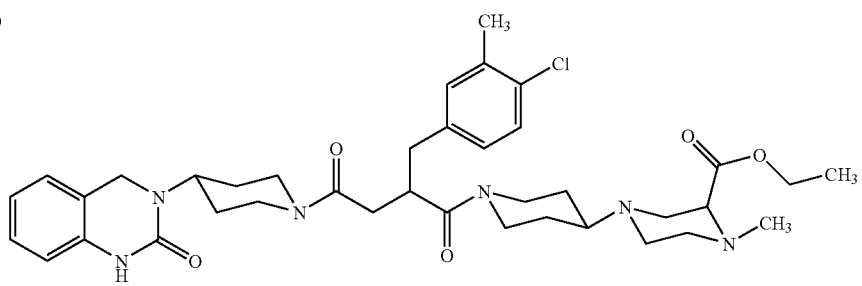 | ethyl 4-(1-{2-(4-chloro-3-methyl-benzyl)-4-oxo-4-[4-(2-oxo-1,4-dihydro-2H-quinazolin-3-yl)-piperidin-1-yl]-butyryl}-piperidin-4-yl)-1-methyl-piperazin-2-carboxylate |
| (158) | 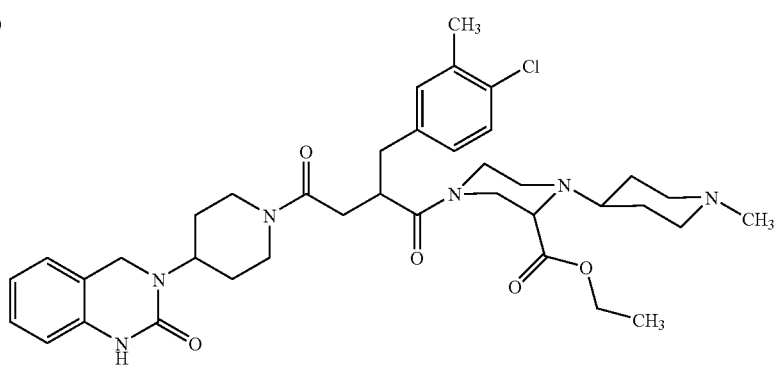 | ethyl 4-{2-(4-chloro-3-methyl-benzyl)-4-oxo-4-[4-(2-oxo-1,4-dihydro-2H-quinazolin-3-yl)-piperidin-1-yl]-butyryl}-1-(1-methyl-piperidin-4-yl)-piperazin-2-carboxylate |

| | Structure | Name |
|---|---|---|
| (159) | | 2-(4-chloro-3-methyl-benzyl)-4-[4-(2-oxo-1,4-dihydro-2H-quinazolin-3-yl)-piperidin-1-yl]-1-[1'-(2,2,2-trifluoro-ethyl)-[4,4']bi-piperidinyl-1-yl]-butan-1,4-dione |
| (160) | | 2-(4-chloro-3-methyl-benzyl)-4-[4-(2-oxo-1,4-dihydr-2H-quinazolin-3-yl)-piperidin-1-yl]-1-{4-[4-(2,2,2-trifluoro-ethyl)-piperazin-1-yl]-piperidin-1-yl}-butan-1,4-dione |
| (161) | | [4-(1-{2-(4-chloro-3-methyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid |
| (162) | | methyl (1'-{2-(4-chloro-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate |

| | Structure | Name |
|---|---|---|
| (163) | | (1'-{2-(4-chloro-3-methyl-benzyl)-4-oxo-4-[4-(2-oxo-1,4-dihydro-2H-quinazolin-3-yl)-piperidin-1-yl]-butyryl}-[4,4']bi-piperidinyl-1-yl)-acetic acid |
| (164) | | 1-{2-(4-chloro-3-methyl-benzyl)-4-oxo-4-[4-(2-oxo-1,4-dihydro-2H-quinazolin-3-yl)-piperidin-1-yl]-butyryl}-4-(1-methyl-piperidin-4-yl)-piperazin-2-carboxylic acid |
| (165) | | 1-(1-{2-(4-chloro-3-methyl-benzyl)-4-oxo-4-[4-(2-oxo-1,4-dihydro-2H-quinazolin-3-yl)-piperidin-1-yl]-butyryl}-piperidin-4-yl)-4-methyl-piperazin-2-carboxylic acid |
| (166) | | 4-(1-{2-(4-chloro-3-methyl-benzyl)-4-oxo-4-[4-(2-oxo-1,4-dihydro-2H-quinazolin-3-yl)-piperidin-1-yl]-butyryl}-piperidin-4-yl)-1-methyl-piperazin-2-carboxylic acid |

-continued

| | Structure | Name |
|---|---|---|
| (167) | | 2-(4-chloro-3-methyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione |
| (168) | | 2-(4-chloro-3-methyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione |
| (169) | | [4-(1-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-piperidin-4-yl)-piperazin-1-yl]-acetic acid |
| (170) | | (methyl 1'-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-4,4'-bipiperidinyl-1-yl)-acetate |

-continued

| | Structure | Name |
|---|---|---|
| (171) | | (1'-{2-(4-chloro-33-methyl-benzyl)-4-oxo-4-[4-(5-oxo-3-phenyl-4,5-dihydro-1,2,4-triazol-01-yl)-piperidin-1-yl]-butyryl}-4,4'-bipiperidinyl-1-yl)-acetic acid |
| (172) | | 2-(3-bromo-4-chloro-5-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione |
| (173) | | 2-(3-bromo-4-chloro-5-methyl-benzyl)-1-(1'-methyl-[4,4']-bipiperidinyl-1-yl)-4-[4-(2-oxo-1,4-dihydro-2H-quinazolin-3-yl)-piperidin-1-yl]-butan-1,4-dione |
| (174) | | 2-(3-bromo-4-chloro-5-methyl-benzyl)-4-[4-(2-oxo-1,4-dihydro-2H-quinazolin-3-yl)-piperidin-1-yl]-1-(4-pyridin-4-yl-piperazin-1-yl)-butan-1,4-dione |

-continued

| | Structure | Name |
|---|---|---|
| (175) | | 2-(3-bromo-4-cchloro-5-methyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione |
| (176) | | [4-(1-{2-(3-bromo-4-chloro-5-methyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid |
| (177) | | methyl (1'-{2-(3-bromo-4-chloro-5-methyl-benzyl)-4-oxo-4-[4-(2-oxo-1,4-dihydro-2H-quinazolin-3-yl)-piperidin-1-yl]-butyryl}-[4,4']-bipiperidinyl-1-yl)-acetate |
| (178) | | (1'-{2-(3-bromo-4-chloro-5-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid |

| Structure | Name |
|---|---|
| (179) 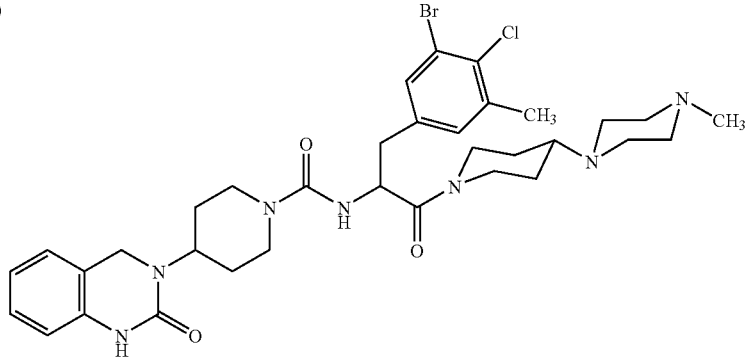 | 4-(2-oxo-1,4-dihydro-2H-quinazolin-3-yl)-piperidin-1-carboxylic acid{1-(3-bromo-4-chloro-5-methyl-benzyl)-2-[4-(4-methyl-piperazin-1-yl)-piperidin-1-yl]-2-oxo-ethyl}-amide |
| (180) 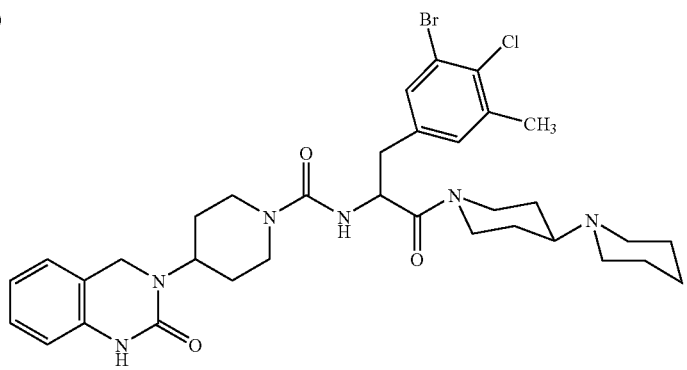 | 4-(2-oxo-1,4-dihydro-2H-quinazolin-3-yl)-piperidin-1-carboxylic acid-[2-[1,4']bipiperidinyl-1'-yl-1-(3-bromo-4-chloro-5-methyl-benzyl)-2-oxo-ethyl]-amide |
| (181) 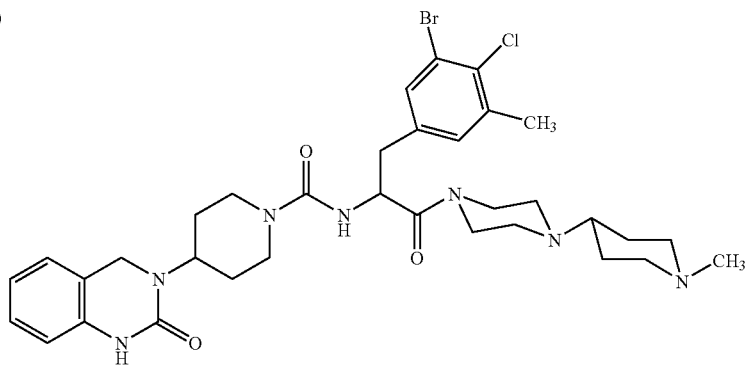 | 4-(2-oxo-1,4-dihydro-2H-quinazolin-3-yl)-piperidin-1-carboxylic acid-{1-(3-bromo-4-chloro-5-methyl-benzyl)-3-[4-(1-methyl-piperidin-4-yl)-piperazin-1-yl]-2-oxo-ethyl}-amide |
| (182) 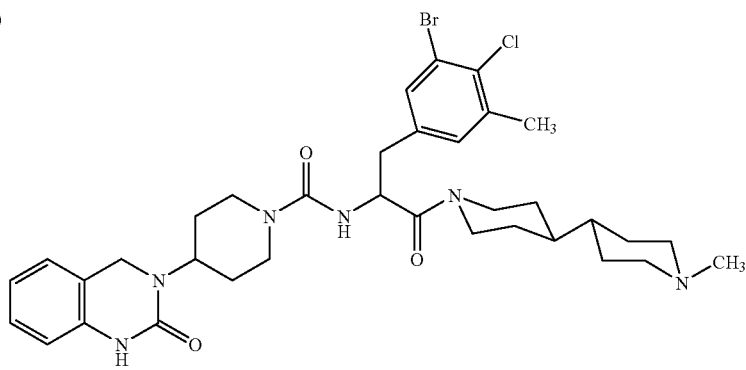 | 4-(2-oxo-1,4-dihydro-2H-quinazolin-3-yl)-piperidin-1-carboxylic acid-[1-(3-bromo-4-chloro-5-methyl-benzyl)-2-(1'-methyl-[4,4']bipiperidinyl-1-yl)-2-oxo-ethyl]-amide |

| Structure | Name |
|---|---|
| (183) 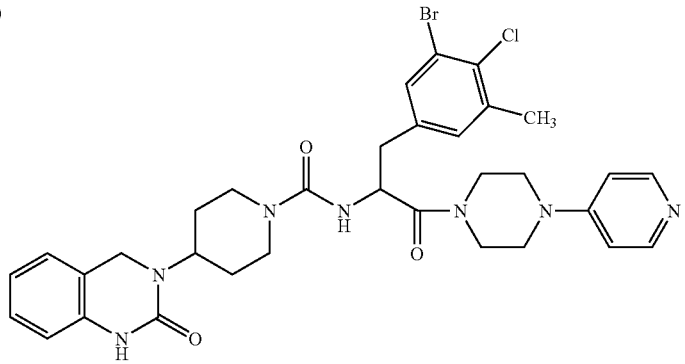 | 4-(2-oxo-1,4-dihydro-2H-quinazolin-3-yl)-piperidin-1-carboxylic acid-[1-(3-bromo-4-chloro-5-methyl-benzyl)-2-oxo-2-(4-pyridin-4-yl-piperazin-1-yl)-ethyl]-amide |
| (184) 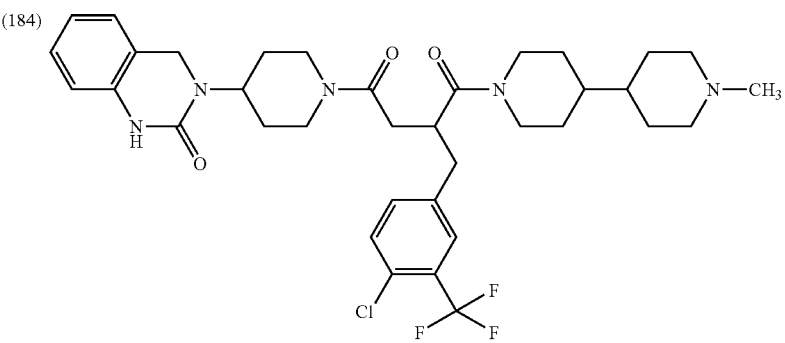 | 2-(4-chloro-3-trifluoromethyl-benzyl)-1-(1'-methyl-[4,4']bipiperidinyl-1-yl)-4-[4-(2-oxo-2,4-dihydro-2H-quinazolin-3-yl)-piperidin-1-yl]-butan-1,4-dione |
| (185) 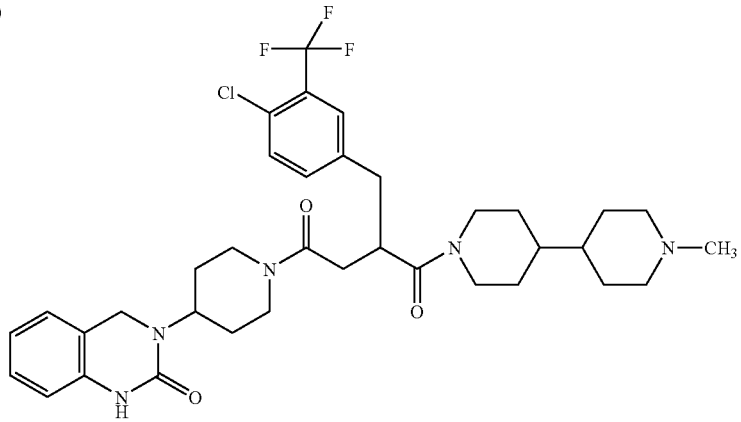 | 2-(4-chloro-3-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione |
| (186) 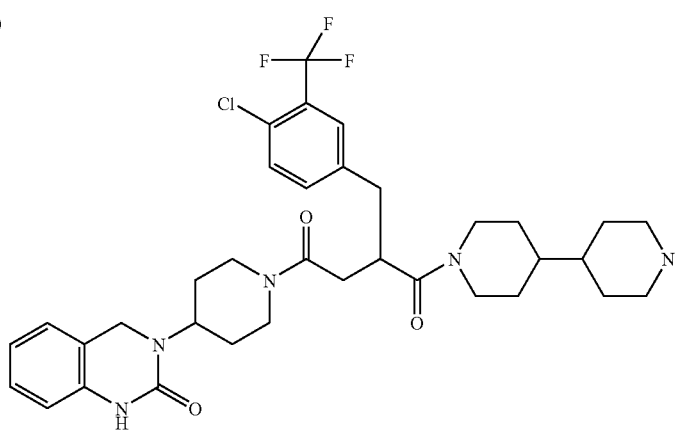 | 1-[1,4']bipiperidinyl-1'-yl-2-(4-chloro-33-trifluoromethyl-benzyl)-4-[4-(2-oxxo-1,4-dihydro-2H-quinazolin-3-yl)-piperidin-1-yl]-butan-1,4-dione |

-continued

| | Structure | Name |
|---|---|---|
| (187) | 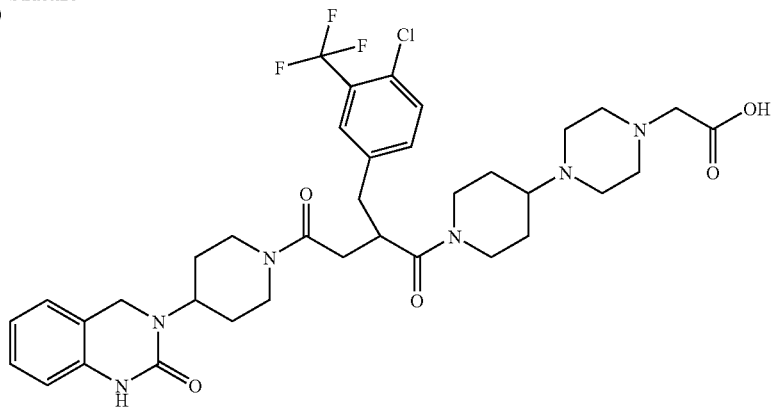 | [4-(1-{2-(4-chloro-0 3-trifluoromethyl-benzyl)-4-oxo-4-4-(2-oxo-1,4-di-hydro-2H-quinazolin-3-yl)-piperidin-1-yl]-butyryl}-piperidin-4-yl)-piperazin-1-yl]-acetic acid |
| (188) | 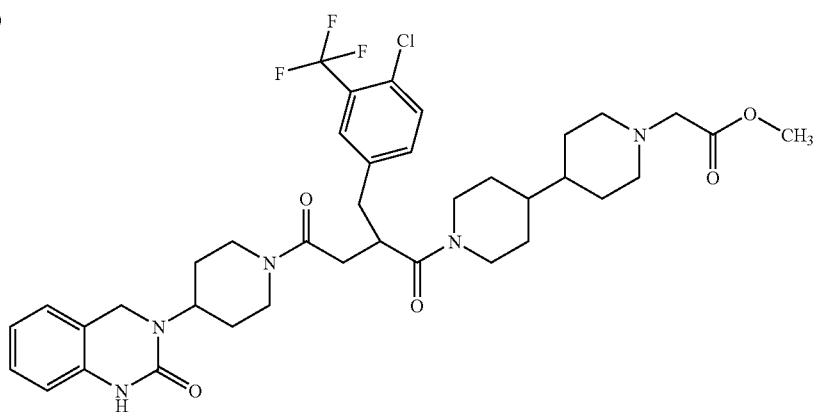 | methyl (1'-{2-(4-chloro-3-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate |
| (189) | 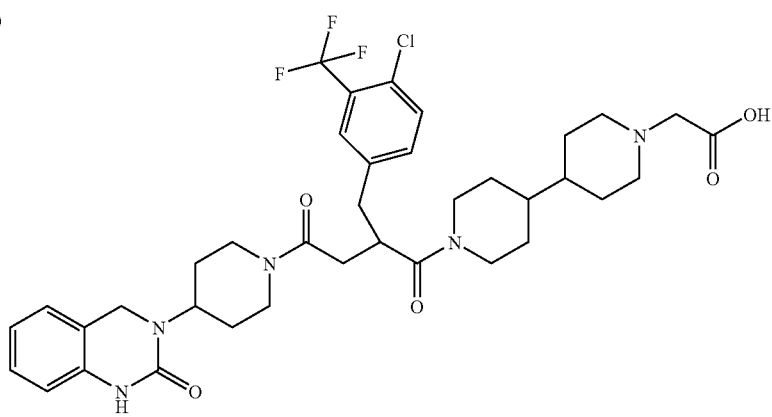 | (1'-{2-(4-chloro-3-trifluoromethyl-benzyl)-4-oxo-4-[4-(2-oxo-1,4-dihydro-2H-quinazolin-3-yl)-piperidin-1-yl]-butyryl}-[4,4']-bipiperidinyl-1-yl)-acetic acid |
| (190) | 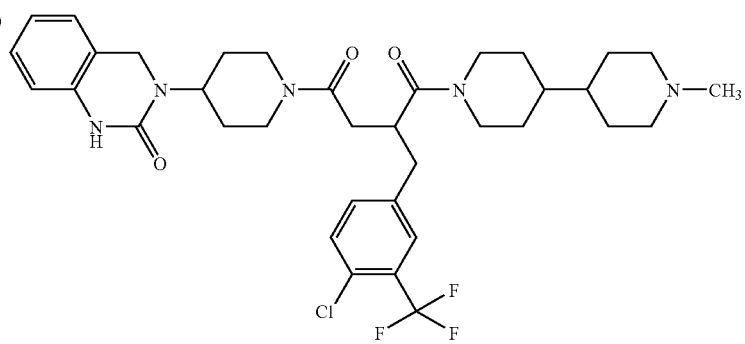 | 2-(4-chloro-3-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione | the enantiomers, the diastereomers and the salts thereof, while the compounds

(14) 4-(2-oxo-1,2,4,5-tetrahydro-1,3-benzodiazepin-3-yl)-piperidin-1-carboxylic acid-{(R)-1-(4-amino-3-chloro-5-trifluoromethyl-benzyl)-2-[4-(1-methyl-piperidin-4-yl)-piperazin-1-yl]-2-oxo-ethyl}-amide,

(15) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-(4-azetidin-1-yl-piperidin-1-yl)-2-oxo-ethyl]-amide,

(16) 4-(2-oxo-1,2,4,5-tetrahydro-1,3-benzodiazepin-3-yl)-piperidin-1-carboxylic acid-{(R)-1-(4-amino-3-chloro-5-trifluoromethyl-benzyl)-2-[4-(5-methyl-2,5-diaza-bicyclo[2.2.1]hept-2-yl)-piperidin-1-yl]-2-oxo-ethyl}-amide,

(17) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-oxo-2-(4-piperazin-1-yl-piperidin-1-yl)-ethyl]-amide,

(18) [1'-((R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionyl)-4,4'-bipiperidinyl-1-yl]-acetic acid,

(19) 4-(2-oxo-1,2,4,5-tetrahydro-1,3-benzodiazepin-3-yl)-piperidin-1-carboxylic acid-[1-(4-amino-3-chloro-5-trifluoromethyl-benzyl)-2-1,4'-bipiperidinyl-1'-yl-2-oxo-ethyl]-amide,

(20) (S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(21) (S)-2-(4-amino-3-bromo-5-trifluoromethyl-benzyl)-4-[4-(2-oxo-1,2,4,5-tetrahydro-1,3-benzodiazepin-3-yl)-piperidin-1-yl]-1-(4-pyridin-4-yl-piperazin-1-yl)-butan-1,4-dione,

(22) (S)-2-(4-amino-3-bromo-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(23) (S)-2-(4-amino-3-bromo-5-trifluoromethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(24) (S)-2-(4-amino-3-bromo-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(25) (S)-2-(4-amino-3-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(26) (S)-2-(4-amino-3-chloro-5-trifluoromethyl-benzyl)-1-(4-dimethylamino-piperidin-1-yl)-4-[4-(2-oxo-1,2,4,5-tetrahydro-1,3-benzodiazepin-3-yl)-piperidin-1-yl]-butan-1,4-dione,

(27) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyrrolidin-1-yl-piperidin-1-yl)-butan-1,4-dione,

(28) (S)-2-(4-amino-3-chloro-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(29) (S)-2-(4-amino-3-chloro-5-trifluoromethyl-benzyl)-1-[4-(4-cyclopropylmethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(30) (S)-2-(4-amino-3-chloro-5-trifluoromethyl-benzyl)-1-(4-morpholine-4-yl-piperidin-1-yl)-4-[4-(2-oxo-1,2,4,5-tetrahydro-1,3-benzodiazepin-3-yl)-piperidin-1-yl]-butan-1,4-dione,

(31) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione,

(32) (S)-2-(4-amino-3-chloro-5-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione,

(33) (S)-2-(4-amino-3-chloro-5-trifluoromethyl-benzyl)-1-[4-(4-isopropyl-piperazin 1-yl)-piperidin-1-yl]-4-[4-(2-oxo-1,2,4,5-tetrahydro-1,3-benzodiazepin-3-yl)-piperidin-1-yl]-butan-1,4-dione,

(34) (S)-2-(4-amino-3-chloro-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(35) (S)-2-(4-amino-3-chloro-5-trifluoromethyl-benzyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butan-1,4-dione,

(36) (S)-2-(4-amino-3-chloro-5-trifluoromethyl-benzyl)-1-[3-(4-methyl-piperazin-1-yl)-azetidin-1-yl]-4-[4-(2-oxo-1,2,4,5-tetrahydro-1,3-benzodiazepin-3-yl)-piperidin-1-yl]-butan-1,4-dione,

(37) (S)-2-(4-amino-3-chloro-5-trifluoromethyl-benzyl)-4-[4-(2-oxo-1,2,4,5tetrahydro-1,3-benzodiazepin-3-yl)-piperidin-1-yl]-1-(3-pyrrolidin-1-yl-azetidin-1-yl)-butan-1,4-dione,

(38) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3-piperidin-1-yl-azetidin-1-yl)-butan-1,4-dione,

(39) (S)-2-(4-amino-3-chloro-5-trifluoromethyl-benzyl)-1-(4-azetidin-1-yl-piperidin-1-yl)-4-[4-(2-oxo-1,2,4,5-tetrahydro-1,3-benzodiazepin-3-yl)-piperidin-1-yl]-butan-1,4-dione,

(40) (S)-1-[4-(4-acetyl-piperazin-1-yl)-piperidin-1-yl]-2-(4-amino-3-chloro-5-trifluoromethyl-benzyl)-4-[4-(2-oxo-1,2,4,5-tetrahydro-1,3-benzodiazepin-3-yl)-piperidin-1-yl]-butan-1,4-dione,

(41) (S)-2-(4-amino-3-chloro-5-trifluoromethyl-benzyl)-1-(4-diethylaminomethyl-piperidin-1-yl)-4-[4-(2-oxo-1,2,4,5-tetrahydro-1,3-benzodiazepin-3-yl)-piperidin-1-yl]-butan-1,4-dione,

(42) (S)-2-(4-amino-3-chloro-5-trifluoromethyl-benzyl)-1-[4-(4-ethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(43) (S)-2-(4-amino-3-chloro-5-trifluoromethyl-benzyl)-1-[4-(1-ethyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(44) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3,4,5,6-tetrahydro-2H-4,4'-bipyridinyl-1-yl)-butan-1,4-dione,

(45) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyridin-4-yl-piperazin-1-yl)-butan-1,4-dione,

(46) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3-perhydro-azepin-1-yl-azetidin-1-yl)-butan-1,4-dione,

(47) (S)-2-(4-amino-3-chloro-5-trifluoromethyl-benzyl)-[4-(1-benzyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(48) (S)-2-(4-amino-3-chloro-5-trifluoromethyl-benzyl)-1-[4-(4-benzyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(49) (S)-2-(4-amino-3-chloro-5-trifluoromethyl-benzyl)-1-(7-dimethylaminomethyl-1,2,4,5-tetrahydro-3-benzazepin-3-yl)-4-[4-(2-oxo-1,2,4,5-tetrahydro-1,3-benzodiazepin-3-yl)-piperidin-1-yl]-butan-1,4-dione,

(50) (S)-2-(4-amino-3-chloro-5-trifluoromethyl-benzyl)-1-[4-(4-dimethylaminomethyl-phenyl)-piperidin-1-yl]-4-[4-(2-oxo-1,2,4,5-tetrahydro-1,3-benzodiazepin-3-yl)-piperidin-1-yl]-butan-1,4-dione,

(51) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-ethyl)-piperazin-1-yl]-piperidin-1-yl}-butan-1,4-dione,

(52) (S)-2-(4-amino-3-chloro-5-trifluoromethyl-benzyl)-1-(1'-methanesulphonyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(53) (S)-2-(4-amino-3-chloro-5-trifluoromethyl-benzyl)-1-(9-methyl-3,9-diaza-spiro[5.5]undec-3-yl)-4-[4-(2-oxo-1,2,4,5-tetrahydro-1,3-benzodiazepin-3-yl)-piperidin-1-yl]-butan-1,4-dione,

(54) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperidin-1-yl-methyl-piperidin-1-yl)-butan-1,4-dione,

(55) (S)-2-(4-amino-3-chloro-5-trifluoromethyl-benzyl)-1-[4-(2-dimethylamino-ethyl)-piperidin-1-yl]-4-[4-(2-oxo-1,2,4,5-tetrahydro-1,3-benzodiazepin-3-yl)-piperidin-1-yl]-butan-1,4-dione,

(56) (S)-2-(4-amino-3-chloro-5-trifluoromethyl-benzyl)-N-methyl-N-[2-(1-methyl-piperidin-4-yl)-ethyl]-4-oxo-4-[4-(2-oxo-1,2,4,5-tetrahydro-1,3-benzodiazepin-3-yl)-piperidin-1-yl]-butyramide,

(57) (S)-2-(4-amino-3-chloro-5-trifluoromethyl-benzyl)-N-methyl-N-(1-methyl-piperidin-4-ylmethyl)-4-oxo-4-[4-(2-oxo-1,2,4,5-tetrahydro-1,3-benzodiazepin-3-yl)-piperidin-1-yl]-butyramide,

(58) (S)-2-(4-amino-3-chloro-5-trifluoromethyl-benzyl)-1-[4-(2-diethylamino-ethyl)-piperidin-1-yl]-4-[4-(2-oxo-1,2,4,5-tetrahydro-1,3-benzodiazepin-3-yl)-piperidin-1-yl]-butan-1,4-dione,

(59) (S)-2-(4-amino-3-chloro-5-trifluoromethyl-benzyl)-1-[4-(cyclopentyl-methyl-amino)-piperidin-1-yl]-4-[4-(2-oxo-1,2,4,5-tetrahydro-1,3-benzodiazepin-3-yl)-piperidin-1-yl]-butan-1,4-dione,

(60) (S)-2-(4-amino-3-chloro-5-trifluoromethyl-benzyl)-1-[4-(1,1-dioxo-1,6-isothiazolidin-2-yl)-piperidin-1-yl]-4-[4-(2-oxo-1,2,4,5-tetrahydro-1,3-benzodiazepin-3-yl)-piperidin-1-yl]-butan-1,4-dione,

(61) (S)-2-(4-amino-3-chloro-5-trifluoromethyl-benzyl)-1-[4-(2-oxo-perhydro-1,3-oxazin-3-yl)-piperidin-1-yl]-4-[4-(2-oxo-1,2,4,5-tetrahydro-1,3-benzodiazepin-3-yl)-piperidin-1-yl]-butan-1,4-dione,

(62) methyl 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-carboxylate,

(63) 8-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-1,3,8-triaza-spiro[4.5]decan-2,4-dione,

(64) (S)-2-(4-amino-3-chloro-5-trifluoromethyl-benzyl)-1-[4-(2-oxo-imidazolidin-1-yl)-piperidin-1-yl]-4-[4-(2-oxo-1,2,4,5-tetrahydro-1,3-benzodiazepin-3-yl)-piperidin-1-yl]-butan-1,4-dione,

(65) (S)-2-(4-amino-3-chloro-5-trifluoromethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(66) (S)-2-(4-amino-3-chloro-5-trifluoromethyl-benzyl)-1-(2-amino-4,5,7,8-tetrahydro-thiazolo[4,5-d]azepin-6-yl)-4-[4-(2-oxo-1,2,4,5-tetrahydro-1,3-benzodiazepin-3-yl)-piperidin-1-yl]-butan-1,4-dione,

(67) (S)-2-(4-amino-3-chloro-5-trifluoromethyl-benzyl)-1-[4-(2-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(68) (S)-2-(4-amino-3-chloro-5-trifluoromethyl-benzyl)-1-[4-(4-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(69) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-thiazol-2-yl-piperazin-1-yl)-butan-1,4-dione,

(70) (S)-2-(4-amino-3-chloro-5-trifluoromethyl-benzyl)-1-[4-(2,4-dimethyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(71) (S)-2-(4-amino-3-chloro-5-trifluoromethyl-benzyl)-1-(4-imidazol-1-yl-piperidin-1-yl)-4-[4-(2-oxo-1,2,4,5-tetrahydro-1,3-benzodiazepin-3-yl)-piperidin-1-yl]-butan-1,4-dione,

(72) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-1,2,4-triazol-1-yl-piperidin-1-yl)-butan-1,4-dione,

(73) (S)-2-(4-amino-3-chloro-5-trifluoromethyl-benzyl)-1-[4-(1-aza-bicyclo[2.2.2]oct-3-yl)-piperazin-1-yl]-4-[4-(2-oxo-1,2,4,5-tetrahydro-1,3-benzodiazepin-3-yl)-piperidin-1-yl]-butan-1,4-dione,

(74) (S)-2-(4-amino-3-chloro-5-trifluoromethyl-benzyl)-N-(5-amino-pentyl)-4-oxo-4-[4-(2-oxo-1,2,4,5-tetrahydro-1,3-benzodiazepin-3-yl)-piperidin-1-yl]-butyramide,

(75) (S)-2-(4-amino-3-chloro-5-trifluoromethyl-benzyl)-N-(3-aminomethyl-benzyl)-4-oxo-4-[4-(2-oxo-1,2,4,5-tetrahydro-1,3-benzodiazepin-3-yl)-piperidin-1-yl]-butyramide,

(76) (S)-2-(4-amino-3-chloro-5-trifluoromethyl-benzyl)-1-[4-(8-methyl-8-aza-bicyclo[3.2.1]oct-3-yl)-piperazin-1-yl]-4-[4-(2-oxo-1,2,4,5-tetrahydro-1,3-benzodiazepin-3-yl)-piperidin-1-yl]-butan-1,4-dione,

(77) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione,

(78) (S)-2-(4-amino-3-chloro-5-trifluoromethyl-benzyl)-1-[4-(1H-imidazol-4-yl)-piperidin-1-yl]-4-[4-(2-oxo-1,2,4,5-tetrahydro-1,3-benzodiazepin-3-yl)-piperidin-1-yl]-butan-1,4-dione,

(79) (S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione,

(80) (S)-2-(4-amino-3-chloro-5-trifluoromethyl-benzyl)-1-[4-(4-methyl-piperazin-1-yl)-piperidin-1-yl]-4-[4-(5-oxo-3-phenyl-4,5-dihydro-1,2,4-triazol-1-yl)-piperidin-1-yl]-butan-1,4-dione,

(81) (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-imidazo[4,5-c]quinolin-3-yl)-piperidin-1-yl]-butan-1,4-dione,

(82) (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-4H-thieno[3,4-d]pyrimidin-3-yl)-piperidin-1-yl]-butan-1,4-dione,

(83) (S)-2-(4-amino-3-chloro-5-trifluoromethyl-benzyl)-1-[4-(5-methyl-2,5-diaza-bicyclo[2.2.1]hept-2-yl)-piperidin-1-yl]-4-[4-(2-oxo-1,2,4,5-tetrahydro-1,3-benzodiazepin-3-yl)-piperidin-1-yl]-butan-1,4-dione,

(84) (S)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione,

(85) (S)-2-(4-amino-3,5-bis-trifluoromethyl-benzyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butan-1,4-dione,

(86) (S)-2-(4-amino-3,5-bis-trifluoromethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(87) (S)-2-(4-amino-3,5-bis-trifluoromethyl-benzyl)-1-[4-(1-aza-bicyclo[2.2.2]oct-3-yl)-piperazin-1-yl]-4-[4-(2-oxo-1,2,4,5-tetrahydro-1,3-benzodiazepin-3-yl)-piperidin-1-yl]-butan-1,4-dione,

(88) (S)-2-(4-amino-3,5-bis-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(89) (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione,

(90) (S)-2-(4-amino-3,5-bis-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(91) (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione,

(92) 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(4-methyl-piperazin-1-yl)-piperidin-1-yl]-2-oxo-ethyl}-amide,

(93) 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(1-methyl-piperidin-4-yl)-piperazin-1-yl]-2-oxo-ethyl}-amide,

(94) 4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-1,4'-bipiperidinyl-1'-yl-2-oxo-ethyl]-amide,

(95) 4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-oxo-2-(4-piperazin-1-yl-piperidin-1-yl)-ethyl]-amide,

(96) 4-(2-oxo-1,2,4,5-tetrahydro-1,3-benzodiazepin-3-yl)-piperidin-1-carboxylic acid-(R)-1-(4-amino-3-chloro-5-trifluoromethyl-benzyl)-2-[4-(4-methyl-piperazin-1-yl)-piperidin-1-yl]-2-oxo-ethyl ester,

(97) 4-(2-oxo-1,4-dihydro-2H-quinazolin-3-yl)-piperidin-1-carboxylic acid-[1-(4-bromo-3-methyl-benzyl)-2-(1'-methyl-[4,4']bipiperidinyl-1-yl)-2-oxo-ethyl]-amide,

(98) 4-(2-oxo-1,4-dihydro-2H-quinazolin-3-yl)-piperidin-1-carboxylic acid-{1-(4-bromo-3-methyl-benzyl)-2-[4-(4-methyl-piperazin-1-yl)-piperidin-1-yl]-2-oxo-ethyl}-amide,

(99) 4-(2-oxo-1,4-dihydro-2H-quinazolin-3-yl)-piperidin-1-carboxylic acid-{1-(4-bromo-3-methyl-benzyl)-2-[4-(1-methyl-piperidin-4-yl)-piperazin-1-yl]-2-oxo-ethyl}-amide, (100) 2-(4-bromo-3-methyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione, (101) 1-[1,4']Bipiperidinyl-1'-yl-2-(4-bromo-3-methyl-benzyl)-4-[4-(2-oxo-1,4-dihydro-2H-quinazolin-3-yl)-piperidin-1-yl]-butan-1,4-dione, (102) 4-(2-oxo-1,4-dihydro-2H-quinazolin-3-yl)-piperidin-1-carboxylic acid {1-(4-chloro-3-methyl-benzyl)-2-[4-(4-methyl-piperazin-1-yl)-piperidin-1-yl]-2-oxo-ethyl}-amide, (103) 4-(2-oxo-1,4-dihydro-2H-quinazolin-3-yl)-piperidin-1-carboxylic acid-{1-(4-chloro-3-methyl-benzyl)-2-[4-(1-methyl-piperidin-4-yl)-piperazin-1-yl]-2-oxo-ethyl}-amide, (104) 4-(2-oxo-1,4-dihydro-2H-quinazolin-3-yl)-piperidin-1-carboxylic acid-[1-(4-chloro-3-methyl-benzyl)-2-(1'-methyl-[4,4']bipiperidinyl-1-yl)-2-oxo-ethyl]-amide, (105) 2-(4-chloro-3-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione, (106) 2-(4-chloro-3-methyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione, (107) 2-(4-chloro-3-methyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, (108) 2-(3-bromo-4-chloro-5-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione, (109) 2-(3-bromo-4-chloro-5-methyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione, (110) 2-(3-bromo-4-chloro-5-methyl-benzyl)-1-[4-(1-methyl-piperidin-4-yl)-piperazin-1-yl]-4-[4-(2-oxo-1,4-dihydro-2H-quinazolin-3-yl)-piperidin-1-yl]-butan-1,4-dione, (111) 4-(2-oxo-1,4-dihydro-2H-quinazolin-3-yl)-piperidin-1-carboxylic acid {1-(3-bromo-4-chloro-5-methyl-benzyl)-2-[4-(4-methyl-piperazin-1-yl)-piperidin-1-yl]-2-oxo-ethyl}-amide, (112) 4-(2-oxo-1,4-dihydro-2H-quinazolin-3-yl)-piperidin-1-carboxylic acid-{1-(3-bromo-4-chloro-5-methyl-benzyl)-2-[4-(1-methyl-piperidin-4-yl)-piperazin-1-yl]-2-oxo-ethyl}-amide, (113) 4-(2-oxo-1,4-dihydro-2H-quinazolin-3-yl)-piperidin-1-carboxylic acid-[1-(3-bromo-4-chloro-5-methyl-benzyl)-2-(1'-methyl-[4,4']bipiperidinyl-1-yl)-2-oxo-ethyl]-amide, (114) 2-(4-chloro-3-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione, the enantiomers, the diastereomers and the salts thereof are of particular importance and the compounds (1) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, (2) 2-(4-amino-3-chloro-5-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione, (3) 2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione, (4) 2-(4-amino-3-chloro-5-trifluoromethyl-benzyl)-1-[1,4']bipiperidinyl-1'-yl-4-[4-(2-oxo-1,4-dihydro-2H-quinazolin-3-yl)-piperidin-1-yl]-butan-1,4-dione, (5) 2-(4-amino-3-chloro-5-trifluoromethyl-benzyl)-4-[4-(2-oxo-1,4-dihydro-2H-quinazolin-3-yl)-piperidin-1-yl]-1-(4-pyridin-4-yl-piperazin-1-yl)-butan-1,4-dione, (6) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-1,4'-bipiperidinyl-1'-yl-2-oxo-ethyl]-amide, (7) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-(4-dimethylamino-piperidin-1-yl)-2-oxo-ethyl]-amide, (8) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-oxo-2-(4-pyridin-4-yl-piperazin-1-yl)-ethyl]-amide, (9) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-(1'-methyl-4,4'-bipiperidinyl-1-yl)-2-oxo-ethyl]-amide,

(10) ethyl[1'-((R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionyl)-4,4'-bipiperidinyl-1-yl]-acetate,

(11) 4-(2-oxo-1,2,4,5-tetrahydro-1,3-benzodiazepin-3-yl)-piperidin-1-carboxylic acid-{(R)-(4-amino-3-chloro-5-trifluoromethyl-benzyl)-2-[4-(4-methyl-piperazin-1-yl)-piperidin-1-yl]-2-oxo-ethyl}-amide,

(12) 4-(2-oxo-1,2,4,5-tetrahydro-1,3-benzodiazepin-3-yl)-piperidin-1-carboxylic acid-{(R)-1-(4-amino-3-chloro-5-trifluoromethyl-benzyl)-2-[4-(1-methyl-piperidin-4-yl)-piperazin-1-yl]-2-oxo-ethyl}-amide,

(13) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-(4-azetidin-1-yl-piperidin-1-yl)-2-oxo-ethyl]-amide,

(14) 4-(2-oxo-1,2,4,5-tetrahydro-1,3-benzodiazepin-3-yl)-piperidin-1-carboxylic acid-{(R)-(4-amino-3-chloro-5-trifluoromethyl-benzyl)-2-[4-(5-methyl-2,5-diaza-bicyclo[2.2.1]hept-2-yl)-piperidin-1-yl]-2-oxo-ethyl}-amide,

(15) 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-oxo-2-(4-piperazin-1-yl-piperidin-1-yl)-ethyl]-amide,

(16) [1'-((R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionyl)-4,4'bipiperidinyl-1-yl]-acetic acid,

(17) 4-(2-oxo-1,2,4,5-tetrahydro-1,3-benzodiazepin-3-yl)-piperidin-1-carboxylic acid-[1-(4-amino-3-chloro-5-trifluoromethyl-benzyl)-2-1,4'-bipiperidinyl-1'-yl-2-oxo-ethyl]-amide,

(18) (S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(19) (S)-2-(4-amino-3-bromo-5-trifluoromethyl-benzyl)-4-[4-(2-oxo-1,2,4,5-tetrahydro-1,3-benzodiazepin-3-yl)-piperidin-1-yl]-1-(4-pyridin-4-yl-piperazin-1-yl)-butan-1,4-dione,

(20) (S)-2-(4-amino-3-bromo-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(21) (S)-2-(4-amino-3-bromo-5-trifluoromethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(22) (S)-2-(4-amino-3-bromo-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(23) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyrrolidin-1-yl-piperidin-1-yl)-butan-1,4-dione,

(24) (S)-2-(4-amino-3-chloro-5-trifluoromethyl-benzyl)-1-(1'-methyl-4,4'bipiperidinyl-1-yl)-4-[4-(2-oxo-1,2,4,5-tetrahydro-1,3-benzodiazepin-3-yl)-piperidin-1-yl]-butan-1,4-dione,

(25) (S)-2-(4-amino-3-chloro-5-trifluoromethyl-benzyl)-1-[4-(4-cyclopropylmethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(26) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione,

(27) (S)-2-(4-amino-3-chloro-5-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione,

(28) (S)-2-(4-amino-3-chloro-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(29) (S)-2-(4-amino-3-chloro-5-trifluoromethyl-benzyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butan-1,4-dione,

(30) (S)-2-(4-amino-3-chloro-5-trifluoromethyl-benzyl)-1-[3-(4-methyl-piperazin-1-yl)-azetidin-1-yl]-4-[4-(2-oxo-1,2,4,5-tetrahydro-1,3-benzodiazepin-3-yl)-piperidin-1-yl]-butan-1,4-dione,

(31) (S)-2-(4-amino-3-chloro-5-trifluoromethyl-benzyl)-1-(4-azetidin-1-yl-piperidin-1-yl)-4-[4-(2-oxo-1,2,4,5-tetrahydro-1,3-benzodiazepin-3-yl)-piperidin-1-yl]-butan-1,4-dione,

(32) (S)-1-[4-(4-acetyl-piperazin-1-yl)-piperidin-1-yl]-2-(4-amino-3-chloro-5-trifluoromethyl-benzyl)-4-[4-(2-oxo-1,2,4,5-tetrahydro-1,3-benzodiazepin-3-yl)-piperidin-1-yl]-butan-1,4-dione,

(33) (S)-2-(4-amino-3-chloro-5-trifluoromethyl-benzyl)-1-(4-diethylaminomethyl-piperidin-1-yl)-4-[4-(2-oxo-1,2,4,5-tetrahydro-1,3-benzodiazepin-3-yl)-piperidin-1-yl]-butan-1,4-dione,

(34) (S)-2-(4-amino-3-chloro-5-trifluoromethyl-benzyl)-1-[4-(4-ethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(35) (S)-2-(4-amino-3-chloro-5-trifluoromethyl-benzyl)-1-[4-(1-ethyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(36) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3,4,5,6-tetrahydro-2H-4,4'-bipyridinyl-1-yl)-butan-1,4-dione,

(37) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyridin-4-yl-piperazin-1-yl)-butan-1,4-dione,

(38) (S)-2-(4-amino-3-chloro-5-trifluoromethyl-benzyl)-1-[4-(1-benzyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(39) (S)-2-(4-amino-3-chloro-5-trifluoromethyl-benzyl)-1-(1'-methanesulphonyl-4,4'-30 bipiperidinyl-1-yl)-4-[4-(2-oxo-1,2,4,5-tetrahydro-1,3-benzodiazepin-3-yl)-piperidin-1-yl]-butan-1,4-dione,

(40) (S)-2-(4-amino-3-chloro-5-trifluoromethyl-benzyl)-1-(9-methyl-3,9-diaza-spiro[5.5]undec-3-yl)-4-[4-(2-oxo-1,2,4,5-tetrahydro-1,3-benzodiazepin-3-yl)-piperidin-1-yl]-butan-1,4-dione,

(41) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperidin-1-yl-methyl-piperidin-1-yl)-butan-1,4-dione,

(42) (S)-2-(4-amino-3-chloro-5-trifluoromethyl-benzyl)-1-[4-(2-dimethylamino-ethyl)-piperidin-1-yl]-4-[4-(2-oxo-1,2,4,5-tetrahydro-1,3-benzodiazepin-3-yl)-piperidin-1-yl]-butan-1,4-dione,

(43) (S)-2-(4-amino-3-chloro-5-trifluoromethyl-benzyl)-N-methyl-N-[2-(1-methyl-piperidin-4-yl)-ethyl]-4-oxo-4-[4-(2-oxo-1,2,4,5-tetrahydro-1,3-benzodiazepin-3-yl)-piperidin-1-yl]-butyramide,

(44) (S)-2-(4-amino-3-chloro-5-trifluoromethyl-benzyl)-N-methyl-N-(1-methyl-piperidin-4-ylmethyl)-4-oxo-4-[4-(2-oxo-1,2,4,5-tetrahydro-1,3-benzodiazepin-3-yl)-piperidin-1-yl]-butyramide,

(45) (S)-2-(4-amino-3-chloro-5-trifluoromethyl-benzyl)-1-[4-(2-diethylamino-ethyl)-piperidin-1-yl]-4-[4-(2-oxo-1,2,4,5-tetrahydro-1,3-benzodiazepin-3-yl)-piperidin-1-yl]-butan-1,4-dione,

(46) (S)-2-(4-amino-3-chloro-5-trifluoromethyl-benzyl)-1-[4-(2-oxo-perhydro-1,3-oxazin-3-yl)-piperidin-1-yl]-4-[4-(2-oxo-1,2,4,5-tetrahydro-1,3-benzodiazepin-3-yl)-piperidin-1-yl]-butan-1,4-dione,

(47) (S)-2-(4-amino-3-chloro-5-trifluoromethyl-benzyl)-1-[4-(2-oxo-imidazolidin-1-yl)-piperidin-1-yl]-4-[4-(2-oxo-1,2,4,5-tetrahydro-1,3-benzodiazepin-3-yl)-piperidin-1-yl]-butan-1,4-dione,

(48) (S)-2-(4-amino-3-chloro-5-trifluoromethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(49) (S)-2-(4-amino-3-chloro-5-trifluoromethyl-benzyl)-1-[4-(2-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(50) (S)-2-(4-amino-3-chloro-5-trifluoromethyl-benzyl)-1-[4-(4-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(51) (S)-2-(4-amino-3-chloro-5-trifluoromethyl-benzyl)-1-[4-(2,4-dimethyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(52) (S)-2-(4-amino-3-chloro-5-trifluoromethyl-benzyl)-1-(4-imidazol-1-yl-piperidin-1-yl)-4-[4-(2-oxo-1,2,4,5-tetrahydro-1,3-benzodiazepin-3-yl)-piperidin-1-yl]-butan-1,4-dione,

(53) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-1,2,4-triazol-1-yl-piperidin-1-yl)-butan-1,4-dione,

(54) (S)-2-(4-amino-3-chloro-5-trifluoromethyl-benzyl)-1-[4-(1-aza-bicyclo[2.2.2]oct-3-yl)-piperazin-1-yl]-4-[4-(2-oxo-1,2,4,5-tetrahydro-1,3-benzodiazepin-3-yl)-piperidin-1-yl]-butan-1,4-dione,

(55) (S)-2-(4-amino-3-chloro-5-trifluoromethyl-benzyl)-1-[4-(8-methyl-8-aza-bicyclo[3.2.1]oct-3-yl)-piperazin-1-yl]-4-[4-(2-oxo-1,2,4,5-tetrahydro-1,3-benzodiazepin-3-yl)-piperidin-1-yl]-butan-1,4-dione,

(56) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione,

(57) (S)-2-(4-amino-3-chloro-5-trifluoromethyl-benzyl)-1-[4-(1H-imidazol-4-yl)-piperidin-1-yl]-4-[4-(2-oxo-1,2,4,5-tetrahydro-1,3-benzodiazepin-3-yl)-piperidin-1-yl]-butan-1,4-dione,

(58) (S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione,

(59) (S)-2-(4-amino-3-chloro-5-trifluoromethyl-benzyl)-1-[4-(4-methyl-piperazin-1-yl)-piperidin-1-yl]-4-[4-(5-oxo-3-phenyl-4,5-dihydro-1,2,4-triazol-1-yl)-piperidin-1-yl]-butan-1,4-dione,

(60) (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-imidazo[4,5-c]quinolin-3-yl)-piperidin-1-yl]-butan-1,4-dione,

(61) (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-4H-thieno[3,4-d]pyrimidin-3-yl)-piperidin-1-yl]-butan-1,4-dione,

(62) (S)-2-(4-amino-3-chloro-5-trifluoromethyl-benzyl)-1-[4-(5-methyl-2,5-diaza-bicyclo[2.2.1]hept-2-yl)-piperidin-1-yl]-4-[4-(2-oxo-1,2,4,5-tetrahydro-1,3-benzodiazepin-3-yl)-piperidin-1-yl]-butan-1,4-dione,

(63) (S)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione,

(64) (S)-2-(4-amino-3,5-bis,(1-piperidin-4-yl)-perhydro-1,4-diazepin-1-yl]-4-[4-(2-oxo-1,2,4,5-tetrahydro-1,3-benzodiazepin-3-yl)-piperidin-1-yl]-butan-1,4-dione,

(65) (S)-2-(4-amino-3,5-bis-trifluoromethyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione,

(66) (S)-2-(4-amino-3,5-bis-trifluoromethyl-benzyl)-1-[4-(1-aza-bicyclo[2.2.2]oct-3-yl)-piperazin-1-yl]-4-[4-(2-oxo-1,2,4,5-tetrahydro-1,3-benzodiazepin-3-yl)-piperidin-1-yl]-butan-1,4-dione,

(67) (S)-2-(4-amino-3,5-bis-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(68) (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione,

(69) (S)-2-(4-amino-3,5-bis-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(70) (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione,

(71) 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(4-methyl-piperazin-1-yl)-piperidin-1-yl]-2-oxo-ethyl}-amide,

(72) 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(1-methyl-piperidin-4-yl)-piperazin-1-yl]-2-oxo-ethyl}-amide,

(73) 4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-1,4'-bipiperidinyl-1'-yl-2-oxo-ethyl]-amide,

(74) 4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-oxo-2-(4-piperazin-1-yl-piperidin-1-yl)-ethyl]-amide,

(75) 4-(2-oxo-1,2,4,5-tetrahydro-1,3-benzodiazepin-3-yl)-piperidin-1-carboxylic acid-(R)-1-(4-amino-3-chloro-5-trifluoromethyl-benzyl)-2-[4-(4-methyl-piperazin-1-yl)-piperidin-1-yl]-2-oxo-ethyl ester,

(76) 4-(2-oxo-1,4-dihydro-2H-quinazolin-3-yl)-piperidin-1-carboxylic acid-[1-(4-bromo-3-methyl-benzyl)-2-(1'-methyl-[4,4']bipiperidinyl-1-yl)-2-oxo-ethyl]-amide,

(77) 4-(2-oxo-1,4-dihydro-2H-quinazolin-3-yl)-piperidin-1-carboxylic acid-{1-(4-bromo-3-methyl-benzyl)-2-[4-(4-methyl-piperazin-1-yl)-piperidin-1-yl]-2-oxo-ethyl}-amide,

(78) 4-(2-oxo-1,4-dihydro-2H-quinazolin-3-yl)-piperidin-1-carboxylic acid-{1-(4-bromo-3-methyl-benzyl)-2-[4-(1-methyl-piperidin-4-yl)-piperazin-1-yl]-2-oxo-ethyl}-amide,

(79) 4-(2-oxo-1,4-dihydro-2H-quinazolin-3-yl)-piperidin-1-carboxylic acid {1-(4-chloro-3-methyl-benzyl)-2-[4-(4-methyl-piperazin-1-yl)-piperidin-1-yl]-2-oxo-ethyl}-amide,

(80) 4-(2-oxo-1,4-dihydro-2H-quinazolin-3-yl)-piperidin-1-carboxylic acid-{1-(4-chloro-3-methyl-benzyl)-2-[4-(1-methyl-piperidin-4-yl)-piperazin-1-yl]-2-oxo-ethyl}-amide,

(81) 4-(2-oxo-1,4-dihydro-2H-quinazolin-3-yl)-piperidin-1-carboxylic acid {1-(3-bromo-4-chloro-5-methyl-benzyl)-2-[4-(4-methyl-piperazin-1-yl)-piperidin-1-yl]-2-oxo-ethyl}-amide,

(82) 4-(2-oxo-1,4-dihydro-2H-quinazolin-3-yl)-piperidin-1-carboxylic acid-{1-(3-bromo-4-chloro-5-methyl-benzyl)-2-[4-(1-methyl-piperidin-4-yl)-piperazin-1-yl]-2-oxo-ethyl}-amide, the enantiomers, the diastereomers and the salts thereof are of exceptional importance.

The compounds of general formula (I) are prepared by methods known in principle. The following methods have proved particularly satisfactory for preparing the compounds of general formula (I) according to the invention:

(a) In order to prepare compounds of general formula (I) wherein X denotes an oxygen atom or the NH group and $R^1$ to $R^3$ are as hereinbefore defined, with the proviso that these groups $R^2$ and $R^3$ do not contain any free carboxylic acid function:

Reacting piperidines of general formula

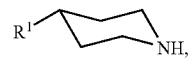

wherein $R^1$ is as hereinbefore defined, (i) with carbonic acid derivatives of general formula

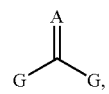

wherein A is as hereinbefore defined and G denotes a nucleofugic group, preferably the phenoxy, 1H-imidazol-1-yl, 1H-1,2,4-triazol-1-yl, trichloromethoxy or the 2,5-dioxo-pyrrolidin-1-yloxy group, with the proviso that X denotes the NH group, or (ii) with carbonic acid derivatives of general formula

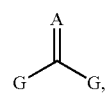

wherein A denotes the oxygen atom and G denotes a nucleofugic group which may be identical or different, preferably the chlorine atom or the p-nitrophenoxy or trichloro-methoxy group, with the proviso that X denotes the oxygen atom, and with compounds of general formula

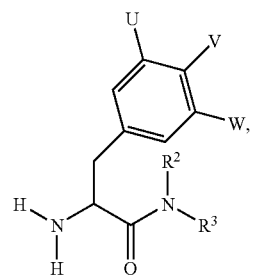

wherein X denotes the oxygen atom or an —NH group and U, V, W, $R^2$ and $R^3$ are as hereinbefore defined, with the proviso that $R^2$ and $R^3$ do not contain any free carboxylic acid and/or any other free primary or secondary aliphatic amino function or any other free hydroxy functions.

The fundamentally two-step reactions are normally carried out as one-pot processes, in which, preferably, in the first step, one of the two components (III) or (V) is reacted with equimolar amounts of the carbonic acid derivative of general formula (IV) in a suitable solvent at lower temperature, then at least equimolar amounts of the other component (III) or (V) are added and the reaction is completed at a higher temperature. The reactions with bis-(trichloromethyl)-carbonate are preferably carried out in the presence of at least 2 equivalents (based on bis-(trichloromethyl)-carbonate) of a tertiary base, for example triethylamine, N-ethyldiisopropylamine, pyridine, 1,5-diaza-bicyclo-[4.3.0]-non-5-ene, 1,4-diazabicyclo[2.2.2]octane or 1,8-diazabicyclo-[5.4.0]-undec-7-ene. The solvents used, which should be anhydrous, may be for example tetrahydrofuran, dioxane, dimethylformamide, dimethylacetamide, N-methyl-2-pyrrolidone, 1,3-dimethyl-2-imidazolidinone or acetonitrile, while if bis-(trichloromethyl)-carbonate is used as the carbonyl component anhydrous chlorohydrocarbons, for example dichloromethane, 1,2-dichloroethane or trichloroethylene are preferred. The reaction temperatures for the first reaction step are between −30° C. and +25° C., preferably −5° C. and +10° C., for the second reaction step between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Volume V, p. 53-93, Verlag Chemie, Weinheim/Bergstr., 1967; P. Majer and R. S. Randad, J. Org. Chem. 59, p. 1937-1938 (1994); K. Takeda, Y. Akagi, A. Saiki, T. Sukahara and H. Ogura, Tetrahedron Letters 24 (42), 4569-4572 (1983)); S. R. Sandler and W. Karo in "Organic Functional Group Preparations", Vol. 1, S. 223-245, Academis Press, New York 1971).

(b) In order to prepare compounds of general formula (I) wherein X denotes the methylene group and $R^1$ to $R^3$ are as hereinbefore defined, with the proviso that these groups do not contain any free carboxylic acid and/or other free primary or secondary aliphatic amino function:

Coupling a carboxylic acid of general formula

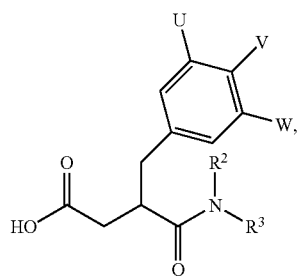

(VI)

wherein U, V, W, $R^2$ and $R^3$ are as hereinbefore defined, to a piperidine of general formula

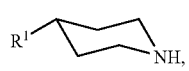

(III)

wherein $R^1$ has the meanings given hereinbefore.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexa-fluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (DIEA) (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (VI) which is to be coupled and monoisobutyl carbonate is obtained, using isobutyl chlorocarbonate in the presence of bases such as 4-methyl-morpholine or 4-ethylmorpholine. The preparation of this mixed anhydride and the coupling with amines are carried out in a one-pot process, using the abovementioned solvents and at temperatures between −20 and +25° C., preferably 0° C. and +25° C.

(c) In order to prepare compounds of general formula (I) wherein X denotes the methylene group and $R^2$ and $R^3$ are as hereinbefore defined, with the proviso that these groups do not contain any free primary or secondary amine:

Coupling a compound of general formula

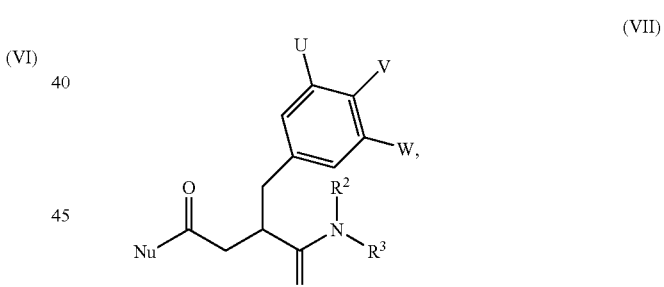

(VII)

wherein U, V, W, $R^2$ and $R^3$ are as hereinbefore defined, with the proviso that $R^2$ and $R^3$ do not contain any free primary or secondary amine, and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzotriazol-1-yloxy or azide group, with a piperidine of general formula

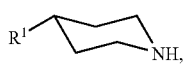

wherein R¹ is as hereinbefore defined.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2.2.2]octane or 1,8-diazabicyclo[5.4.0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

(d) In order to prepare compounds of general formula (I) wherein all the groups are as hereinbefore defined:

Coupling a carboxylic acid of general formula

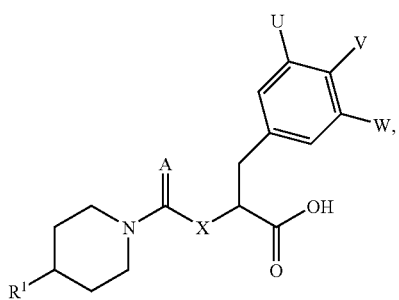

wherein all the groups are as hereinbefore defined, with an amine of general formula HNR²R³, wherein R² and R³ are as hereinbefore defined, with the proviso that it does not contain any free carboxylic acid and/or other free primary or secondary aliphatic amino function.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexa-fluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (DIEA) (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (VI) which is to be coupled and monoisobutyl carbonate is obtained, using isobutyl chlorocarbonate in the presence of bases such as 4-methyl-morpholine or 4-ethylmorpholine. The preparation of this mixed anhydride and the coupling with amines are carried out in a one-pot process, using the abovementioned solvents and at temperatures between −20 and +25° C., preferably 0° C. and +25° C.

(e) In order to prepare compounds of general formula (I) wherein R¹ is as hereinbefore defined, with the proviso that no free primary or secondary amine is present:

Coupling a compound of general formula

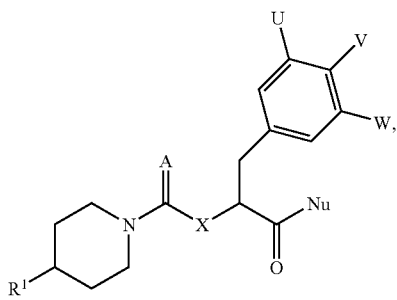

wherein all the groups are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with an amine of general formula HNR²R³, wherein R² and R³ are as hereinbefore defined, with the proviso that no free carboxylic acid and/or other free primary or secondary aliphatic amino function is present.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents.

The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2.2.2]octane or 1,8-diazabicyclo[5.4.0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting compounds of general formula (III) may be obtained, if they are not known from the literature or even commercially available, according to the processes described in WO 98/11128 and DE 199 52 146. The starting compounds of general formula (IV) are commercially available. Compounds of general formula (V) may be obtained by methods familiar to the peptide chemist from protected phenylalanines and amines of general formula $HNR^2R^3$.

The phenylalanine derivatives needed to prepare the optically pure compounds of general formula (V) may be prepared from the compounds of general formula

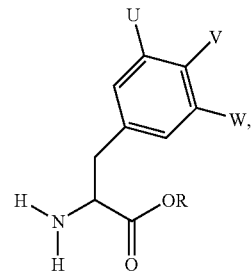

(X)

wherein U, V and W are as hereinbefore defined and R denotes an unbranched alkyl group, preferably the methyl or ethyl group, by racemate cleavage.

This racemate cleavage can be carried out using enzymatic methods, while only one enantiomer of the racemate is transformed and the mixture produced is then separated using physicochemical methods, preferably using chromatographic methods. A suitable enzyme system for this step consists of the enzyme Alcalase 2.4 L FG (Novozymes A/S; DK 2880 Bagsvaerd). The compounds of general formula (X) can then be converted into the enantiomerically pure compounds of general formula (V) by methods familiar to the peptide chemist.

If the group X in compounds of general formula (V) denotes the oxygen atom, the hydroxycarboxylic acids needed for the synthesis, of general formula

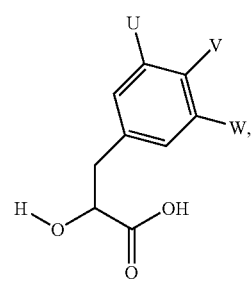

(XI)

wherein U, V and W are as hereinbefore defined, may be prepared from compounds of general formula (X), with the proviso that R denotes the hydrogen atom.

With the proviso that V does not denote the amino or methylamino group, the compounds of general formula (XI) may be obtained by diazotisation of compounds of general formula (X) with a suitable diazotising reagent, preferably sodium nitrite in an acidic medium. If enantiomerically pure compounds are used, the corresponding enantiomerically pure hydroxycarboxylic acid compounds are obtained, and the configuration is retained during the reaction.

Another method of obtaining compounds of general formula (XI) wherein U, V and W are as hereinbefore defined comprises alkylating the compound

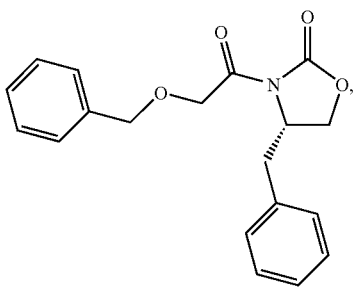

(XII)

with correspondingly substituted benzyl chlorides, benzyl bromides or benzyl iodides of general formula (XIII)

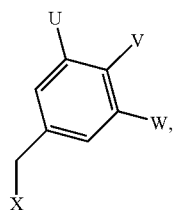

(XIII)

wherein U, V and W are as hereinbefore defined and X denotes a chlorine, bromine or iodine atom, analogously to methods known from the literature (Michael T. Crimmins, Kyle A. Emmitte and Jason D. Katz, Org. Lett. 2, 2165-2167 [2000]).

The diastereomeric products obtained can then be separated by physicochemical methods, preferably using chromatographic methods. The hydrolytic cleaving of the chiral auxiliary, coupling with amines of general formula $HNR^2R^3$ and cleaving the benzyl protecting group also provides access to enantiomerically pure hydroxycarboxylic acid compounds of general formula (V).

The starting compounds of general formula (VI) are obtained for example by reacting amines of general formula $HNR^2R^3$ with 2-(alkoxycarbonylmethyl)-3-aryl-propanoic acids and subsequently hydrolytically cleaving the alkyl group. The 2-(alkoxycarbonylmethyl)-3-aryl-propanoic acids required may be prepared analogously to methods known from the literature (David A. Evans, Leester D. Wu, John J. M. Wiener, Jeffrey S. Johnson, David H. B. Ripin and Jason S. Tedrow, J. Org. Chem 64, 6411-6417 [1999]; Saul G. Cohen and Aleksander Milovanovic, J. Am. Chem. Soc. 90, 3495-3502 [1968]; Hiroyuki Kawano, Youichi Ishii, Takao Ikariya, Masahiko Saburi, Sadao Yoshikawa, Yasuzo Uchida and Hidenori Kumobayashi, Tetrahedron Letters 28, 1905-1908 [1987]). Carboxylic acids of general formula (VIII) may be prepared from generally available starting materials in accordance with the processes described in WO 98/11128.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain a carboxylic acid function, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the abovementioned racemates are made up.

Also included in the subject matter of this invention are the compounds according to the invention, including the salts thereof, in which one or more hydrogen atoms are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds of general formula I and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the abovementioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, $NaHCO_3$ 16.2, $MgSO_4$ 0.8, $NaHPO_4$ 1.0, $CaCl_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM $MgCl_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM $MgCl_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds mentioned hereinbefore show $IC_{50}$ values $\leq 10000$ nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($11^{-11}$ to $10^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds of general formula I exhibit CGRP-antagonistic properties in the in vitro test model described, in a dosage range between $10^{-12}$ and $10^{-5}$ M.

In view of their pharmacological properties the compounds of general formula I and the salts thereof with physiologically acceptable acids are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect. The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone substitution, it is advisable to reduce the doses specified above, in which case the dosage may be from ⅕ of the lower limits mentioned above up to ⅕ of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. antiemetics, prokinetics, neuroleptics, antidepressants, neurokinine antagonists, anti-convulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, 5-$HT_{1B/1D}$ agonists or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib and celecoxib.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenytoin, valproate, amitryptiline, lidocaine or diltiazem and other 5-$HT_{1B/1D}$-agonists such as, for example, almotriptan, avitriptan, eletriptan, frovatriptan, naratriptan, rizatriptan, sumatriptan and zolmitriptan.

The dosage of these active substances is expediently ⅕ of the lowest recommended dose to ⅕ of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

EXPERIMENTAL SECTION

As a rule, IR, $^1$H-NMR and/or mass spectra have been obtained for the compounds prepared. Unless otherwise stated, $R_f$ values were obtained using ready-made silica gel TLC plates 60 F254 (E. Merck, Darmstadt, Item no. 1.05714) without chamber saturation. The $R_f$ values obtained under the name Alox were obtained using ready-made aluminium oxide 60 F254 TLC plates (E. Merck, Darmstadt, item no. 1.05713) without chamber saturation. The ratios given for the eluants relate to units by volume of the solvent in question. The units by volume given for NH$_3$ are based on a concentrated solution of NH$_3$ in water.

Unless otherwise stated the acid, base and saline solutions used for working up the reaction solutions are aqueous solutions having the concentrations specified.

For chromatographic purification, silica gel made by Millipore (MATREX™, 35-70 µm) was used. For chromatographic purification Alox (E. Merck, Darmstadt, standardised aluminium oxide 90, 63-200 µm, Article no. 1.01097.9050) is used.

The HPLC data provided are measured using the parameters specified below: Analytical column: Zorbax column (Agilent Technologies), SB (Stable Bond)-C18; 3.5 µm; 4.6× 75 mm; column temperature: 30° C.; flow: 0.8 mL/min; injection volume: 5 µL; detection at 254 nm

| | Method A: | |
|---|---|---|
| time (min) | percent by volume of water (with 0.1% formic acid) | percent by volume of acetonitrile (with 0.1% formic acid) |
| 0 | 90 | 10 |
| 9 | 10 | 90 |
| 10 | 10 | 90 |
| 11 | 90 | 10 |

In preparative HPLC purifications as a rule the same gradients are used as were used to raise the analytical HPLC data.

The products are collected under mass control and the fractions containing the product are combined and freeze-dried.

If no detailed information is given as to the configuration, it is not clear whether it is a pure enantiomer or whether partial or even complete racemisation has occurred.

The following abbreviations are used in the description of the experiments:

| abs. | absolute |
|---|---|
| Boc | tert.-butoxycarbonyl |
| CDI | N,N'-carbonyldiimidazole |
| CDT | 1,1'-carbonyldi-(1,2,4-triazole) |
| Cyc | cyclohexane |
| DCM | dichloromethane |
| DMF | N,N-dimethylformamide |
| EtOAc | ethyl acetate |
| EtOH | ethanol |
| semiconc. | semiconcentrated |
| HCl | hydrochloric acid |
| HOAc | acetic acid |
| HOBt | 1-hydroxybenzotriazole-hydrate |
| i. vac. | in vacuo (in a vacuum) |
| KOH | potassium hydroxide |
| conc. | concentrated |
| MeOH | methanol |
| NaCl | sodium chloride |
| NaOH | sodium hydroxide |
| org. | organic |
| PE | petroleum ether |
| RT | room temperature |
| TBTU | 2-(1H-benzotriazol-1-yl)-1,1,3,3-tetramethyluronium-tetrafluoroborate |
| TFA | trifluoroacetic acid |
| THF | tetrahydrofuran |

Instructions for Preparing the Amines Used (Starting Compounds)

Example A1

2-methyl-5-piperidin-4-yl-2,5-diaza-bicyclo[2.2.1]heptane (Examples 7.9 and 10.79)

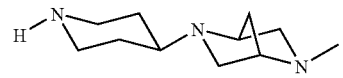

A1a 2-(1-benzyl-piperidin-4-yl)-5-methyl-2,5-diaza-bicyclo[2.2.1]heptane 0.73 mL (12.7 mmol) acetic acid were added to a solution of 2.38 mL (12.7 mmol) 1-benzyl-piperidin-4-one and 3.5 g (12.77 mmol) of 2-methyl-2,5-diaza-bicyclo[2.2.1]heptane in 100 mL MeOH and the reaction mixture was stirred for 3 h at RT. Under a nitrogen current 0.99 g (15.0 mmol) NaBH$_3$CN were added and the reaction solution was stirred overnight at RT. It was acidified with 7 mL of conc. HCl, stirred for 1 h at RT and evaporated down i.vac. The residue was combined with 200 mL of 15% K$_2$CO$_3$ solution, extracted twice with 200 mL DCM in each case and the combined organic phases were dried over Na$_2$SO$_4$. After the desiccant and solvent had been eliminated the residue was purified by chromatography (silica gel, gradient: DCM to DCM/MeOH/NH$_3$ 10:85:5).

Yield: 2.1 g (58% of theory) ESI-MS: (M+H)$^+$=286 R$_f$=0.15 (silica gel, DCM/MeOH/NH$_3$ 80:20:2)

A1b 2-methyl-5-piperidin-4-yl-2,5-diaza-bicyclo[2.2.1]heptane

A solution of 2.1 g (7.36 mmol) 2-(1-benzyl-piperidin-4-yl)-5-methyl-2,5-diaza-bicyclo[2.2.1]heptane in 100 mL MeOH was combined with 500 mg of 10% Pd/C and hydrogenated at RT and 50 psi H$_2$ for 3 h. The catalyst was suction filtered and the solvent eliminated i.vac. The product was used for further reactions without being purified.

Yield: 1.4 g (97% of theory) ESI-MS: (M+H)$^+$=196 R$_f$=0.10 (silica gel, DCM/MeOH/NH$_3$ 80:20:2)

Example A2

1-cyclopropylmethyl-4-piperidin-4-yl-piperazine (Example 10.4)

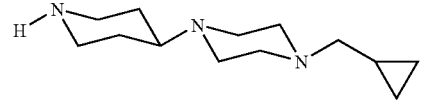

A2a tert. butyl 4-(4-cyclopropylmethyl-piperazin-1-yl)-piperidine-1-carboxylate 1.26 g (20.0 mmol) NaBH$_3$CN were added in 4 batches at RT to a solution of 1.71 g (5.0 mmol) tert. butyl 4-piperazin-1-yl-piperidine-1-carboxylate and 0.75 mL (10.0 mmol) cyclopropanecarbaldehyde in 100 mL of EtOH and the reaction mixture was stirred overnight at RT. The mixture was evaporated down i.vac., the residue was taken up in saturated NaHCO$_3$ solution, extracted exhaustively with EtOAc and the organic phase was dried over Na$_2$SO$_4$. After the desiccant and solvent had been eliminated the residue was purified by chromatography (silica gel, EtOAc/MeOH/NH$_3$ 90:10:0.5).

Yield: 1.36 g (84% of theory) EI: (M)$^+$=323

A2b 1-cyclopropylmethyl-4-piperidin-4-yl-piperazine 5 mL TFA were added to a solution of 1.36 g (4.2 mmol) tert. butyl 4-(4-cyclopropylmethyl-piperazin-1-yl)-piperidine-1-carboxylate in 30 mL DCM and the reaction mixture was stirred for 4 h at RT. The reaction solution was evaporated down i.vac., the residue combined with diethyl ether, the precipitate was suction filtered and dried. The product was precipitated as the tris-trifluoroacetate salt.

Yield: 1.86 g (78% of theory) EI: (M)$^+$=223

Example A3

4-azetidin-1-yl-piperidine (Example 10.15)

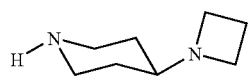

A3a 4-azetidin-1-yl-1-benzyl-piperidine 1.0 mL (17.49 mmol) acetic acid was added to a solution of 3.0 mL (16.45 mmol) of 1-benzyl-piperidin-4-one and 1.0 g (17.51 mmol) azetidine in 100 mL DCM and the reaction mixture was stirred for 1 h at RT. 6.0 g (39.55 mmol) of NaBH(OAc)$_3$ were added in 4 batches within 1 h while cooling with ice and the reaction solution was stirred overnight at RT. 15% K$_2$CO$_3$ solution was added and stirring was continued for another hour. 200 mL EtOAc were added, the organic phase was separated off and dried over MgSO$_4$. After the desiccant and solvent had been eliminated the residue was purified by chromatography (silica gel, gradient: DCM to MeOH/NH$_3$ 9:1).

Yield: 3.2 g (84% of theory) EI: (M)$^+$=230 R$_f$=0.57 (silica gel, DCM/MeOH/cyc/NH$_3$ 70:15:15:2)

A3b 4-azetidin-1-yl-piperidine

A solution of 3.2 g (13.89 mmol) 4-azetidin-1-yl-1-benzyl-piperidine in 50 mL MeOH was combined with 500 mg 10% Pd/C and hydrogenated for 7.5 h at RT and 3 bar H$_2$. The catalyst was suction filtered and the solvent eliminated i.vac. The product was used for further reactions without being purified.

Yield: 1.9 g (98% of theory) ESI-MS: (M+H)$^+$=141 R$_f$=0.19 (silica gel, DCM/MeOH/NH$_3$ 70:25:5)

Example A4

1-azetidin-3-yl-perhydro-azepine (Example 10.22)

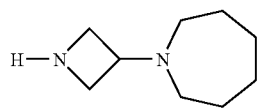

A4a 1-(1-benzhydryl-azetidin-3-yl)-perhydro-azepine

Under a nitrogen atmosphere 31.7 g (320 mmol) of perhydro-azepine were added to a solution of 31.7 g (100 mmol) 1,1-dibenzyl-azetidin-3-yl methanesulphonate in 200 mL of DMF and the mixture was stirred for 7 days at 50° C. The reaction solution was combined with 1 L water, the aqueous phase was extracted twice with EtOAc, the combined organic phases were washed twice with water and dried over Na$_2$SO$_4$. After the desiccant and solvent had been eliminated the residue was twice purified by chromatography (silica gel, 1st column: DCM/MeOH/NH$_3$ 19:1:0.025 and 2nd column: tert-butylmethylether).

Yield: 22.2 g (69% of theory) R$_f$=0.82 (silica gel, DCM/MeOH/NH$_3$ 19:1:0.025)

A4b 1-azetidin-3-yl-perhydro-azepine 5 g 10% Pd/C were added to a solution of 22.0 g (68.6 mmol) of 1-(1-benzhydryl-azetidin-3-yl)-perhydro-azepine in 400 mL MeOH and 69 mL of 2 N HCl and the reaction mixture was hydrogenated for 3 h at 45° C. until the theoretical uptake of H$_2$ had been achieved. After filtration the solvent was eliminated i.vac. and the product, which was obtained as the bis-hydrochloride, was further reacted without being purified.

Yield: 15.5 g (100% of theory) melting point: 205-220° C. R$_f$=0.08 (silica gel, DCM/MeOH/NH$_3$ 9:1:0.1)

Example A5

1-benzyl-4-piperidin-4-yl-piperazine (Example 10.24)

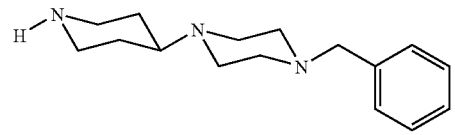

A5a tert. butyl 4-(4-benzyl-piperazin-1-yl)-piperidine-1-carboxylate

A solution of 66.7 mL (381 mmol) 1-benzyl-piperazine and 75.8 g (380 mmol) tert. butyl 4-oxo-piperidine-1-carboxylate in 1 L THF was adjusted to pH 5 with glacial acetic acid and then 100 g (448 mmol) NaBH(OAc)$_3$ was added batchwise within 2 h while cooling with ice and the reaction mixture was stirred overnight at RT. The reaction solution was carefully made alkaline with 2.2 M K$_2$CO$_3$ solution, stirred for 1 h, exhaustively extracted with EtOAc and the combined organic phases were dried over Na$_2$SO$_4$. After the desiccant and solvent had been eliminated the residue was further reacted without being purified.

Yield: 114 g (83% of theory) ESI-MS: (M+Na)$^+$=382 R$_f$=0.74 (silica gel, DCM/MeOH/cyc/NH$_3$ 70:15:15:2)

A5b 1-benzyl-4-piperidin-4-yl-piperazine 20 mL TFA were added to a solution of 5 g (13.91 miol) tert. butyl 4-(4-benzyl-piperazin-1-yl)-piperidine-1-carboxylate in 200 mL DCM and the reaction mixture was stirred overnight at RT. The mixture was evaporated down i. vac., the residue was combined with 200 mL 15% K$_2$CO$_3$ solution, extracted three times with 100 mL DCM in each case and the combined organic phases were dried over MgSO$_4$. After the desiccant and solvent had been eliminated the desired product was obtained, which was further reacted without being purified.

Yield: 2.9 g (80% of theory) ESI-MS: (M+H)$^+$=260 R$_f$=0.58 (silica gel, DCM/MeOH/NH$_3$ 70:25:5)

Example A6

Dimethyl-(2,3,4,5-tetrahydro-1H-3-benzazepin-7-ylmethyl)-amine (Example 10.25)

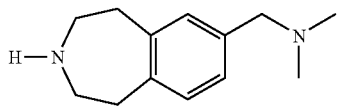

A6a 1-(7-dimethylaminomethyl-1,2,4,5-tetrahydro-3-benzazepin-3-yl)-2,2,2-trifluoro-ethanone 11.7 mL (23.4 mmol) of a 2 M dimethylamine solution in THF were added to a solution of 4.5 g (16.59 mmol) 3-(2,2,2-trifluoro-acetyl)-2,3,4,5-tetrahydro-1H-3-benzazepin-7-carbaldehyde in 150 mL THF and the solution was adjusted to pH 5 with 1 mL glacial acetic acid. After 30 min 4.62 g (21.79 mmol) $NaBH(OAc)_3$ were added and the reaction mixture was stirred overnight at RT. The reaction solution was carefully combined with saturated $NaHCO_3$ solution, stirred for 30 min, exhaustively extracted with EtOAc, the organic phase was separated off and dried over $Na_2SO_4$. After the desiccant and solvent had been eliminated the desired product was obtained, which was further reacted without being purified.

Yield: 4.5 g (90% of theory) ESI-MS: $(M+H)^+=301$ $R_f=0.76$ (silica gel, DCM/MeOH/cyc/$NH_3$ 70:15:15:2)

A6b dimethyl-(2,3,4,5-tetrahydro-1H-3-benzazepin-7-ylmethyl)-amine 50 mL water and 8.5 g (61.51 mmol) $K_2CO_3$ were added to a solution of 4.5 g (14.98 mmol) 1-(7-dimethylaminomethyl-1,2,4,5-tetrahydro-3-benzazepin-3-yl)-2,2,2-trifluoro-ethanone in 50 mL MeOH and the reaction mixture was stirred for 72 h at RT. The reaction solution was evaporated down i.vac., the residue combined with DCM, filtered to remove insoluble constituents and evaporated down i.vac. The desired product was obtained in the form of a light brown oil.

Yield: 2.9 g (95% of theory) ESI-MS: $(M+H)^+=205$ $R_f=0.39$ (silica gel, DCM/MeOH/cyc/$NH_3$ 70:15:15:2)

Example A7

1-piperidin-4-yl-4-(2,2,2-trifluoro-ethyl)-piperazine (Example 10.27)

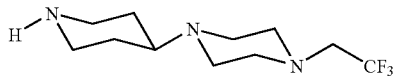

A7a 1-[4-(1-benzyl-piperidin-4-yl)-piperazin-1-yl]-2,2,2-trifluoro-ethanone

A solution of 8.21 mL (57.83 mmol) trifluoroacetic anhydride in 40 mL DCM was added dropwise to a solution, cooled to 0° C., of 15.0 g (57.83 mmol) 1-(1-benzyl-piperidin-4-yl)-piperazine and 20.1 mL (145 mmol) triethylamine in 200 DCM and the reaction mixture was stirred for 5 h at RT. Water was added, the organic phase was separated off and dried over $Na_2SO_4$. After the desiccant and solvent had been eliminated the crude product was further reacted without being purified.

Yield: 8.3 g (40% of theory) EI: $(M)^+=205$ $R_f=0.48$ (silica gel, DCM/MeOH/$NH_3$ 90:10:1)

A7b 1-(1-benzyl-piperidin-4-yl)-4-(2,2,2-trifluoro-ethyl)-piperazine 0.53 g (14.07 mmol) $NaBH_4$ were added to a solution of 1.0 g (2.81 mmol) 1-[4-(1-benzyl-piperidin-4-yl)-piperazin-1-yl]-2,2,2-trifluoro-ethanone in 9 mL of 1,4-dioxane and 1 mL of THF and then a solution of 1.08 mL (14.07 mmol) TFA in 10 mL 1,4-dioxane was added dropwise to the resulting suspension within 10 min. The reaction solution was refluxed for 5 h, after cooling it was decomposed with water and evaporated down i.vac. The residue obtained was purified by chromatography (silica gel, EtOAc/MeOH/$NH_3$ 95:5:0.5).

Yield: 0.41 g (43% of theory) ESI-MS: $(M+H)^+=342$ $R_f=0.45$ (silica gel, EtOAc/MeOH/$NH_3$ 80:20:2)

A7c 1-piperidin-4-yl-4-(2,2,2-trifluoro-ethyl)-piperazine 50 mg of 10% Pd/C were added to a solution of 0.41 g (1.20 mmol) of 1-(1-benzyl-piperidin-4-yl)-4-(2,2,2-trifluoro-ethyl)-piperazine in 30 mL MeOH and the reaction mixture was hydrogenated for 2.5 h at RT and 3 bar $H_2$. To complete the reaction a spatula tip of $Pd(OH)_2$ was added and hydrogenation was continued for a further 1.5 h. After the catalyst had been removed by suction filtering and the solvent had been eliminated the desired product was obtained.

Yield: 0.28 g (94% of theory) ESI-MS: $(M+H)^+=252$ $R_f=0.05$ (silica gel, EtOAc/MeOH/$NH_3$ 70:30:3)

Example A8

Methyl-[2-(1-methyl-piperidin-4-yl)-ethyl]-amine (Example 10.32)

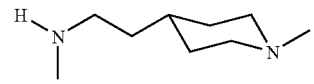

A8a (N,N-dimethyl-2-(1-methyl-piperidin-4-yl)-acetamide

A solution of 9.3 g (50 mmol) ethyl N-methylpiperidinyl-4-acetate in 50 mL 40% aqueous methylamine solution was stirred for 15 h at 80° C. in a bomb tube. The solvent was eliminated i.vac. and the residue dissolved in EtOAc. The organic phase was dried over $MgSO_4$ and the solvent was eliminated i.vac.

Yield: 4.7 g (55% of theory) $R_f=0.53$ (silica gel, DCM/MeOH 21:1)

A8b methyl-[2-(1-methyl-piperidin-4-yl)-ethyl]-amine 3.1 g (20 mmol) N,N-dimethyl-2-(1-methyl-piperidin-4-yl)-acetamide in 40 mL THF were added dropwise to a solution of 1.1 g (30 mmol) lithium aluminium hydride in 50 mL diethyl ether. The mixture was refluxed for 2 h and then stirred overnight at RT. After the addition of water, 6 N NaOH and more water the solution was stirred for 30 min. After filtration the solvent was eliminated i.vac. The residue was dissolved in diethyl ether, dried over MgSO₄ and the solvent was eliminated i.vac.

Yield: 2.5 g (80% of theory) R$_f$=0.29 (Alox, DCM/MeOH 21:1)

Example A9

Cyclopentyl-methyl-piperidin-4-yl-amine (Example 10.41)

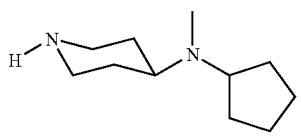

A9a (1-benzyl-piperidin-4-yl)-cyclopentyl-methyl-amine 6.0 mL (105 mmol) glacial acetic acid were added to a solution of 6.5 g (31.8 mmol) (1-benzyl-piperidin-4-yl)-methyl-amine and 2.7 g (32.0 mmol) cyclopentanone in 200 mL THF and the reaction mixture was heated to 55° C. for 10 min. After cooling to 15° C. 10.6 g (50.0 mmol) NaBH(OAc)₃ were added batchwise and the reaction solution was stirred overnight at RT. To complete the reaction another 3.0 g (14.2 mmol) NaBH(OAc)₃ were added and the mixture was stirred for a further 5 h at RT. 100 mL of water were carefully added, the pH was made alkaline using Na₂CO₃, the mixture was extracted exhaustively with diethyl ether, the combined organic phases were washed with water and evaporaoted down i.vac. After elimination of the solvent the residue was purified by chromatography (silica gel, EtOAc/MeOH/NH₃ 9:1:0.3).

Yield: 5.0 g (58% of theory) EI: (M)⁺=272 R$_f$=0.6 (silica gel, EtOAc/MeOH/NH₃ 9:1:0.3)

A9b cyclopentyl-methyl-piperidin-4-yl-amine 1.0 g 10% Pd/C were added to a solution of 5.0 g (18.35 mmol) (1-benzyl-piperidin-4-yl)-cyclopentyl-methyl-amine in 100 mL MeOH and the reaction mixture was hydrogenated for 3 h at RT and 5 bar H₂. After the catalyst had been removed by suction filtering and the solvent had been eliminated the desired product was obtained, which was further reacted without being purified.

Yield: 3.0 g (90% of theory) R$_f$=0.05 (silica gel, EtOAc/MeOH/NH₃ 9:1:0.4)

Example A10

4-(1,1-dioxo-1□⁶-isothiazolidin-2-yl)-piperidine (Example 10.46)

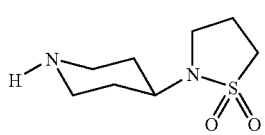

A10a 1-benzyl-4-(1,1-dioxo-1□⁶-isothiazolidin-2-yl)-piperidine 3-chloro-propan-1-sulphonyl chloride was added dropwise at RT to a solution of 19.0 g (100 mmol) 1-benzyl-piperidin-4-ylamine and 27.2 g (197 mmol) K₂CO₃ in 200 mL acetonitrile. The reaction solution was left to stand overnight. After filtration the solvent was distilled off. The residue was taken up in 120 mL EtOH and combined with 6.2 g (111 mmol) KOH. The mixture was refluxed for 1 h and after cooling acidified with HCl. The precipitate was suction filtered and dried.

Yield: 15.4 g (46% of theory) melting point: 255-257° C.

A10b 4-(1,1-dioxo-1□⁶-isothiazolidin-2-yl)-piperidine

Analogously to Example 17d the product was prepared from 16.5 g (56.1 mmol) 1-benzyl-4-(1,1-dioxo-1□⁶-isothiazolidin-2-yl)-piperidine.

Yield: 8.5 g (74% of theory) melting point: 89-92° C. R$_f$=0.13 (silica gel, DCM/MeOH 8:2)

Example A11 tert-butyl-piperidin-4-yl-amine (Example 10.50)

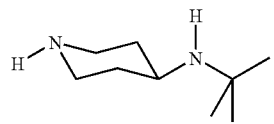

A11a (1-benzyl-piperidin-4-yl)-tert-butyl-amine

Under an argon atmosphere a solution of 8.6 mL (78 mmol) TiCl₄ in 100 mL toluene was added dropwise to a solution, cooled to 0° C., of 24.1 mL (130 mmol) 1-benzyl-piperidin-4-one and 55 mL (519 mmol) of tert-butylamine in 200 mL toluene in such a way that the internal temperature did not exceed 15° C. The reaction mixture was stirred overnight at RT, the precipitate formed was suction filtered and the solution remaining after the addition of 65 mg of platinum oxide was hydrogenated until the theoretical uptake of H₂ had been achieved. After hydrogenation had ended, 160 mL of 2 N NaOH solution were added to the suspension, it was filtered, the organic phase was separated off, the aqueous solution was extracted three times with toluene and the combined organic phases were dried over Na₂SO₄. After the desiccant and solvent had been eliminated the product was further reacted without being purified.

Yield: 13.9 g (43% of theory)

A11b tert-butyl-piperidin-4-yl-amine 1.5 g 10% Pd/C were added to a solution of 13.9 g (56.0 mmol) (1-benzyl-piperidin-4-yl)-tert-butyl-amine in 140 mL MeOH and the reaction mixture was hydrogenated at RT until the theoretical uptake of H₂ had been achieved (2 h). After the catalyst had been removed by suction filtering and the solvent was eliminated, the desired product was obtained, which was farther reacted without being purified.

Yield: 8.3 g (95% of theory)

Example A12

4-(2-methyl-imidazol-1-yl)-piperidine (Example 10.58)

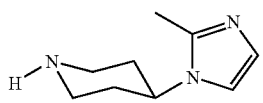

A12a tert. butyl 4-(2-methyl-imidazol-1-yl)-piperidine-1-carboxylate

Under a nitrogen atmosphere 1.0 g (22.92 mmol) NaH (55% in mineral oil) were added batchwise to a solution of 2.0 g (21.92 mmol) 2-methyl-1H-imidazole in 20 mL DMF at RT within 20 min and the reaction mixture was stirred for 30 min at this temperature. Then a solution of 4.0 g (14.32 mmol) tert. butyl 4-methanesulphonyloxy-piperidine-1-carboxylate in 50 mL DMF was slowly added dropwise and the reaction solution was then stirred for 2.5 h at 100° C. The mixture was evaporated down i. vac., the residue was taken up in 150 mL DCM, the organic phase was washed twice with 50 mL water in each case and dried over MgSO$_4$. After the desiccant and solvent had been eliminated the residue was further reacted without being purified.

Yield: 0.65 g (17% of theory) ESI-MS: (M+H)$^+$=266 R$_f$=0.56 (silica gel, DCM/MeOH/cyc/NH$_3$ 70:15:15:2)

A12b 4-(2-methyl-imidazol-1-yl)-piperidine

A solution of 650 mg (2.45 mmol) tert. butyl 4-(2-methyl-imidazol-1-yl)-piperidine-1-carboxylate was dissolved in 10 mL of 4 M HCl in 1,4-dioxane and the reaction mixture was stirred for 2 h at RT. The mixture was evaporated down i. vac., the residue was combined with diisopropylether and a little isopropanol, the precipitate was removed by suction filtering and dried in the circulating air dryer. The desired product was obtained as the dihydrochloride.

Yield: 430 mg (74% of theory) ESI-MS: (M+H)$^+$=166 R$_f$=0.54 (silica gel, DCM/MeOH/NH$_3$ 75:25:5)

Example A13

4-(2,4-dimethyl-imidazol-1-yl)-piperidine (Example 10.61)

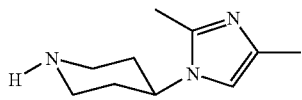

A13a tert. butyl 4-(2,4-dimethyl-imidazol-1-yl)-piperidine-1-carboxylate

Prepared analogously to Example A12a from 2.2 g (22.20 mmol) of 2,4-dimethyl-1H-imidazole and 4.0 g (14.32 mmol) of tert. butyl 4-methanesulphonyloxy-piperidine-1-carboxylate.

Yield: 0.45 g (11% of theory) ESI-MS: (M+H)$^+$=280 R$_f$=0.51 (silica gel, DCM/MeOH/cyc/NH$_3$ 70:15:15:2)

A13b 4-(2,4-dimethyl-imidazol-1-yl)-piperidine

Prepared analogously to Example A12b from 450 mg (1.61 mmol) of tert. butyl 4-(2,4-dimethyl-imidazol-1-yl)-piperidine-1-carboxylate. The desired product was obtained as the dihydrochloride.

Yield: 300 mg (74% of theory) ESI-MS: (M+H)$^+$=180 R$_f$=0.63 (silica gel, DCM/MeOH/NH$_3$ 75:25:5)

Example A14 piperazin-1-sulphonic acid-(1-methyl-piperidin-4-yl)-amide (Example 10.66)

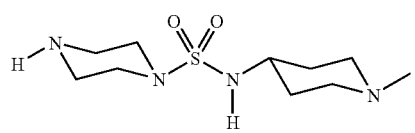

A14a 4-benzyl-piperazin-1-sulphonic acid-(1-methyl-piperidin-4-yl)-amide 1.89 g (11.0 mmol) 1,3,2-benzodioxathiole-2,2-dioxide were added to a solution of 1.0 g (8.76 mmol) 1-methyl-piperidin-4-ylamine and 1.25 mL (9.0 mmol) triethylamine in 50 mL of DCM cooled to 0° C., the cooling bath was removed and the reaction mixture was stirred overnight at RT. The mixture was evaporated down i. vac., the residue was stirred with diethyl ether/diisopropylether, filtered and the crude product was dried. Under a nitrogen atmosphere this crude product (2.5 g) and 3.16 g (17.4 mmol) 1-benzyl-piperazine were dissolved in 100 mL 1,4-dioxane and the reaction mixture was refluxed for 2 h. The mixture was evaporated down i. vac. and the residue was purified by chromatography (silica gel, DCM/MeOH/NH$_3$ 90:10:1).

Yield: 1.1 g (36% of theory) ESI-MS: (M+H)$^+$=353 R$_f$=0.50 (silica gel, DCM/MeOH/NH$_3$ 80:20:1)

A14b piperazin-1-sulphonic acid-(1-methyl-piperidin-4-yl)-amide 500 mg of 10% Pd/C were added to a solution of 1.1 g (3.12 mmol) of 4-benzyl-piperazin-1-sulphonic acid-(1-methyl-piperidin-4-yl)-amide in 100 mL MeOH and the reaction mixture was hydrogenated at RT until the theoretical uptake of H$_2$ had been achieved (2.5 h). After the catalyst had been removed by suction filtering and the solvent had been eliminated the desired product was obtained, which was further reacted without being purified.

Yield: 0.82 g (100% of theory) ESI-MS: (M+H)$^+$=263 R$_f$=0.05 (silica gel, EtOAc/MeOH/NH$_3$ 90:10:1)

Example A15 ethyl 1-(1-methyl-piperidin-4-yl)-piperazin-2-carboxylate

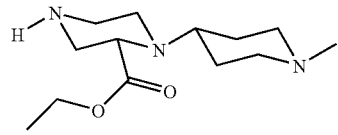

A15a 1-tert-butyl, 3-ethyl 4-(1-methyl-piperidin-4-yl)-piperazin-1,3-dicarboxylate A solution of 1.0 g (3.87 mmol) 1-tert-butyl, 3-ethyl piperazin-1,3-dicarboxylate and 0.45 mL (3.87 mmol) of 1-methyl-piperidin-4-one in 25 mL THF was adjusted to a pH of between 5 and 6 with glacial acetic acid and then 1.0 g (4.48 mmol) NaBH(OAc)$_3$ were added batchwise and the reaction mixture was stirred overnight at RT. To complete the reaction another 1 mL (8.6 mmol) of 1-methyl-piperidin-4-one and 0.2 g (0.9 mmol) of NaBH(OAc)$_3$ were added and the mixture was stirred for a further 2 h at RT. The excess NaBH(OAc)$_3$ was destroyed by the addition of a little water, the mixture was saturated with K$_2$CO$_3$ and stirred. The K$_2$CO$_3$ was filtered, the organic phase was evaporated down and purified by chromatography (silica gel, EtOAc/MeOH/NH$_3$ 90:10:1).

Yield: 0.78 g (57% of theory) ESI-MS: (M+H)$^+$=356 R$_f$=0.46 (silica gel, EtOAc/MeOH/NH$_3$ 80:20:2)

A15b ethyl 1-(1-methyl-piperidin-4-yl)-piperazin-2-carboxylate 2.0 mL TFA were added to a solution of 0.78 g (2.20 mmol) 1-tert-butyl, 3-ethyl 4-(1-methyl-piperidin-4-yl)-piperazin-1,3-dicarboxylate in 30 mL DCM while cooling with ice and the reaction mixture was stirred for 3 h at RT. The mixture was evaporated down i. vac. and the product, which was obtained as the tris-trifluoroacetate salt, was further reacted without any purification.

Yield: quantitative EI: (M)$^+$=255 R$_f$=0.11 (silica gel, EtOAc/MeOH/NH$_3$ 70:30:3)

Example A16 ethyl 4-(1-methyl-piperidin-4-yl)-piperazin-2-carboxylate

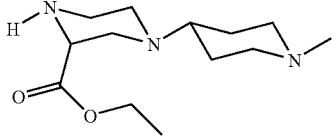

A16a 1-tert-butyl, 3-ethyl 4-benzyl-piperazin-1,3-dicarboxylate

A solution of 5.0 mL (42.10 mmol) benzylbromide in 50 mL THF was added dropwise to a solution of 10.69 g (41.39 mmol) 1-tert-butyl, 3-ethyl piperazine-1,3-dicarboxylate and 7.32 mL (42 mmol) of ethyl diisopropylamine in 150 mL of THF, the mixture was stirred for 2 h at RT and then refluxed for 3 h. To complete the reaction another 0.5 mL (4.21 mmol) of benzylbromide were added and the mixture was refluxed for a further 3 h. After cooling the reaction solution was filtered, the filtrate was evaporated down i.vac. and the residue was purified by chromatography (silica gel, cyc/EtOAc 8:2).

Yield: 13.04 g (90% of theory) ESI-MS: (M+H)$^+$=349 R$_f$=0.51 (silica gel, cyc/EtOAc 8:2)

A16b ethyl 1-benzyl-piperazin-2-carboxylate 35 mL TFA were added to a solution of 13.04 g (37.42 mmol) 1-tert-butyl, 3-ethyl 4-benzyl-piperazin-1,3-dicarboxylate in 200 mL DCM while cooling with ice and the reaction mixture was stirred for 5 h at RT. The mixture was evaporated down i. vac. and the product, which was obtained as the bis-trifluoroacetate salt, was further reacted without any purification.

Yield: quantitative ESI-MS: (M+H)$^+$=249

A16c ethyl 1-benzyl-4-(1-methyl-piperidin-4-yl)-piperazin-2-carboxylate 4.0 g (17.93 mmol) NaBH(OAc)$_3$ were added to a solution of 8.15 g (17.11 mmol) ethyl 1-benzyl-piperazin-2-carboxylate (used as the bis-trifluoroacetate salt) and 2.05 mL (17.22 mmol) of 1-methyl-piperidin-4-one in 200 mL of THF and the reaction mixture was stirred overnight at RT. The mixture was evaporated down i. vac. and the residue was purified by chromatography (silica gel, gradient: EtOAc to EtOAc/MeOH/NH$_3$ 50:50:2).

Yield: 5.91 g (100% of theory) ESI-MS: (M+H)$^+$=346 R$_f$=0.53 (silica gel, EtOAc/MeOH/NH$_3$ 80:20:2)

A16d ethyl 4-(1-methyl-piperidin-4-yl)-piperazin-2-carboxylate 0.5 g Pd(OH)$_2$ were added to a solution of 5.91 g (17.11 mmol) ethyl 1-benzyl-4-(1-methyl-piperidin-4-yl)-piperazin-2-carboxylate in 150 mL EtOH and the reaction mixture was hydrogenated for 3.5 h at RT and 3 bar H$_2$. After the catalyst had been removed by suction filtering and the solvent had been eliminated the desired product was obtained, which was further reacted without being purified.

Yield: 4.44 g (100% of theory) ESI-MS: (M+H)$^+$=256 R$_f$=0.24 (silica gel, EtOAc/MeOH/NH$_3$ 70:30:3)

Example A17 ethyl 1-methyl-4-piperidin-4-yl-piperazin-2-carboxylate

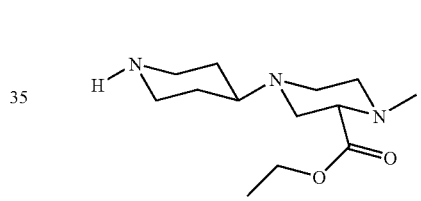

A17a 1-tert-butyl, 3-ethyl 4-methyl-piperazin-1,3-dicarboxylate

At RT a solution of 1.25 mL (19.90 mmol) of iodomethane in 20 mL of THF was slowly added dropwise to a solution of 5.04 g (19.51 mmol) of 1-tert-butyl, 3-ethyl piperazine-1,3-dicarboxylate and 3.4 mL (19.52 mmol) of ethyldiisopropylamine in 100 mL THF, the reaction mixture was stirred for 20 min and then heated to 60° C. for 3 h. To complete the reaction a further 0.2 mL (3.18 mmol) of iodomethane were added and the mixture was heated to 75° C. for a further 3 h. After cooling the mixture was filtered to remove insoluble constituents, the filtrate was evaporated down and the residue was purified by chromatography (silica gel, EtOAc).

Yield: 4.2 g (79% of theory) ESI-MS: (M+H)$^+$=273 R$_f$=0.58 (silica gel, EtOAc)

A17b ethyl 1-methyl-piperazin-2-carboxylate 20 mL TFA were added to a solution of 4.20 g (15.42 mmol) 1-tert-butyl, 3-ethyl 4-methyl-piperazin-1,3-dicarboxylate in 80 mL of DCM while cooling with ice and the reaction mixture was stirred for 1 h at RT. The mixture was evaporated down i. vac. and the product, which was obtained as the bis-trifluoroacetate salt, was further reacted without being purified.

Yield: quantitative ESI-MS: (M+H)$^+$=173 R$_f$=0.16 (silica gel, EtOAc/MeOH/NH$_3$ 70:30:3)

A17c ethyl 4-(1-benzyl-piperidin-4-yl)-1-methyl-piperazin-2-carboxylate 4.5 g (20.17 mmol) NaBH(OAc)₃ were added batchwise to a solution of 6.17 g (15.41 mmol) ethyl 1-methyl-piperazin-2-carboxylate (used as the bis-trifluoroacetate salt) and 3.77 mL (19.93 mmol) 1-benzyl-piperidin-4-one in 80 mL THF and the reaction mixture was stirred for 2 h at RT. Excess NaBH(OAc)₃ was destroyed by the addition of a little water, the reaction solution was evaporated down i.vac. and the residue was purified by chromatography (silica gel, gradient: EtOAc/MeOH/NH₃ 90:10:1 to EtOAc/MeOH/NH₃ 80:20:2).

Yield: quantitative ESI-MS: (M+H)⁺=345 $R_f$=0.41 (silica gel, EtOAc/MeOH/NH₃ 80:20:2)

A17d ethyl 1-methyl-4-piperidin-4-yl-piperazin-2-carboxylate 1 g 10% Pd/C was added to a solution of the crude product from A17c in 200 mL EtOH and the reaction mixture was hydrogenated for 17.5 h at RT and 3 bar H₂. After the catalyst had been removed by suction filtering and the solvent had been eliminated the desired product was obtained, which was further reacted without being purified.

Yield: 5.32 g (100% of theory, based on A17a) ESI-MS: (M+H)⁺=256 $R_f$=0.1 (silica gel, EtOAc/MeOH/NH₃ 50:50:5)

Example A18 ethyl 4-methyl-1-piperidin-4-yl-piperazin-2-carboxylate

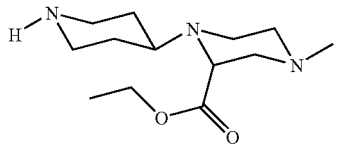

A18a ethyl 1-benzyl-4-methyl-piperazin-2-carboxylate

A solution of 1.4 mL (22.29 mmol) iodomethane in 50 mL of THF was slowly added dropwise to a solution of 10.3 g (21.64 mmol) of ethyl 1-benzyl-piperazin-2-carboxylate (see Example A16b, used as the bis-trifluoroacetate salt) and 12 mL (68.89 mmol) of ethyldiisopropylamine in 200 mL THF and the reaction mixture was stirred overnight at RT. To complete the reaction another 0.2 mL (3.18 mmol) of iodomethane were added and the mixture was stirred for another 2 h at RT. The precipitate formed was filtered, the filtrate was evaporated down i.vac. and the residue was purified by chromatography (silica gel, EtOAc/MeOH/NH₃ 90:10:1).

Yield: 4.1 g (72% of theory) ESI-MS: (M+Na)⁺=285 $R_f$=0.83 (silica gel, EtOAc/MeOH/NH₃ 90:10:1)

A18b ethyl 4-methyl-piperazin-2-carboxylate 450 mg 10% Pd/C were added to a solution of 4.1 g (15.63 mmol) ethyl 1-benzyl-4-methyl-piperazine-2-carboxylate in 100 mL EtOH and the reaction mixture was hydrogenated for 11 h at RT and 5 bar H₂. To complete the reaction 450 mg Pd(OH)₂ were added and the reaction mixture was hydrogenated for a further 2.5 h at 50° C. and 3 bar H₂. The catalyst was suction filtered, the filtrate was evaporated down and the residue was purified by chromatography (silica gel, EtOAc/MeOH/NH₃ 80:20:2).

Yield: 2.18 g (81% of theory) ESI-MS: (M+H)⁺=173 $R_f$=0.56 (silica gel, EtOAc/MeOH/NH₃ 80:20:2)

A18c ethyl 1-(1-benzyl-piperidin-4-yl)-4-methyl-piperazin-2-carboxylate

A solution of 1.58 g (9.17 mmol) ethyl 4-methyl-piperazin-2-carboxylate and 1.68 mL (9.2 mmol) 1-benzyl-piperidin-4-one in 30 mL THF was adjusted to a pH of 5 with glacial acetic acid and then 2.2 g (9.86 mmol) NaBH(OAc)₃ were added batchwise and the reaction mixture was stirred overnight at RT. Excess NaBH(OAc)₃ was destroyed by the addition of a little water and the reaction solution was dried over K₂CO₃. The supernatant solution was decanted off, evaporated down i.vac. and the residue was purified by chromatography (silica gel, gradient: EtOAc to EtOAc/MeOH/NH₃ 90:9:1).

Yield: 0.71 g (22% of theory) ESI-MS: (M+H)⁺=346 $R_f$=0.84 (silica gel, EtOAc/MeOH/NH₃ 70:30:3)

A18d ethyl 4-methyl-1-piperidin-4-yl-piperazin-2-carboxylate 200 mg Pd(OH)₂ were added to a solution of 2.28 g (6.6 mmol) ethyl 1-(1-benzyl-piperidin-4-yl)-4-methyl-piperazin-2-carboxylate in 100 mL of EtOH and the reaction mixture was hydrogenated for 9.5 h at RT and 3 bar H₂. To complete the reaction another 100 mg Pd(OH)₂ were added and the reaction mixture was hydrogenated for a further 6 h. The catalyst was suction filtered, the filtrate was evaporated down and the residue was further reacted without being purified.

Yield: 1.7 g (100% of theory) ESI-MS: (M+H)⁺=256 $R_f$=0.21 (silica gel, EtOAc/MeOH/NH₃ 60:40:4)

Example A19 tert-butyl(4-piperidin-4-yl-piperazin-1-yl)-acetate

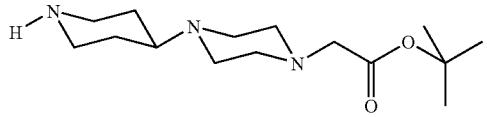

A19a tert. butyl[4-(1-benzyl-piperidin-4-yl)-piperazin-1-yl]-acetate 100 g (709 mmol) K₂CO₃ were added to a solution of 74 g (123 mmol) 1-(1-benzyl-piperidin-4-yl)-piperazine (used as the tris-trifluoroacetate salt) in 1 L acetonitrile and the suspension was stirred for 10 min at RT. Then 20 mL (133 mmol) of tert. butyl bromoacetate were added. The reaction mixture was stirred for 3 h at RT and combined with MgSO₄ to dry it. The insoluble constituents were filtered off, the solvent was evaporated down i.vac., the residue was combined with water, the precipitate formed was suction filtered and dried at 50° C. in a circulating air dryer.

Yield: 30 g (65% of theory) ESI-MS: (M+H)⁺=374 $R_f$=0.51 (silica gel, DCM/MeOH/cyc/NH₃ 70:15:15:2)

A19b tert. butyl(4-piperidin-4-yl-piperazin-1-yl)-acetate 6 g 10% Pd/C were added to a solution of 30 g (80.3 mmol) tert. butyl[4-(1-benzyl-piperidin-4-yl)-piperazin-1-yl]-acetate in 300 mL THF and the reaction mixture was hydrogenated at 50° C. and 3 bar H₂ until the theoretical uptake of H₂ had been achieved. After the catalyst had been removed by suction filtering and the solvent had been eliminated the desired product was obtained, which was further reacted without being purified.

Example A20 ethyl(4-piperidin-4-yl-piperazin-1-yl)-acetate

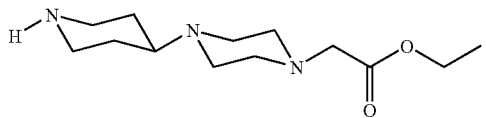

A20a tert. butyl 4-(4-ethoxycarbonylmethyl-piperazin-1-yl)-piperidine-1-carboxylate A solution of 1.42 mL (13.3 mmol) ethyl chloroacetate in 10 mL acetonitrile was added to a solution of 4.0 g (13.08 mmol) tert. butyl 4-piperazin-1-yl-piperidine-1-carboxylate (used as the hydrochloride) and 6.54 mL (39.23 mmol) ethyldiisopropylamine in 50 mL acetonitrile, cooled to 0° C. After the cooling bath had been removed a spatula tip of NaI was added and the reaction mixture was stirred overnight at RT. The mixture was combined with saturated NaHCO$_3$ solution, extracted exhaustively with DCM and the organic phase was dried over Na$_2$SO$_4$. After the desiccant and solvent had been eliminated the residue was further reacted without being purified.

Yield: 4.25 g (91% of theory) ESI-MS: (M+H)$^+$=356 R$_f$=0.67 (silica gel, DCM/MeOH 9:1)

A20b ethyl(4-piperidin-4-yl-piperazin-1-yl)-acetate 6 mL TFA were added to a solution of 4.25 g (11.96 mmol) tert. butyl 4-(4-ethoxycarbonylmethyl-piperazin-1-yl)-piperidine-1-carboxylate in 80 mL DCM, cooled to 0° C., and the reaction mixture was stirred overnight at RT. The mixture was evaporated down i. vac., the residue was stirred with tert-butylmethylether, the precipitate was suction filtered and the product, which was obtained as the tris-trifluoroacetate salt, was dried.

Yield: 6.7 g (94% of theory) ESI-MS: (M+H)$^+$=256 R$_f$=0.38 (silica gel, DCM/MeOH/NH$_3$ 75:25:5)

Example A21 ethyl[4,4']bipiperidinyl-1-yl-acetate

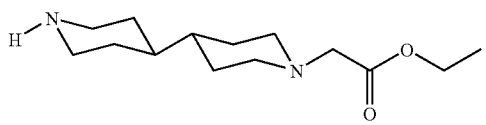

A21a tert. butyl 1'-ethoxycarbonylmethyl-[4,4']bipiperidinyl-1-carboxylate

The product was obtained analogously to Example A19a from 8.40 g (31.1 mmol) of tert. butyl[4,4']bipiperidinyl-1-carboxylate and 3.53 mL (31.1 mmol) of ethyl bromoacetate.

Yield: 9.4 g (85% of theory) EI-MS: (M)$^+$=355 R$_f$=0.64 (silica gel, EtOAc/MeOH 9:1)

A21b ethyl[4,4']bipiperidinyl-1-yl-acetate

The product was obtained as the bis-trifluoroacetate salt analogously to Example 20b from 7.50 g (21.2 mmol) tert. butyl 1'-ethoxycarbonylmethyl-[4,4']bipiperidinyl-1carboxylate.

Yield: 10.1 g (99% of theory) ESI-MS: (M+H)$^+$=255 R$_f$=0.15 (silica gel, DCM)

Example A22 ethyl(4-piperazin-1-yl-piperidin-1-yl)-acetate

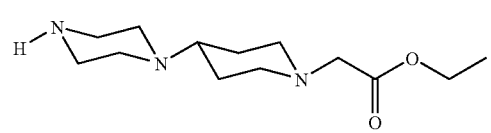

A22a tert. butyl 4-(4-benzyl-piperazin-1-yl)-piperidine-1-carboxylate

A solution of 66.7 mL (381 mmol) of 1-benzylpiperazine and 75.6 g (380 mmol) tert. butyl 4-oxo-piperidine-1-carboxylate was adjusted to pH 5 with glacial acetic acid. 100 g (380 mmol) of NaBH(OAc)$_3$ were added over 2 h while cooling with ice and the mixture was stirred overnight at RT. The reaction mixture was made alkaline with K$_2$CO$_3$ solution (300 g/L), stirred for one hour at RT and extracted three times with EtOAc. The organic phase was dried over MgSO$_4$ and the solvent was eliminated i.vac.

Yield: 114 g (83% of theory) ESI-MS: (M+H)$^+$=369 R$_f$=0.74 (silica gel, DCM/cyc/MeOH/NH$_3$ 70:15:15:2)

A22b 1-benzyl-4-piperidin-4-yl-piperazine

The product was obtained as the tris-trifluoroacetate salt analogously to Example 20b from 40.0 g (111 mmol) tert. butyl 4-(4-benzyl-piperazin-1-yl)-piperidine-1-carboxylate.

Yield: 54.8 g (82% of theory)
ESI-MS: (M+H)$^+$=260
R$_f$=0.18 (silica gel, DCM/cyc/MeOH/NH$_3$ 70:15:15:2)

A22c ethyl[4-(4-benzyl-piperazin-1-yl)-piperidin-1-yl]-acetate

The product was obtained analogously to Example A19a from 51.8 g (86 mmol) of 1-benzyl-4-piperidin-4-yl-piperazine (used as the tris-trifluoroacetate) and 10.3 mL (91 mmol) of ethyl bromoacetate.

Yield: 25.3 g (85% of theory) EI-MS: (M)$^+$=346 R$_f$=0.58 (silica gel, DCM/cyc/MeOH/NH$_3$ 70:15:15:2)

A22d ethyl(4-piperazin-1-yl-piperidin-1-yl)-acetate

The product was obtained analogously to Example A19b from 25.3 g (73.3 mmol) ethyl [4-(4-benzyl-piperazin-1-yl)-piperidin-1-yl]-acetate. The product contains 59% methyl (4-piperazin-1-yl-piperidin-1-yl)-acetate.

Yield: 17.4 g (93% of theory) ESI-MS: (M+H)$^+$=256 and for the methyl ester: (M+H)$^+$=242 R$_f$=0.15 (silica gel, DCM/cyc/MeOH/NH$_3$ 70:15:15:2)

Example A23

1-(2,2,2-trifluoro-ethyl)-[4,4']bipiperidinyl

A23a tert. butyl 1'-(2,2,2-trifluoro-acetyl)-[4,4']bipiperidinyl-1-carboxylate

The product was prepared analogously to Example A7a from 15.0 g (55.9 mmol) of tert. butyl[4,4']bipiperidinyl-1-carboxylate.

Yield: 19.0 g (93% of theory) ESI-MS: $(M+Na)^+=387$

A23b tert. butyl 1'-(2,2,2-trifluoro-ethyl)-[4,4']bipiperidinyl-carboxylate

The product was prepared analogously to Example A7b from 20.7 g (56.7 mmol) tert. butyl 1'-(2,2,2-trifluoro-acetyl)-[4,4']bipiperidinyl-1-carboxylate.

Yield: 19.9 g (100% of theory) ESI-MS: $(M+H)^+=351$ $R_f=0.78$ (silica gel, PE/EtOAc 1:1)

A23c 1-(2,2,2-trifluoro-ethyl)-[4,4']bipiperidinyl

The product was obtained in the form of the bis-trifluoroacetate analogously to Example A20b from 21.4 g (61.1 mmol) tert. butyl 1'-(2,2,2-trifluoro-ethyl)-[4,4']bipiperidinyl-1-carboxylate.

Yield: 26.8 g (92% of theory) ESI-MS: $(M+H)^+=251$ $R_f=0.17$ (silica gel, DCM/MeOH/NH$_3$ 9:1:0.1)

Example A24 dimethyl-[3-(4-piperazin-1-yl-phenyl)-propyl]-amine

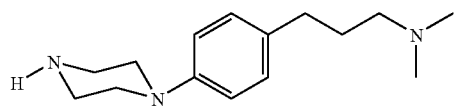

A24a 1-[4-(4-benzyl-piperazin-1-yl)-phenyl]-ethanone

A solution of 35.3 g (200 mmol) benzylpiperazine and 13.8 g (100 mmol) of 4-fluoroacetophenone in 34 mL (200 mmol) ethyldiisopropylamine was refluxed for 2 days. After cooling the residue was stirred with tert-butylmethylether, suction filtered and dried in the air. The product was further reacted without being purified.

Yield: 12.2 g (42% of theory) EI-MS: $(M)^+=294$ $R_f=0.53$ (silica gel, PE/EtOAc 3:2)

A24b 1-[4-(4-benzyl-piperazin-1-yl)-phenyl]-3-dimethylamino-propan-1-one 1.40 g paraformaldehyde were added to a solution of 6.9 g (23.4 mmol) of 1-[4-(4benzyl-piperazin-1-yl)-phenyl]-etha-none and 2.90 g (35.1 mmol) dimethylamine hydrochloride in 100 mL EtOH and 10 mL conc. HCl. The reaction mixture was refluxed for 20 h. The solvent was eliminated i.vac. and the residue combined with acetonitrile. The precipitate was suction filtered and dried at 30° C. in the circulating air dryer.

Yield: 4.4 g (48% of theory as the hydrochloride) EI-MS: $(M)^+=351$ $R_f=0.35$ (silica gel, DCM/EtOAc/cyc/MeOH/NH$_3$ 60:16:5:5:0.6)

A24c dimethyl-[3-(4-piperazin-1-yl-phenyl)-propyl]-amine 2 g 10% Pd/C were added to a solution of 8.00 g (20.6 mmol) 1-[4-(4-benzyl-piperazin-1-yl)-phenyl]-3-dimethy-lamino-propan-1-one in 6.7 mL of conc. HCl and 300 mL of MeOH. The reaction mixture was stirred at 3 bar H$_2$ and 50° C. for 3 h. After filtration the filtrate was evaporated to dryness. The residue was combined with EtOH and EtOAc and stirred overnight. The precipitate was suction filtered under nitrogen and dried at 20° C. in the circulating air dryer.

Yield: 5.7 g (86% of theory as the bis-hydrochloride) EI-MS: $(M)^+=247$ $R_f=0.35$ (DCM/cyc/MeOH/NH$_3$ 70:15:15:2)

The other amines used in the preparation of the final compounds are either commercially obtainable or were prepared by methods known from the literature.

Preparation of the Final Compounds

Example 1

(S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione

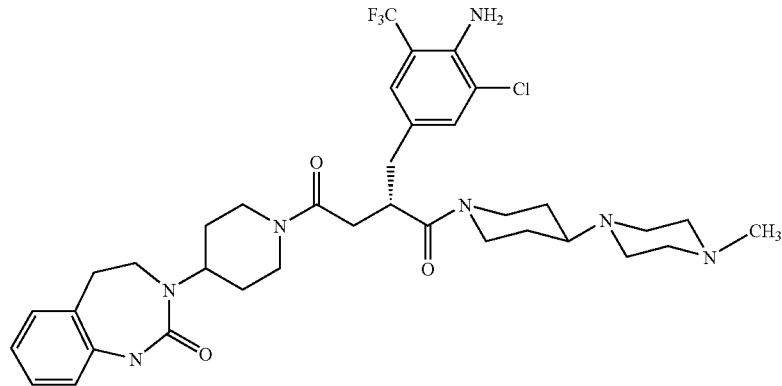

1a (4-amino-3-chloro-5-trifluoromethyl-phenyl)-methanol 69.56 g (0.43 mol) CDI were added to a solution of 93.4 g (0.39 mol) 4-amino-3-chloro-5-trifluoromethyl-benzoic acid (described in Arzneim.-Forsch. 1984, 34(11A), 1612-1624) in 1 L THF and the mixture was stirred for 1 h at 40° C. The reaction mixture was then carefully added to a solution of 51.4 g (1.36 mol) NaBH$_4$ in 450 mL of water at RT under a nitrogen atmosphere and with cooling. The mixture was stirred for 2 h at RT, combined with 500 mL water and 300 mL semiconc. HCl, stirred for another hour and then exhaustively extracted with EtOAc. The combined org. phases were dried over Na$_2$SO$_4$ and evaporated down i. vac. The oil remaining was combined with 500 mL PE and stirred while cooling with ice. The precipitate was suction filtered, washed with PE and dried. 29.7 g of the desired product were obtained.

The mother liquor was evaporated down again, combined with PE and cooled. The precipitate obtained was again washed with PE and dried. A further 21.8 g of the desired product were obtained.

Yield: 51.5 g (59% of theory) of a white solid $R_f$=0.73 (silica gel: PE/EtOAc=1:1)

1b 4-amino-3-chloro-5-trifluoromethyl-benzaldehyde

A mixture of 17.0 g (75.4 mmol) of (4-amino-3-chloro-5-trifluoromethyl-phenyl)-methanol, 100 g (1.15 mol) of manganese dioxide and 300 mL of DCM was stirred overnight at RT. The precipitate was suction filtered and the solution evaporated down i. vac. The desired product was obtained as a white solid.

Yield: 16.0 g (95% of theory) ESI-MS: (M+H)$^+$=224/226 (Cl)

1c diethyl[2-((R)-4-benzyl-2-oxo-oxazolidin-3-yl)-2-oxo-ethyl]-phosphonate

A solution of 168.0 g (0.56 mol) (R)-4-benzyl-3-(2-bromo-acetyl)-oxazolidin-2-one and 188.6 mL (1.1 mol) of triethylphosphite was stirred for 1.5 h at 60° C., while the ethylbromide formed was distilled off. The reaction mixture was concentrated by evaporation i. vac. and the residue remaining was purified by chromatography on silica gel. The desired product was obtained in the form of a yellowish-brown oil.

Yield: 130 g (65% of theory) ESI-MS: (M+H)$^+$=356

1d (R)-3-[(E)-3-(4-amino-3-chloro-5-trifluoromethyl-phenyl)-acryloyl]-4-benzyl-oxazolidin-2-one Under a nitrogen atmosphere 3.93 g (90.0 mmol) of NaH (55% in mineral oil) were added batchwise to a solution of 31.98 g (90.0 mmol) of diethyl[2-((R)-4-benzyl-2-oxo-oxazolidin-3-yl)-2-oxo-ethyl]-phosphonate in 400 mL of THF. The reaction mixture was stirred for 30 min at RT and for a further 35 min at 35° C. After the development of gas had ended, 16.0 g (71.5 mmol) of 4-amino-3-chloro-5-trifluoromethyl-benzaldehyde, dissolved in 50 mL THF, were added dropwise and stirred for a further 12 h at RT. The reaction solution was combined with saturated NH$_4$Cl solution, the mixture was extracted exhaustively with EtOAc and the combined extracts were dried and evaporated down i. vac. The residue remaining was purified by chromatography on silica gel. The desired product was obtained in the form of a yellow oil.

Yield: 38.2 g (62% of theory) ESI-MS: (M+H)$^+$=425/427 (Cl) $R_f$=0.55 (silica gel: PE/EtOAc=2:1)

1 e (R)-3-[3-(4-amino-3-chloro-5-trifluoromethyl-phenyl)-propionyl]-4-benzyl-oxazolidin-2-one A mixture of 23.7 g (55.8 mmol) of (R)-3-[(E)-3-(4-amino-3-chloro-5-trifluoromethyl-phenyl)-acryloyl]-4-benzyl-oxazolidin-2-one, 400 mL of MeOH and 5.0 g of Raney nickel was shaken for 2 h at RT and 3 bar of H$_2$ in a Parr autoclave. The catalyst was suction filtered and the solvent removed i. vac. The desired product was obtained in the form of a yellow oil.

Yield: 22.5 g (95% of theory) ESI-MS: (M+H)$^+$=427/429 (Cl)

1f tert.-butyl (S)-3-(4-amino-3-chloro-5-trifluoromethyl-benzyl)-4-((R)-4-benzyl-2-oxo-oxazolidin-3-yl)-4-oxo-butanoate Under an argon atmosphere 63.24 mL (63.24 mmol) of a sodium-bis(trimethylsilyl)-amide solution (1 M in THF) was added dropwise to a solution of 22.5 g (52.71 mmol) of (R)-3-[3-(4-amino-3-chloro-5-trifluoromethyl-phenyl)-propionyl]-4-benzyl-oxazolidin-2-one in 105 mL THF which had been cooled to −78° C. and the mixture was stirred for 2 h at −78° C. 38.9 mL (263.5 mmol) of tert.butyl bromoacetate were added dropwise to the reaction mixture at −78° C., this was stirred for a further 24 h at −78° C. and then heated to RT. After the addition of 200 mL of a saturated NH$_4$Cl solution the mixture was extracted twice with 300 mL of EtOAc, the combined org. phases were dried over Na$_2$SO$_4$ and evaporated down i. vac. The residue remaining was purified by chromatography on silica gel. The desired product was obtained in the form of a yellow oil.

Yield: 15.6 g (55% of theory) ESI-MS: (M+H)$^+$=541/543 (Cl) $R_f$=0.35 (silica gel, PE/EtOAc=8:2)

1g 4-tert.-butyl (S)-2-(4-amino-3-chloro-5-trifluoromethyl-benzyl)-succinate 11.75 ml (115.1 mmol) H$_2$O$_2$ (35% in water) were added to a solution of 2.51 g (57.6 mmol) lithium hydroxide hydrate in 150 mL of water. This mixture was then added dropwise to an ice-cooled solution of 15.6 g (28.8 mmol) of tert.-butyl (S)-3-(4-amino-3-chloro-5-trifluoromethyl-benzyl)-4-((R)-4-benzyl-2-oxo-oxazolidin-3-yl)-4-oxo-butanoate in 600 mL of THF and the reaction mixture was stirred for a further 2 h while cooling with ice. Then 150 mL of saturated sodium sulphite solution were added to the reaction mixture and acidified with citric acid solution. The org. phase was separated off, dried and evaporated down i. vac. 15.6 g of a viscous yellow oil were obtained.

The aqueous phase was exhaustively extracted with EtOAc, the combined org. phases were washed with water, dried and evaporated down i. vac. A further 5.5 g of a yellow oil were obtained.

The crude product, which still contained (R)-4-benzyl-oxazolidin-2-one, was further reacted without purification.

Yield: 21.1 g crude product ESI-MS: (M+H)$^+$=380/382 (Cl)

1g tert. butyl (S)-3-(4-amino-3-chloro-5-trifluoromethyl-benzyl)-4-[4-(4-methyl-piperazin-1-yl)-piperidin-1-yl]-4-oxo-butanoate A mixture of 15.4 g (40.3 mmol) of 4-tert. butyl (S)-2-(4-amino-3-chloro-5-trifluoromethyl-benzyl)-succinate, 7.4 g (40.3 mmol) of (1-methyl-4-piperidin-4-yl)-piperazine, 5.45 g (40.3 mmol) of HOBt, 12.94 g (40.3 mmol) of TBTU, 11.77 mL (85.0 mmol) of triethylamine and 400 mL of THF was stirred for 12 h at RT. Then the mixture was evaporated down i. vac. and the residue remaining was distributed between EtOAc and NaHCO$_3$ solution. The org. phase was separated off, dried and evaporated down i. vac. The residue obtained was purified by chromatography on aluminium oxide. The desired product was obtained in the form of a yellow oil.

Yield: 11.0 g (50% of theory) ESI-MS: (M+H)$^+$=547/549 (Cl) $R_f$=0.35 (Alox; EtOAc/CH$_2$Cl$_2$=6:4)

1 h (S)-3-(4-amino-3-chloro-5-trifluoromethyl-benzyl)-4-[4-(4-methyl-piperazin-1-yl)-piperidin-1-yl]-4-oxo-butanoic acid 5.75 g (38.4 mmol) of NaI, 3 mL of anisol and 4.92 mL (38.4 mmol) of trimethylsilylchloride were added to the solution of 7.0 g (12.8 mmol) of tert. butyl (S)-3-(4-amino-3-chloro-5-trifluoromethyl-benzyl)-4-[4-(4-methyl-piperazin-1-yl)-piperidin-1-yl]-4-oxo-butanoate in 375 mL acetonitrile. The reaction mixture was stirred for 90 min at 40° C., combined with another 5.75 g (38.4 mmol) of NaI and 4.92 mL (38.4 mmol) of trimethylsilylchloride and stirred for a further 2 h at 40° C. The mixture was evaporated down i. vac. and further reacted as the crude product.

1i (S)-2-(4-amino-3-chloro-5-trifluoromethyl-benzyl) 1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione A mixture of 6.3 g (12.8 mmol) of (S)-3-(4-amino-3-chloro-5-trifluoromethyl-benzyl)-4-[4-(4-methyl-piperazin-1-yl)-piperidin-1-yl]-4-oxo-butanoic acid, 3.16 g (12.9 mmol) of 3-piperidin-4-yl-1,3,4,5-tetrahydro-1,3-benzodiazepin-2-one, 4.66 g (14.5 mmol) of TBTU, 1.96 g (14.5 mmol) of HOBt, 9.45 mL (68 mmol) of triethylamine and 300 mL DMF was stirred for 12 h at RT. The reaction mixture was evaporated down i. vac., the residue was distributed between EtOAc and saturated NaHCO₃ solution. The org. phase was separated off, dried and evaporated down i. vac. The residue was purified by chromatography on silica gel. The yellow oil obtained was triturated with ether and suction filtered. The desired product was obtained in the form of a white solid.

Yield: 3.8 g (39% of theory) ESI-MS: (M+H)⁺=718/20 (Cl) $R_f$=0.22 (silica gel, EtOAc/MeOH/conc. aqueous NH₃=70:30:3)

Example 2

2-(4-amino-3-chloro-5-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione CF₃ ice-cold NaHCO₃ solution, dried over Na₂SO₄, filtered through activated charcoal and evaporated down i. vac. The crude product was used in the following reaction step without any further purification.

Yield: 1.08 g (quantitative yield) EI-MS: M⁺=243/245/247 (Cl₂) $R_f$=0.81 (silica gel, PE/EtOAc=2:1)

2b tert.butyl 4-(4-amino-3-chloro-5-trifluoromethyl-phenyl)-3,3-bis-ethoxycarbonyl-butyrate 193 mg (4.43 mmol) of NaH (55% in mineral oil) were added batchwise to a solution of 1.20 g (4.43 mmol) of 1-tert.-butyl-4-ethyl 3-ethoxycarbonyl-succinate in 50 mL of abs. THF under a nitrogen atmosphere and while cooling with ice and the mixture was stirred for 1 h at RT. 1.1 g (4.43 mmol) of 2-chloro-4-chloromethyl-6-trifluoromethyl-phenylamine, dissolved in 10 mL abs. THF, was added dropwise and the mixture was stirred for 16 h at RT. The reaction mixture was diluted with water and the aqueous phase extracted with EtOAc. The org. phase was dried over MgSO₄ and evaporated down i. vac. The crude product was used in the next reaction step without any further purification.

Yield: 2.1 g (98% of theory) ESI-MS: (M+H)⁺=482/484 (Cl) $R_f$=0.48 (silica gel, PE/EtOAc=4:1)

2c 4-(4-amino-3-chloro-5-trifluoromethyl-phenyl)-3,3-bis-ethoxycarbonyl-butanioc acid 20 mL of TFA was added to a solution of 30.0 g (62.25 mmol) of tert.butyl 4-(4-amino-3-chloro-5-trifluoromethyl-phenyl)-3,3-bis-ethoxycarbonyl-butanoate in 200 mL DCM while cooling with ice and the mixture was stirred for 16 h at RT. The reaction mixture was evaporated down i. vac. and the residue recrystallised from PE. The precipitate was filtered off, washed with PE and dried.

Yield: 23.6 g (89% of the yield) ESI-MS: (M−H)⁻=424/426 (Cl)

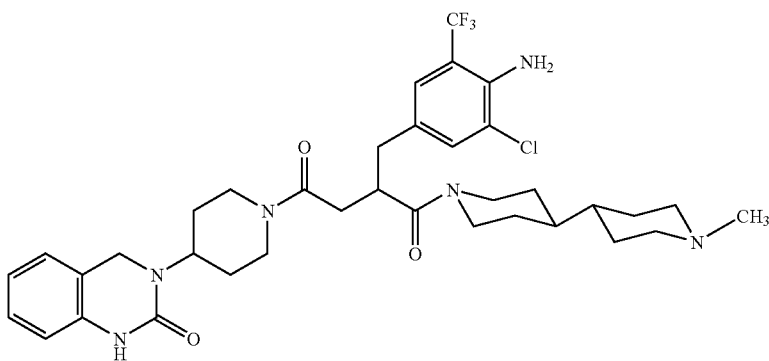

2a 2-chloro-4-chloromethyl-6-trifluoromethyl-phenylamine 0.94 mL (13.00 mmol) of SOCl₂ was added at RT to a solution of 1.00 g (4.43 mmol) of (4-amino-3-chloro-5-trifluoromethyl-phenyl)-methanol in 50 mL DCM and the mixture was stirred for 3 h at RT. The reaction mixture was poured onto ice and the aqueous phase was exhaustively extracted with DCM. The combined org. phases were washed with 2d diethyl 2-(4-amino-3-chloro-5-trifluoromethyl-benzyl)-2-{2-oxo-2-[4-(2-oxo-1,4-dihydro-2H-quinazolin-3-yl)-piperidin-1-yl]-ethyl}-malonate 3.2 mL (23.0 mmol) of triethylamine were added dropwise to a solution of 8.00 g (19.0 mmol) of 4-(4-amino-3-chloro-5-trifluoromethyl-phenyl)-3,3-bis-ethoxycarbonyl-butanoic acid, 4.39 g (19.0 mmol) of 3-piperidin-4-yl-3,4-dihydro-1H- quinazolin-2-one, 6.00 g (18.0 mmol) of TBTU and 2.75 g (18.0 mmol) of HOBT in 100 mL of THF and the mixture was stirred for 16 h at RT. The solid formed was filtered off, washed with diethyl ether and dried i. vac.

Yield: 10.45 g (87% of theory)

2e 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid 3.13 g (78.25 mmol) of NaOH, dissolved in 300 mL water, were added to a solution of 10.00 g (15.65 mmol) of diethyl 2-(4-amino-3-chloro-5-trifluoromethyl-benzyl)-2-{2-oxo-2-[4-(2-oxo-1,4-dihydro-2H-quinazolin-3-yl)-piperidin-1-yl]-ethyl}-malonate in 600 mL EtOH and the mixture was refluxed for 4 h. EtOH was evaporated off i. vac., the reaction mixture was acidified to pH 1 with conc. HCl and 1 hour at RT. The precipitate formed was filtered off, washed with water and dried i. vac.

Yield: 8.01 g (95% of theory)

2f 2-(4-amino-3-chloro-5-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione 2.0 mL triethylamine were added to a solution of 0.80 g (1.48 mmol) of 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid, 0.28 g (1.50 mmol) of 1-methyl-[4,4']bipiperidinyl, 0.49 g (1.50 mmol) of TBTU and 0.23 g (1.50 mmol) of HOBT in 100 mL of THF and the mixture was stirred for 16 h at RT. The reaction mixture was evaporated down i. vac., the residue was combined with saturated NaHCO$_3$ solution and the mixture was exhaustively extracted with EtOAc. The combined org. extracts were dried over MgSO$_4$ and evaporated down i. vac. The residue was purified by column chromatography (silica gel, gradient: EtOAc/MeOH/NH$_3$ 94/5/1 to 70/25/5).

Yield: 253 mg (24% of theory) ESI-MS: (M+H)$^+$=703/705 (Cl) R$_f$=0.66 (silica gel, DCM/cyc/MeOH/NH$_3$ 70/15/15/2)

Example 3

2-(4-amino-3-chloro-5-trifluoromethyl-benzyl)-1-[4-(4-methyl-piperazin-1-yl)-piperidin--yl]-4-[4-(2-oxo-1,4-dihydro-2H-quinazolin-3-yl)-piperidin-1-yl]-butan-1,4-dione The product was obtained analogously to Example 2f starting from 0.80 g (1.48 mmol) of 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 0.30 g (1.50 mmol) of 1-methyl-4-piperidin-4-yl-piperazine.

Yield: 600 mg (57% of theory) EI-MS: M$^+$=703/705 (Cl) R$_f$=0.56 (silica gel, DCM/cyc/MeOH/NH$_3$ 70:15:15:2)

Example 4

2-(4-amino-3-chloro-5-trifluoromethyl-benzyl)-1-[1,4']bipiperidinyl-1'-yl-4-[4-(2-oxo-1,4-dihydro-2H-quinazolin-3-yl)-piperidin-1-yl]-butan-1,4-dione

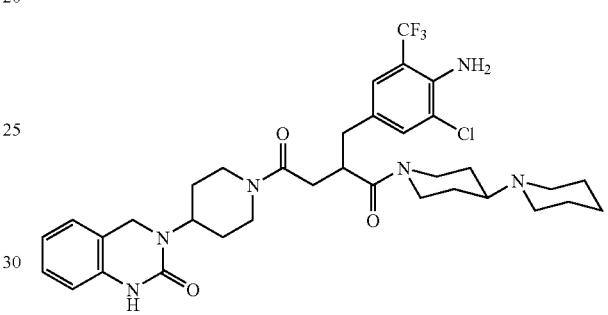

The product was obtained analogously to Example 2f starting from 0.80 g (1.48 mmol) of 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 0.27 g (1.50 mmol) of [1,4']bipiperidinyl.

Yield: 240 mg (24% of theory) ESI-MS: (M+H)$^+$=689/691 (Cl) R$_f$=0.59 (silica gel, DCM/cyc/MeOH/NH$_3$ 70:15:15:2)

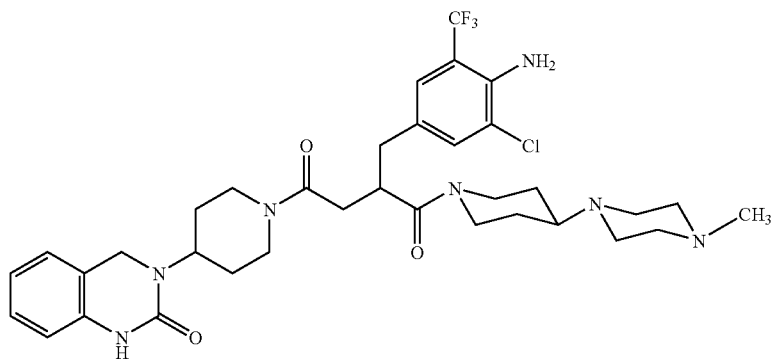

Example 5

2-(4-amino-3-chloro-5-trifluoromethyl-benzyl)-4-[4-(2-oxo-1,4-dihydro-2H-quinazolin-3-yl)-piperidin-1-yl]-1-(4-pyridin-4-yl-piperazin-1-yl)-butan-1,4-dione

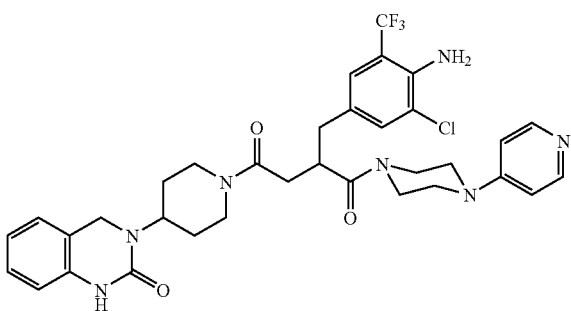

The product was obtained analogously to Example 2f starting from 0.80 g (1.48 mmol) of 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 0.24 g (1.48 mmol) of 1-pyridin-4-yl-piperazine.

Yield: 500 mg (50% of theory) EI-MS: M$^+$=683/685 (Cl) R$_f$=0.35 (silica gel, MeOH)

Example 6

2-(4-amino-3-chloro-5-trifluoromethyl-benzyl)-1-[4-(1-methyl-piperidin-4-ylamino)-piperidin-1-yl]-4-[4-(2-oxo-1,4-dihydro-2H-quinazolin-3-yl)-piperidin-1-yl]-butan-1,4-dione 6a (1-benzyl-piperidin-4-yl)-(1-methyl-piperidin-4-yl)-amine A solution of 15.0 g (78.8 mmol) of 1-benzyl-piperidin-4-ylamine and 10 mL (78.8 mmol) of 1-methyl-piperidin-4-one in 300 mL of THF was acidified with HOAc to pH 5 and stirred for 1 h at RT. 19.0 g (90.0 mmol) of NaBH(OAc)$_3$ was added and the mixture was stirred for 16 h. The mixture was evaporated down i. vac., the residue was dissolved in MeOH and precipitated by the addition of HCl in MeOH. The precipitate formed was filtered off, washed with MeOH and dried i. vac.

Yield: 21.8 g (70% of theory) R$_f$=0.30 (silica gel, DCM/cyc/MeOH/NH$_3$ 70:15:15:2)

6b (1-methyl-piperidin-4-yl)-piperidin-4-yl-amine-trihydrochloride

A solution of 10.0 g (25.3 mmol) of (1-benzyl-piperidin-4-yl)-(1-methyl-piperidin-4-yl)-amine in 120 mL MeOH was added to a suspension of 5 g of 10% Pd/C in 80 mL water and the mixture was hydrogenated for 2 h at 50° C. under 3 bar H$_2$. The reaction mixture was filtered and the filtrate was evaporated down i. vac. The residue was combined with EtOH, the precipitate formed was filtered off, washed with EtOH and ether and dried i. vac.

Yield: 7.75 g (quantitative yield)

6c 2-(4-amino-3-chloro-5-trifluoromethyl-benzyl)-1-[4-(1-methyl-piperidin-4-ylamino)-piperidin-1-yl]-4-[4-(2-oxo-1,4-dihydro-2H-quinazolin-3-yl)-piperidin-1-yl]-butan-1,4-dione The product was obtained analogously to Example 2f starting from 0.80 g (1.48 mmol) of 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 0.24 g (1.48 mmol) of (1-methyl-piperidin-4-yl)-piperidin-4-yl-amine-trihydrochloride.

Yield: 300 mg (25% of theory) EI-MS: M$^+$=717/719 (Cl) R$_f$=0.20 (silica gel, MeOH)

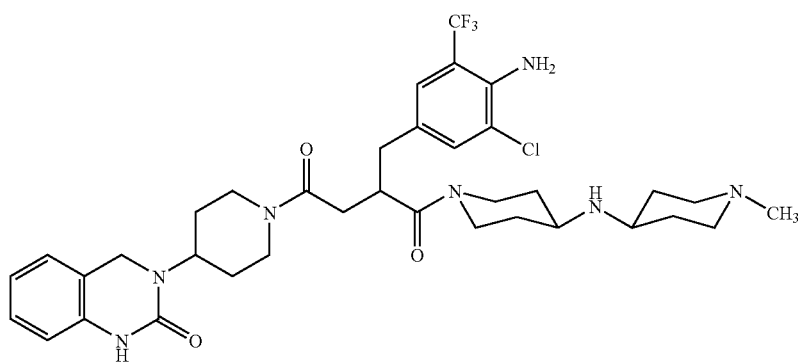

Example 6.1

[4-(1-{2-(4-amino-3-chloro-5-trifluoromethyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid

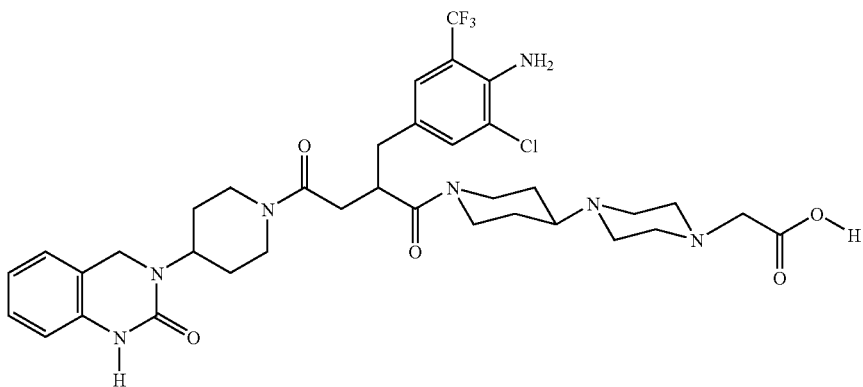

Prepared analogously to Example 16.4 from 108 mg (0.20 mmol) 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 51 mg (0.20 mmol) ethyl(4-piperidin-4-yl-piperazin-1-yl)-acetate.

Yield: 16 mg (10% of theory) ESI-MS: $(M+H)^+=748/750$ (Cl)

Example 6.2

Methyl(1'-{2-(4-amino-3-chloro-5-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate

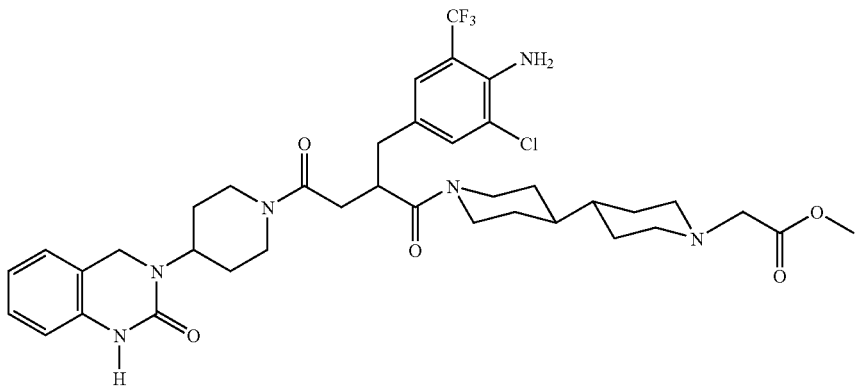

Prepared analogously to Example 16.5 from 216 mg (0.4 mmol) 2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 102 mg (0.2 mmol) ethyl[4,4']bipiperidinyl-1-yl-acetate.

Yield: 22 mg (22% of theory) ESI-MS: $(M+H)^+=761/763$ (Cl) $R_f=0.33$ (silica gel, DCM/MeOH 9:1)

Example 6.3

(1'-{2-(4-amino-3-chloro-5-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid

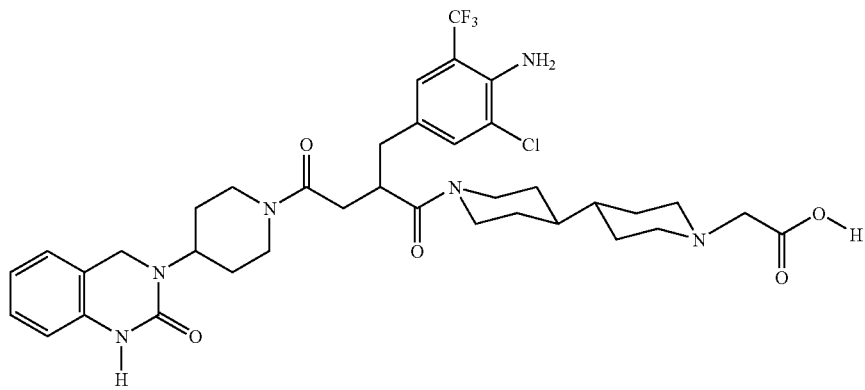

Prepared analogously to Example 16.6 from 201 mg (0.26 mmol) methyl(1'-{2-(4-amino-3-chloro-5-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate.

Yield: 22 mg (22% of theory) ESI-MS: (M+H)$^+$=761/763 (Cl) R$_f$=0.21 (silica gel, DCM/MeOH 9:1)

Example 7

4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-1,4'-bipiperidinyl-1'-yl-2-oxo-ethyl]-amide

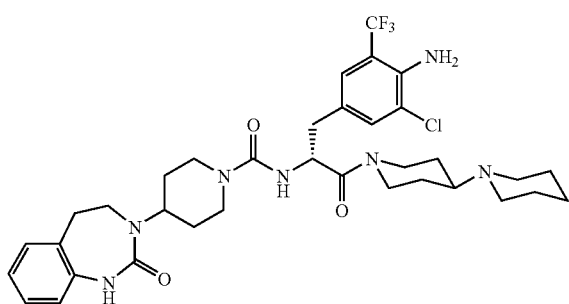

7a (R)-2-amino-3-(4-amino-3-chloro-5-trifluoromethyl-phenyl)-N-((1S,2S)-2-hydroxy-1-methyl-2-phenyl-ethyl)-N-methyl-propionamide The alkylation was carried out in accordance with the general procedure described by A. G. Myers et al. (J. Org. Chem. 1999, 64, 3322-3327.) starting from 31.72 g (132 mmol) of 2-amino-N-((1S,2S)-2-hydroxy-1-methyl-2-phenyl-ethyl)-N-methyl-acetamide-monohydrate and 33.8 g (138 mmol) of 2-chloro-4-chloromethyl-6-trifluoromethyl-phenylamine. The crude product was purified by column chromatography (silica gel, DCM/cyc/MeOH/NH$_3$ 70:15:15:2) purified.

Yield: 10.0 g (18% of theory) ESI-MS: (M+H)$^+$=430/432 (Cl) R$_f$=0.48 (silica gel, DCM/cyc/MeOH/NH$_3$ 70:15:15:2)

7b (R)-2-amino-3-(4-amino-3-chloro-5-trifluoromethyl-phenyl)-propionic acid

The hydrolysis was carried out in accordance with the general procedure described by A.

G. Myers et al. (J. Org. Chem. 1999, 64, 3322-3327.) starting from 10.0 g (23.0 mmol) of (R)-2-amino-3-(4-amino-3-chloro-5-trifluoromethyl-phenyl)-N-((1S,2S)-2-hydroxy-1-methyl-2-phenyl-ethyl)-N-methyl-propionamide. The crude product was used in the next synthesis step without any further purification.

7c (R)-3-(4-amino-3-chloro-5-trifluoromethyl-phenyl)-2-tert.-butoxycarbonylamino-propionic acid A solution of 3.71 g (35.0 mmol) of NaHCO$_3$ in 100 mL water was added to a solution of 6.5 g (23.0 mmol) of (R)-2-amino-3-(4-amino-3-chloro-5-trifluoromethyl-phenyl)-propionic acid in 140 mL of THF. 15.28 g (70.0 mmol) of Boc-anhydride was added and the mixture was stirred for 3 h at RT. THF was evaporated off i. vac., the aqueous phase was washed with EtOAc and acidified with 10% citric acid solution. The aqueous phase was exhaustively extracted with EtOAc, the combined org. extracts were dried over Na$_2$SO$_4$ and evaporated down i. vac. The crude product was used in the next reaction step without any further purification.

Yield: 2.00 g (15% of theory) ESI-MS: (M–H)$^-$=381/383 (Cl)

7d tert.-butyl [(R)-1-(4-amino-3-chloro-5-trifluoromethyl-benzyl)-2-[1,4']bipiperidinyl-1'-yl-2-oxo-ethyl]-carbaminate 1.53 mL (11.00 mmol) of triethylamine were added to a solution of 2.00 g (5.22 mmol) of (R)-3-(4-amino-3-chloro-5-trifluoromethyl-phenyl)-2-tert.-butoxycarbonylamino-propionic acid, 0.99 g (5.30 mmol) of [1,4']bipiperidinyl, 1.77 g (5.50 mmol) of TBTU and 0.74 g (5.50 mmol) of HOBt in 150 mL of THF and the mixture was stirred for 16 h at RT. The reaction mixture was evaporated down i. vac., the residue was combined with saturated NaHCO$_3$ solution and the mixture was exhaustively extracted with EtOAc. The combined org. extracts were dried over MgSO$_4$ and evaporated down i. vac. The residue was purified by column chromatography (aluminium oxide (neutral, activity II), DCM/MeOH 99:1).

Yield: 500 mg (18% of theory)

7e (R)-2-amino-3-(4-amino-3-chloro-5-trifluoromethyl-phenyl)-1-[1,4']bipiperidinyl-1'-yl-propan-1-one-dihydrochloride 5 mL HCl (12 M in EtOH) were added at RT to a solution of 500 mg (0.75 mmol) of tert. butyl [(R)-1-(4-amino-3-chloro-5-trifluoromethyl-benzyl)-2-[1,4']bipiperidinyl-1'- yl-2-oxo-ethyl]-carbaminate in 50 mL EtOH and the mixture was stirred for 3 h and then evaporated down i. vac. The crude product was used in the next reaction step without any further purification.

Yield: 380 mg (quantitative yield)

7f 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-1,4'-bipiperidinyl-1'-yl-2-oxo-ethyl]-amide 180 mg (1.10 mmol) of CDT were added at 0° C. to a solution of 380 mg (0.75 mmol) of (R)-2-amino-3-(4-amino-3-chloro-5-trifluoromethyl-phenyl)-1-[1,4']bipiperidinyl-1'-yl-propan-1-one-dihydrochloride in 50 mL of DMF and 0.56 mL (4.00 mmol) of triethylamine and the mixture was stirred for 1.5 h at 0° C. 242 mg (0.99 mmol) of 3-piperidin-4-yl-1,3,4,5-tetrahydro-1,3-benzodiazepin-2-one were added and the reaction mixture was stirred for 1.5 h at 100° C. DMF was evaporated off i. vac. and the residue was purified by column chromatography (silica gel, DCM/cyc/MeOH/NH$_3$ 70:15:15:2) followed by HPLC.

Yield: 140 mg (20% of theory) ESI-MS: (M+H)$^+$=704/706 (Cl) R$_f$=0.58 (silica gel, DCM/cyc/MeOH/NH$_3$ 70:15:15:2)

Example 7.1

4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-(4-dimethylamino-piperidin-1-yl)-2-oxo-ethyl]-amide

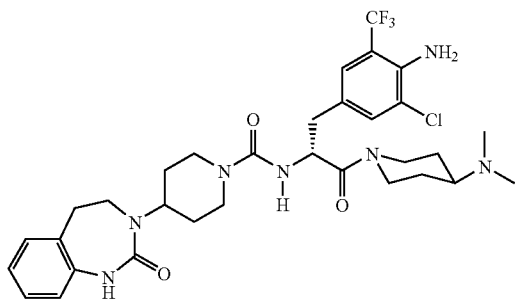

7.1a ethyl (R)-2-amino-3-(4-amino-3-chloro-5-trifluoromethyl-phenyl)-propionate

A solution of 3.5 g (10.97 mmol) (R)-2-amino-3-(4-amino-3-chloro-5-trifluoromethyl-phenyl)-propionic acid in 100 mL EtOH and 70 mL ethanolic HCl (11.5 M) was stirred overnight at RT. The mixture was evaporated down i.vac., the residue was taken up in 150 mL water, combined with 30 mL of 15% K$_2$CO$_3$ solution, extracted with 150 mL EtOAc, the organic phase was separated off and dried over Na$_2$SO$_4$. After removal of the desiccant and solvent the desired product was obtained.

Yield: 3.5 g (92% of theory) ESI-MS: (M+H)$^+$=311/313 (Cl)

7.1b ethyl (R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionate 1.8 g (11.0 mmol) CDT were added to a solution of 3.2 g (10.2 mmol) of ethyl (R)-2-amino-3-(4-amino-3-chloro-5-trifluoromethyl-phenyl)-propionate and 1.8 mL (10.3 mmol) ethyldiisopropylamine in 150 mL THF cooled to 0° C. and the reaction mixture was stirred for 45 min at this temperature and after removal of the ice bath stirred for a further 30 min. Then 2.5 g (10.2 mmol) 3-piperidin-4-yl-1,3,4,5-tetrahydro-1,3-benzodiazepin-2-one suspended in 50 mL THF were added. 40 mL DMF were added to the reaction solution and this was stirred for 2 h at 80° C. It was evaporated down i.vac., combined with 200 mL EtOAc and 200 mL 10% citric acid solution, the organic phase was separated off, extracted with 150 mL NaHCO$_3$ solution and dried over Na$_2$SO$_4$. After elimination of the desiccant and solvent the desired product was obtained.

Yield: 5.9 g (100% of theory) ESI-MS: (M+H)$^+$=582/584 (Cl) R$_f$=0.4 (silica gel, EtOAc)

7.1c (R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid To a suspension of 6.0 g (10.31 mmol) ethyl (R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionate in 50 mL THF was added a solution of 0.64 g (15 mmol) lithium hydroxide hydrate in 100 mL of water. A further 100 mL each of water and THF were added to this suspension, and after 5 min a solution was formed. It was stirred for 1 h at RT, the THF was eliminated i.vac., diluted with 100 mL of water and 1 M HCl was added dropwise while cooling with ice until an acidic reaction was obtained. The substance precipitated was filtered, washed with water and dried in the air.

Yield: 5.5 g (96% of theory) ESI-MS: (M+H)$^+$=554/556 (Cl)

7.1 d 4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-(4-dimethylamino-piperidin-1-yl)-2-oxo-ethyl]-amide 241 mg (0.75 mmol) TBTU, 0.21 mL (1.5 mmol) triethylamine and 103 mg (0.8 mmol) dimethyl-piperidin-4-yl-amine were added to a solution of 400 mg (0.72 mmol) of (R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid in 10 mL DMF and the reaction mixture was stirred overnight at RT. The reaction solution was poured onto 150 mL of 15% K$_2$CO$_3$ solution, stirred for 10 min at RT, the substance precipitated was suction filtered, washed with 30 mL water and dried overnight in the air. The crude product was suspended in isopropanol, stirred overnight at RT, suction filtered and dried at 40° C.

Yield: 350 mg (73% of theory) ESI-MS: (M+H)$^+$=664/666 (Cl) Retention time (HPLC): 6.0 min (method A)

The following compounds were prepared analogously from (R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid and the corresponding amount of amine:

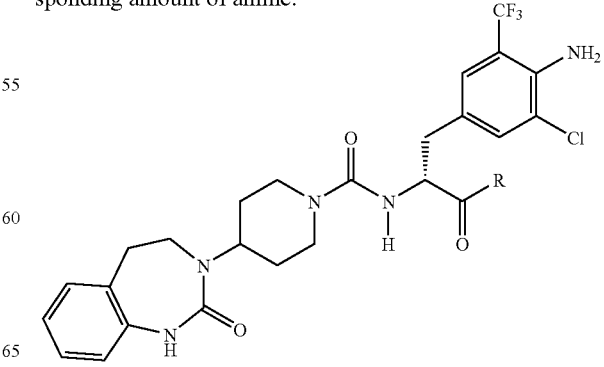

| Example | R | Yield (%) | Mass spectrum | Retention time HPLC (method) |
|---|---|---|---|---|
| 7.2 | 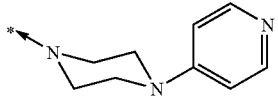 | 44 | 699/701 [M + H]+ | 6.1 min (A) |
| 7.3 |  | 27 | 718/720 [M + H]+ | 6.2 min (A) |
| 7.4 | 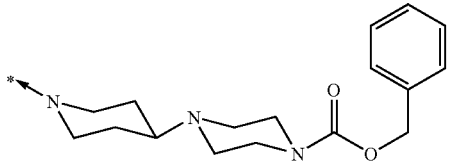 | 79 | 839/841 [M + H]+ | 7.1 min (A) |

The following compounds were prepared analogously from (R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid and the corresponding amount of amine, the crude product being purified by chromatography (silica gel, gradient: DCM to

| Example | R | Yield (%) | Mass spectrum | Retention time HPLC (method) |
|---|---|---|---|---|
| 7.5 | 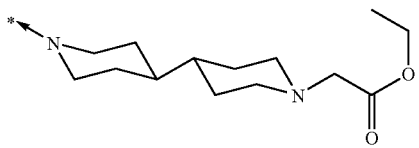 | 53 | 790/792 [M + H]+ | 6.6 min (A) |
| 7.6 | 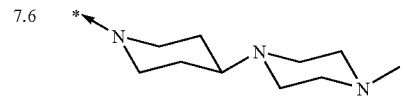 | 84 | 719/721 [M + H]+ | 5.7 min (A) |
| 7.7 | 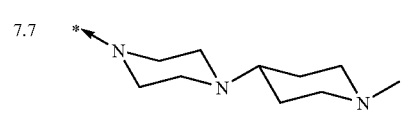 | 43 | 719/721 [M + H]+ | 5.0 min (A) |

The following compounds were prepared analogously from (R)-3-(4-amino-3-chloro-5trifluoromethyl-phenyl)-2-{[4-(2-oxo-1,2,4,5-tetrahydro-1,3-benzodiazepin-3-yl)-piperidin-1-carbonyl]-amino}-propionic acid and the corresponding amount of amine, while the crude product was purified directly by HPLC:

A solution of 600 mg (0.72 mmol) benzyl 4-[1-((R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionyl)-piperidin-4-yl]-piperazin-1-carboxylate (Example 7.4) and 200 mg Raney nickel in 50 mL

| Example | R | Yield (%) | Mass spectrum | Retention time HPLC (method) |
|---|---|---|---|---|
| 7.8 | ![structure] | 17 | 676/678 [M + H]⁺ | 6.2 min (A) |
| 7.9 | ![structure] | 52 | 731/733 [M + H]⁺ | 5.5 min (A) |

Example 7.10

4-(2-oxo-1,2,4,5-tetrahydro-1,3-benzodiazepin-3-yl)-piperidin-1-carboxylic acid-[(R)-1-(4-amino-3-chloro-5-trifluoromethyl-benzyl)-2-oxo-2-(4-piperazin-1-yl-piperidin-1-yl)-ethyl]-amide

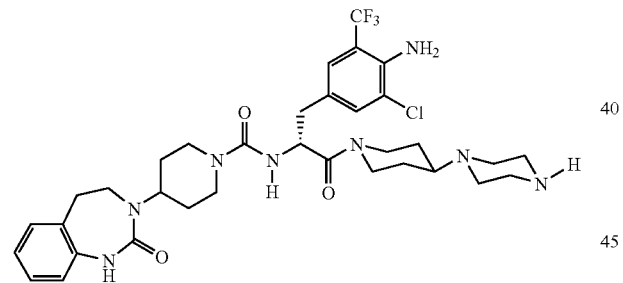

MeOH were hydrogenated at RT and 50 psi of $H_2$ for 12 h. The catalyst was filtered off, the solvent evaporated down i.vac. and the residue purified by HPLC.

Yield: 160 mg (32% of theory) ESI-MS: $(M+H)^+=705/707$ (Cl) Retention time (HPLC): 5.5 min (method A)

Example 7.11

[1'-((R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionyl)-4,4'-bipiperidinyl-1-yl]-acetic acid

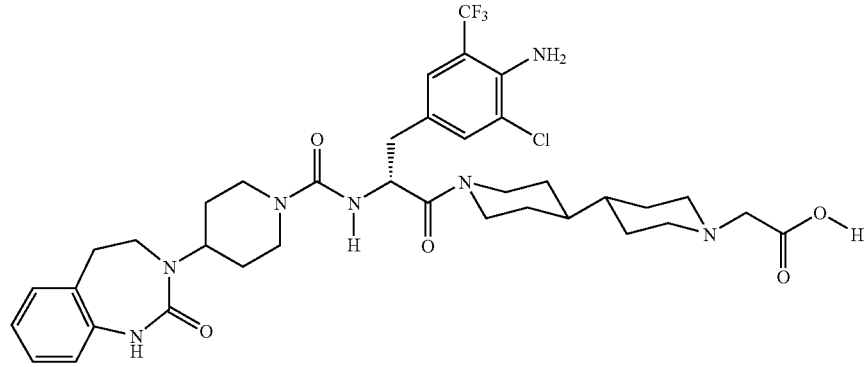

A solution of 20.1 mg (0.47 mmol) lithium hydroxide hydrate in 10 mL water was added to a solution of 250 mg (0.32 mmol) ethyl[1'-((R)-3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionyl)-4,4'-bipiperidinyl-1-yl]-acetate (Example 7.5) in 5 mL THF and the reaction mixture was stirred for 2 h at RT. 0.5 mL 1 M HCl were added, the substance precipitated was filtered off and dried at 50° C. The crude product was purified by HPLC.

Yield: 85 mg (35% of theory) ESI-MS: (M+H)$^+$=762/764 (Cl) Retention time (HPLC): 6.2 min (method A)

The following Examples may be prepared analogously:

| Example | Structure |
|---------|-----------|
| 7.12 | 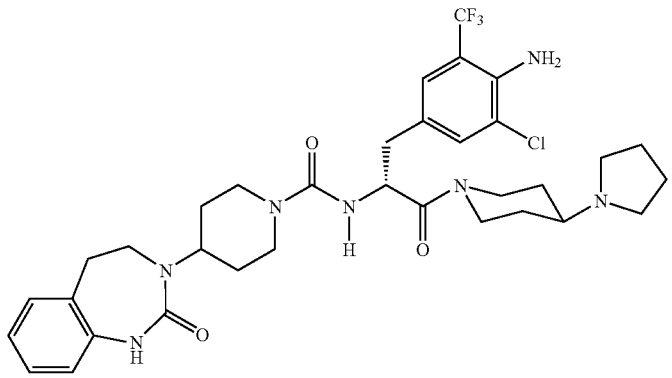 |
| 7.13 | 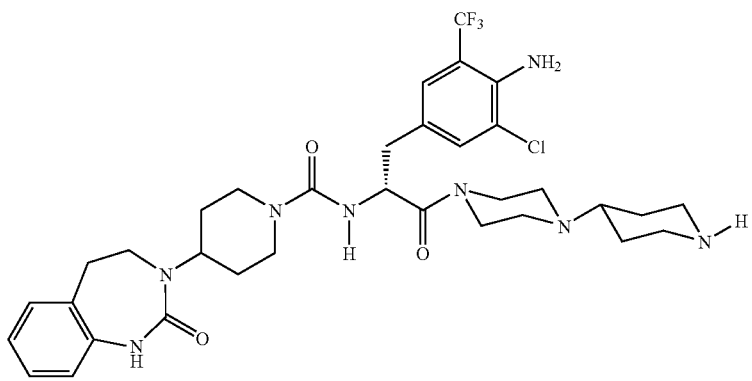 |
| 7.14 | 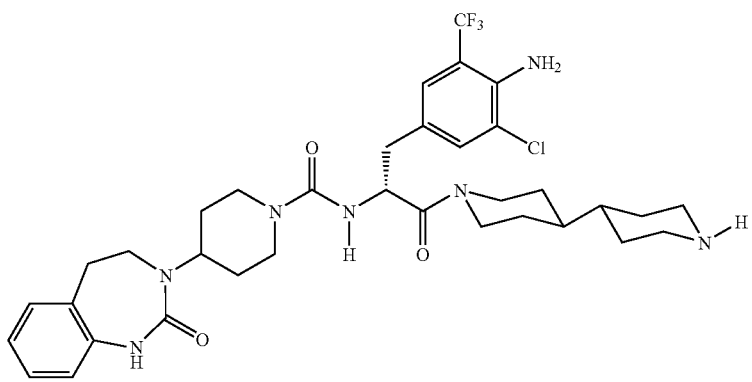 |

Example 8

4-(2-oxo-1,2,4,5-tetrahydro-1,3-benzodiazepin-3-yl)-piperidin-1-carboxylic acid-[1-(4-amino-3-chloro-5-trifluoromethyl-benzyl)-2-1,4'-bipiperidinyl-1'-yl-2-oxo-ethyl]-amide

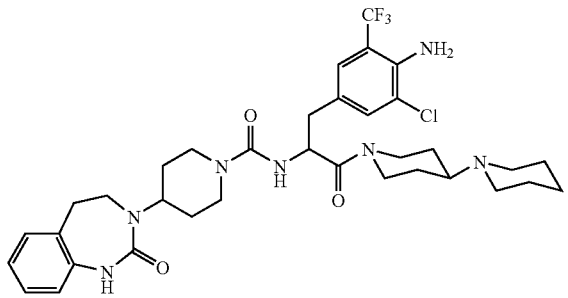

8a diethyl 2-acetylamino-2-(4-amino-3-chloro-5-trifluoromethyl-benzyl)-malonate 24.11 g (0.11 mol) diethyl 2-acetylamino-malonate was added to a freshly prepared solution of 2.55 g (0.11 mol) sodium in 200 mL abs. EtOH under a nitrogen atmosphere and the mixture was stirred for 15 min at RT. A solution of 27.00 g (0.11 mol) 2-chloro-4-chloromethyl-6-trifluoromethyl-phenylamine (Example 2a) in 100 mL of 1,4-dioxane was rapidly added dropwise and the mixture was stirred for 4 h at RT. 500 mL of water were added and the mixture was stirred for a further 16 h. The precipitate formed was filtered off, washed with water and dried i. vac.

Yield: 40.0 g (84% of theory) $R_f$=0.14 (silica gel, PE/EtOAc=2/1)

8b 2-amino-3-(4-amino-3-chloro-5-trifluoromethyl-phenyl)-propionic acid-hydrochloride 50 mL conc. HCl were added to a solution of 40.0 g (94.16 mmol) of diethyl 2-acetylamino-2-(4-amino-3-chloro-5-trifluoromethyl-benzyl)-malonate in 110 mL AcOH and 150 mL of water and the reaction mixture was heated to 140° C. for 4 h. The precipitate formed was filtered off and discarded. The filtrate was evaporated down i. vac., combined with 100 mL of EtOH and stirred for 15 min at RT. The precipitate formed was filtered off, washed with EtOH and dried i. vac. The crude product was used in the next reaction step without any further purification.

Yield: 16 g (53% of theory) ESI-MS: (M–H)⁻=281/283 (Cl)

8c ethyl 2-amino-3-(4-amino-3-chloro-5-trifluoromethyl-phenyl)-propionate 16 g (50.14 mmol) of 2-amino-3-(4-amino-3-chloro-5-trifluoromethyl-phenyl)-propionic acid-hydrochloride were dissolved in 350 mL of HCl (12 M in EtOH) and stirred for 5 h at RT. The reaction mixture was evaporated down to 100 mL i. vac. and combined with 200 mL diethylether. The precipitate formed was filtered off, washed with diethylether and dried i. vac.

Yield: 12.2 g (70% of theory) ESI-MS: (M+H)⁺=311/313 (Cl)

8d ethyl 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionate 4.15 g (23.04 mmol) of CDT were added at 0° C. to a suspension of 8.00 g (23.04 mmol) of ethyl 2-amino-3-(4-amino-3-chloro-5-trifluoromethyl-phenyl)-propionate and 16.0 mL (115.00 mmol) of triethylamine in 100 mL of DMF and the mixture was stirred for 1.5 h at 0° C. A solution of 5.64 g (23.00 mmol) of 3-piperidin-4-yl-1,3,4,5-tetrahydro-1,3-benzodiazepin-2-one in 200 mL of DMF was added and the mixture was heated to 100° C. for 2 h. The reaction mixture was cooled to RT, diluted with 1.5 L water and stirred for a further 10 min. The precipitate formed was filtered off, washed with water and dried i. vac.

Yield: 13.0 g (97% of theory) ESI-MS: (M+H)⁺=582/584 (Cl)

8e 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid 45 mL of 1 M NaOH were added to a solution of 13.00 g (22.34 mmol) of ethyl 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionate in 100 mL EtOH and the mixture was stirred, for 16 h at RT. EtOH was evaporated off i. vac., 45 mL of 1M HCl were added and the mixture was stirred for 15 min. The precipitate formed was filtered off, washed with water and dried i. vac. at 75° C.

Yield: 10.5 g (85% of theory) ESI-MS: (M–H)⁻=552/554 (Cl)

8f 4-(2-oxo-1,2,4,5-tetrahydro-1,3-benzodiazepin-3-yl)-piperidin-1-carboxylic acid-[1-(4-amino-3-chloro-5-trifluoromethyl-benzyl)-2-1,4'-bipiperidinyl-1'-yl-2-oxo-ethyl]-amide 0.69 mL (5.00 mmol) of triethylamine were added to a solution of 1.00 g (1.81 mmol) of 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid, 0.34 g (1.81 mmol) of [1,4']bipiperidinyl and 0.64 g (2.00 mmol) of TBTU in 150 mL of THF and the mixture was stirred for 16 h at RT. The reaction mixture was evaporated down i. vac., the residue was combined with saturated NaHCO₃ solution and the mixture was exhaustively extracted with EtOAc. The combined org. extracts were dried over MgSO₄ and evaporated down i. vac. The residue was purified by column chromatography (silica gel, EtOAc/MeOH/NH₃=75:25:2.5).

Yield: 350 mg (28% of theory) ESI-MS: (M+H)⁺=704/706 (Cl) $R_f$=0.58 (silica gel, DCM/cyc/MeOH/NH₃=70/15/15/2)

Example 9

(S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione

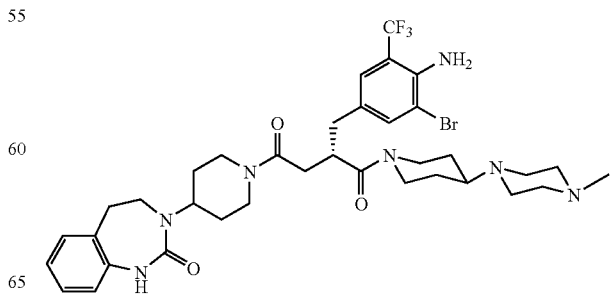

9a ethyl 4-amino-3-trifluoromethyl-benzoate

A solution of 150 g (0.66 mol) N-(4-cyano-2-trifluoromethyl-phenyl)-acetamide in 360 mL dry EtOH and 540 mL 10 M ethanolic HCL was heated to 70° C. for 2 h 45 min in a pressure apparatus. After the solution had cooled the precipitate formed was suction filtered, washed with EtOH and the filtrate was evaporated down i.vac. The residue was combined with 300 mL water and EtOH in each case, vigorously stirred, suction filtered and washed with water/EtOH 1:1.

The crude product was further reacted without purification.

Yield: 153 g (100% of theory) $R_f$=0.4 (silica gel, PE/EtOAc 1:1)

9b 4-amino-3-trifluoromethyl-benzoic acid

At RT a solution of 153 g (0.66 mol) ethyl 4-amino-3-trifluoromethyl-benzoate in 350 mL EtOH was added to a solution of 100 g (2.5 mol) NaOH in 250 mL water and the reaction mixture was stirred for 2 h at 45° C. EtOH was eliminated i. vac., the remaining aqueous solution was acidified with conc. HCl, the precipitated product was suction filtered, washed with water and dried in the air.

Yield: 129 g (96% of theory) ESI-MS: $(M-H)^-$=204

9c 4-amino-3-bromo-5-trifluoromethyl-benzoic acid

A solution of 6 mL (117 mmol) bromine in 50 mL acetic acid was slowly added dropwise to a solution of 21.0 g (102 mmol) 4-amino-3-trifluoromethyl-benzoic acid in 250 mL acetic acid and then heated to 60° C. for 2 h. After cooling it was combined with 1 L water and the precipitate was suction filtered. The residue was dissolved in DCM, the organic phase made alkaline with NaOH solution, the aqueous phase was separated off and acidified with conc. HCl. The precipitate was suction filtered and dried at 60° C.

Yield: 18 g (62% of theory) ESI-MS: $(M-H)^-$=282/284 (Br) $R_f$=0.6 (silica gel, PE/EtOAc/AcOH 50:50:1)

9d (4-amino-3-bromo-5-trifluoromethyl-phenyl)-methanol 12 g (74 mmol) CDI were added to a solution of 18 g (63.4 mmol) 4-amino-3-bromo-5-trifluoromethyl-benzoic acid in 400 mL THF, stirred for 1 h at RT and heated to 40° C. for 1 h. The activated acid was then added dropwise to a solution of 8.0 g (212 mmol) NaBH$_4$ in 200 mL water, while the temperature should not exceed 40° C. The reaction mixture was stirred for 2.5 h at RT, combined with 300 mL of semiconc. HCl, stirred for 1 h and exhaustively extracted with EtOAc. The organic phase was washed with 15% K$_2$CO$_3$ solution and dried over Na$_2$SO$_4$. After the desiccant and solvent had been eliminated the residue was dissolved in isopropanol at 50° C.; after cooling the precipitate was suction filtered, taken up in PE and suction filtered again.

Yield: 12.5 g (73% of theory) EI: $(M)^+$=269/271 (Br) $R_f$=0.9 (silica gel, MeOH)

9e 4-amino-3-bromo-5-trifluoromethyl-benzaldehyde 53 g (0.61 mol) MnO$_2$ were added to a solution of 12.5 g (46.3 mmol) (4-amino-3-bromo-5-trifluoromethyl-phenyl)-methanol in 150 mL DCM and the reaction mixture was stirred overnight at RT. The MnO$_2$ was suction filtered, washed with DCM, the solvent was eliminated i. vac. and the residue stirred with PE. The precipitate was suction filtered, washed with a little PE and dried.

Yield: 9.5 g (77% of theory) ESI-MS: $(M+H)^+$=268/270 (Br) $R_f$=0.6 (silica gel, PE/EtOAc 2:1)

9f 1-methyl 2-[1-(4-amino-3-bromo-5-trifluoromethyl-phenyl)-meth-(E)-ylidene]-succinate 27.9 g (71.0 mmol) 1-methyl 2-(triphenyl-□$^5$-phosphanylidene)-succinate were added to a solution of 9.5 g (35.4 mmol) 4-amino-3-bromo-5-trifluoromethyl-benzaldehyde in 80 mL THF and the reaction mixture was heated to 40° C. for 120 h. The precipitate was suction filtered, the filtrate evaporated down i.vac., the residue combined with water and EtOAc, the organic phase was separated off, washed three times with water and extracted three times with 5% K$_2$CO$_3$ solution. The aqueous phase was acidified with conc. HCl, the precipitate formed was separated off, washed with water and dried at 60° C.

Yield: 5.9 g (44% of theory) ESI-MS: $(M+H)^+$=382/384 (Br)

9g 1-methyl (S)-2-(4-amino-3-bromo-5-trifluoromethyl-benzyl)-succinate

Under an argon atmosphere 130 mg (+)-1,2-bis((2R,5R)-2,5-diethylphospholano)benzol(cyclooctadiene)rhodium(I) tetrafluoroborate were added to a solution of 5.9 g (15.44 mmol) 1-methyl 2-[1-(4-amino-3-bromo-5-trifluoromethyl-phenyl)-meth-(E)-ylidene]-succinate in 50 mL degassed MeOH and 5.9 mL triethylamine and the reaction mixture was hydrogenated at 50 psi H$_2$ for 4 h. Then the reaction solution was evaporated down i.vac., the residue was dissolved in 100 mL EtOAc, washed twice with 2 M HCl and exhaustively extracted with 5% K$_2$CO$_3$ solution. The aqueous phase was acidified with conc. HCl, exhaustively extracted with EtOAc and the organic phase was dried over Na$_2$SO$_4$. After the desiccant and solvent had been eliminated the desired product was obtained.

Yield: 5.8 g (98% of theory) ESI-MS: $(M-H)^-$=382/384 (Br)

9h methyl (S)-2-(4-amino-3-bromo-5-trifluoromethyl-benzyl)-4-oxo-4-[4-(2-oxo-1,2,4,5-tetrahydro-1,3-benzodiazepin-3-yl]-piperidin-1-yl-butanoate 3.70 g (15.1 mmol) 3-piperidin-4-yl-1,3,4,5-tetrahydro-1,3-benzodiazepin-2-one were added to a solution of 5.80 g (15.1 mmol) 1-methyl (S)-2-(4-amino-3-bromo-5trifluoromethyl-benzyl)-succinate, 4.98 g (15.1 mmol) TBTU, 2.04 g (15.1 mmol) HOBt and 4.87 mL (35 mmol) triethylamine in 200 mL THF and the reaction mixture was stirred overnight at RT. The reaction solution was evaporated down i.vac., combined with EtOAc and 20% citric acid solution, the organic phase was separated off, washed with saturated NaHCO$_3$ solution and dried over Na$_2$SO$_4$. After the desiccant and solvent had been eliminated the desired product was obtained.

Yield: 9.2 g (100% of theory) ESI-MS: $(M+H)^+$=611/613 (Br)

9i (S)-2-(4-amino-3-bromo-5-trifluoromethyl-benzyl)-4-oxo-4-[4-(2-oxo-1,2,4,5-tetrahydro-1,3-benzodiazepin-3-yl)-piperidin-1-yl]-butanoic acid A solution of 1.04 g (24.30 mmol) lithium hydroxide hydrate in 30 mL water was added at RT to a solution of 9.2 g (15.05 mmol) methyl (S)-2-(4-amino-3-bromo-5-trifluoromethyl-benzyl)-4-oxo-4-[4-(2-oxo-1,2,4,5-tetrahydro-1,3-benzodiazepin-3-yl)-piperidin-1-yl]-butanoate in 70 mL THF and the reaction mixture was stirred for 3 h at RT. The THF was eliminated i.vac., the aqueous solution was acidified with conc. HCl, exhaustively extracted with EtOAc, the organic phase was separated off and dried over Na$_2$SO$_4$. After the desiccant and solvent had been eliminated the desired product was obtained.

Yield: 7.8 g (87% of theory) ESI-MS: $(M+H)^+$=597/599 (Br)

Analogously to the sequence described in 9f to 9i, 1-methyl (S)-2-(4-amino-3-chloro-5-trifluoromethyl-benzyl)-succinate and (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid were able to be obtained from 4-amino-3-chloro-5-trifluoromethyl-benzaldehyde (see Example 1b).

9k (S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione 154 mg (0.84 mmol) 1-methyl-4-piperidin-4-yl-piperazine were added to a solution of 500 mg (0.84 mmol) of (S)-2-(4-amino-3-bromo-5-trifluoromethyl-benzyl)-4-oxo-4-[4-(2-oxo-1,2,4,5-tetrahydro-1,3-benzodiazepin-3-yl)-piperidin-1-yl]-butanoic acid, 289 mg (0.9 mmol) TBTU, 122 mg (0.9 mmol) HOBt and 0.35 mL (2.5 mmol) triethylamine in 40 mL THF and 5 mL DMF and the reaction mixture was stirred overnight at RT. The reaction solution was evaporated down i.vac., combined with EtOAc and saturated NaHCO$_3$ solution, the organic phase was separated off and dried over Na$_2$SO$_4$. After the desiccant and solvent had been eliminated the residue was purified by chromatography (silica gel, gradient: DCM to MeOH/NH$_3$ 95:5).

Yield: 423 mg (66% of theory) ESI-MS: (M+H)$^+$=762/764 (Br) Retention time (HPLC): 5.9 min (method A)

The following compounds were prepared analogously from in each case 500 mg (S)-2-(4-amino-3-bromo-5-trifluoromethyl-benzyl)-4-oxo-4-[4-(2-oxo-1,2,4,5-tetrahydro-1,3-benzodiazepin-3-yl)-piperidin-1-yl]-butanoic acid and the corresponding amount of amine:

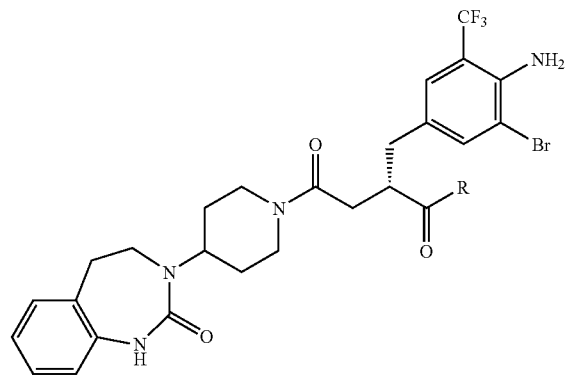

| Example | R | Yield (%) | Mass spectrum | Retention time HPLC (method) |
|---|---|---|---|---|
| 9.1 | | 50 | 742/744 [M + H]$^+$ | 6.4 min (A) |
| 9.2 | | 48 | 747/749 [M + H]$^+$ | 6.5 min (A) |
| 9.3 | | 61 | 762/764 [M + H]$^+$ | 5.4 min (A) |
| 9.4 | | 34 | 761/763 [M + H]$^+$ | 6.3 min (A) |

The following Examples may be prepared analogously:
| Example | Structure |
|---------|-----------|
| 9.5 | 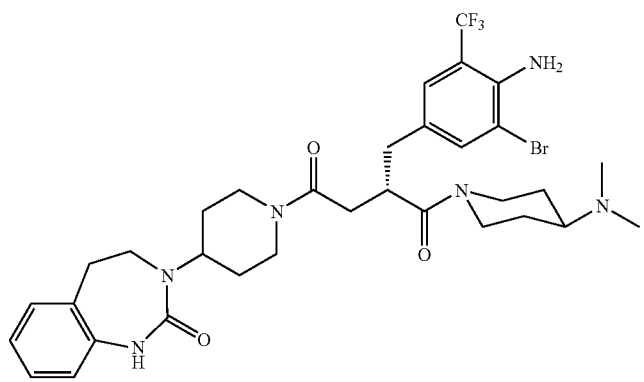 |
| 9.6 | 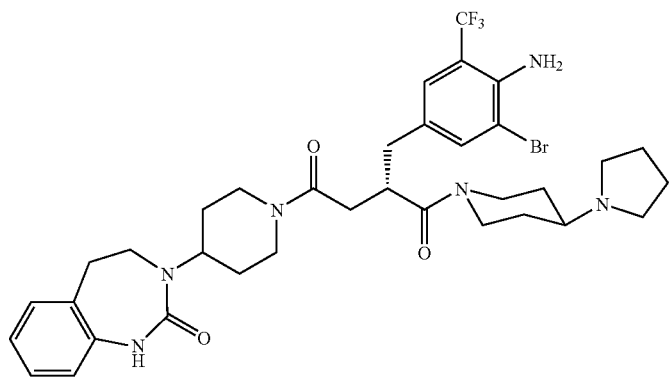 |
| 9.7 | 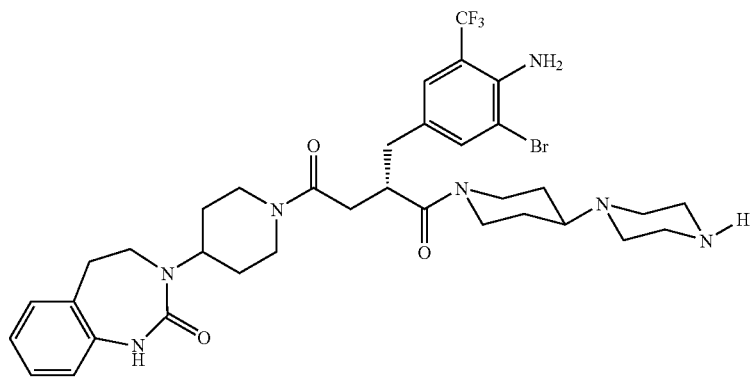 |

-continued

| Example | Structure |
|---|---|
| 9.8 | 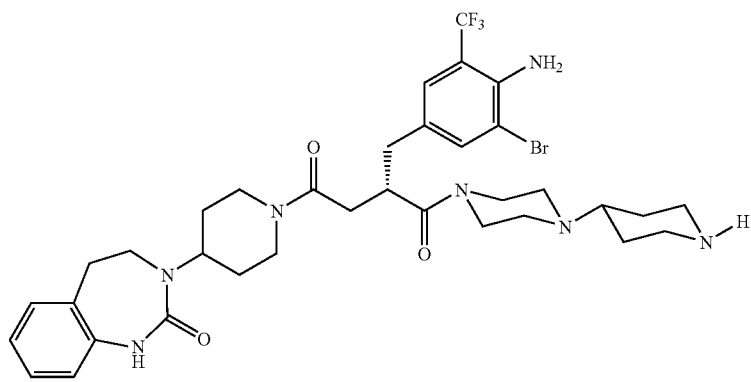 |
| 9.9 | 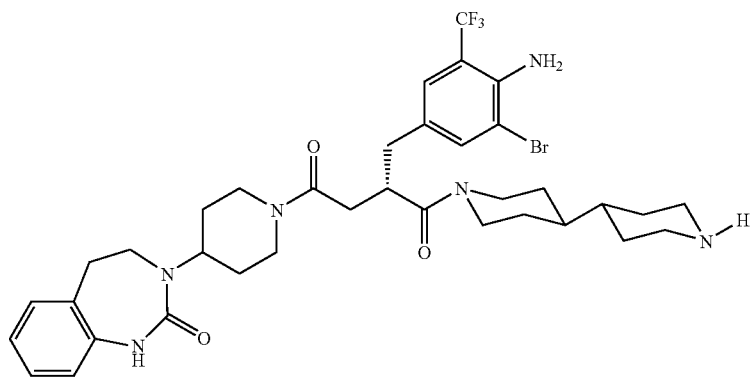 |

Example 9, 10

(S)-2-(4-amino-3-trifluoromethyl-benzyl)-1-[4-(4-methyl-piperazin-1-yl)-piperidin-1-yl-]-4-[4-(2-oxo-1,2,4,5-tetrahydro-1,3-benzodiazepin-3-yl)-piperidin-1-yl]-butan-1,4-dione

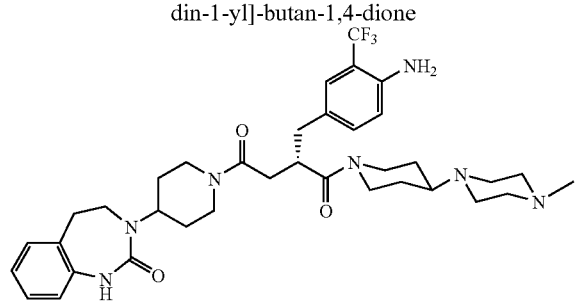

100 mg 10% Pd/C were added to a solution of 150 mg (0.2 mmol) (S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione in 20 mL MeOH and the reaction mixture was hydrogenated at 50 psi H$_2$ for 3 h at RT. The catalyst was suction filtered, the solvent was evaporated down i.vac., the residue was combined with 5% K$_2$CO$_3$ solution and EtOAc, the organic phase was separated off and evaporated down i.vac. The residue was triturated with diisopropylether and suction filtered.

Yield: 134 mg (100% of theory) ESI-MS: (M+H)$^+$=684
Retention time (HPLC): 5.5 min (method A)

Example 10

(S)-2-(4-amino-3-chloro-5-trifluoromethyl-benzyl)-1-(4-dimethylamino-piperidin-1-yl)-4-[4-(2-oxo-1,2,4,5-tetrahydro-1,3-benzodiazepin-3-yl)-piperidin-1-yl]-butan-1,4-dione

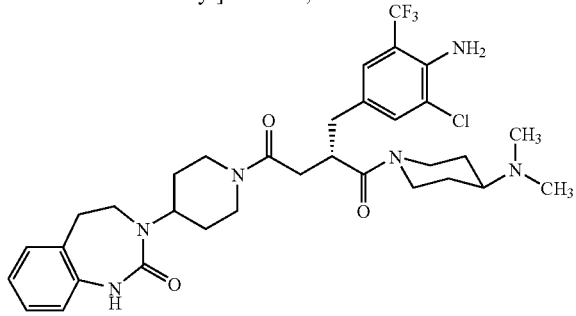

80.3 mg (0.25 mmol) TBTU, 0.21 mL (1.2 mmol) ethyldiisopropylamine and 38.5 mg (0.3 mmol) dimethyl-piperidin-4-yl-amine were added to a solution of 130 mg (0.24 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid in 10 mL DMF and the reaction mixture was stirred overnight at RT. The reaction solution was poured into 80 mL 15% K$_2$CO$_3$ solution, stirred for 10 min at RT, the precipitated substance was suction filtered, washed with 5 mL water and dried in the air over the weekend. Then the product was purified by chromatography using HPLC.

Yield: 82 mg (53% of theory) ESI-MS: (M+H)$^+$=663/665 (Cl) Retention time (HPLC): 6.1 min (method A)

The following compounds were prepared analogously:

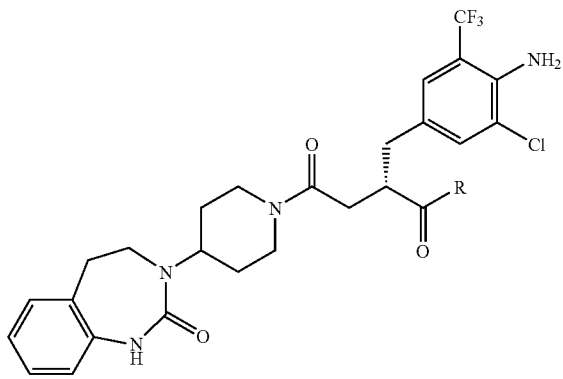

| Example | R | Yield (%) | Mass spectrum | Retention time HPLC (method) |
|---|---|---|---|---|
| 10.1 | *-N(piperidine)-N(CH3)2 | 55 | 663/665 [M + H]+ | 6.3 min 6.5 min (A) |
| 10.2 | *-N(piperidine)-N(pyrrolidine) | 51 | 689/691 [M + H]+ | 6.4 min (A) |
| 10.3 | *-N(piperidine)-cyclohexyl-N-CH3 | 56 | 717/719 [M + H]+ | 6.2 min (A) |
| 10.4 | *-N(piperidine)-N(piperazine)-CH2-cyclopropyl | 49 | 758/760 [M + H]+ | 6.0 min (A) |
| 10.5 | *-N(piperidine)-N(morpholine) | 45 | 705/707 [M + H]+ | 6.2 min (A) |
| 10.6 | *-N(piperidine)-N(azepane) | 58 | 717/719 [M + H]+ | 6.6 min (A) |
| 10.7 | *-N(piperidine)-N(N-methylhomopiperazine)-CH3 | 54 | 732/734 [M + H]+ | 5.4 min (A) |
| 10.8 | *-N(piperidine)-N(piperazine)-iPr | 50 | 746/748 [M + H]+ | 5.9 min (A) |
| 10.9 | *-N(piperidine)-N(piperidine) | 67 | 703/705 [M + H]+ | 6.4 min (A) |

-continued

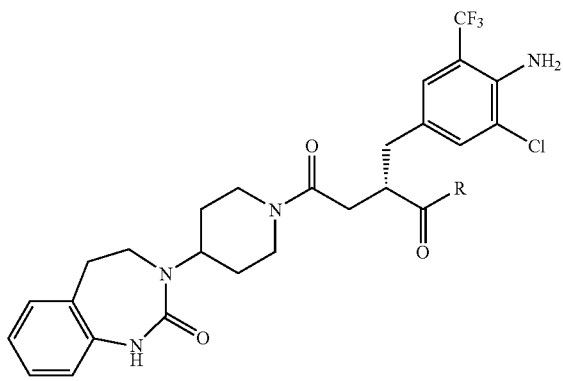

| Example | R | Yield (%) | Mass spectrum | Retention time HPLC (method) |
|---|---|---|---|---|
| 10.10 | *-N(CH2CH2)2N-piperidine-N-CH3 (homopiperazine-N-methylpiperidine) | 53 | 732/734 [M + H]+ | 5.5 min (A) |
| 10.11 | *-azetidine-N-piperazine-N-CH3 | 25 | 690/692 [M + H]+ | 6.0 min (A) |
| 10.12 | *-azetidine-pyrrolidine | 48 | 661/663 [M + H]+ | 6.3 min (A) |
| 10.13 | *-azetidine-piperidine | 56 | 675/677 [M + H]+ | 6.5 min (A) |
| 10.14 | *-azetidine-N(Et)2 | 53 | 663/665 [M + H]+ | 6.4 min (A) |
| 10.15 | *-piperidine-azetidine | 52 | 675/677 [M + H]+ | 6.3 min (A) |
| 10.16 | *-piperidine-piperazine-N-C(O)CH3 | 36 | 746/748 [M + H]+ | 6.1 min (A) |
| 10.17 | *-piperidine-CH2-N(Et)2 | 38 | 705/707 [M + H]+ | 6.4 min (A) |

-continued

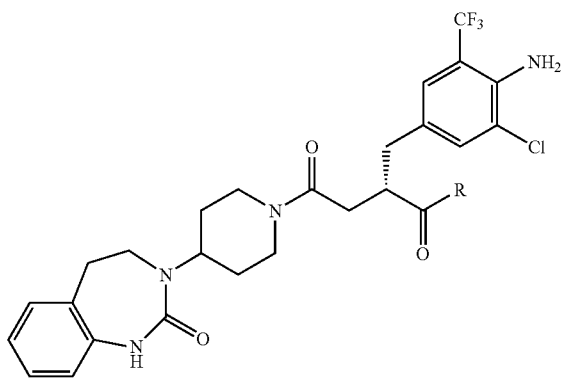

| Example | R | Yield (%) | Mass spectrum | Retention time HPLC (method) |
|---|---|---|---|---|
| 10.18 | *-N(piperidine)-N(piperidine)-N-ethyl | 52 | 732/734 [M + H]+ | 5.8 min (A) |
| 10.19 | *-N(piperidine)-N(piperidine)-N-ethyl | 40 | 732/734 [M + H]+ | 5.4 min (A) |
| 10.20 | *-N(piperidine)-4-pyridyl | 53 | 697/699 [M + H]+ | 6.3 min (A) |
| 10.21 | *-N(piperazine)-4-pyridyl | 60 | 698/700 [M + H]+ | 6.3 min (A) |
| 10.22 | *-N(azetidine)-N(azepane) | 53 | 689/691 [M + H]+ | 6.7 min (A) |
| 10.23 | *-N(piperidine)-N(piperidine)-N-benzyl | 58 | 794/796 [M + H]+ | 5.7 min (A) |
| 10.24 | *-N(piperidine)-N(piperazine)-N-benzyl | 21 | 794/796 [M + H]+ | 6.8 min (A) |
| 10.25 | *-N(benzazepine)-CH2-N(CH3)2 | 47 | 739/741 [M + H]+ | 6.6 min (A) |

Example 10.26

(S)-2-(4-amino-3-chloro-5-trifluoromethyl-benzyl)-1-[4-(4-dimethylaminomethyl-phenyl)-piperidin-1-yl]-4-[4-(2-oxo-1,2,4,5-tetrahydro-1,3-benzodiazepin-3-yl)-piperidin-1-yl]-butan-1,4-dione

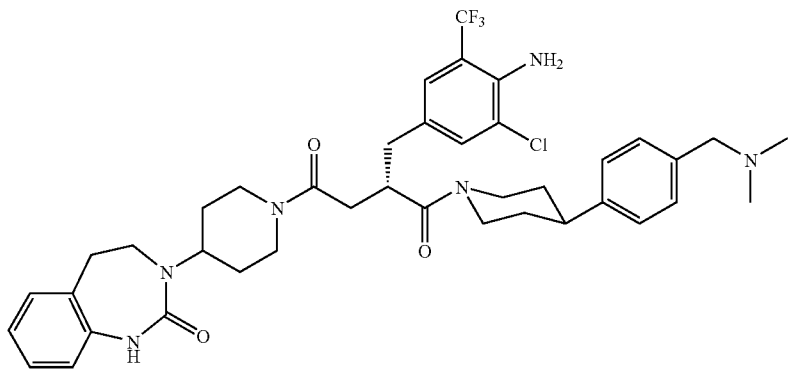

80 mg (0.25 mmol) TBTU and 87 μL (0.5 mmol) ethyldiisopropylamine were added to a solution of 130 mg (0.24 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid in 2 mL DMF and the mixture was stirred for 30 min at RT. Then 80 mg (0.31 mmol) dimethyl-(4-piperidin-4-yl-benzyl)-amine (used as the hydrochloride) were added and the reaction mixture was stirred overnight at RT. The reaction solution was filtered through an injection filter and purified directly by chromatography using HPLC.

Yield: 80 mg (45% of theory) ESI-MS: (M+H)$^+$=753/755 (Cl) Retention time (HPLC): 6.6 min (method A)

The following compounds were prepared analogously from in each case 130 mg (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and the corresponding amount of amine (with 1.07 eq. of ethyldiisopropylamine in the case of the free amines and the additional amount of base required when using amine salts):

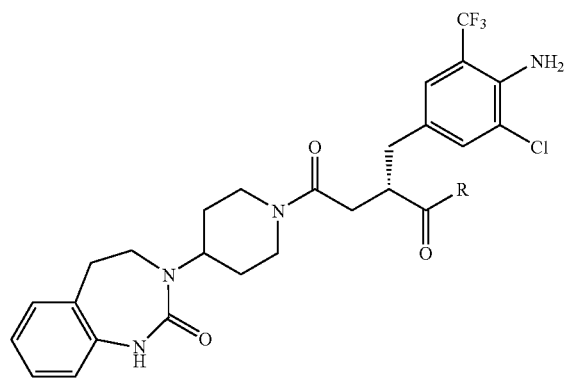

| Example | R | Yield (%) | Mass spectrum | Retention time HPLC (method) |
|---|---|---|---|---|
| 10.27 | | 51 | 786/788 [M + H]$^+$ | 6.9 min (A) |
| 10.28 | | 41 | 781/783 [M + H]$^+$ | 8.1 min (A) |

-continued
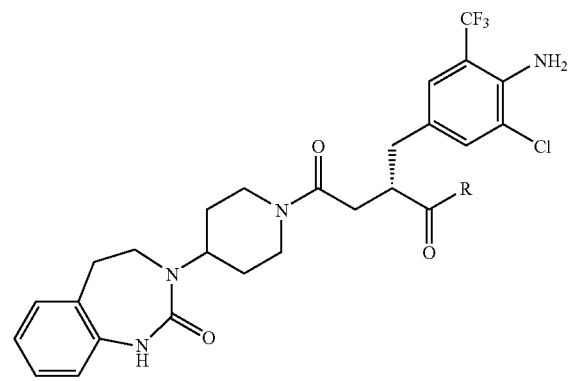
| Example | R | Yield (%) | Mass spectrum | Retention time HPLC (method) |
|---|---|---|---|---|
| 10.29 | *-N(piperidine)-(piperidine)-N-CH₃ | 61 | 703/705 [M + H]⁺ | 6.2 min (A) |
| 10.30 | *-N(piperidine)-CH₂-(piperidine)-N | 48 | 717/719 [M + H]⁺ | 6.4 min (A) |
| 10.31 | *-N(piperidine)-CH₂CH₂-N(CH₃)₂ | 31 | 691/693 [M + H]⁺ | 6.2 min (A) |
| 10.32 | *-N(CH₃)-CH₂CH₂-(piperidine)-N-CH₃ | 31 | 691/693 [M + H]⁺ | 6.3 min (A) |
| 10.33 | *-N(CH₃)-CH₂-(piperidine)-N-CH₃ | 19 | 677/679 [M + H]⁺ | 6.3 min (A) |

Example 10.34

(S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-piperidin-1-yl-butan-1,4-dione

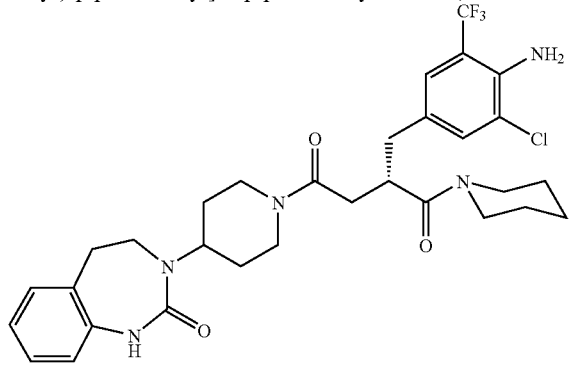

62 mg (0.19 mmol) TBTU and 34 µL (0.2 mmol) ethyldiisopropylamine were added to a solution of 100 mg (0.18 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid in 2 mL DMF and this was stirred for 30 min at RT. Then 24 µL (0.24 mmol) piperidine were added and the reaction mixture was stirred for 64 h at RT. The reaction solution was purified directly by chromatography using HPLC.

Yield: 54 mg (48% of theory) ESI-MS: $(M+H)^+=620/622$ (Cl) Retention time (HPLC): 8.4 min (method A)

The following compounds were prepared analogously from in each case 100 mg (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and the corresponding amount of amine:

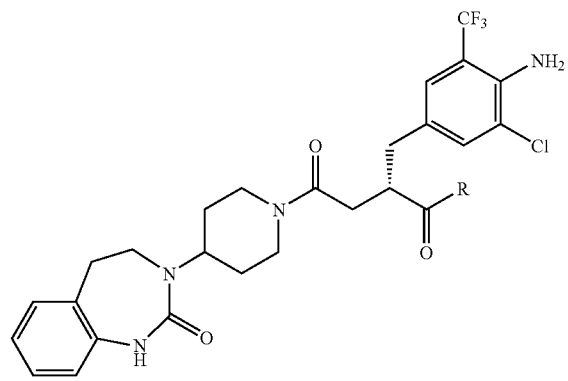

| Example | R | Yield (%) | Mass spectrum | Retention time HPLC (method) |
|---|---|---|---|---|
| 10.35 | *–N⟨piperidine⟩–propyl | 46 | 662/664 $[M + H]^+$ | 9.6 min (A) |
| 10.36 | *–N⟨piperidine⟩–CH₂–phenyl | 47 | 710/712 $[M + H]^+$ | 9.6 min (A) |
| 10.37 | *–N⟨piperidine⟩–CH₂CH₂–N(Et)₂ | 23 | 719/721 $[M + H]^+$ | 6.4 min (A) |
| 10.38 | *–N⟨piperidine⟩–cyclohexyl | 53 | 688/690 $[M + H]^+$ | 9.9 min (A) |
| 10.39 | *–N⟨piperidine⟩–N(CH₃)SO₂CH₃ | 51 | 727/729 $[M + H]^+$ | 7.7 min (A) |

-continued

| Example | R | Yield (%) | Mass spectrum | Retention time HPLC (method) |
|---------|---|-----------|---------------|------------------------------|
| 10.40 | *-N(piperidine)-NH-S(O)₂-CH₃ | 50 | 713/715 [M + H]⁺ | 7.4 min (A) |
| 10.41 | *-N(piperidine)-N(CH₃)(cyclopentyl) | 39 | 717/719 [M + H]⁺ | 6.6 min (A) |
| 10.42 | *-N(piperidine)-cyclohexyl | 56 | 634/636 [M + H]⁺ | 8.7 min (A) |
| 10.43 | *-N(piperidine)-CH₂-C(O)-OCH₃ | 48 | 692/694 [M + H]⁺ | 8.2 min (A) |
| 10.44 | *-N(piperidine)-OH | 52 | 636/638 [M + H]⁺ | 7.0 min (A) |
| 10.45 | *-N(piperidine)-CF₃ | 58 | 688/690 [M + H]⁺ | 8.7 min (A) |
| 10.46 | *-N(piperidine)-N(isothiazolidine dioxide) | 50 | 739/741 [M + H]⁺ | 7.6 min (A) |
| 10.47 | *-N(piperidine)-N(tetrahydro-oxazin-2-one) | 41 | 719/721 [M + H]⁺ | 7.2 min (A) |
| 10.48 | *-N(piperidine)-C(O)-OCH₃ | 23 | 678/680 [M + H]⁺ | 8.0 min (A) |

-continued
| Example | R | Yield (%) | Mass spectrum | Retention time HPLC (method) |
|---|---|---|---|---|
| 10.49 | 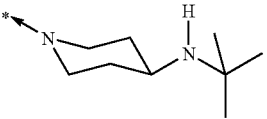 | 24 | 702/704 [M + H]⁺ | 10.5 min (A) |
| 10.50 |  | 32 | 691/693 [M + H]⁺ | 6.6 min (A) |
| 10.51 | 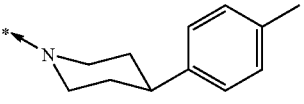 | 44 | 696/698 [M + H]⁺ | 9.2 min (A) |
| 10.52 | 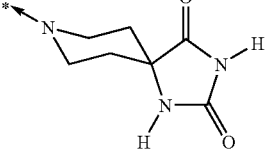 | 44 | 710/712 [M + H]⁺ | 9.6 min (A) |
| 10.53 | 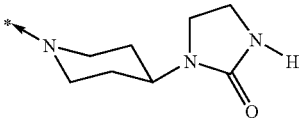 | 43 | 704/706 [M + H]⁺ | 7.0 min (A) |
| 10.54 | 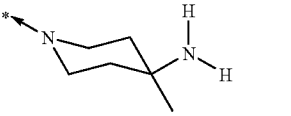 | 51 | 704/706 [M + H]⁺ | 7.0 min (A) |
| 10.55 | 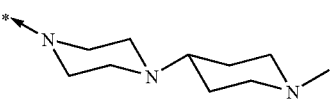 | 54 | 649/651 [M + H]⁺ | 6.2 min (A) |
| 10.56 |  | 68 | 719/721 [M + H]⁺ | 5.4 min (A) |

Example 10.57

(S)-2-(4-amino-3-chloro-5-trifluoromethyl-benzyl)-1-(2-amino-4,5,7,8-tetrahydro-thiazolo[4,5-d]azepin-6-yl)-4-[4-(2-oxo-1,2,4,5-tetrahydro-1,3-benzodiazepin-3-yl)-piperidin-1-yl]-butan-1,4-dione

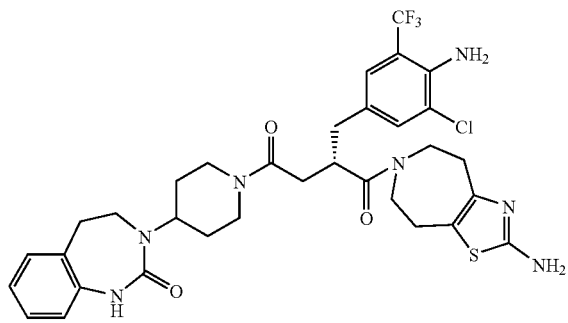

A solution of 300 mg (0.54 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and 190 mg (0.59 mmol) TBTU in 0.4 mL (2.27 mmol) ethyldiisopropylamine and 15 mL DMF was stirred for 1 h at RT. Then 160 mg (0.64 mmol) 5,6,7,8-tetrahydro-4H-thiazolo[4,5-d]azepin-2-ylamine was added (used as the hydrobromide) and the reaction solution was stirred for a further 3 h at RT. The reaction mixture was poured into 50 mL 15% $K_2CO_3$ solution, the precipitated product was suction filtered and purified by chromatography (silica gel, gradient: DCM to DCM/MeOH/$NH_3$ 10:9:1).

Yield: 100 mg (26% of theory) ESI-MS: $(M+H)^+=704/706$ (Cl) Retention time (HPLC): 6.1 min (method A)

The following compounds were prepared analogously from in each case 300 mg (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and the corresponding amount of amine (used as the free amine or as the amine-hydrochloride):

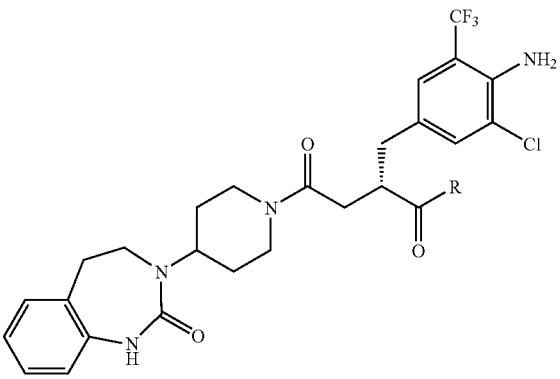

| Example | R | Yield (%) | Mass spectrum | Retention time HPLC (method) |
|---|---|---|---|---|
| 10.58 | | 40 | 700/702 $[M + H]^+$ | 6.4 min (A) |
| 10.59 | | 42 | 700/702 $[M + H]^+$ | 6.4 min (A) |
| 10.60 | | 50 | 704/706 $[M + H]^+$ | 7.5 min (A) |
| 10.61 | ![](dimethyl imidazole) | 31 | 714/716 $[M + H]^+$ | 6.5 min (A) |
| 10.62 | | 62 | 686/688 $[M + H]^+$ | 6.3 min (A) |

-continued

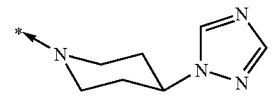

| Example | R | Yield (%) | Mass spectrum | Retention time HPLC (method) |
|---|---|---|---|---|
| 10.63 | | 62 | 687/689 [M + H]⁺ | 7.2 min (A) |
| 10.64 | | 15 | 730/732 [M + H]⁺ | 6.0 min (A) |
| 10.65 | | 18 | 621/623 [M + H]⁺ | 6.1 min (A) |

The compounds of Examples 10.64 and 10.65 could both be isolated from one reaction mixture as the 3-piperazin-1-yl-1-aza-bicyclo[2.2.2]octane used was contaminated with piperazine.

Example 10.66

4-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperazin-1-sulphonic acid (1-methyl-piperidin-4-yl)-amide A solution of 500 mg (0.90 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and 320 mg (1.00 mmol) TBTU in 0.2 mL (1.14 mmol) ethyldiisopropylamine and 50 mL THF was stirred for 1 h at RT. Then 270 mg (1.03 mmol) piperazin-1-sulphonic acid-(1-methyl-piperidin-4-yl)-amide and 5 mL DMF were added. The reaction solution was stirred overnight at RT. The reaction mixture was diluted with 50 mL EtOAc, extracted with 30 mL 15% K₂CO₃ solution and the organic phase was

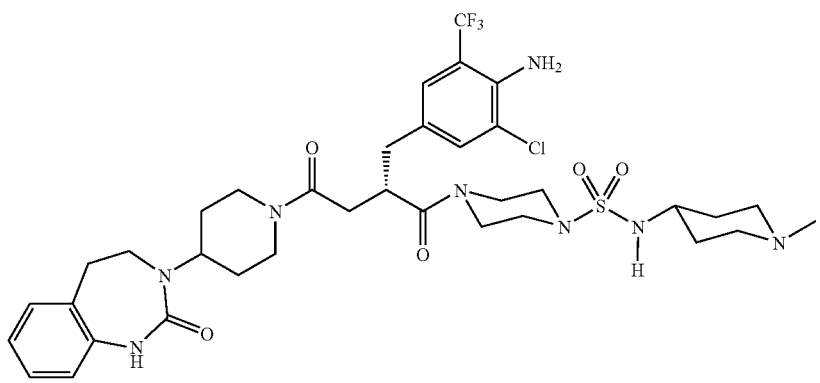

dried over Na$_2$SO$_4$. After the desiccant and solvent had been eliminated the residue was purified by chromatography (silica gel, gradient: DCM to DCM/MeOH/NH$_3$ 10:9:1).

Yield: 170 mg (24% of theory) ESI-MS: (M+H)$^+$=797/799 (Cl) Retention time (HPLC): 6.4 min (method A)

Example 10.67

(S)-2-(4-amino-3-chloro-5-trifluoromethyl-benzyl)-N-(5-amino-pentyl)-4-oxo-4-[4-(2-oxo-1,2,4,5-tetrahydro-1,3-benzodiazepin-3-yl)-piperidin-1-yl]-butyramide

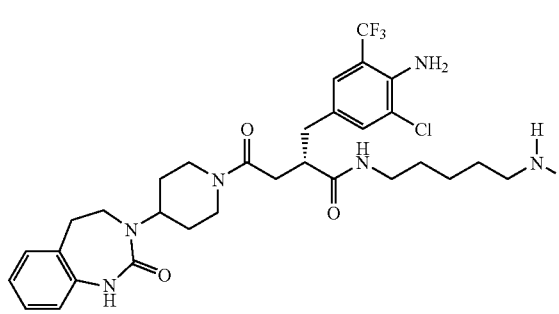

61 mg (0.3 mmol) of tert-butyl(5-amino-pentyl)-carbaminate were added to a solution of 260 mg (0.47 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and 161 mg (0.50 mmol) TBTU in 0.43 mL (2.50 mmol) ethyldiisopropylamine and 10 mL DMF and the reaction mixture was stirred overnight at RT. 80 mL of 15% K$_2$CO$_3$ solution were added, the resulting mixture was stirred for 10 min, the precipitated substance was suction filtered; it was then washed with water and dried in the air. The crude product was dissolved in 20 mL DCM, combined with 2 mL TFA and stirred for 2 h at RT. The reaction mixture was neutralised with 15% K$_2$CO$_3$ solution, the organic phase was separated off and evaporated down. The crude product thus obtained was purified directly by HPLC.

Yield: 110 mg (37% of theory) ESI-MS: (M+H)$^+$=637/639 (Cl) Retention time (HPLC): 6.0 min (method A)

The following compound was prepared analogously from 260 mg (0.47 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and 142 mg (0.6 mmol) tert. butyl(2-aminomethyl-benzyl)-carbaminate:

Example 10.69

1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidine-4-carboxylic acid

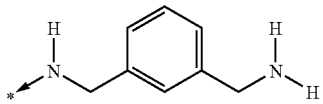

2 mg (0.05 mmol) lithium hydroxide hydrate, dissolved in a little water, were added to a solution of 15 mg (0.02 mmol) methyl 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-carboxylate (Example 10.48) in 5 mL THF and the reaction mixture was stirred for 3 h at RT. The solvent was eliminated i. vac., the residue was taken up in water and acetonitrile and lyophilised.

Yield: 14 mg (96% of theory) ESI-MS: (M+H)$^+$=664/666 (Cl) Retention time (HPLC): 7.2 min (method A)

The following compound was prepared analogously from 20 mg (0.03 mmol) methyl(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-acetate (Example 10.43):

| Example | R | Yield (%) | Mass spectrum | Retention time HPLC (method) |
|---|---|---|---|---|
| 10.68 | ![structure] | 47 | 671/673 [M + H]$^+$ | 6.4 min (A) |

| Example | R | Yield (%) | Mass spectrum | Retention time HPLC (method) |
|---|---|---|---|---|
| 10.70 | 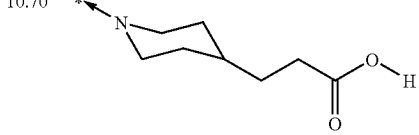 | 96 | 678/680 [M + H]+ | 7.3 min (A) |

Example 10.71

(S)-2-(4-amino-3-chloro-5-trifluoromethyl-benzyl)-1-[4-(8-methyl-8-aza-bicyclo[3.2.1]oct-3-yl)-piperazin-1-yl]-4-[4-(2-oxo-1,2,4,5-tetrahydro-1,3-benzodiazepin-3-yl)-piperidin-1-yl]-butan-1,4-dione

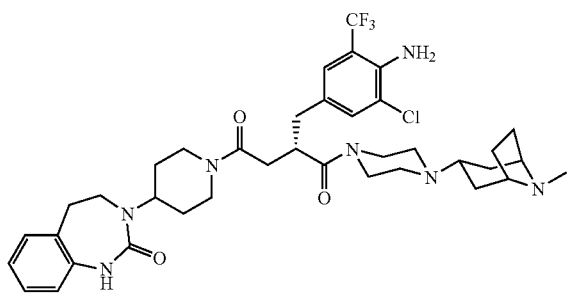

850 mg (2.4 mmol) 8-methyl-3-piperazin-1-yl-8-aza-bicyclo[3.2.1]octan were added to a solution of 1.04 g (1.88 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid, 642 mg (2.0 mmol) TBTU and 1.64 mL (9.6 mmol) ethyldiisopropylamine in 20 mL DMF and the reaction mixture was stirred overnight at RT. The reaction solution was combined with 15% K$_2$CO$_3$ solution, stirred for 10 min at RT, the precipitated substance was suction filtered, washed with 50 mL water and dried in the air and purified by chromatography (silica gel, gradient: DCM to DCM/MeOH/NH$_3$ 10:85:5).

Yield: 1.07 g (77% of theory) ESI-MS: (M+H)+=744/746 (Cl) Retention time (HPLC): 5.4 min (method A)

Example 10.72

(S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione

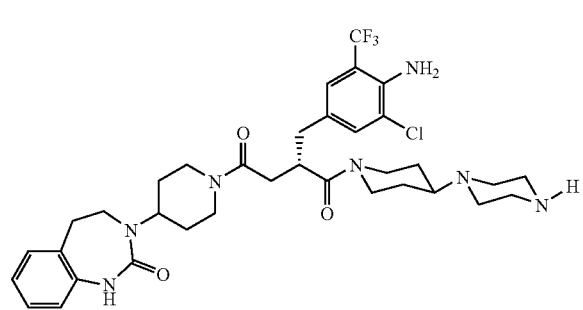

10.72a benzyl 4-(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-piperazin-1-carboxylate 241 mg (0.75 mmol) TBTU, 0.62 mL (3.6 mmol) ethyldiisopropylamine and 215 mg (0.71 mmol) benzyl 4-piperidin-4-yl-piperazin-1-carboxylate were added to a solution of 390 mg (0.71 mmol) (S)-2-(4-amino-3-chloro-5-trifluoromethyl-benzyl)-4-oxo-4-[4-(2oxo-1,2,4,5-tetrahydro-1,3-benzodiazepin-3-yl)-piperidin-1-yl]-butanoic acid in 10 mL DMF and the reaction mixture was stirred overnight at RT. The reaction solution was poured into 80 mL 15% K$_2$CO$_3$ solution, stirred for 10 min at RT, the precipitated substance was suction filtered, washed with 5 mL water and dried in the air over the weekend.

Yield: 580 mg (98% of theory) ESI-MS: (M+H)+=838/840 (Cl)

10.72b (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione 100 mg Raney nickel were added to a solution of 250 mg (0.30 mmol) benzyl 4-(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-piperazin-1-carboxylate in 30 mL MeOH and the reaction mixture was stirred for 5 h at RT and 50 psi H$_2$. To complete the reaction another 100 mg of Raney nickel were added and the mixture was stirred for a further 10 h at RT. The catalyst was suction filtered, the solvent eliminated i. vac. and the residue purified by HPLC.

Yield: 88 mg (42% of theory) ESI-MS: (M+H)+=704/706 (Cl) Retention time (HPLC): 5.6 min (method A)

Example 10.73

(S)-2-(4-amino-3-chloro-5-trifluoromethyl-benzyl)-1-[4-(1H-imidazol-4-yl)-piperidin-1-yl]-4-[4-(2-oxo-1,2,4,5-tetrahydro-1,3-benzodiazepin-3-yl)-piperidin-1-yl]-butan-1,4-dione

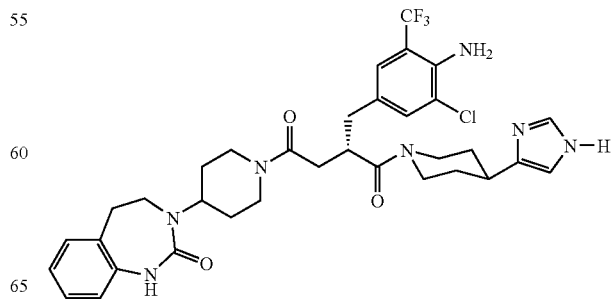

400 mg (1.25 mmol) TBTU and 0.65 mL (3.73 mmol) ethyldiisopropylamine were added to a solution of 650 mg (1.18 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid in 20 mL DMF and this was stirred for 30 min at RT. Then 340 mg (1.52 mmol) 4-(1H-imidazol-4-yl)-piperidin (used as the bis-hydrochloride) were added and the reaction mixture was stirred overnight at RT. It was evaporated down i.vac., combined with 30 mL of 15% $K_2CO_3$ solution, extracted twice with in each case 15 mL of DCM and the organic phase was dried with $MgSO_4$. After the desiccant and solvent had been eliminated the residue was purified by chromatography (silica gel, gradient: DCM to $DCM/MeOH/NH_3$ 20:75:5).

Yield: 460 mg (57% of theory) ESI-MS: $(M+H)^+$=686/688 (Cl) $R_f$=0.35 (silica gel, $DCM/cyc/MeOH/NH_3$ 70:15:15:2)

Example 10.74

(S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-acetyl)-phenyl]-piperazin-1-yl}-butan-1,4-dione mL dry THF cooled to −78° C. and this was then stirred for 15 min at this temperature. Then a solution of 0.43 mL (3.0 mmol) of N,N-diethyl-2,2,2-trifluoroacetamide in 10 mL of THF was slowly added dropwise. After the addition had ended the reaction mixture was kept for 2 h at −78° C., then poured onto 100 mL water, extracted twice with in each case 50 mL EtOAc, the organic phase was suction filtered through $Na_2SO_4$, evaporated down i.vac. and purified by chromatography (silica gel, cyc/EtOAc 3:1).

Yield: 267 mg (25% of theory) EI: $(M)^+$=358 $R_f$=0.37 (silica gel, cyc/EtOAc 3:1)

10.74c 2,2,2-trifluoro-1-(4-piperazin-1-yl-phenyl)-ethanone 2.0 mL TFA were added to a solution of 267 mg (0.75 mmol) tert. butyl 4-[4-(2,2,2-trifluoro-acetyl)-phenyl]-piperazin-1-carboxylate in 30 mL DCM cooled to 0° C. and the reaction mixture was stirred for 24 h, while warming up to RT. It was evaporated down i.vac.; the crude product was further reacted without purification.

ESI-MS: $(M+H)^+$=259

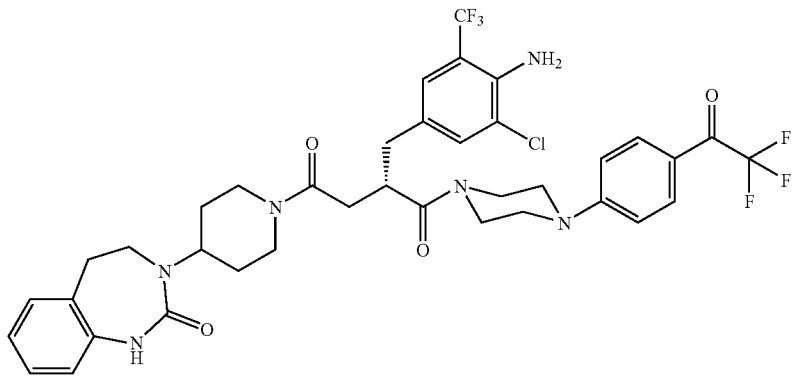

10.74a tert. butyl 4-(4-bromo-phenyl)-piperazine-1-carboxylate

Boc-anhydride was added batchwise to a suspension of 10.0 g (36 mmol) 4-(4-bromo-phenyl)-piperazine (used as the hydrochloride) and 15 mL (108 mmol) triethylamine in 150 mL THF and the reaction mixture was heated to 60° C. for 3 h. After cooling it was poured onto water, the precipitate was extracted with EtOAc, the organic phase was washed with water and dried over $Na_2SO_4$. After the desiccant and solvent had been eliminated the desired product was obtained.

Yield: 12.0 g (98% of theory) $R_f$=0.6 (silica gel, cyc/EtOAc 2:1)

10.74b tert. butyl 4-[4-(2,2,2-trifluoro-acetyl)-phenyl]-piperazin-1-carboxylate Under a nitrogen atmosphere a solution of 1.02 g (3.0 mmol) tert. butyl 4-(4-bromo-phenyl)-piperazine-1-carboxylate in 20 mL THF was slowly added dropwise to a solution of 2.06 mL (3.3 mmol) n-butyllithium (1.6 M in n-hexane) in 40

10.74d (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-acetyl)-phenyl]-piperazin-1-yl}-butan-1,4-dione The crude product obtained in 10.74c was added to a solution of 234 mg (0.42 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid, 136 mg (0.42 mmol) TBTU, 57 mg (0.42 mmol) HOBt and 0.14 mL (1.0 mmol) triethylamine in 20 mL THF and 2 mL DMF and the reaction mixture was stirred for 2 h at RT. The reaction solution was combined with semisaturated $NaHCO_3$ solution and extracted with 30 mL EtOAc. The organic phase was suction filtered through $Na_2SO_4$, the filtrate was evaporated down i.vac. and the residue was purified by chromatography (silica gel, EtOAc/MeOH 95:5).

Yield: 246 mg (73% of theory) ESI-MS: $(M+H)^+$=793/795 (Cl) $R_f$=0.27 (silica gel, EtOAc)

Example 10.75

(S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

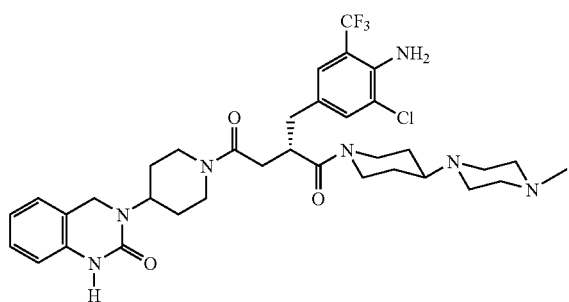

10.75a methyl (S)-2-(4-amino-3-chloro-5-trifluoromethyl-benzyl)-4-oxo-4-[4-(2-oxo-1,4-dihydro-2H-quinazolin-3-yl)-piperidin-1-yl]-butanoate A solution of 3.0 g (8.83 mmol) 1-methyl (S)-2-(4-amino-3-chloro-5-trifluoromethyl-benzyl)-succinate and 3.05 g (9.5 mmol) TBTU, 1.28 g (9.47 mmol) HOBT in 1.7 mL (9.76 mmol) ethyldiisopropylamine and 1100 mL DMF was stirred for 1 h at RT. Then 2.2 g (9.51 mmol) 3-piperidin-4-yl-3,4-dihydro-1H-quinazolin-2-one were added and the reaction solution was stirred overnight at RT. The reaction mixture was evaporated down i.vac., the residue was taken up in DCM, washed with 10% citric acid solution and 15% $K_2CO_3$ solution and dried over $Na_2SO_4$. The desiccant was eliminated by filtering through activated charcoal; after elimination of the solvent the desired product was obtained.

Yield: 4.8 g (98% of theory) ESI-MS: $(M+H)^+$=553/555 (Cl) $R_f$=0.71 (silica gel, DCM/cyc/MeOH/$NH_3$ 70:15:15:2)

10.75b (S)-2-(4-amino-3-chloro-5'-trifluoromethyl-benzyl)-4-oxo-4-[4-(2-oxo-1,4-dihydro-2H-quinazolin-3-yl)-piperidin-1-yl]-butanoic acid A solution of 558 mg (113.02 mmol) lithium hydroxide hydrate in 12 mL water was added to a solution of 4.8 g (8.68 mmol) methyl (S)-2-(4-amino-3-chloro-5-trifluoromethyl-benzyl)-4-oxo-4-[4-(2-oxo-1,4-dihydro-2H-quinazolin-3-yl)-piperidin-1-yl]-butanoate in 28 mL THF and the reaction mixture was stirred for 7 h at RT. It was evaporated down i.vac., combined with 100 mL water, acidified with 1 M HCl and the precipitate formed was suction filtered. The residue was dissolved in EtOAc, extracted with 15% $K_2CO_3$ solution and the aqueous phase was again acidified with 1 M HCl. The precipitate formed was suction filtered and dried.

Yield: 4.2 g (90% of theory) ESI-MS: $(M+H)^+$=539/541 (Cl) $R_f$=0.09 (silica gel, DCM/cyc/MeOH/$NH_3$ 70:15:15:2)

10.75c (S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione The crude product was obtained analogously to 10.75a from 500 mg (0.93 mmol) (S)-2-(4-amino-3-chloro-5-trifluoromethyl-benzyl)-4-oxo-4-[4-(2-oxo-1,4-dihydro-2H-quinazolin-3-yl)-piperidin-1-yl]-butanoic acid and 180 mg (0.98 mmol) 1-methyl-4-piperidin-4-yl-piperazine. After being worked up as described it was purified first by chromatography (silica gel, gradient: DCM to DCM/MeOH/$NH_3$ 70:27:3) and then by HPLC.

Yield: 120 mg (18% of theory) ESI-MS: $(M+H)^+$=704/706 (Cl) $R_f$=0.43 (silica gel, DCM/cyc/MeOH/$NH_3$ 70:15:15:2) Retention time (HPLC): 5.6 min (method A)

Example 10.76

(S)-2-(4-amino-3-chloro-5-trifluoromethyl-benzyl)-1-[4-(4-methyl-piperazin-1-yl)-piperidin-1-yl]-4-[4-(5-oxo-3-phenyl-4,5-dihydro-1,2,4-triazol-1-yl]-piperidin-1-yl)-butan-1,4-dione

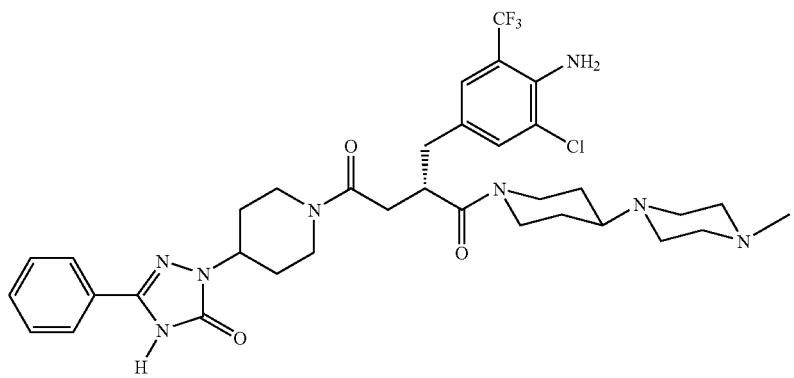

10.76a methyl (S)-2-(4-amino-3-chloro-5-trifluoromethyl-benzyl)-4-oxo-4-[4-(5-oxo-3-phenyl-4,5-dihydro-1,2,4-triazol-1-yl)-piperidin-1-yl]-butanoate The desired product was obtained analogously to 10.75a from 3.0 g (8.31 mmol) 1-methyl (S)-2-(4-amino-3-chloro-5-trifluoromethyl-benzyl)-succinate and 3.55 g (9.45 mmol) 5-phenyl-2-piperidin-4-yl-2,4-dihydro-1,2,4-triazol-3-one.

Yield: 2.5 g (50% of theory) ESI-MS: $(M+H)^+$=566/568 (Cl) $R_f$=0.67 (silica gel, DCM/cyc/MeOH/NH$_3$ 70:15:15:2)

10.76b (S)-2-(4-amino-3-chloro-5-trifluoromethyl-benzyl)-4-oxo-4-[4-(5-oxo-3-phenyl-4,5-dihydro-1,2,4-triazol-1-yl)-piperidin-1-yl]-butanoic acid The desired product was obtained analogously to 10.75b from 2.5 g (4.42 mmol) methyl (S)-2-(4-amino-3-chloro-5-trifluoromethyl-benzyl)-4-oxo-4-[4-(5-oxo-3-phenyl-4,5-dihydro-1,2,4-triazol-1-yl)-piperidin-1-yl]-butanoate.

Yield: 2.5 g (50% of theory) ESI-MS: $(M+H)^+$=552/554 (Cl) $R_f$=0.14 (silica gel, DCM/cyc/MeOH/NH$_3$ 70:15:15:2)

10.76c (S)-2-(4-amino-3-chloro-5-trifluoromethyl-benzyl)-1-[4-(4-methyl-piperazin-1-yl)-piperidin-1-yl]-4-[4-(5-oxo-3-phenyl-4,5-dihydro-1,2,4-triazol-1-yl)-piperidin-1-yl]-butan-1,4-dione The crude product was obtained analogously to 10.75a from 500 mg (0.91 mmol) (S)-2-(4-amino-3-chloro-5-trifluoromethyl-benzyl)-4-oxo-4-[4-(5-oxo-3-pheny 1-4,5-dihydro-1,2,4-triazol-1-yl)-piperidin-1-yl]-butanoic acid and 180 mg (0.98 mmol) 1-methyl-4-piperidin-4-yl-piperazine. After being worked up as described it was purified by chromatography (silica gel, gradient: DCM to DCM/MeOH/NH$_3$ 70:27:3).

Yield: 350 mg (54% of theory) ESI-MS: $(M+H)^+$=717/719 (Cl) $R_f$=0.44 (silica gel, DCM/cyc/MeOH/NH$_3$ 70:15:15:2) Retention time (HPLC): 5.6 min (method A)

Example 10.77

(S)-2-(4-amino-3-chloro-5-trifluoromethyl-benzyl)-1-[4-(4-methyl-piperazin-1-yl)-piperidin-1-yl]-4-[4-(2-oxo-1,2-dihydro-imidazo[4,5-c]quinoline-3-yl)-piperidin-1-yl]-butan-1,4-dione 10.77a methyl (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoate The desired product was obtained analogously to 10.75a from 3.0 g (8.31 mmol) 1-methyl (S)-2-(4-amino-3-chloro-5-trifluoromethyl-benzyl)-succinate and 2.55 g (9.40 mmol) 3-piperidin-4-yl-1,3-dihydro-imidazo[4,5-c]quinolin-2-one.

Yield: 5.2 g (100% of theory) ESI-MS: $(M+H)^+$=590/592 (Cl) $R_f$=0.66 (silica gel, DCM/cyc/MeOH/NH$_3$ 70:15:15:2)

10.77b (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoic acid The desired product was obtained analogously to 10.75b from 5.2 g (8.81 mmol) methyl (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoate.

Yield: 2.75 g (54% of theory) ESI-MS: $(M+H)^+$=576/578 (Cl) $R_f$=0.09 (silica gel, DCM/cyc/MeOH/NH$_3$ 70:15:15:2)

10.77c (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-imidazo[4,5-c]quinolin-3-yl)-piperidin-1-yl]-butan-1,4-dione The crude product was obtained analogously to 10.75a from 500 mg (0.87 mmol) (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoic acid and 170 mg (0.93 mmol) 1-methyl-4-piperidin-4-yl-piperazine. After being worked up as described the residue was combined with diisopropylether and treated in an ultrasound bath, the product was suction filtered and dried.

Yield: 520 mg (81% of theory) ESI-MS: $(M+H)^+$=741/743 (Cl) $R_f$=0.40 (silica gel, DCM/cyc/MeOH/NH$_3$ 70:15:15:2) Retention time (HPLC): 4.5 min (method A)

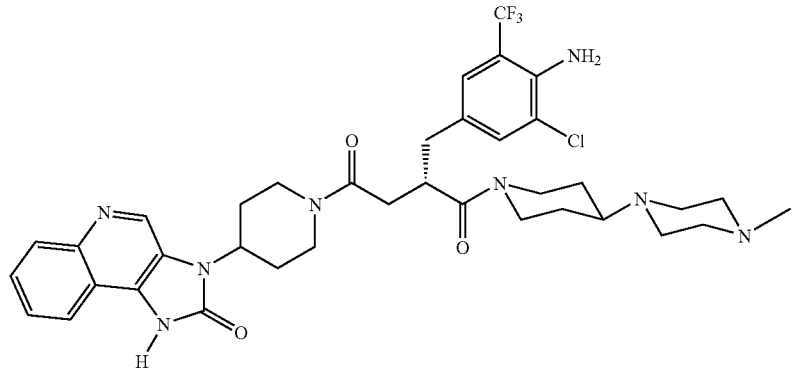

Example 10.78

(S)-2-(4-amino-3-chloro-5-trifluoromethyl-benzyl)-1-[4-(4-methyl-piperazin-1-yl)-piperidin-1-yl]-4-[4-(2-oxo-1,2-dihydro-4H-thieno[3,4-d]pyrimidin-3-yl)-piperidin-1-yl]-butan-1,4-dione

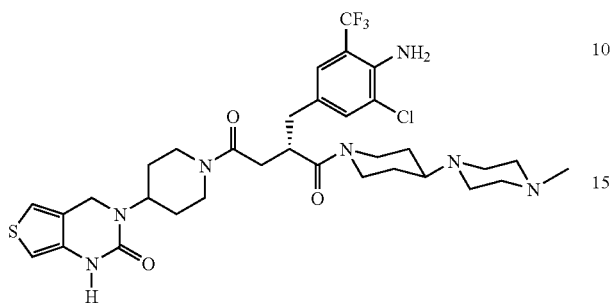

10.78a methyl (S)-2-(4-amino-3-chloro-5-trifluoromethyl-benzyl)-4-oxo-4-[4-(2-oxo-1,2-dihydro-4H-thieno[3,4-d]pyrimidin-3-yl)-piperidin-1-yl]-butanoate The desired product was obtained analogously to 10.75a from 3.0 g (8.31 mmol) 1-methyl (S)-2-(4-amino-3-chloro-5-trifluoromethyl-benzyl)-succinate and 3.34 g (9.51 mmol) 3-piperidin-4-yl-3,4-dihydro-1H-thieno[3,4-d]pyrimidin-2-one.

Yield: 2.2 g (45% of theory) ESI-MS: (M+H)$^+$=559/561 (Cl) R$_f$=0.56 (silica gel, DCM/cyc/MeOH/NH$_3$ 70:15:15:2)

10.78b (S)-2-(4-amino-3-chloro-5-trifluoromethyl-benzyl)-4-oxo-4-[4-(2-oxo-1,2-dihydro-4H-thieno[3,4-d]pyrimidin-3-yl)-piperidin-1-yl]-butanoic acid The desired product was obtained analogously to 10.75b from 2.2 g (3.94 mmol) methyl (S)-2-(4-amino-3-chloro-5-trifluoromethyl-benzyl)-4-oxo-4-[4-(2-oxo-1,2-dihydro-4H-thieno[3,4-d]pyrimidin-3-yl)-piperidin-1-yl]-butanoate.

Yield: 1.10 g (51% of theory) ESI-MS: (M+H)$^+$=545/547 (Cl) R$_f$=0.24 (silica gel, DCM/cyc/MeOH/NH$_3$ 70:15:15:2)

10.78c (S)-2-(4-amino-3-chloro-5-trifluoromethyl-benzyl)-1-[4-(4-methyl-piperazin-1-yl)-piperidin-1-yl]-4-[4-(2-oxo-1,2-dihydro-4H-thieno[3,4-d]pyrimidin-3-yl)-piperidin-1-yl]-butan-1,4-dione The crude product was obtained analogously to 10.75a from 500 mg (0.92 mmol) (S)-2(4-amino-3-chloro-5-trifluoromethyl-benzyl)-4-oxo-4-[4-(2-oxo-1,2-dihydro-4H-thieno[3,4-d]pyrimidin-3-yl)-piperidin-1-yl]-butanoic acid and 180 mg (0.98 mmol) 1-methyl-4-piperidin-4-yl-piperazine. After being worked up as described it was purified by chromatography (silica gel, gradient: DCM to DCM/MeOH/NH$_3$ 70:27:3).

Yield: 100 mg (81% of theory) ESI-MS: (M+H)$^+$=710/712 (Cl) R$_f$=0.43 (silica gel, DCM/cyc/MeOH/NH$_3$ 70:15:15:2) Retention time (HPLC): 5.5 min (method A)

Example 10.79

(S)-2-(4-amino-3-chloro-5-trifluoromethyl-benzyl)-1-[4-(5-methyl-2,5-diaza-bicyclo[2.2.1]hept-2-yl)-piperidin-1-yl]-4-[4-(2-oxo-1,2,4,5-tetrahydro-1,3-benzodiazepin-3-yl)-piperidin-1-yl]-butan-1,4-dione

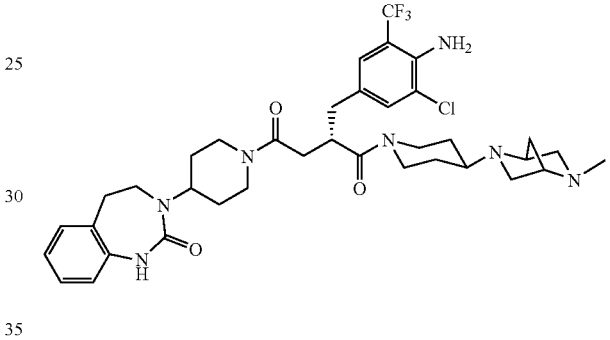

Prepared analogously to Example 10.26 from 100 mg (0.18 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid and 39.1 mg (0.2 mmol) 2-methyl-5-piperidin-4-yl-2,5-diaza-bicyclo[2.2.1]heptane using triethylamine as the base.

Yield: 83 mg (63% of theory) ESI-MS: (M+H)$^+$=730/732 (Cl) Retention time (HPLC): 5.6 min (method A)

The following compounds may be prepared analogously to the methods described:

| Example | Structure |
|---|---|
| 10.80 | 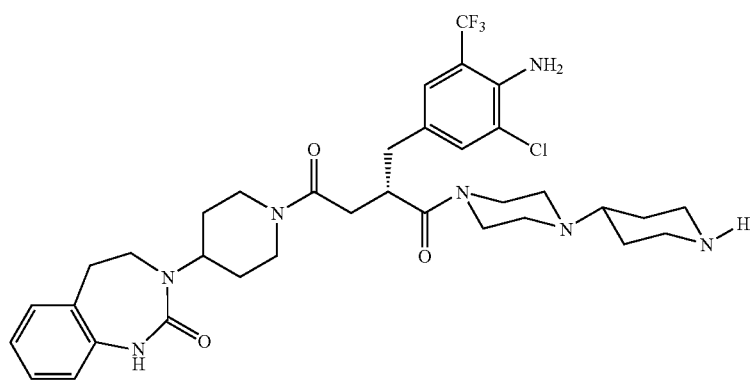 |

| Example | Structure |
|---|---|
| 10.81 | 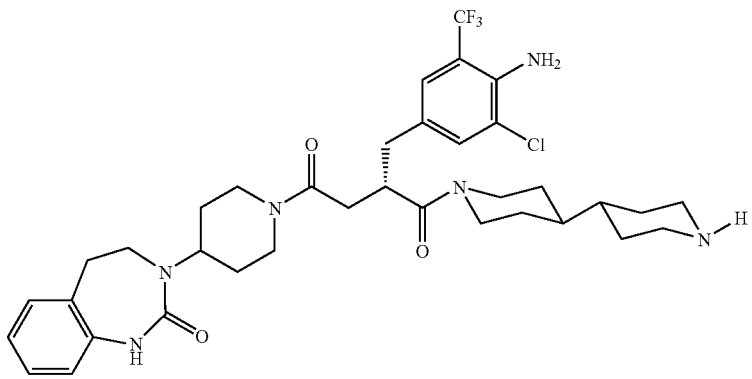 |

Example 11

(S)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione

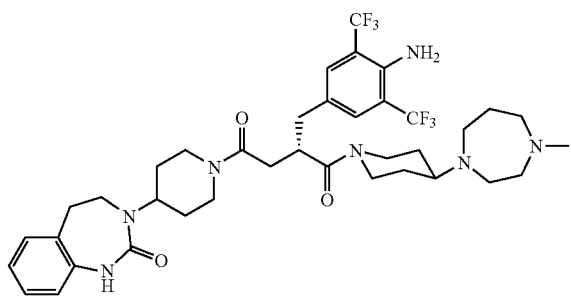

11a 4-amino-3,5-bis-trifluoromethyl-benzaldehyde

A solution of 5 g (19.67 mmol) 4-amino-3,5-bis-trifluoromethyl-benzonitrile in 30 mL formic acid was shaken in 10 equal portions in pressurised containers for 20 h at 110° C.

The individual portions were combined, filtered, washed with formic acid and evaporated down i.vac. The residue was purified by chromatography (silica gel, PE/EtOAc 9:1).

Yield: 3.8 g (75% of theory) ESI-MS: (M−H)=256

11b 1-methyl 2-[1-(4-amino-3,5-bis-trifluoromethyl-phenyl)-meth-(E)-ylidene]-succinate 12.79 g (32.6 mmol) 1-methyl 2-(triphenyl-$\square^5$-phosphanylidene)-succinate were added to a solution of 4.2 g (16.33 mmol) 4-amino-3,5-bis-trifluoromethyl-benzaldehyde in 80 mL THF and the reaction mixture was heated to 40° C. for 120 h. It was evaporated down i. vac., the residue was combined with water and EtOAc, the organic phase was separated off, washed with water and extracted three times with in each case 80 mL 5% $K_2CO_3$ solution. The combined aqueous phases were acidified with conc. HCl, the oily precipitate was extracted twice with in each case 100 mL EtOAc and dried over $Na_2SO_4$. After the desiccant and solvent had been eliminated the desired product was obtained.

Yield: 5.9 g (97% of theory) EI: (M)$^+$=371

11c 1-methyl (S)-2-(4-amino-3,5-bis-trifluoromethyl-benzyl)-succinate

Prepared analogously to Example 9g from 5.9 g 1-methyl 2-[1-(4-amino-3,5-bis-trifluoromethyl-phenyl)-meth-(E)-ylidene]-succinate.

Yield: 5.9 g (97% of theory) ESI-MS: (M+H)$^+$=374

11d methyl (S)-2-(4-amino-3,5-bis-trifluoromethyl-benzyl)-4-oxo-4-[4-(2-oxo-1,2,4,5-tetrahydro-1,3-benzodiazepin-3-yl)-piperidin-1-yl]-butanoate Prepared analogously to Example 9h from 4.40 g (11.79 mmol) 1-methyl (S)-2-(4-amino-3,5-bis-trifluoromethyl-benzyl)-succinate and 2.89 g (11.78 mmol) 3-piperidin-4-yl-1,3,4,5-tetrahydro-1,3-benzodiazepin-2-one.

Yield: 6.75 g (95% of theory) ESI-MS: (M+H)$^+$=601 $R_f$=0.13 (silica gel, PE/EtOAc 1:1)

11e (S)-2-(4-amino-3,5-bis-trifluoromethyl-benzyl)-4-oxo-4-[4-(2-oxo-1,2,4,5-tetrahydro-1,3-benzodiazepin-3-yl)-piperidin-1-yl]-butanoic acid A solution of 0.72 g (16.75 mmol) lithium hydroxide hydrate in 30 mL water was added to a solution of 6.7 g (11.16 mmol) methyl (S)-2-(4-amino-3,5-bis-trifluoromethyl-benzyl)-4-oxo-4-[4-(2-oxo-1,2,4,5-tetrahydro-1,3-benzodiazepin-3-yl)-piperidin-1-yl]-butanoate in 50 mL THF at RT and the reaction mixture was stirred for 5 h at RT. The THF was eliminated i. vac., the aqueous solution cooled to 10° C. and adjusted to pH 1 with conc. HCl, during which time the product was precipitated. This was suction filtered and dried at 65° C. The dried substance was combined with 300 mL diisopropylether, stirred overnight, suction filtered, washed with diisopropylether and dried.

Yield: 5.6 g (86% of theory) ESI-MS: (M+H)$^+$=587

11f (S)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione 197 mg (1.0 mmol) 1-methyl-4-piperidin-4-yl-perhydro-1,4-diazepine were added to a solution of 400 mg (0.68 mmol) (S)-2-(4-amino-3,5-bis-trifluoromethyl-benzyl)-4-oxo-4-[4-(2-oxo-1,2,4,5-tetrahydro-1,3-benzodiazepin-3-yl)-piperidin-1-yl]-butanoic acid, 241 mg (0.75 mmol) TBTU and 0.25 mL (1.8 mmol) triethylamine in 5 mL DMF and the reaction mixture was stirred overnight at RT. The reaction solution was slowly poured into 150 mL of 15% $K_2CO_3$ solution, the precipitated product was suction filtered and dried in the air. The crude product was purified by chromatography (silica gel, gradient: DCM to MeOH/NH$_3$ 95:5).

Yield: 400 mg (77% of theory) ESI-MS: (M+H)$^+$=767 R$_f$=0.2 (silica gel, DCM/MeOH/NH$_3$ 85:15:1.5) Retention time (HPLC): 5.6 min (method A)

The following compounds were prepared analogously from in each case 400 mg (Example 11.7: 387 mg) (S)-2-(4-amino-3,5-bis-trifluoromethyl-benzyl)-4-oxo-4-[4-(2-oxo-1,2,4,5-tetrahydro-1,3-benzodiazepin-3-yl)-piperidin-1-yl]-butanoic acid and the corresponding amount of amine:

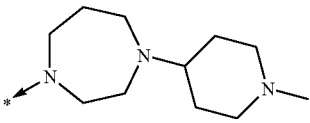

| Example | R | Yield (%) | Mass spectrum | Retention time HPLC (method) |
|---|---|---|---|---|
| 11.1 | 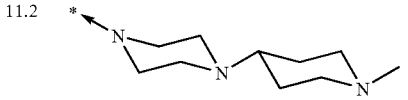 | 52 | 766 [M + H]$^+$ | 5.7 min (A) |
| 11.2 | 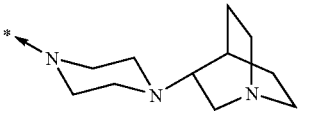 | 64 | 752 [M + H]$^+$ | 5.6 min (A) |
| 11.3 | 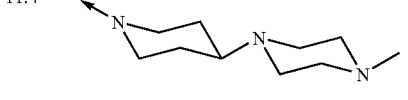 | 21 | 764 [M + H]$^+$ | 6.2 min (A) |
| 11.4 | 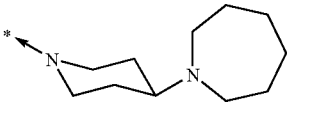 | 74 | 752 [M + H]$^+$ | 6.0 min (A) |
| 11.5 | 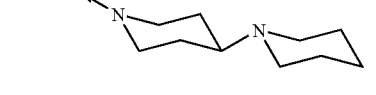 | 55 | 751 [M + H]$^+$ | 6.8 min (A) |
| 11.6 | 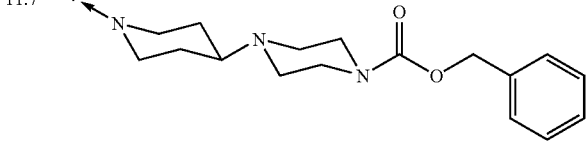 | 62 | 737 [M + H]$^+$ | 6.7 min (A) |
| 11.7 |  | 100 | 872 [M + H]$^+$ | |

Example 11.7 was further reacted without purification.

Example 11.8

(S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione

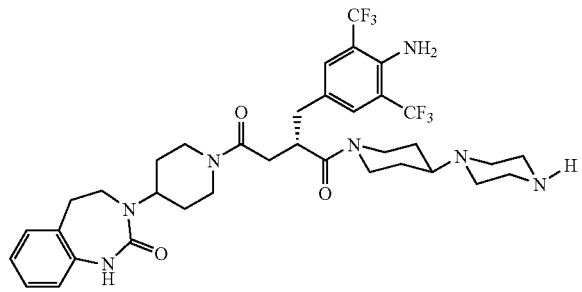

A solution of 560 mg (0.64 mmol) benzyl 4-(1-{(S)-2-(4-amino-3,5-bis-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-piperazin-1-carboxylate (crude product from Example 11.7) in 50 mL MeOH was combined with 200 mg 10% Pd/C and the reaction mixture was hydrogenated for 3 h at RT and 3 bar $H_2$. The catalyst was suction filtered, the solution evaporated down i.vac. and the residue purified by chromatography (silica gel, gradient: DCM to DCM/MeOH/$NH_3$ 10:85:5).

Yield: 230 mg (49% of theory) ESI-MS: $(M+H)^+=738$ $R_f=0.27$ (silica gel, DCM/MeOH/$NH_3$ 50:50:5)

The following compounds may be prepared analogously:

| Example | Structure |
|---|---|
| 11.9 | 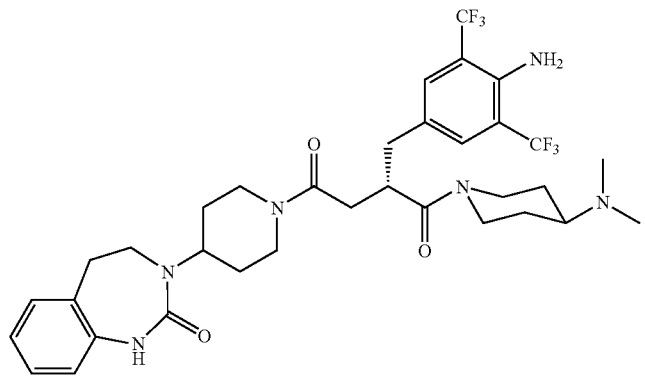 |
| 11.10 | 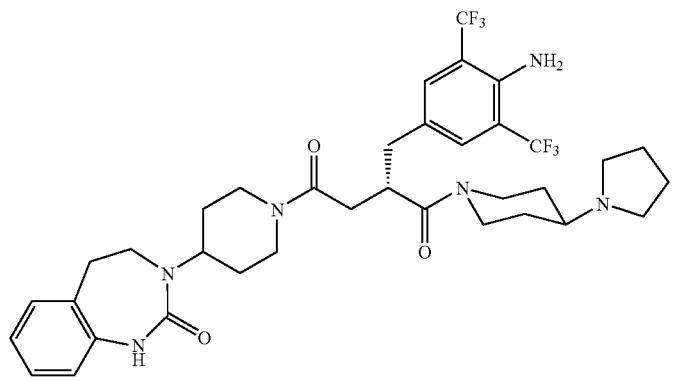 |

| Example | Structure |
|---|---|
| 11.11 | 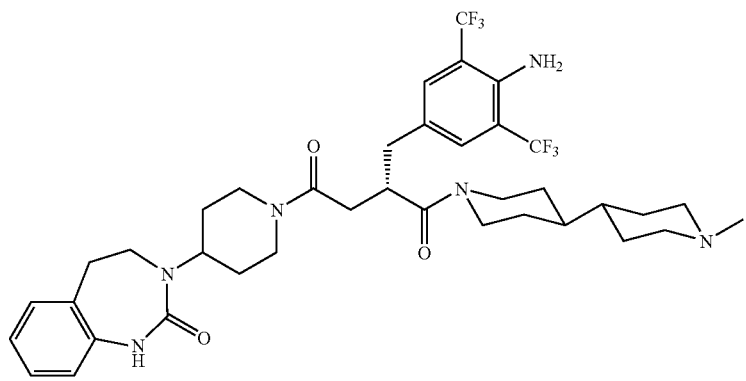 |
| 11.12 | 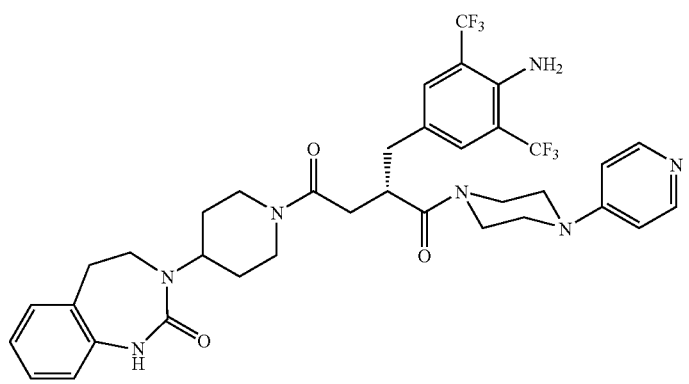 |
| 11.13 | 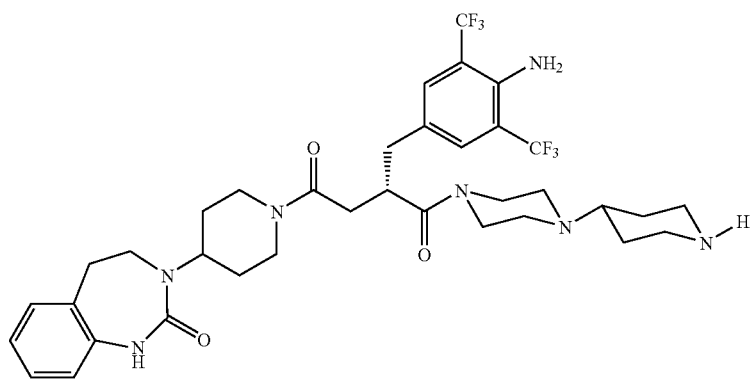 |
| 11.14 | 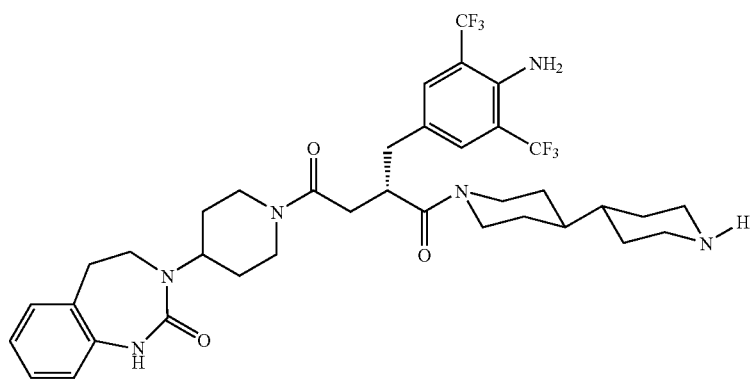 |

Example 12

4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(4-methyl-piperazin-1-yl)-piperidin-1-yl]-2-oxo-ethyl}-amide

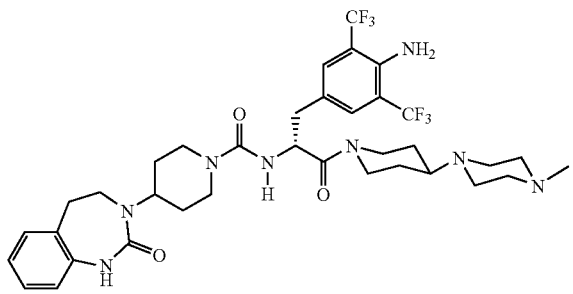

12a (4-amino-3,5-bis-trifluoromethyl-phenyl)-methanol

Under a nitrogen atmosphere 1.06 g (28 mmol) NaBH$_4$ were added batchwise to a solution of 7.2 g (28.0 mmol) 4-amino-3,5-bis-trifluoromethyl-benzaldehyde (Example 11a) in 100 mL MeOH and the reaction mixture was stirred for 2 h at RT. The reaction solution was acidified with 1 M HCl, evaporated down i.vac., the residue was combined with 150 mL water and 150 mL EtOAc, the organic phase was separated off and dried over Na$_2$SO$_4$. After the desiccant and solvent had been eliminated the residue was purified by chromatography (silica gel, PE/EtOAc 9:1).

Yield: 5.1 g (70% of theory) ESI-MS: (M−H)$^−$=258 R$_f$=0.15 (silica gel, PE/EtOAc 9:1)

12b 4-chloromethyl-2,6-bis-trifluoromethyl-phenylamine 4.35 mL (60 mmol) thionyl chloride were added to a solution of 5.1 g (19.68 mmol) (4-amino-3,5-bis-trifluoromethyl-phenyl)-methanol in 80 mL DCM at RT and the reaction mixture was stirred for 3 h at RT. The reaction solution was poured onto ice and ice-cold NaHCO$_3$ solution, the organic phase was separated off and dried over Na$_2$SO$_4$. After the desiccant and solvent had been eliminated the residue was further reacted without purification.

Yield: 5.4 g (99% of theory) R$_f$=0.55 (silica gel, PE/EtOAc 4:1)

12c diethyl 2-acetylamino-2-(4-amino-3,5-bis-trifluoromethyl-benzyl)-malonate

Under a nitrogen atmosphere 4.34 g (20.0 mmol) diethyl 2-acetylamino-malonate were added to a solution of sodium ethoxide (prepared by reacting 0.46 g (20.0 mmol) sodium with EtOH) in 50 mL dry EtOH and the reaction mixture was stirred for 15 min at RT. Then a solution of 5.4 g (19.45 mmol) of 4-chloromethyl-2,6-bis-trifluoromethyl-phenylamine in 100 mL 1,4-dioxane was added dropwise within 5 min, the reaction solution was stirred for a further 4 h at RT, combined with 1 L water and stirred overnight. The precipitate formed was filtered off, washed with water and dried in the air.

Yield: 5.2 g (57% of theory) ESI-MS: (M+H)$^+$=459 R$_f$=0.65 (silica gel, PE/EtOAc 2:1)

12d monoethyl 2-acetylamino-2-(4-amino-3,5-bis-trifluoromethyl-benzyl)-malonate 2.0 mL 6 M NaOH solution were added to a solution of 5.1 g (11.13 mmol) diethyl 2-acetylamino-2-(4-amino-3,5-bis-trifluoromethyl-benzyl)-malonate in 80 mL dry EtOH and the reaction mixture was stirred overnight at RT. It was evaporated down i. vac., the residue was taken up in 150 mL water, acidified with 1 M HCl, the aqueous phase was extracted with 150 mL EtOAc and the organic phase was dried over Na$_2$SO$_4$. After the desiccant and solvent had been eliminated the residue was further reacted without purification.

Yield: 4.3 g (90% of theory) ESI-MS: (M+H)$^+$=431 R$_f$=0.1 (silica gel, PE/EtOAc 2:1)

12e ethyl 2-acetylamino-3-(4-amino-3,5-bis-trifluoromethyl-phenyl)-propionate

A solution of 4.3 g (10.0 mmol) monoethyl 2-acetylamino-2-(4-amino-3,5-bis-trifluoromethyl-benzyl)-malonate in 200 mL isopropanol and 80 mL toluene was heated to 100° C. for 15 h. It was evaporated down i. vac. and the residue was further reacted without being purified.

Yield: 3.8 g (98% of theory) R$_f$=0.60 (silica gel, PE/EtOAc 1:1)

12f ethyl (R)-2-acetylamino-3-(4-amino-3,5-bis-trifluoromethyl-phenyl)-propionate 4 mL Alcalase 2.4 L FG (Novozymes A/S; DK 2880 Bagsvaerd) was added to a solution of 3.65 g (20.5 mmol) Na$_2$HPO$_4$ dihydrate in 130 mL water warmed to 37° C. and the pH was adjusted to 7.5 by the addition of NaH$_2$PO$_4$ dihydrate. Then a solution of 3.8 g (9.84 mmol) ethyl 2-acetylamino-3-(4-amino-3,5-bis-trifluoromethyl-phenyl)-propionate in 40 mL acetone was added dropwise at 37° C. with stirring. The pH value of the reaction mixture was constantly kept in the range from 7.4-7.6 by the addition of 1 M NaOH. After the addition had ended the mixture was stirred for 4 h at 37° C. After cooling to RT the reaction mixture was combined with 300 mL DCM, 300 mL 15% K$_2$CO$_3$ solution and 200 mL water. The organic phase was separated off, washed with 7% K$_2$CO$_3$ solution and dried over Na$_2$SO$_4$. After the desiccant and solvent had been eliminated the crude product (2.2 g) was further reacted without purification. ESI-MS: (M+H)$^+$387 R$_f$=0.60 (silica gel, PE/EtOAc 1:1)

12g ethyl (R)-2-amino-3-(4-amino-3,5-bis-trifluoromethyl-phenyl)-propionate

A solution of 2.2 g of the above crude product was refluxed in 4 M HCl for 1.5 h. It was evaporated down i. vac., the residue was taken up in 50 mL EtOH and 50 mL ethanolic HCl (11.5 M) and the reaction mixture was stirred overnight at RT. It was evaporated down again i.vac., combined with 50 mL 15% K$_2$CO$_3$ solution, extracted with 200 mL EtOAc, the organic phase was separated off and evaporated down i.vac. The crude product (1.8 g) was further reacted without purification. ESI-MS: (M+H)$^+$345 R$_f$=0.50 (silica gel, DCM/MeOH/NH$_3$ 90:10:1)

12h ethyl (R)-3-(4-amino-3,5-bis-trifluoromethyl-phenyl)-2-{[4-(2-oxo-1,2,4,5-tetrahydro-1,3-benzodiazepin-3-yl)-piperidin-1-carbonyl]-amino}-propionate 0.94 g (5.7 mmol) CDT were added to a solution of 1.8 g of the above crude product in 50 mL THF cooled to −5° C. and the reaction mixture was stirred for 45 min at this temperature and after removal of the ice bath stirred for a further 30 min.

Then a solution of 1.28 g (5.2 mmol) 3-piperidin-4-yl-1,3,4,5-tetrahydro-1,3-benzodiazepin-2-one in 50 mL DMF was added. The reaction solution was heated to 80° C. for 2 h, after cooling it was evaporated down i.vac., the residue was combined with 150 mL EtOAc and 150 mL 10% citric acid solution, the organic phase was separated off, washed with 150 mL saturated NaHCO$_3$ solution and dried over Na$_2$SO$_4$. After the desiccant and solvent had been eliminated the crude product (3.7 g) was further reacted without purification. ESI-MS: (M+H)$^+$616 R$_f$=0.25 (silica gel, EtOAc)

12i (R)-3-(4-amino-3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid A solution of 0.4 g (9.5 mmol) lithium hydroxide hydrate in 50 mL water was added to a solution of 3.7 g of the above crude product in 50 mL THF and the reaction mixture was stirred overnight at RT. The THF was eliminated i.vac., mixed with 100 mL water and acidified with 1 M HCl. The precipitated product was suction filtered, washed with 50 mL water and dried in the drying cupboard at 60° C.

Yield: 2.6 g (90% of theory based on 12f) ESI-MS: (M−H)$^−$= 586 Retention time (HPLC): 7.1 min (method A)

12k 4-(2-oxo-1,2,4,5-tetrahydro-1,3-benzodiazepin-3-yl)-piperidin-1-carboxylic acid-{(R)-1-(4-amino-3,5-bis-trifluoromethyl-benzyl)-2-[4-(4-methyl-piperazin-1-yl)-piperidin-1-yl]-2-oxo-ethyl}-amide 155 mg (0.85 mmol) 1-methyl-4-piperidin-4-yl-piperazine were added to a solution of 500 mg (0.85 mmol) (R)-3-(4-amino-3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid, 289 mg (0.9 mmol) TBTU and 0.28 mL (2.0 mmol) triethylamine in 50 mL THF and the reaction mixture was stirred overnight at RT. It was evaporated down i. vac., the residue was taken up in 100 mL EtOAc and 100 mL 10% citric acid solution, the organic phase was separated off and the solvent was eliminated i.vac. Then the residue was purified by chromatography (silica gel, gradient: DCM to DCM/MeOH/NH$_3$ 10:85:5).

Yield: 570 mg (89% of theory) ESI-MS: (M+H)$^+$=753 R$_f$=0.5 (silica gel, DCM/MeOH/NH$_3$ 85:15:1.5)

The following compounds were prepared analogously from (R)-3-(4-amino-3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid and the corresponding amount of amine:

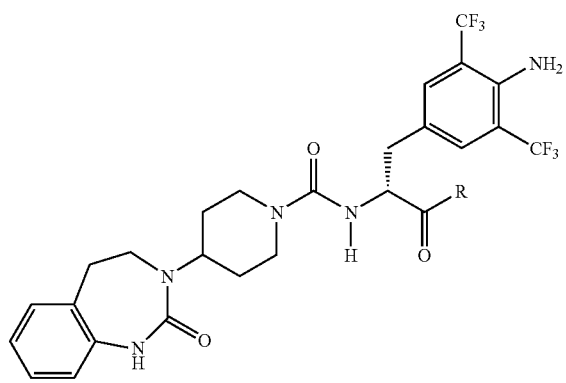

| Example | R | Yield (%) | Mass spectrum | R$_f$ value on silica gel (eluant) |
|---|---|---|---|---|
| 12.1 | ![structure] | 89 | 753 [M + H]$^+$ | 0.4 (DCM/MeOH/NH$_3$ 85:15:1.5) |
| 12.2 | ![structure] | 64 | 738 [M + H]$^+$ | 0.5 (DCM/MeOH/NH$_3$ 85:15:1.5) |
| 12.3 | ![structure] | 80 | 873 [M + H]$^+$ | |

Example 12.3 was further reacted without purification.

Example 12.4

4-(2-oxo-1,2,4,5-tetrahydro-1,3-benzodiazepin-3-yl)-piperidin-1-carboxylic acid-[(R)-1-(4-amino-3,5-bis-trifluoromethyl-benzyl)-2-oxo-2-(4-piperazin-1-yl-piperidin-1-yl)-ethyl]-amide

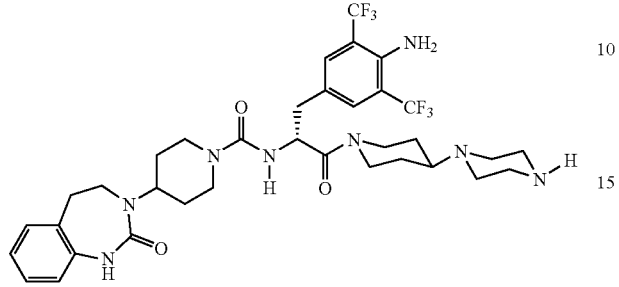

Prepared analogously to Example 11.8 from 450 mg (0.52 mmol) benzyl 4-[1-((R)-3-(4-amino-3,5-bis-trifluoromethyl-phenyl)-2-{[4-(2-oxo-1,2,4,5-tetrahydro-1,3-benzodiaz-epin-3-yl)-piperidin-1-carbonyl]-amino}-propionyl)-piperidin-4-yl]-piperazin-1-carboxylate (crude product from Example 12.3).

Yield: 200 mg (53% of theory) ESI-MS: $(M+H)^+=739$
$R_f=0.3$ (silica gel, DCM/MeOH/NH$_3$ 50:50:5)

The following compounds may be prepared analogously:

| Example | Structure |
|---|---|
| 12.5 | 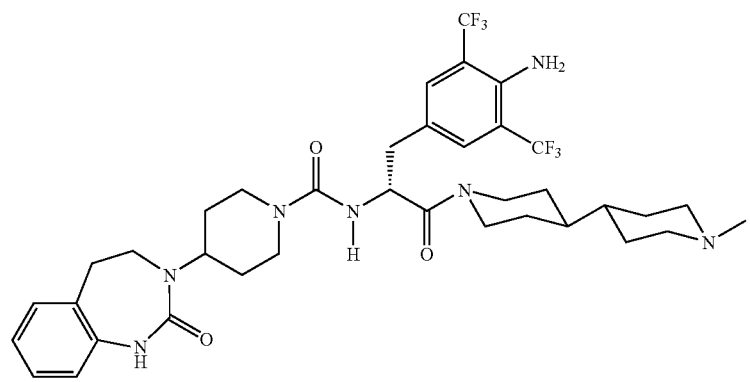 |
| 12.6 | 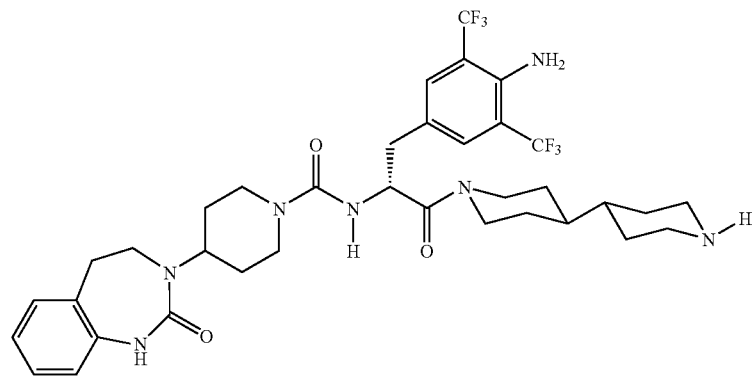 |
| 12.7 | 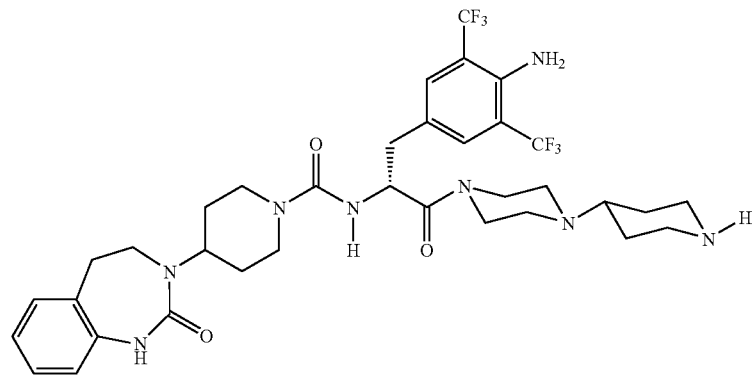 |

| Example | Structure |
|---|---|
| 12.8 | 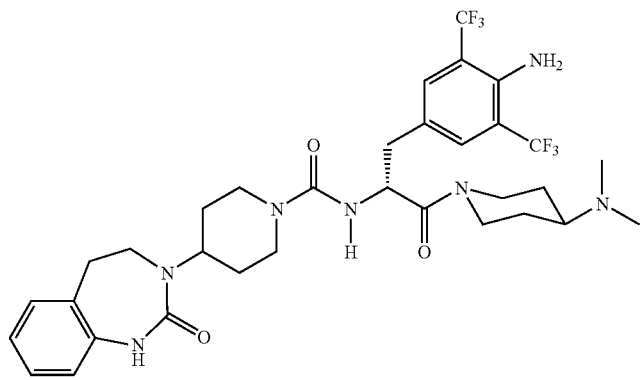 |
| 12.9 | 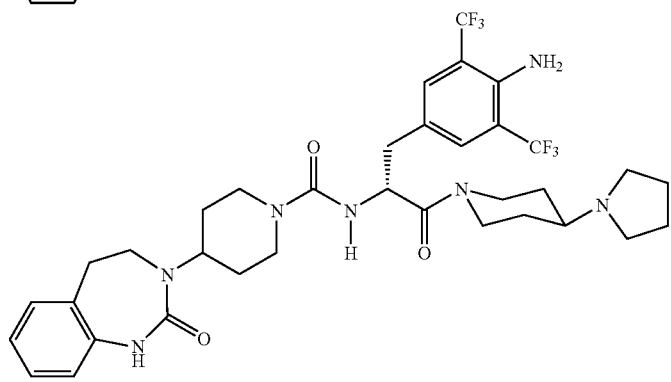 |
| 12.10 | 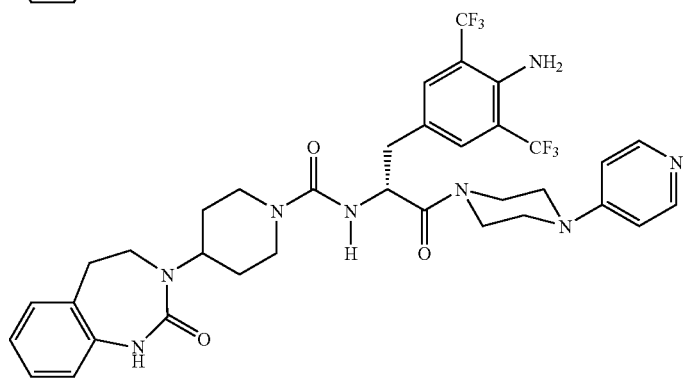 |

Example 13

(R)-1-(4-amino-3-chloro-5-trifluoromethyl-benzyl)-2-[4-(4-methyl-piperazin 1-yl)-piperidin-1-yl]-2-oxo-ethyl 4-(2-oxo-1,2,4,5-tetrahydro-1,3-benzodiazepin-3-yl)-piperidin-1-carboxylate

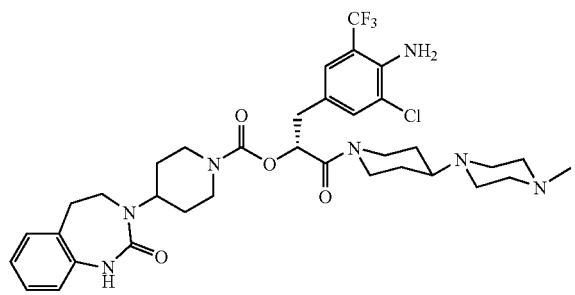

13a (S)-3-[(R)-3-(4-amino-3-chloro-5-trifluoromethyl-phenyl)-2-benzyloxy-propionyl]-4-benzyl-oxazolidin-2-one Under a nitrogen atmosphere a solution of 1.33 g (4.1 mmol) (S)-4-benzyl-3-(2-benzyloxy-acetyl)-oxazolidin-2-one in 15 mL THF, cooled to −60° C., was added dropwise within 10 min to a solution of 5.1 mL (5.1 mmol, 1 M in THF) sodium-bis-trimethylsilylamide in 4 mL THF cooled to −60° C. and the reaction mixture was stirred for for 1 h at this temperature. Then it was cooled to −70° C. and a solution of 2.0 g (8.2 mmol) 2-chloro-4-chloromethyl-6-trifluoromethyl-phenylamine (Example 2a) in 15 mL of THF was slowly added dropwise. The reaction solution was kept for 1 h at −70° C. and then allowed to warm up to RT within 2 h. 50 mL saturated NH₄Cl solution were added, the mixture was extracted with 50 mL EtOAc, the organic phase was separated off, the aqueous phase was extracted again with 50 mL EtOAc, the combined organic phases were washed with 100 mL saturated NaCl and 1 M KHSO₄ solution and dried over Na$_2$SO$_4$. After the desiccant and solvent had been eliminated the residue was purified by chromatography (silica gel, PE/EtOAc 4:1).

Yield: 2.1 g (96% of theory) ESI-MS: (M+H)$^+$=533/535 R$_f$=0.15 (silica gel, PE/EtOAc 4:1)

13b (R)-3-(4-amino-3-chloro-5-trifluoromethyl-phenyl)-2-benzyloxy-propionic acid A solution of 0.34 g (8.0 mmol) lithium hydroxide hydrate and 1.38 mL (16 mmol, 35% in water) H$_2$O$_2$ in 25 mL water was added to a solution, cooled to 0° C., of 2.1 g (3.94 mmol) (S)-3-[(R)-3-(4-amino-3-chloro-5-trifluoromethyl-phenyl)-2-benzyloxy-propionyl]-4-benzyl-oxazolidin-2-one in 50 mL THF and the reaction mixture was stirred for 2 h at 0° C. 5 mL of saturated Na$_2$SO$_3$ solution and 5 mL of saturated NaHCO$_3$ solution were added, the mixture was stirred for another 30 min and then the THF was eliminated i.vac. The aqueous residue was extracted twice with 50 mL EtOAc in each case and the combined organic phases were dried over MgSO$_4$. After the desiccant and solvent had been eliminated the crude product was further reacted without purification.

13c (R)-3-(4-amino-3-chloro-5-trifluoromethyl-phenyl)-2-benzyloxy-1-[4-(4-methyl-piperazin-1-yl)-piperidin-1-yl]-propan-1-one 1.35 g (4.20 mmol) TBTU, 0.70 mL (5.0 mmol) triethylamine and 0.75 g (4.01 mmol) 1-methyl-4-piperidin-4-yl-piperazine were added to a solution of 1.5 g (4.01 mmol) (R)-3-(4-amino-3-chloro-5-trifluoromethyl-phenyl)-2-benzyloxy-propionic acid in 50 mL THF and the reaction mixture was stirred overnight at RT. The reaction solution was evaporated down i.vac., the residue was combined with 200 mL EtOAc and 200 mL saturated NaHCO$_3$ solution, the organic phase was separated off and extracted with 100 mL of 5% citric acid solution. The citric acid extract was made alkaline with K$_2$CO$_3$ and extracted twice with 100 mL EtOAc in each case. The combined organic phases were evaporated down i.vac. and the residue further reacted without purification.

Yield: 1.75 g (81% of theory) ESI-MS: (M+H)$^+$=539/541 (Cl) Retention time (HPLC): 5.9 min (method A)

13d (R)-3-(4-amino-3-chloro-5-trifluoromethyl-phenyl)-2-hydroxy 1-[4-(4-methyl-piperazin-1-yl)-piperidin-1-yl]-propan-1-one 0.32 mL (2.5 mmol) chloro-trimethyl-silane were added to a suspension of 450 mg (0.84 mmol) (R)-3-(4-amino-3-chloro-5-trifluoromethyl-phenyl)-2-benzyloxy-1-[4-(4-methyl-piperazin-1-yl)-piperidin-1-yl]-propan-1-one and 380 mg (2.5 mmol) NaI in 30 mL acetonitrile and the reaction mixture was stirred for 7 h at 80° C. 30 mL EtOH and 20 mL isopropanol were added, the mixture was stirred for 30 min at RT, 15 mL of NH$_3$ solution were added and the mixture was stirred for a further 30 min. It was evaporated down i. vac., the residue was combined with 100 mL 15% K$_2$CO$_3$ solution, extracted with 100 mL EtOAc, the organic phase was separated off, washed with 3% Na$_2$SO$_3$ solution and trocknete over Na$_2$SO$_4$. After the desiccant and solvent had been eliminated the residue was further reacted without purification.

Yield: 300 mg (80% of theory) Retention time (HPLC): 3.7 min (method A)

13e 4-(2-oxo-1,2,4,5-tetrahydro-1,3-benzodiazepin-3-yl)-piperidin-1-carbonyl chloride 6 g (12.1 mmol) of phosgene (20 wt. % in toluene) were added to a solution cooled to 0° C. of 2.5 g (10.2 mmol) 3-piperidin-4-yl-1,3,4,5-tetrahydro-1,3-benzodiazepin-2-one and 2.6 mL (14.9 mmol) ethyldiisopropylamine in 75 mL DCM and the reaction mixture was stirred for 30 min at this temperature. It was allowed to warm up to RT, evaporated down i.vac. to approx. 50 mL and filtered through silica gel, washed with 200 mL DCM/EtOAc (1:1) and the combined filtrates were evaporated down again i.vac. The residue was stirred with diisopropylether, suction filtered and dried i.vac.

Yield: 2.42 g (77% of theory) R$_f$=0.43 (silica gel, DCM/EtOAc 1:1)

13f (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidin-1-carboxylate Under a nitrogen atmosphere 31 mg (0.7 mmol) NaH (55% in mineral oil) were added to a solution, cooled to 0° C., of 300 mg (0.67 mmol) (R)-3-(4-amino-3-chloro-5-trifluoromethyl-phenyl)-2-hydroxy-1-[4-(4-methyl-piperazin-1-yl)-piperidin-1-yl]-propan-1-one in 30 mL THF and the reaction mixture was stirred for 30 min at this temperature. Then 246 mg (0.8 mmol) 4-(2-oxo-1,2,4,5-tetrahydro-1,3-benzodiazepin-3-yl)-piperidin-1-carbonylchloride were added batchwise and after the removal of the cooling bath the reaction solution was stirred for 3 h at RT. It was evaporated down i. vac., the residue was combined with 4 mL acetonitrile and purified by HPLC-MS.

Yield: 88 mg (15% of theory) ESI-MS: (M+H)$^+$=720/722 (Cl) Retention time (HPLC): 6.0 min (method A)

The following compounds can be prepared from (R)-3-(4-amino-3-chloro-5-trifluoromethyl-phenyl)-2-benzyloxy-propionic acid and the appropriate amines analogously to Example 13c, 13d and 13f:

| Example | Structure |
|---|---|
| 13.1 | 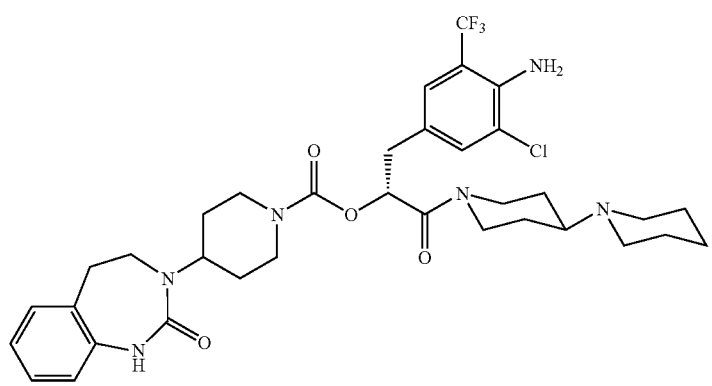 |

| Example | Structure |
|---|---|
| 13.2 | 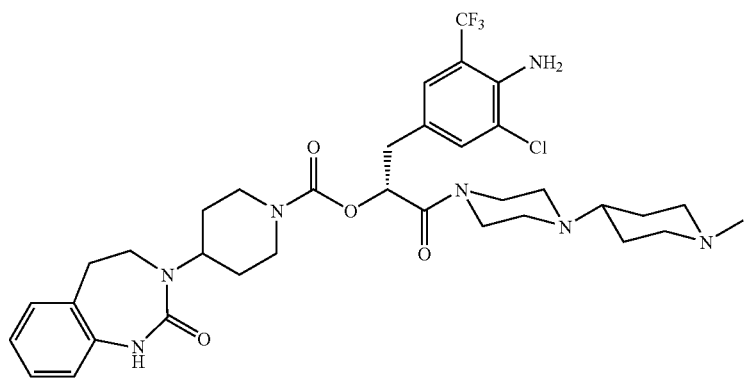 |
| 13.3 | 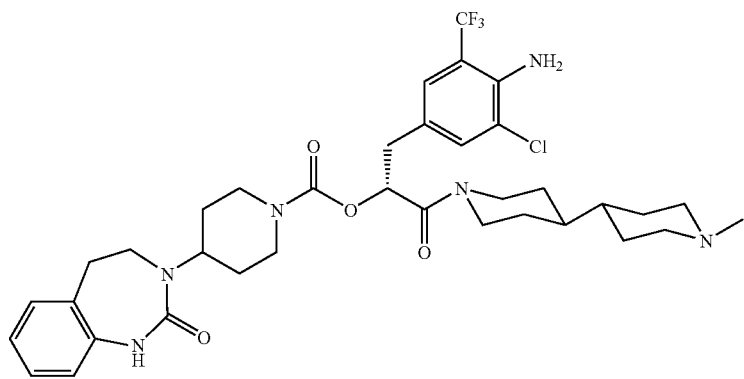 |
| 13.4 | 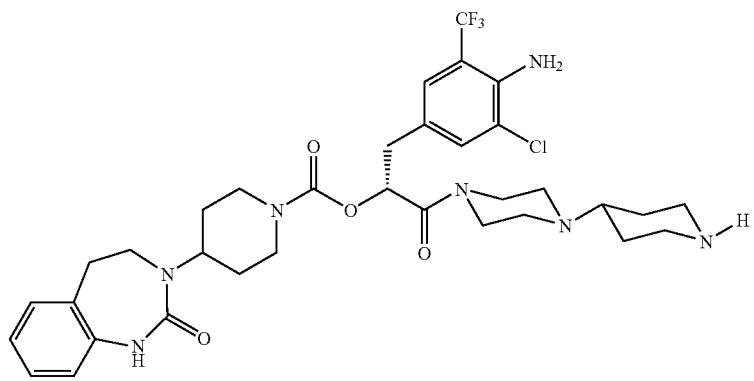 |
| 13.5 | 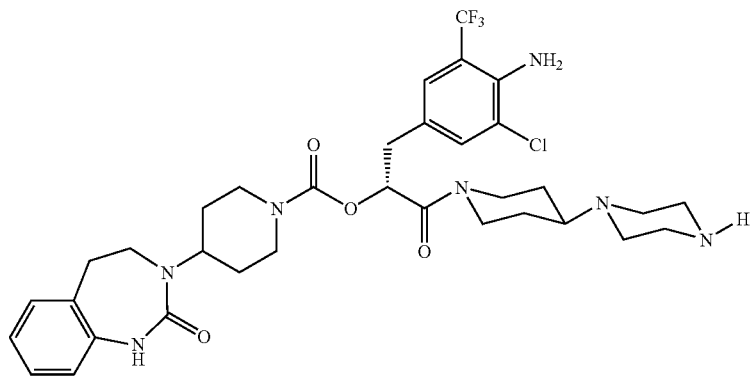 |

-continued
| Example | Structure |
|---|---|
| 13.6 | 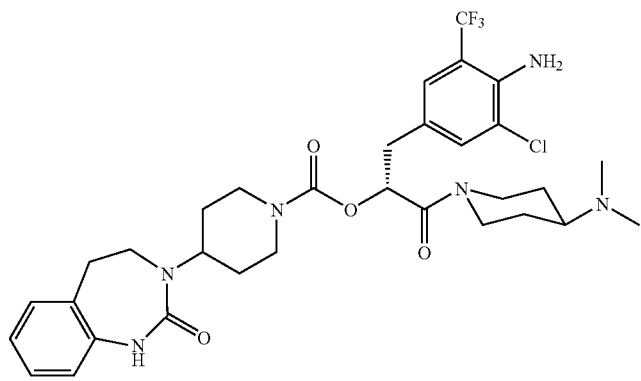 |
| 13.7 | 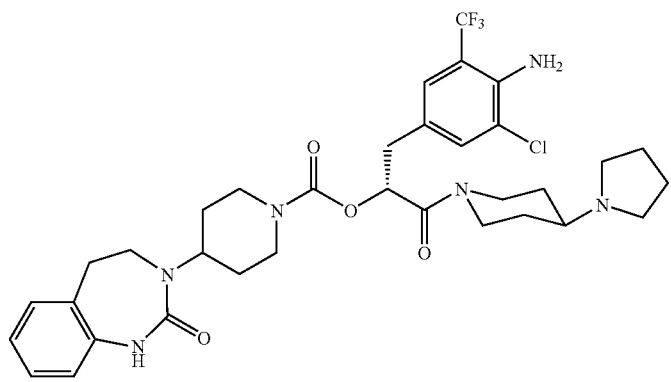 |
| 13.8 | 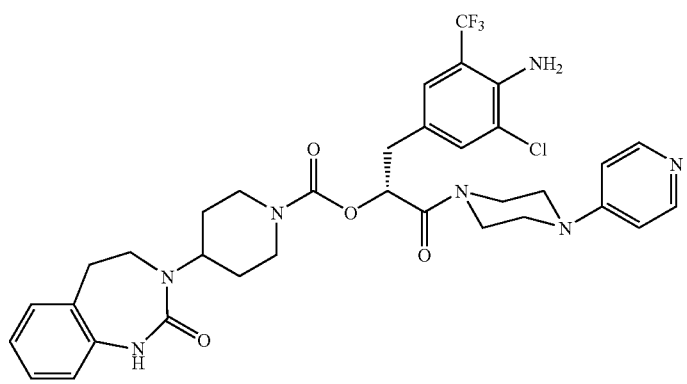 |

| Example | Structure |
|---|---|
| 13.9 | 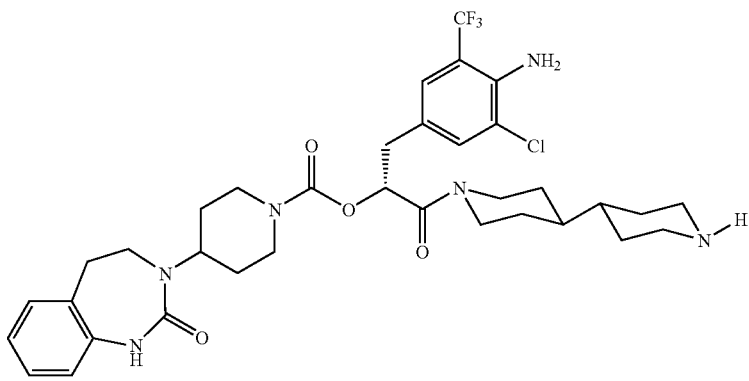 |

Example 14

4-(2-oxo-1,4-dihydro-2H-quinazolin-3-yl)-piperidin-1-carboxylic acid[2-[1,4']bipiperidinyl-1'-yl-1-(4-bromo-3-methyl-benzyl)-2-oxo-ethyl]-amide

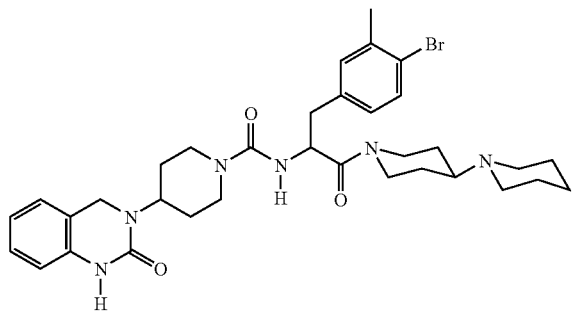

14a ethyl 2-amino-3-(4-bromo-3-methyl-phenyl)-propionate hydrochloride

The mixture of 31.4 g (115 mmol) N-(diphenylmethylene)-glycinethylester, 28.5 g (108 mmol) (4-bromo-3-methylphenyl)-methylbromide, 3.55 g (11.0 mmol) tetrabutylammonium bromide, 116 g (550 mmol) $K_2CO_3$ and 400 mL acetonitrile was refluxed for 4 h. The solid was filtered off, the mother liquor was concentrated by evaporation in vacuo. The residue was taken up in 500 mL tert-butylmethylether and after the addition of 200 mL 10% HCl it was stirred overnight at RT. The organic phase was separated off, the aqueous phase was washed twice more with 50 mL tert-butylmethylether, then neutralised with 10% $Na_2CO_3$ solution while being externally cooled with ice and exhaustively extracted with DCM. The combined organic phases were washed twice more with 50 mL water, dried over $MgSO_4$, filtered through activated charcoal and evaporated down in vacuo. The oily residue remaining was dissolved in 50 mL anhydrous EtOH, combined with ethereal HCl solution and then diluted with tert-butylmethylether to give a total volume of 500 mL. After 20 minutes' stirring a colourless crystalline precipitate was formed which was suction filtered and dried in the air.

Yield: 17.6 g (47% of theory) $R_f$=0.45 (silica gel, DCM/MeOH/$NH_3$ 9:1:0.1)

14b ethyl 3-(4-bromo-3-methyl-phenyl)-2-{[4-(2-oxo-1,4-dihydro-2H-quinazolin-3-yl)-piperidin-1-carbonyl]-amino}-propionate 3.28 g (20.0 mmol) CDT and 2.77 mL (20.0 mmol) triethylamine were added to an ice-cooled suspension of 6.45 g (20.0 mmol) ethyl 2-amino-3-(4-bromo-3-methyl-phenyl)-propionate hydrochloride in 50 mL DMF. The reaction mixture was then stirred for 1 h at 0° C. and 1 hour at RT, then combined with the suspension of 4.63 g (20.0 mmol) 3-piperidin-4-yl-3,4-dihydro-1H-quinazoline-2-one in 50 mL DMF. The mixture was heated to 80° C. for 1.5 h and then stirred into in 500 mL water. The precipitate which solidified after some time was ground up using an Ultra-Turrax stirrer, washed thoroughly with water, suction filtered and dried at 50° C. in the circulating air dryer.

Yield: 11.9 g (97% of theory; contains 1.0 eq. DMF) $R_f$=0.40 (silica gel, DCM/MeOH/$NH_3$ 9:1:0.1)

14c 3-(4-bromo-3-methyl-phenyl)-2-{[4-(2-oxo-1,4-dihydro-2H-quinazolin-3-yl)-piperidin-1-carbonyl]-amino}-propionic acid 60 mL of 1 M NaOH were added to a solution of 10.9 g (20 mmol) ethyl 3-(4-bromo-3-methyl-phenyl)-2-{[4-(2-oxo-1,4-dihydro-2H-quinazolin-3-yl)-piperidin-1-carbonyl]-amino}-propionate in 60 mL EtOH and the mixture was then refluxed for 2 h. After cooling it was diluted with 50 mL water and acidified with 20% citric acid solution. The precipitate obtained was suction filtered, washed thoroughly with water and dried at 50 CC in the circulating air dryer.

Yield: 9.6 g (93% of theory) ESI-MS: $(M-H)^-$=513/515 (Br) $R_f$=0.10 (silica gel, DCM/MeOH 9:1)

14d 4-(2-oxo-1,4-dihydro-2H-quinazolin-3-yl)-piperidin-1-carboxylic acid[2-[1,4']bipiperidinyl-1'-yl-1-(4-bromo-3-methyl-benzyl)-2-oxo-ethyl]-amide The product was obtained analogously to Example 2f from 515 mg (1.00 mmol) 3-(4-bromo-3-methyl-phenyl)-2-{[4-(2-oxo-1,4-dihydro-2H-quinazolin-3-yl)-piperidin-1-carbonyl]-amino}-propionic acid and 177 mg (1.00 mmol) [1,4']bipiperidinyl.

Yield: 320 mg (48% of theory) ESI-MS: $(M+H)^+$=665/667 (Br) $R_f$=0.33 (silica gel, DCM/MeOH/$NH_3$ 9:1:0.1)

The following compounds were prepared analogously from 3-(4-bromo-3-methyl-phenyl)-2-{[4-(2-oxo-1,4-dihydro-2H-quinazolin-3-yl)-piperidin-1-carbonyl]-amino}-propionic acid and the corresponding amount of amine:

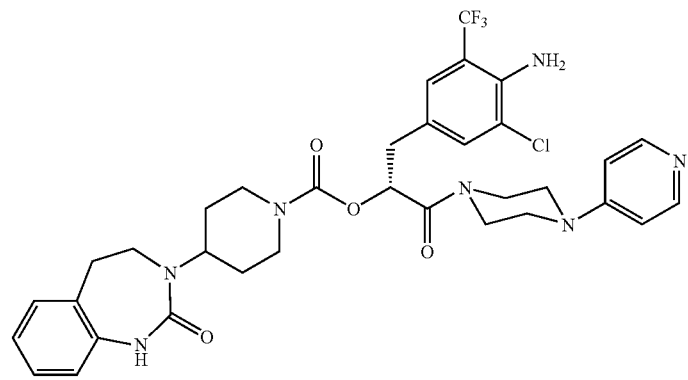

| Example | R | Yield (%) | Mass spectrum | R_f (silica gel) |
|---|---|---|---|---|
| 14.1 | *–N⟨piperidine⟩–⟨cyclohexane⟩–N(CH₃) | 52 | 679/681 [M + H]⁺ | 0.28 (DCM/MeOH/NH₃ 9:1:0.1) |
| 14.2 | *–N⟨piperidine⟩–N–⟨piperidine⟩–CH₃ | 50 | | 0.24 (DCM/MeOH/NH₃ 9:1:0.1) |
| 14.3 | *–N⟨piperidine⟩–⟨piperidine⟩–N–CH₃ | 25 | 680/682 [M + H]⁺ | 0.19 (DCM/MeOH/NH₃ 9:1:0.1) |
| 14.4 | *–N⟨piperidine⟩–N–⟨piperidine⟩–CH₂CO₂Et | 25 | 774/776 [M + Na]⁺ | 0.45 (DCM/MeOH 9:1) |
| 14.5 | *–N⟨piperidine⟩–⟨cyclohexane⟩–N–CH₂CO₂Et | 40 | 751/753 [M + H]⁺ | 0.48 (DCM/MeOH 9:1) |
| 14.6 | *–N⟨piperidine⟩–⟨piperidine⟩–N–CH₂CO₂Et | 28 | 774/776 [M + Na]⁺ | 0.39 (DCM/MeOH 9:1) |

Example 15

{4-[1-(3-(4-bromo-3-methyl-phenyl)-2-{[4-(2-oxo-1,4-dihydro-2H-quinazolin-3-yl)-piperidin-1-carbonyl]-amino}-propionyl)-piperidin-4-yl]-piperazin-1-yl}-acetic acid

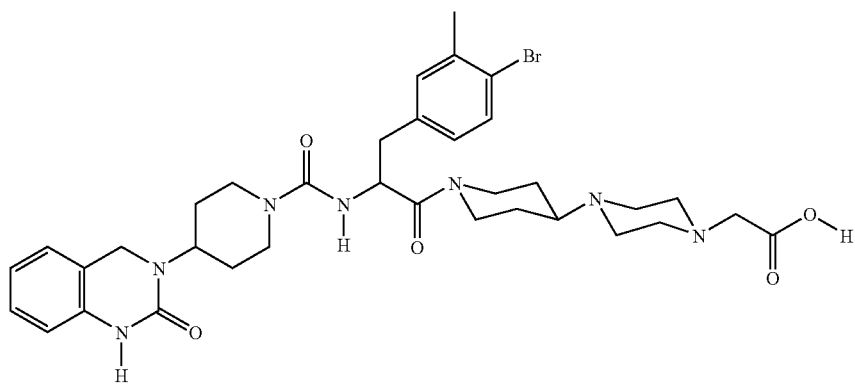

1.0 mL (1.00 mmol) 1 M NaOH were added to a solution of 80 mg (0.11 mmol) ethyl {4-[1-(3-(4-bromo-3-methyl-phenyl)-2-{[4-(2-oxo-1,4-dihydro-2H-quinazolin-3-yl)-piperidin-1-carbonyl]-amino}-propionyl)-piperidin-4-yl]-piperazin-1-yl}-acetate (Example 14.4) in 4 mL THF. The reaction mixture was stirred overnight at RT and the solvent was eliminated i. vac. 1 mL 1 M HCl was added to the residue and it was evaporated to dryness again. The residue was taken up in EtOH and after filtration the mother liquor was concentrated by evaporation i.vac. The residue was triturated with diisopropylether and after filtration dried in the air.

Yield: 80 mg (100% of theory) Retention time (HPLC): 5.9 min (method A)

The following compounds were prepared analogously from the respective ethyl esters (Examples 14.5 and 14.6):

| Example | R | Yield (%) | Mass spectrum | $R_f$ (silica gel) or Retention time HPLC |
|---|---|---|---|---|
| 15.1 | 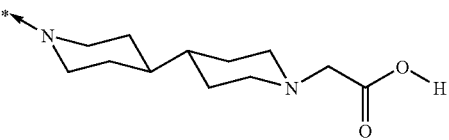 | 59 | 745/747 [M + Na]+ | 0.12 (DCM/MeOH 9:1) |
| 15.2 |  | 81 | 722/724 [M − H]+ | 5.5 min (A) |

Example 16

2-(4-bromo-3-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

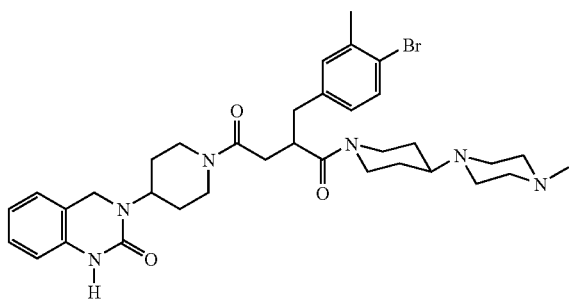

16a 4-tert-butyl, 1-ethyl 2-(4-bromo-3-methyl-benzyl)-2-ethoxycarbonyl-succinicate The product was prepared analogously to Example 2b from 11.4 g (41.7 mmol) 4-tert-butyl, 1-ethyl 2-ethoxycarbonyl-succinate and 11.0 g (41.7 mmol) 1-bromo-4-bromomethyl-2-methyl-benzene.

Yield: 21.3 g (100% of theory) $R_f$=0.64 (silica gel, PE/EtOAc 8:2)

16b ethyl 2-(4-bromo-3-methyl-benzyl)-2-ethoxycarbonyl-succinicate

The product was prepared analogously to Example 2c from 21.3 g (41.7 mmol) 4-tert-butyl, 1-ethyl 2-(4-bromo-3-methyl-benzyl)-2-ethoxycarbonyl-succinate.

Yield: 7.8 g (47% of theory) $R_f$=0.26 (silica gel, PE/EtOAc 8:2)

16c diethyl 2-(4-bromo-3-methyl-benzyl)-2-{2-oxo-2-[4-(2-oxo-1,4-dihydro-2H-quinazolin-3-yl)-piperidin-1-yl]-ethyl}-malonate The product was prepared analogously to Example 2d from 7.80 g (19.4 mmol) ethyl 2-(4-bromo-3-methyl-benzyl)-2-ethoxycarbonyl-succinate and 4.50 g (19.4 mmol) 3-piperidin-4-yl-3,4-dihydro-1H-quinazolin-2-one.

Yield: 8.30 g (70% of theory) EI-MS: (M)$^+$=613/615 (Br) $R_f$=0.80 (silica gel, DCM/cyc/MeOH/NH$_3$ 70:15:15:2)

16d 2-(4-bromo-3-methyl-benzyl)-4-oxo-4-[4-(2-oxo-1,4-dihydro-2H-quinazolin-3-yl)-piperidin-1-yl]-butanoic acid The product was prepared analogously to Example 2e from 8.30 g (13.5 mmol) diethyl 2-(4-bromo-3-methyl-benzyl)-2-{2-oxo-2-[4-(2-oxo-1,4-dihydro-2H-quinazolin-3-yl)-piperidin-1-yl]-ethyl}-malonate.

Yield: 5.10 g (74% of theory) EI-MS: (M)$^+$=513/515 (Br) $R_f$=0.20 (silica gel, DCM/cyc/MeOH/NH$_3$ 70:15:15:2)

16e 2-(4-bromo-3-methyl-benzyl)-1-[4-(4-methyl-piperazin-1-yl]-piperidin-1-yl)-4-[4-(2-oxo-1,4-dihydro-2H-quinazolin-3-yl)-piperidin-1-yl]-butan-1,4-dione The product was prepared analogously to Example 2f from 0.51 g (1.00 mmol) 2-(4-bromo-3-methyl-benzyl)-4-oxo-4-[4-(2-oxo-1,4-dihydro-2H-quinazolin-3-yl)-piperidin-1-yl]-butanoic acid and 0.18 g (1.00 mmol) 1-methyl-4-piperidin-4-yl-piperazine.

Yield: 250 mg (37% of theory) EI-MS: (M)$^+$=678/680 (Br) $R_f$=0.50 (silica gel, DCM/cyc/MeOH/NH$_3$ 70:15:15:2)

The following compounds were prepared analogously from 2-(4-bromo-3-methyl-benzyl)-4-oxo-4-[4-(2-oxo-1,4-dihydro-2H-quinazolin-3-yl)-piperidin-1-yl]-butanoic acid and the corresponding amount of amine:

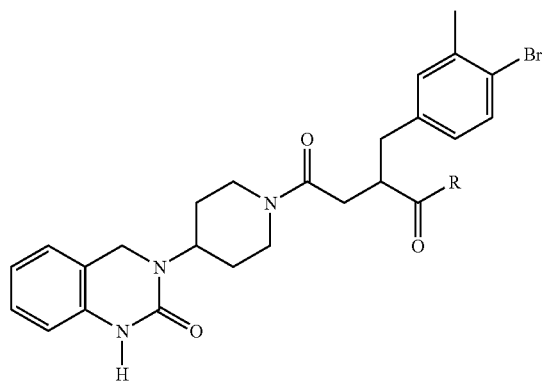

| Example | R | Yield (%) | Mass spectrum | $R_f$ (silica gel) |
|---|---|---|---|---|
| 16.1 | *–N⟨piperidine⟩–⟨piperidine⟩–N–CH$_3$ | 44 | 677/679 [M]$^+$ | 0.50 (DCM/cyc/MeOH/NH$_3$ 70:15:15:2) |
| 16.2 | *–N⟨piperidine⟩–⟨cyclohexane⟩–N⟨piperidine⟩ | 46 | 663/665 [M]$^+$ | 0.52 (DCM/cyc/MeOH/NH$_3$ 70:15:15:2) |

-continued

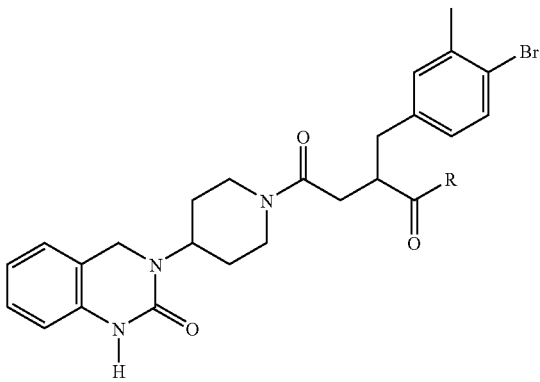

| Example | R | Yield (%) | Mass spectrum | $R_f$ (silica gel) |
|---|---|---|---|---|
| 16.3 | (structure) | 27 | 742/744 [M]$^+$ | 0.56 (DCM/cyc/MeOH/NH$_3$ 70:15:15:2) |

Example 16.4

[4-(1-{2-(4-bromo-3-methyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid

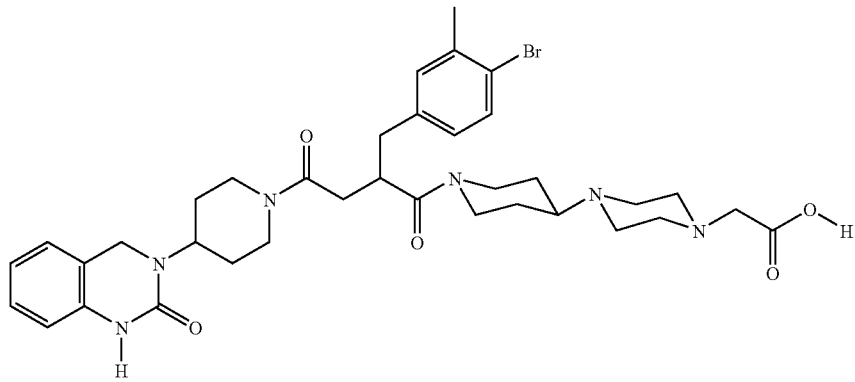

This synthesis was carried out by the Chemspeed ASW2000 synthesising robot (Chemspeed Ltd., Rheinstrale 32, CH-4302 Augst, Switzerland).
Mixture:
AGV 1: 102 mg (0.20 mmol) 2-(4-bromo-3-methyl-benzyl)-4-oxo-4-[4-(2-oxo-1,4-dihydro-2H-quinazolin-3-yl)-piperidin-1-yl]-butanoic acid in 3 mL THF;
AGV 2: 51 mg (0.20 mmol) ethyl(4-piperidin-4-yl-piperazin-1-yl)-acetate in 2 mL THF;
AGV 3: 64 mg (0.20 mmol) TBTU in 2 mL DMF;
AGV 4: 0.14 mL (1.00 mmol) triethylamine;
AGV 5: 1.00 mL 4 M NaOH;
AGV 6: 1.00 mL 4 M HCl;
AGV 7: 6 mL THF.

The AGV's 1 to 4 were positioned accordingly, then pipetted together by the robot and shaken for 8 h at RT. The reaction mixtures were concentrated by evaporation, combined with 7 mL EtOAc, the resulting solutions were each washed with 10 mL of 10% K$_2$CO$_3$ solution and 6 mL water and again freed from solvent. The residues were each dissolved in AGV 7 and after the addition of AGV 5 stirred for 6 h at RT. The reaction mixtures were each neutralised by the addition of AGV 6, then concentrated by evaporation. The residue obtained was dissolved in 1.9 mL DMF and added to a microtitre plate. The samples were separated using an HPLC-MS apparatus (Agilent Technologies, Agilent 1100 Series Modules and Systems for HPLC and LC/MS), the product was collected under mass control. The end product was freeze-dried.
Yield: 4 mg (3% of theory). ESI-MS:
(M−H)$^-$=721/723 (Br)
(M+H)$^+$=723/725 (Br)

Example 16.5 methyl(1'-{2-(4-bromo-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate

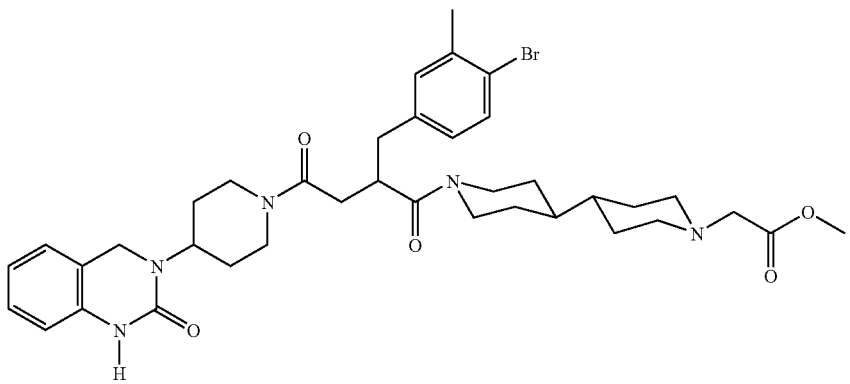

This synthesis was carried out by the Chemspeed ASW2000 synthesising robot (Chemspeed Ltd., RheinstraBe 32, CH-4302 Augst, Switzerland).

Mixture:
AGV 1: 206 mg (0.40 mmol) 2-(4-bromo-3-methyl-benzyl)-4-oxo-4-[4-(2-oxo-1,4-dihydro-2H-quinazolin-3-yl)-piperidin-1-yl]-butanoic acid in 3 mL THF;
AGV 2: 102 mg (0.40 mmol) ethyl[4,4']bipiperidinyl-1-yl-acetate in 4 mL THF;
AGV 3: 128 mg (0.40 mmol) TBTU in 4 mL DMF;
AGV 4: 0.14 mL (1.00 mmol) triethylamine;

The AGV's 1 to 4 were positioned accordingly, then pipetted together by the robot and shaken for 8 h at RT. The reaction mixtures were concentrated by evaporation, combined with 7 mL EtOAc and 6 mL 10% $K_2CO_3$ solution, shaken vigorously, the aqueous phase was removed and discarded. The organic phase was concentrated by evaporation and dissolved in 6 mL of MeOH. One third of this solution was taken and added to a microtitre plate. The samples were separated using an HPLC-MS apparatus (Agilent Technologies, Agilent 1100 Series Modules and Systems for HPLC and LC/MS), the product was collected under mass control. The end product was freeze-dried.

Yield: 9 mg (9% of theory). EI-MS: $(M)^+=735/737$ (Br) $R_f=0.38$ (silica gel, DCM/MeOH 9:1)

The remaining ⅔ of the MeOH solution were concentrated by evaporation and the crude product (195 mg) was further reacted in Example 16.6.

Example 16.6

(1'-{2-(4-bromo-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid

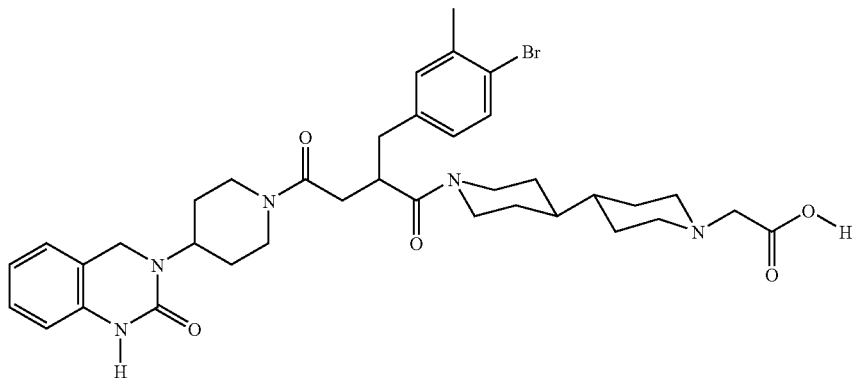

This synthesis was carried out by the Chemspeed ASW2000 synthesising robot (Chemspeed Ltd., Rheinstralβe 32, CH-4302 Augst, Switzerland).

Mixture:
AGV 1: 195 mg (0.26 mmol) methyl(1'-{2-(4-bromo-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate;
AGV 2: 5 mL MeOH
AGV 3: 1.00 mL 4 M NaOH;
AGV 4: 1.00 mL 4 M HCl;

AGV 1 was dissolved in AGV 2 and then AGV 3 was added. The mixture was shaken for 5 h at 20° C. and then neutralised with AGV 4. The reaction mixture was concentrated by evaporation and dissolved in 2 mL DMF. The samples were separated using an HPLC-MS apparatus (Agilent Technologies, Agilent 1100 Series Modules and Systems for HPLC and LC/MS), the product was collected under mass control. The end product was freeze-dried.

Yield: 22 mg (11% of theory). ESI-MS: $(M+H)^+=722/724$ (Br) $R_f=0.22$ (silica gel, DCM/MeOH 9:1)

Example 17

4-(2-oxo-1,4-dihydro-2H-quinazolin-3-yl)-piperidin-1-carboxylic acid {1-(4-chloro-3-methyl-benzyl)-2-[4-(4-methyl-piperazin-1-yl)-piperidin-1-yl]-2-oxo-ethyl}-amide

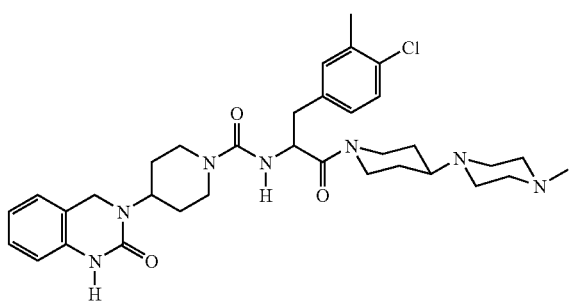

17a ethyl 2-amino-3-(4-chloro-3-methyl-phenyl)-propionate hydrochloride

The product was prepared analogously to Example 14a from 31.4 g (115 mmol) N-(diphenylmethylene)-glycinethylester and 25.2 g (115 mmol) of 4-bromomethyl-1-chloro-2-methyl-benzene.

Yield: 20.4 g (64% of theory) ESI-MS: $(M+H)^+=241/243$ (Cl) $R_f=0.35$ (silica gel, DCM/MeOH/NH$_3$ 9:1:0.1)

17b ethyl 3-(4-chloro-3-methyl-phenyl)-2-{[4-(2-oxo-1,4-dihydro-2H-quinazolin-3-yl)-piperidin-1-carbonyl]-amino}-propionate The product was obtained analogously to Example 14b from 5.56 g (20.0 mmol) ethyl 2-amino-3-(4-chloro-3-methyl-phenyl)-propionate hydrochloride and 4.63 (20.0 mmol) 3-piperidin-4-yl-3,4-dihydro-1H-quinazolin-2-one.

Yield: 9.50 g (95% of theory) ESI-MS: $(M-H)^-=497/499$ (Cl)

17c 3-(4-chloro-3-methyl-phenyl)-2-{[4-(2-oxo-1,4-dihydro-2H-quinazolin-3-yl)-piperidin-1-carbonyl]-amino}-propionic acid The product was obtained analogously to Example 14c from 9.50 g (19.0 mmol) ethyl 3-(4-chloro-3-methyl-phenyl)-2-{[4-(2-oxo-1,4-dihydro-2H-quinazolin-3-yl)-piperidin-1-carbonyl]-amino}-propionate.

Yield: 8.90 g (99% of theory) ESI-MS: (M−H)=469/471 (Cl) $R_f=0.10$ (silica gel, DCM/MeOH 9:1)

17d 4-(2-oxo-1,4-dihydro-2H-quinazolin-3-yl)-piperidin-1-carboxylic acid {1-(4-chloro-3-methyl-benzyl)-2-[4-(4-methyl-piperazin-1-yl)-piperidin-1-yl]-2-oxo-ethyl}-amide The product was prepared analogously to Example 2f from 706 mg (1.50 mmol) of 3-(4-chloro-3-methyl-phenyl)-2-{[4-(2-oxo-1,4-dihydro-2H-quinazolin-3-yl)-piperidin-1-carbonyl]-amino}-propionic acid and 275 g (1.50 mmol) of 1-methyl-4-piperidin-4-yl-piperazine.

Yield: 250 mg (26% of theory) ESI-MS: $(M+H)^+=636/638$ (Cl) $R_f=0.17$ (silica gel, DCM/MeOH/NH$_3$ 9:1:0.1)

The following compounds were prepared analogously from 3-(4-chloro-3-methyl-phenyl)-2-{[4-(2-oxo-1,4-dihydro-2H-quinazolin-3-yl)-piperidin-1-carbonyl]-amino}-propionic acid and the corresponding amount of amine:

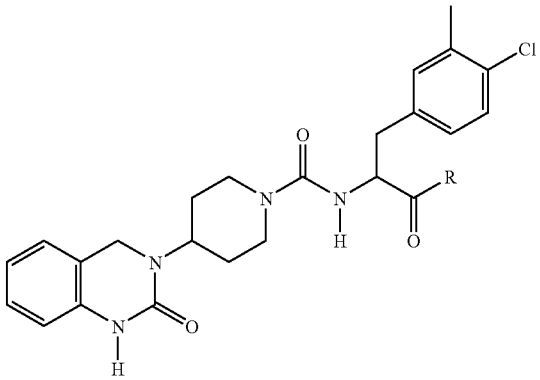

| Example | R | Yield (%) | Mass spectrum | $R_f$ (silica gel) |
|---|---|---|---|---|
| 17.1 | 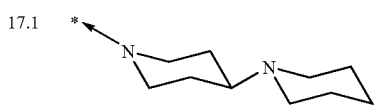 | 54 | 621/623 [M + H]$^+$ | (DCM/MeOH/NH$_3$ 9:1:0.1) |

-continued
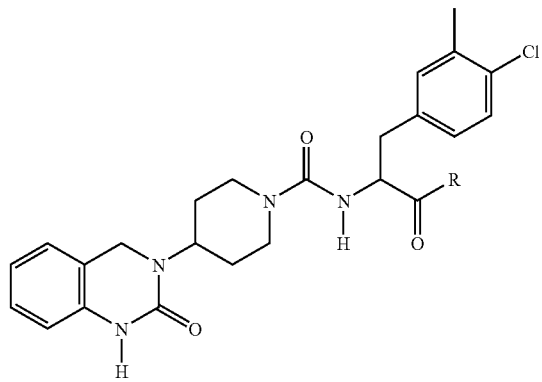
| Example | R | Yield (%) | Mass spectrum | $R_f$ (silica gel) |
|---|---|---|---|---|
| 17.2 | *―N⟨⟩―N⟨⟩―CH₃ | 35 | 636/638 [M + H]⁺ | (DCM/MeOH/NH₃ 9:1:0.1) |
| 17.3 | *―N⟨⟩―⟨⟩―N―CH₃ | 27 | 635/637 [M + H]⁺ | 0.26 (DCM/MeOH/NH₃ 9:1:0.1) |
| 17.4 | *―N⟨⟩―⟨⟩―N―CH₂C(O)OEt | 24 | 707/709 [M + Na]⁺ | 0.49 (DCM/MeOH 9:1) |
| 17.5 | *―N⟨⟩―⟨⟩―N―CH₂C(O)O-tBu | 37 | 736/738 [M + Na]⁺ | 0.39 (DCM/MeOH 9:1) |
| 17.6 | *―N⟨⟩―⟨⟩―N―CH₂CF₃ | 37 | 703/705 [M + Na]⁺ | 0.36 (DCM/MeOH/NH₃ 9:1:0.1) |
| 17.7 | *―N⟨⟩―N⟨⟩―N―CH₂CF₃ | 49 | 704/706 [M + Na]⁺ | 0.40 (DCM/MeOH/NH₃ 9:1:0.1) |

Example 18

[1'-(3-(4-chloro-3-methyl-phenyl)-2-{[4-(2-oxo-1,4-dihydro-2H-quinazolin-3-yl)-piperidin-1-carbonyl]-amino}-propionyl)-[4,4']bipiperidinyl-1-yl]-acetic acid

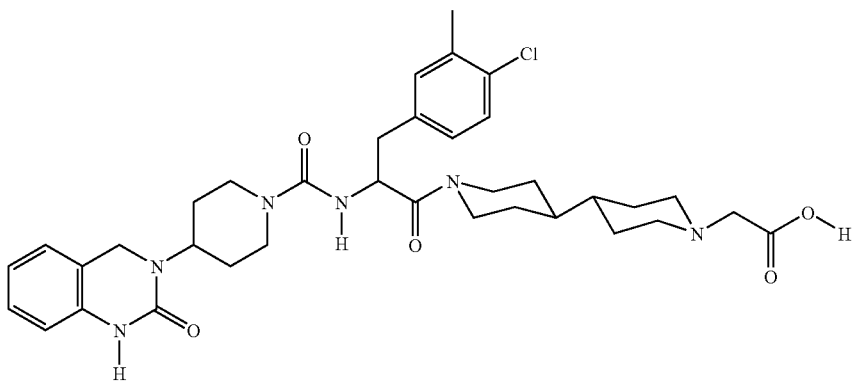

The product was prepared analogously to Example 15 from 220 mg (0.28 mmol) ethyl [1'-(3-(4-chloro-3-methyl-phenyl)-2-{[4-(2-oxo-1,4-dihydro-2H-quinazolin-3-yl)-piperidin-1-carbonyl]-amino}-propionyl)-[4,4']bipiperidinyl-1-yl]-acetate.

Yield: 190 mg (99% of theory) ESI-MS: $(M+H)^+=679/681$ (Cl) $R_f=0.13$ (silica gel, DCM/MeOH 9:1)

Example 19

2-(4-chloro-3-methyl-benzyl)-1-[4-(4-ethyl-piperazin-1-yl)-piperidin-1-yl]-4-[4-(2-oxo-1,4-dihydro-2H-quinazolin-3-yl)-piperidin-1-yl]-butan-1,4-dione

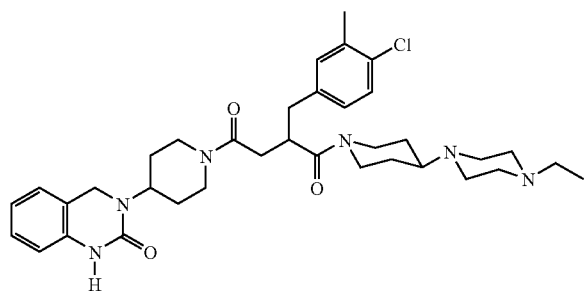

19a 4-tert-butyl, 1-ethyl 2-(4-chloro-3-methyl-benzyl)-2-ethoxycarbonyl-succinate The product was prepared analogously to Example 2b from 19.5 g (71.0 mmol) 4-tert-butyl, 1-ethyl 2-ethoxycarbonyl-succinate and 15.5 g (71.0 mmol) 4-bromomethyl-1-chloro-2-methyl-benzene.

Yield: 25.7 g (88% of theory) $R_f=0.74$ (silica gel, DCM)

19b ethyl 2-(4-chloro-3-methyl-benzyl)-2-ethoxycarbonyl-succinate

The product was prepared analogously to Example 2c from 21.3 g (41.7 mmol) 4-tert-butyl, 1-ethyl 2-(4-chloro-3-methyl-benzyl)-2-ethoxycarbonyl-succinate.

Yield: 22.2 g (100% of theory) $R_f=0.18$ (silica gel, DCM)

19c diethyl 2-(4-chloro-3-methyl-benzyl)-2-{2-oxo-2-[4-(2-oxo-1,4-dihydro-2H-quinazolin-3-yl)-piperidin-1-yl]-ethyl}-malonate The product was prepared analogously to Example 2d from 8.00 g (22.4 mmol) ethyl 2-(4-chloro-3-methyl-benzyl)-2-ethoxycarbonyl-succinate and 5.18 g (22.4 mmol) 3-piperidin-4-yl-3,4-dihydro-1H-quinazolin-2-one.

Yield: 9.20 g (72% of theory) EI-MS: $(M)^+=569/570$ (Cl) $R_f=0.64$ (silica gel, DCM/MeOH/NH$_3$ 9:1:0.1)

19d 2-(4-chloro-3-methyl-benzyl)-4-oxo-4-[4-(2-oxo-1,4-dihydro-2H-quinazolin-3-yl)-piperidin-1-yl]-butanoic acid The product was prepared analogously to Example 2e from 9.20 g (16.2 mmol) diethyl 2-(4-chloro-3-methyl-benzyl)-2-{2-oxo-2-[4-(2-oxo-1,4-dihydro-2H-quinazolin-3-yl)-piperidin-1-yl]-ethyl}-malonate.

Yield: 7.20 g (95% of theory) ESI-MS: $(M-H)^-=468/470$ (Cl)

19e 2-(4-chloro-3-methyl-benzyl)-1-[4-(4-ethyl-piperazin-1-yl)-piperidin-1-yl]-4-[4-(2-oxo-1,4-dihydro-2H-quinazolin-3-yl)-piperidin-1-yl]-butan-1,4-dione The product was prepared analogously to Example 2f from 470 mg (1.00 mmol) 2-(4-chloro-3-methyl-benzyl)-4-oxo-4-[4-(2-oxo-1,4-dihydro-2H-quinazolin-3-yl)-piperidin-1-yl]-butanoic acid and 593 mg (1.10 mmol) 1-ethyl-4-piperidin-4-yl-piperazine tris-trifluoroacetate.

Yield: 280 mg (43% of theory) EI-MS: $(M)^+=648/650$ (Cl) $R_f=0.47$ (silica gel, DCM/MeOH/NH$_3$ 9:1:0.1)

The following compounds were prepared analogously from 2-(4-chloro-3-methyl-benzyl)-4-oxo-4-[4-(2-oxo-1,4-dihydro-2H-quinazolin-3-yl)-piperidin-1-yl]-butanoic acid and the corresponding amount of amine:

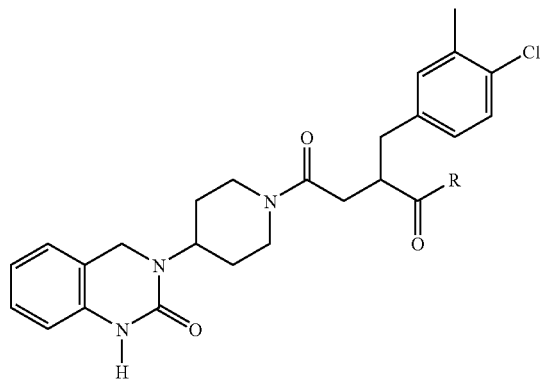

| Example | R | Yield (%) | Mass spectrum | R_f (silica gel) |
|---|---|---|---|---|
| 19.1 | *-N(piperidine)-cyclohexyl-N(CH3) | 48 | 634/636 [M]+ | 0.49 (DCM/cyc/MeOH/NH3 70:15:15:2) |
| 19.2 | *-N(piperidine)-N(piperidine) | 32 | 620/622 [M + H]+ | 0.54 (DCM/cyc/MeOH/NH3 70:15:15:2) |
| 19.3 | *-N(piperidine)-piperazine-CH3 | 44 | 635/637 [M + H]+ | 0.50 (DCM/cyc/MeOH/NH3 70:15:15:2) |
| 19.4 | *-N(piperidine)-piperidine-N-CH3 | 39 | 635/637 [M + H]+ | 0.49 (DCM/cyc/MeOH/NH3 70:15:15:2) |
| 19.5 | *-N(piperidine)-piperidine-N-SO2CH3 | 57 | 698/700 [M]+ | 0.54 (DCM/MeOH/NH3 9:1:0.1) |
| 19.6 | *-N(piperidine)-piperidine-N-iPr | 50 | 662/664 [M]+ | 0.48 (DCM/MeOH/NH3 9:1:0.1) |
| 19.7 | *-N(piperidine)(CO2Et)-piperidine-N-CH3 | 1 | 707/709 [M + H]+ | 0.76 (DCM/MeOH/NH3 8:2:0.2) |
| 19.8 | *-N(piperidine)-piperidine(CO2Et)-N-CH3 | 30 | 707/709 [M + H]+ | 0.77 (DCM/MeOH/NH3 8:2:0.2) |

-continued
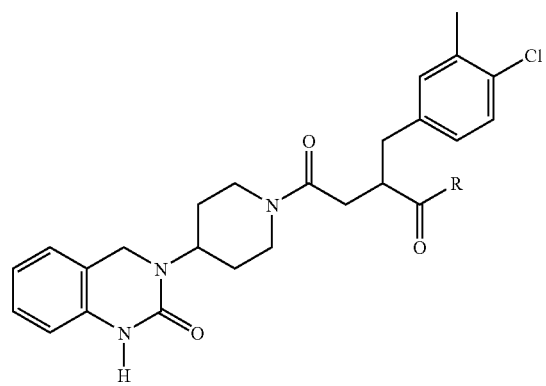
| Example | R | Yield (%) | Mass spectrum | $R_f$ (silica gel) |
|---|---|---|---|---|
| 19.9 | 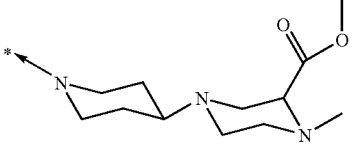 | 11 | 707/709 [M + H]+ | 0.56 (DCM/MeOH/NH$_3$ 8:2:0.2) |
| 19.10 | 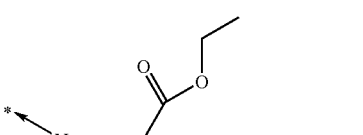 | 8 | 707/709 [M + H]+ | 0.56 (EtOAc/MeOH/NH$_3$ 8:2:0.2) |
| 19.11 |  | 30 | 702/704 [M + H]+ | 0.36 (DCM/MeOH/NH$_3$ 9:1:0.1) |
| 19.12 |  | 41 | 703/705 [M + H]+ | 0.72 (DCM/MeOH/NH$_3$ 8:2:0.1) |

Example 19.13

[4-(1-{2-(4-chloro-3-methyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid

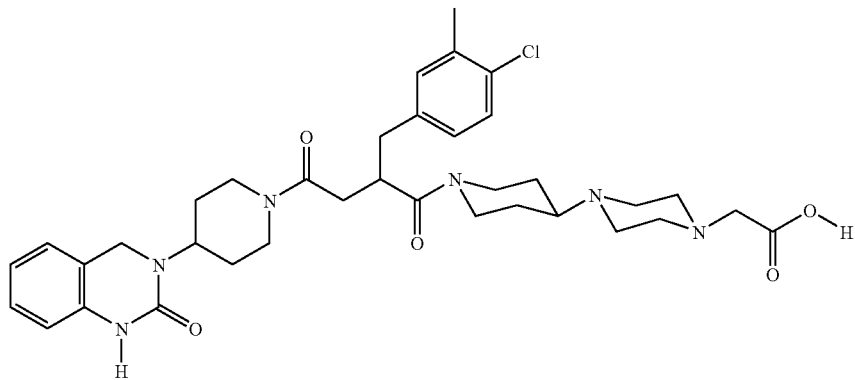

The product was obtained analogously to Example 16.4 from 94 mg (0.20 mmol) 2-(4-chloro-3-methyl-benzyl)-4-oxo-4-[4-(2-oxo-1,4-dihydro-2H-quinazolin-3-yl)-piperidin-1-yl]-butanoic acid and 51 mg (0.20 mmol) ethyl(4-piperidin-4-yl-piperazin-1-yl)-acetate.

Yield: 27 mg (19% of theory) EI-MS: (M)$^+$=679/681 (Cl) Retention time (HPLC): 5.9 min (method A)

Example 19.14 methyl(1'-{2-(4-chloro-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate

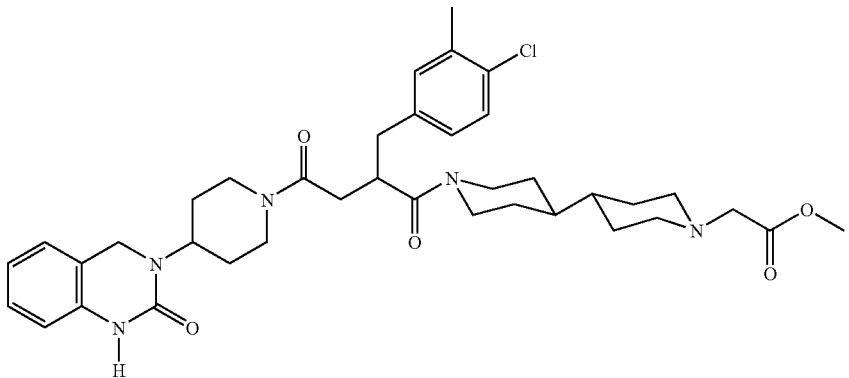

The product was obtained analogously to Example 16.5 from 188 mg (0.40 mmol) 2-(4-chloro-3-methyl-benzyl)-4-oxo-4-[4-(2-oxo-1,4-dihydro-2H-quinazolin-3-yl)-piperidin-1-yl]-butanoic acid and 102 mg (0.40 mmol) ethyl[4,4']bipiperidinyl-1-yl-acetate.

Yield: 27 mg (30% of theory) ESI-MS: (M+H)$^+$=692/694 (Cl) $R_f$=0.36 (silica gel, DCM/MeOH 9:1)

Example 19.15

(1'-{2-(4-chloro-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid

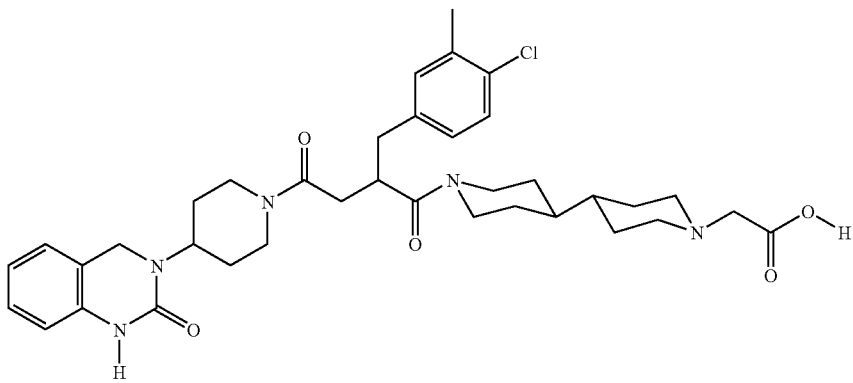

The product was obtained analogously to Example 16.6 from 184 mg (0.26 mmol) methyl(1'-{2-(4-chloro-3-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate.

Yield: 30 mg (16% of theory) ESI-MS: $(M+H)^+$=678/680 (Cl) $R_f$=0.21 (silica gel, DCM/MeOH 9:1)

The following compounds were prepared from the relevant ethyl esters (Examples 19.7 to 19.9) analogously to Example 15:

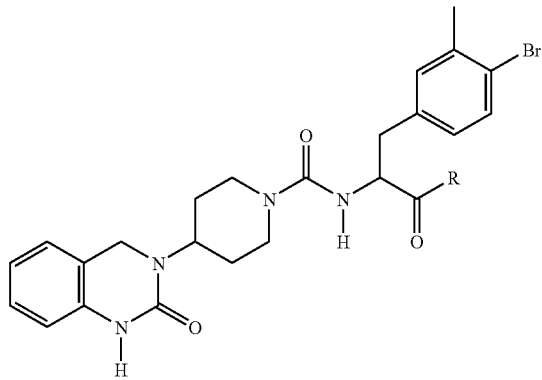

| Example | R | Yield (%) | Mass spectrum | $R_f$ (silica gel) |
|---|---|---|---|---|
| 19.16 | | 18 | 679/681 $[M + H]^+$ | 0.05 (EtOAc/MeOH/NH$_3$ 6:4:0.4) |
| 19.17 | | 50 | 679/681 $[M + H]^+$ | 0.21 (DCM/MeOH/NH$_3$ 8:2:0.2) |

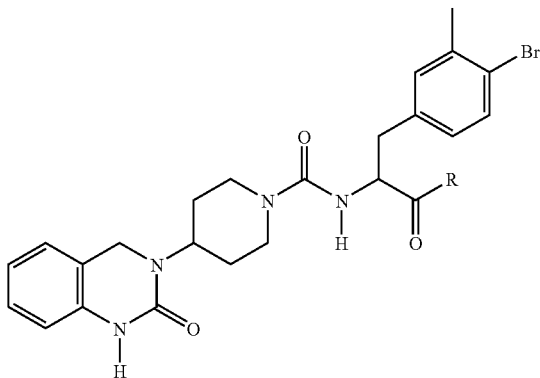

| Example | R | Yield (%) | Mass spectrum | $R_f$ (silica gel) |
|---|---|---|---|---|
| 19.18 | 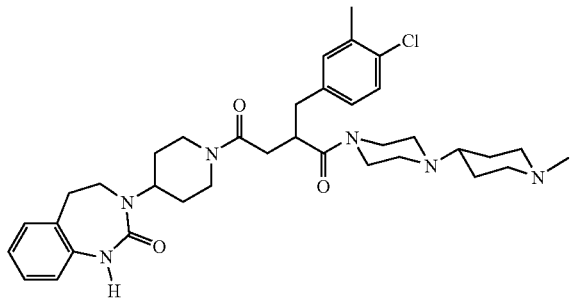 | 48 | 679/681 [M + H]$^+$ | 0.14 (EtOAc/MeOH/NH$_3$ 6:4:0.4) |

Example 20

2-(4-chloro-3-methyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione

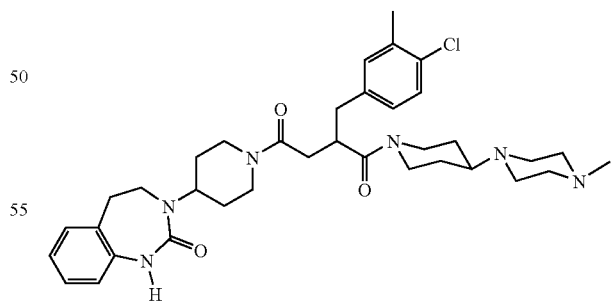

20a diethyl 2-(4-chloro-3-methyl-benzyl)-2-{2-oxo-2-[4-(2-oxo-1,2,4,5-tetrahydro-1,3-benzodiazepin-3-yl)-piperidin-1-yl]-ethyl}-malonate The product was prepared analogously to Example 2d from 1.43 g (4.00 mmol) ethyl 2-(4-chloro-3-methyl-benzyl)-2-ethoxycarbonyl-succinate and 981 mg (4.00 mmol) 3-(1-methyl-piperidin-4-yl)-1,3,4,5-tetrahydro-1,3-benzodiazepin-2-one.

Yield: 2.10 g (90% of theory) $R_f$=0.69 (silica gel, DCM/cyc/MeOH/NH$_3$ 70:15:15:2)

20b 2-(4-chloro-3-methyl-benzyl)-4-oxo-4-[4-(2-oxo-1,2,4,5-tetrahydro-1,3-benzodiazepin-3-yl)-piperidin-1-yl]-butanoic acid The product was prepared analogously to Example 2e from 2.10 g (3.60 mmol) diethyl 2-(4-chloro-3-methyl-benzyl)-2-{2-oxo-2-[4-(2-oxo-1,2,4,5-tetrahydro-1,3-benzodiazepin-3-yl)-piperidin-1-yl]-ethyl}-malonate. The product was further reacted without purification.

Yield: 1.20 g (69% of theory)

20c 2-(4-chloro-3-methyl-benzyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butan-1,4-dione The product was prepared analogously to Example 2f from 800 mg (1.65 mmol) 2-(4-chloro-3-methyl-benzyl)-4-oxo-4-[4-(2-oxo-1,2,4,5-tetrahydro-1,3-benzodiazepin-3-yl)-piperidin-1-yl]-butanoic acid and 302 mg (1.65 mmol) 1-(1-methyl-piperidin-4-yl)-piperazine.

Yield: 400 mg (37% of theory) EI-MS: (M)$^+$=648/650 (Cl) $R_f$=0.50 (silica gel, DCM/cyc/MeOH/NH$_3$ 70:15:15:2)

Example 20.1

2-(4-chloro-3-methyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione The product was prepared analogously to Example 2f from 400 mg (0.83 mmol) 2-(4-chloro-3-methyl-benzyl)-4-oxo-4-[4-(2-oxo-1,2,4,5-tetrahydro-1,3-benzodiazepin-3-yl)-piperidin-1-yl]-butanoic acid and 152 mg (0.83 mmol) 1-methyl-4-piperidin-4-yl-piperazine.

Yield: 200 mg (37% of theory) EI-MS: (M)$^+$=648/650 (Cl) $R_f$=0.51 (silica gel, DCM/cyc/MeOH/NH$_3$ 70:15:15:2)

Example 21

[4-(1-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-piperidin-4-yl)-piperazin-1-yl]-acetic acid

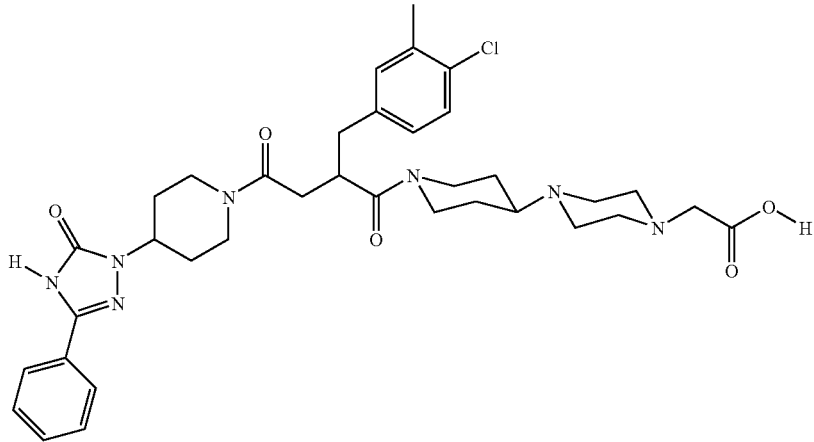

21a diethyl 2-(4-chloro-3-methyl-benzyl)-2-{2-oxo-2-[4-(5-oxo-3-phenyl-4,5dihydro-1,2,4-triazol-1-yl)-piperidin-1-yl]-ethyl}-malonate The product was prepared analogously to Example 2d from 5.00 g (14.0 mmol) ethyl 2-(4-chloro-3-methyl-benzyl)-2-ethoxycarbonyl-succinate and 3.42 g (14.0 mmol) 5-phenyl-2-piperidin-4-yl-2,4-dihydro-1,2,4-triazol-3-one.

Yield: 5.50 g (67% of theory) $R_f$=0.50 (silica gel, DCM/MeOH/NH$_3$ 9:1:0.1)

21 b  2-(4-chloro-3-methyl-benzyl)-4-oxo-4-[4-(5-oxo-3-phenyl-4,5-dihydro-1,2,4-triazol-1-yl)-piperidin-1-yl]-butanoic acid The product was prepared analogously to Example 2e from 5.50 g (9.43 mmol) diethyl 2-(4-chloro-3-methyl-benzyl)-2-{2-oxo-2-[4-(5-oxo-3-phenyl-4,5-dihydro-1,2,4-triazol-1-yl)-piperidin-1-yl]-ethyl}-malonate.

Yield: 2.80 g (62% of theory) ESI-MS: (M–H)$^-$=481/483 (Cl)

21c  [4-(1-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-piperidin-4-yl)-piperazin-1-yl]-acetic acid The product was obtained analogously to Example 16.4 from 96 mg (0.20 mmol) 2-(4-chloro-3-methyl-benzyl)-4-oxo-4-[4-(5-oxo-3-phenyl-4,5-dihydro-1,2,4-triazol-1-yl)-piperidin-1-yl]-butanoic acid and 51 mg (0.20 mmol) ethyl (4-piperidin-4-yl-piperazin-1-yl)-acetate.

Yield: 3 mg (2% of theory) ESI-MS: (M+H)$^+$=692/694 (Cl)

Example 21.1 methyl(1'-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-4,4'-bipiperidinyl-1-yl)-acetate

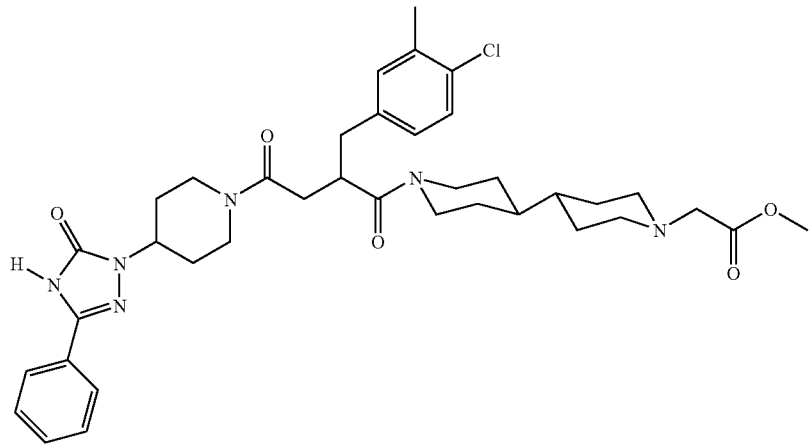

The product was obtained analogously to Example 16.5 from 193 mg (0.40 mmol) 2-(4-chloro-3-methyl-benzyl)-4-oxo-4-[4-(5-oxo-3-phenyl-4,5-dihydro-1,2,4-triazol-1-yl)-piperidin-1-yl]-butanoic acid and 102 mg (0.40 mmol) ethyl [4,4']bipiperidinyl-1-yl-acetate.

Yield: 14 mg (15% of theory) ESI-MS: (M+H)$^+$=705/707 (Cl) R$_f$=0.32 (silica gel, DCM/MeOH 9:1)

Example 21.2

(1'-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-4,4'-bipiperidinyl-1-yl)-acetic acid

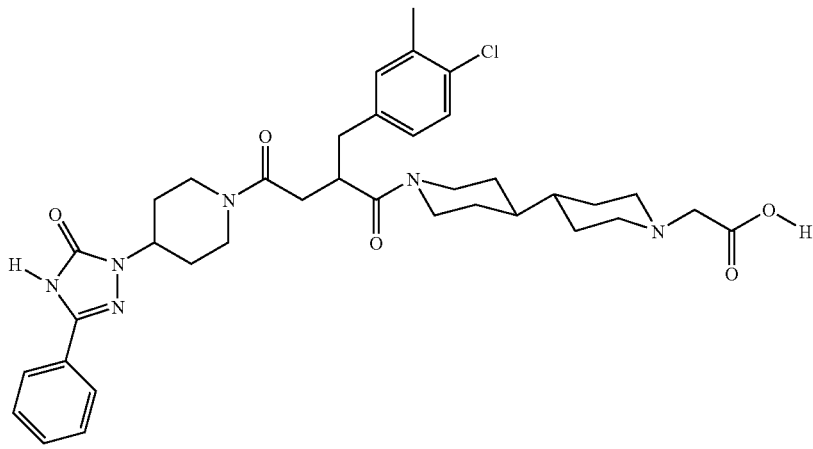

The product was obtained analogously to Example 16.6 from 187 mg (0.26 mmol) methyl(1'-{2-(4-chloro-3-methyl-benzyl)-4-oxo-4-[4-(5-oxo-3-phenyl-4,5-dihydro-1,2,4-triazol-1-yl)-piperidin-1-yl]-butyryl}-4,4'-bipiperidinyl-1-yl)-acetate.

Yield: 11 mg (6% of theory) ESI-MS: (M+H)$^+$=691/693 (Cl) R$_f$=0.21 (silica gel, DCM/MeOH 9:1)

Example 22

2-(3-bromo-4-chloro-5-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

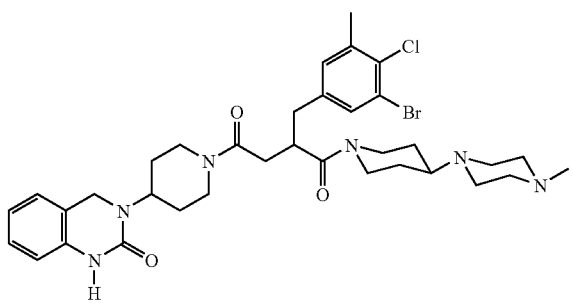

22a 1-(3-bromo-4-chloro-5-methyl-phenyl)-ethanone 25.0 g (148 mmol) 1-(4-chloro-3-methyl-phenyl)-ethanone were added dropwise to 59.2 g (444 mmol) of aluminium trichloride. The temperature rose to 70° C. The mixture was stirred for 30 min at 80° C. and then at this temperature 10.7 mL (170 mmol) bromine were added dropwise. The reaction solution was stirred for 1 h at 80° C. and then added to ice. The aqueous phase was extracted with diethyl ether and the combined organic extracts were washed with saturated NaHCO$_3$ solution. The organic phase was dried over Na$_2$SO$_4$ and the solvent was eliminated i. vac. Purification was carried out by column chromatography on silica gel (toluene).

Yield: 14.0 g (38% of theory) EI-MS: (M)$^+$=246/248/250 (Br, Cl) R$_f$=0.28 (silica gel, toluene)

22b 3-bromo-4-chloro-5-methyl-benzoic acid 8.7 mL (171 mmol) bromine was added dropwise at 0° C. to a solution of 22.8 g (570 mmol) NaOH in 114 mL water so that the temperature did not exceed 10° C. 14.0 g (57.0 mmol) 1-(3-bromo-4-chloro-5-methyl-phenyl)-ethanone in 57 mL 1,4-dioxane was added dropwise at 10° C. and the mixture was stirred for 2 h at RT. The reaction mixture was diluted with water and the bromine form obtained was separated off. The aqueous phase was acidified with semiconc. HCl, the precipitate was suction filtered and washed with water.

Yield: 11.0 g (78% of theory) EI-MS: (M)$^+$=248/250/252 (Br, Cl) melting point: 207-209° C.

22c (3-bromo-4-chloro-5-methyl-phenyl)-methanol 8.1 g (50 mmol) CDI were added to a solution of 11.0 g (44 mmol) 3-bromo-4-chloro-5-methyl-benzoic acid in 285 mL THF at RT. The reaction mixture was for stirred for 1 h at 40° C. This solution was added to a solution of 5.38 g (142 mmol) NaBH$_4$ in 47.5 mL water. The mixture was stirred for 3 h at RT, then diluted with 300 mL water and acidified with semiconc. HCl. The aqueous phase was extracted with EtOAc and the organic phase was washed successively with water and saturated NaHCO$_3$ solution. The organic phase was dried over Na$_2$SO$_4$ and the solvent was eliminated i. vac.

Yield: 9.00 g (87% of theory) ESI-MS: (M–H)$^-$=233/235/237 (Br, Cl) R$_f$=0.62 (silica gel, PE/EtOAc 1:1)

22d 1-bromo-5-bromomethyl-2-chloro-3-methyl-benzene 5.2 mL (19 mmol) phosphorus tribromide was added dropwise to a solution of 9.00 g (38 mmol) (3-bromo-4-chloro-5-methyl-phenyl)-methanol in 250 mL diethyl ether at RT and refluxed for 1 h. The reaction mixture was added to saturated NaHCO$_3$ solution, the organic phase was separated off, washed with water and dried over Na$_2$SO$_4$. After the desiccant and solvent had been eliminated the desired product was obtained.

Yield: 10.7 g (94% of theory) EI-MS: (M)$^+$=296/298/300/302 (2Br, Cl) R$_f$=0.89 (silica gel, PE/EtOAc 1:1)

22e 4-tert-butyl, 1-ethyl 2-(3-bromo-4-chloro-5-methyl-benzyl)-2-ethoxycarbonyl-succinate The product was prepared analogously to Example 2b from 9.86 g (36 mmol) 4-tert-butyl, 1-ethyl 2-ethoxycarbonyl-succinate and 10.7 g (36 mmol) 1-bromo-5-bromomethyl-2-chloro-3-methyl-benzene.

Yield: 17.5 g (99% of theory) ESI-MS: (M+H)$^+$=513/515/517 (Br, Cl) R$_f$=0.57 (silica gel, DCM)

22f 1-ethyl 2-(3-bromo-4-chloro-5-methyl-benzyl)-2-ethoxycarbonyl-succinate

The product was prepared analogously to Example 2c from 18.0 g (37 mmol) 4-tert-butyl, 1-ethyl 2-(3-bromo-4-chloro-5-methyl-benzyl)-2-ethoxycarbonyl-succinate. The crude product which still contained TFA was further reacted without purification. ESI-MS: (M−H)$^-$=433/435/437 (Br, Cl)

22g diethyl 2-(3-bromo-4-chloro-5-methyl-benzyl)-2-{2-oxo-2-[4-(2-oxo-1,4-dihydro-2H-quinazolin-3-yl)-piperidin-1-yl]-ethyl}-malonate The product was prepared analogously to Example 2d from 18.2 g (42 mmol) 1-ethyl 2-(3-bromo-4-chloro-5-methyl-benzyl)-2-ethoxycarbonyl-succinate and 9.60 g (42 mmol) 3-piperidin-4-yl-3,4-dihydro-1H-quinazolin-2-one.

Yield: 15.0 g (56% of theory) EI-MS: (M)$^+$=647/649/651 (Br, Cl) R$_f$=0.60 (silica gel, DCM/MeOH/NH$_3$ 9:1:0.1)

22h 2-(3-bromo-4-chloro-5-methyl-benzyl)-4-oxo-4-[4-(2-oxo-1,4-dihydro-2H-quinazolin-3-yl)-piperidin-1-yl]-butanoic acid The product was prepared analogously to Example 2e from 15.0 g (23 mmol) diethyl 2(3-bromo-4-chloro-5-methyl-benzyl)-2-{2-oxo-2-[4-(2-oxo-1,4-dihydro-2H-quinazolin-3-yl)-piperidin-1-yl]-ethyl}-malonate.

Yield: 11.8 g (93% of theory) R$_f$=0.20 (silica gel, EtOAc/MeOH/acetic acid 8:2:0.1)

22i 2-(3-bromo-4-chloro-5-methyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione The product was prepared analogously to Example 2f from 1.09 g (2.00 mmol) 2-(3-bromo-4-chloro-5-methyl-benzyl)-4-oxo-4-[4-(2-oxo-1,4-dihydro-2H-quinazolin-3-yl)-piperidin-1-yl]-butanoic acid and 367 mg (2.00 mmol) 1-methyl-4-piperidin-4-yl-piperazine.

Yield: 773 mg (54% of theory) EI-MS: (M)$^+$=712/714/716 (Br, Cl) R$_f$=0.24 (silica gel, DCM/MeOH/NH$_3$ 9:1:0.1)

The following compounds were prepared analogously from 2-(3-bromo-4-chloro-5-methyl-benzyl)-4-oxo-4-[4-(2-oxo-1,4-dihydro-2H-quinazolin-3-yl)-piperidin-1-yl]-butanoic acid and the corresponding amount of amine:

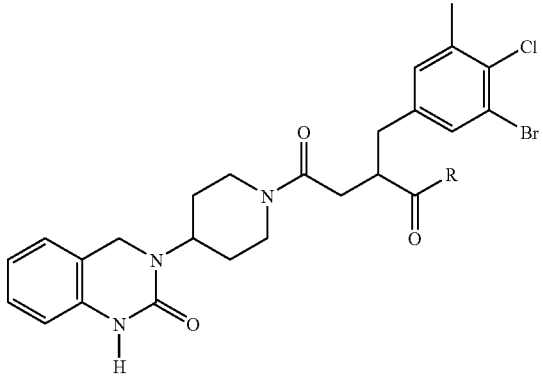

| Example | R | Yield (%) | Mass spectrum | R$_f$ (silica gel) |
|---|---|---|---|---|
| 22.1 | | 74 | 711/13/15 [M]$^+$ | 0.63 (DCM/MeOH/NH$_3$ 8:2:0.1) |
| 22.2 | | 56 | 692/94/96 [M]$^+$ | 0.26 (DCM/MeOH/NH$_3$ 9:1:0.1) |
| 22.3 | | 13 | 713/15/17 [M + H]$^+$ | 0.43 (DCM/MeOH/NH$_3$ 8:2:0.1) |

Example 22.4

[4-(1-{2-(3-bromo-4-chloro-5-methyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid

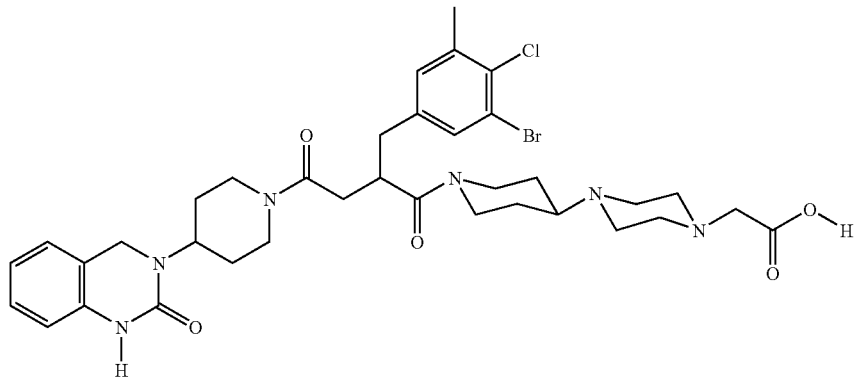

The product was obtained analogously to Example 16.4 from 109 mg (0.20 mmol) 2-(3-bromo-4-chloro-5-methyl-benzyl)-4-oxo-4-[4-(2-oxo-1,4-dihydro-2H-quinazolin-3-yl)-piperidin-1-yl]-butanoic acid and 51 mg (0.20 mmol) ethyl(4-piperidin-4-yl-piperazin-1yl)-acetate.

Yield: 10 mg (6% of theory) ESI-MS: $(M-H)^- = 755/757/759$ (Br, Cl) $R_f = 0.21$ (silica gel, DCM/MeOH 9:1)

Example 22.5 methyl(1'-{2-(3-bromo-4-chloro-5-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate

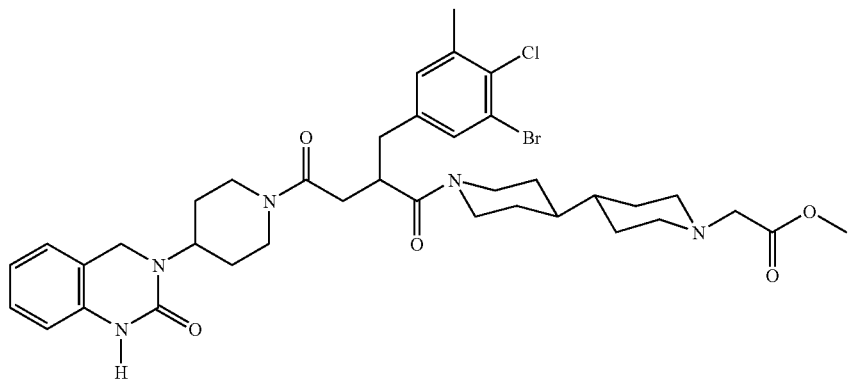

The product was obtained analogously to Example 16.5 from 220 mg (0.40 mmol) 2-(3-bromo-4-chloro-5-methyl-benzyl)-4-oxo-4-[4-(2-oxo-1,4-dihydro-2H-quinazolin-3-yl)-piperidin-1-yl]-butanoic acid and 102 mg (0.40 mmol) ethyl[4,4']bipiperidinyl-1-yl-acetate.

Yield: 19 mg (18% of theory) ESI-MS: $(M+H)^+ = 770/772/774$ (Br, Cl) $R_f = 0.36$ (silica gel, DCM/MeOH 9:1)

Example 22.6

(1'-{2-(3-bromo-4-chloro-5-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid

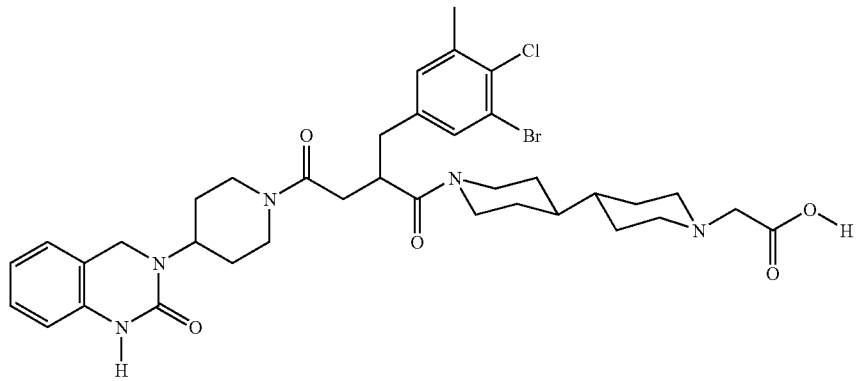

The product was obtained analogously to Example 16.6 from 204 mg (0.26 mmol) methyl(1'-{2-(3-bromo-4-chloro-5-methyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate.

Yield: 25 mg (12% of theory) ESI-MS: $(M+H)^+=756/758/760$ (Br, Cl) $R_f=0.23$ (silica gel, DCM/MeOH 9:1)

Example 23

4-(2-oxo-1,4-dihydro-2H-quinazolin-3-yl)-piperidin-1-carboxylic acid {1-(3-bromo-4-chloro-5-methyl-benzyl)-2-[4-(4-methyl-piperazin-1-yl)-piperidin-1-yl]-2-oxo-ethyl}-amide

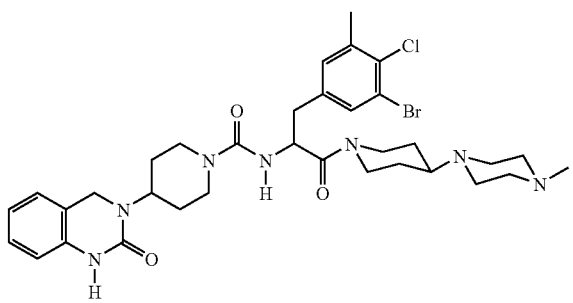

23a ethyl 2-amino-3-(3-bromo-4-chloro-5-methyl-phenyl)-propionate hydrochloride

The product was prepared analogously to Example 14a from 6.06 g (22.2 mmol) N-(diphenylmethylen)-glycinethylester and 6.30 g (115 mmol) 1-bromo-5-bromomethyl-2-chloro-3-methyl-benzene.

Yield: 5.82 g (77% of theory) ESI-MS: $(M+H)^+=320/322/324$ $R_f=0.70$ (silica gel, DCM/MeOH/NH₃ 9:1:0.1)

23b ethyl 3-(3-bromo-4-chloro-5-methyl-phenyl)-2-{[4-(2-oxo-1,4-dihydro-2H-quinazolin-3-yl)-piperidin-1-carbonyl]-amino}-propionate The product was obtained analogously to Example 14b from 5.82 g (16.3 mmol) ethyl 2-amino-3-(3-bromo-4-chloro-5-methyl-phenyl)-propionate hydrochloride and 3.77 (16.3 mmol) 3-piperidin-4-yl-3,4-dihydro-1H-quinazolin-2-one.

Yield: 7.60 g (81% of theory) $R_f=0.52$ (silica gel, DCM/MeOH/NH₃ 9:1:0.1)

23c 3-(3-bromo-4-chloro-5-methyl-phenyl)-2-{[4-(2-oxo-1,4-dihydro-2H-quinazolin-3-yl)-piperidin-1-carbonyl]-amino}-propionic acid The product was obtained analogously to Example 14c from 7.60 g (13.1 mmol) ethyl 3-(3-bromo-4-chloro-5-methyl-phenyl)-2-{[4-(2-oxo-1,4-dihydro-2H-quinazolin-3-yl)-piperidin-1-carbonyl]-amino}-propionate.

Yield: 6.70 g (93% of theory) ESI-MS: $(M-H)^-=547/549/551$ (Br, Cl) $R_f=0.05$ (silica gel, DCM/MeOH/NH₃ 9:1:0.1)

23d 4-(2-oxo-1,4-dihydro-2H-quinazolin-3-yl)-piperidin-1-carboxylic acid {1-(3-bromo-4-chloro-5-methyl-benzyl)-2-[4-(4-methyl-piperazin-1-yl)-piperidin-1-yl]-2-oxo-ethyl}-amide The product was prepared analogously to Example 2f from 1.35 g (2.45 mmol) 3-(3-bromo-4-chloro-5-methyl-phenyl)-2-{[4-(2-oxo-1,4-dihydro-2H-quinazolin-3-yl)-piperidin-1-carbonyl]-amino}-propionic acid and 449 g (2.45 mmol) 1-methyl-4-piperidin-4-yl-piperazine.

Yield: 1.10 g (63% of theory) ESI-MS: $(M+H)^+=714/716/718$ (Br, Cl) $R_f=0.41$ (silica gel, DCM/MeOH/NH₃ 9:1:0.1)

The following compounds were prepared analogously from 3-(3-bromo-4-chloro-5-methyl-phenyl)-2-{[4-(2-oxo-1,4-dihydro-2H-quinazolin-3-yl)-piperidin-1-carbonyl]-amino}-propionic acid and the corresponding amount of amine:

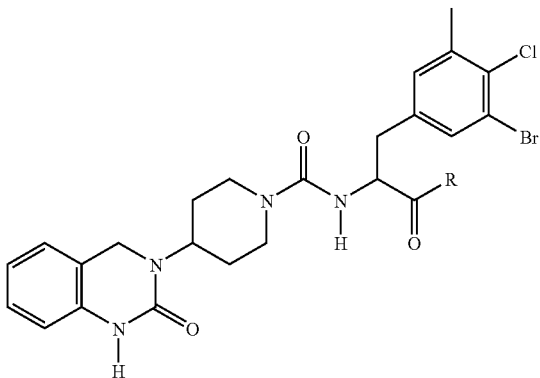

| Example | R | Yield (%) | Mass spectrum | $R_f$ (silica gel) |
|---|---|---|---|---|
| 23.1 | *–N⟨⟩–N⟨⟩ | 44 | 699/701/703 [M + H]⁺ | 0.40 (DCM/MeOH/NH₃ 9:1:0.1) |
| 23.2 | *–N⟨⟩–N⟨⟩–N–CH₃ | 55 | 714/716/718 [M + H]⁺ | 0.24 (DCM/MeOH/NH₃ 9:1:0.1) |
| 23.3 | *–N⟨⟩–⟨⟩–N–CH₃ | 53 | 713/715/717 [M + H]⁺ | 0.37 (DCM/MeOH/NH₃ 9:1:0.1) |
| 23.4 | *–N⟨⟩–N⟨⟩–pyridyl | 39 | 694/696/698 [M + H]⁺ | 0.49 (DCM/MeOH/NH₃ 9:1:0.1) |

Example 24

2-(4-chloro-3-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione

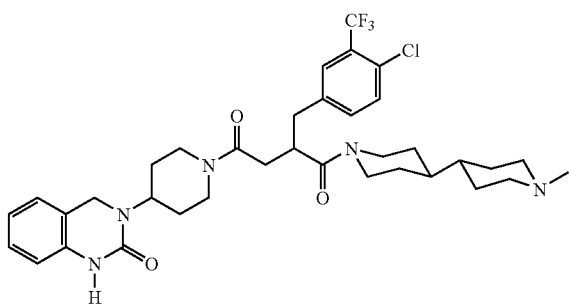

24a 1-methyl 2-[1-(4-chloro-3-trifluoromethyl-phenyl)-meth-(E)-ylidene]-succinate 20.7 mL (158 mmol) dimethyl succinate were added to a freshly prepared sodium methoxide solution (prepared by dissolving 3.64 g (158 mmol) sodium im MeOH) in 300 mL MeOH and the reaction mixture was stirred for 1 h at RT. Then 30 g (144 mmol) 4-chloro-3-trifluoromethyl-benzaldehyde were added and the reaction solution was refluxed for 6 h. It was evaporated down i. vac., the residue was taken up in water, acidified with 20% citric acid solution and extracted exhaustively with EtOAc. The organic phase was extracted five times, each time with 200 mL of 3% NH₃ solution, the combined aqueous phases were acidified with citric acid solution, exhaustively extracted with EtOAc and dried over Na₂SO₄. After the desiccant and solvent had been eliminated the desired product was obtained in the form of a yellow oil.

Yield: 12 g (26% of theory) $R_f$=0.33 (silica gel, PE/EtOAc/AcOH 75:25:5)

24b 1-methyl 2-(4-chloro-3-trifluoromethyl-benzyl)-succinate 200 mg 10% Pt/C were added to a solution of 2.0 g (6.2 mmol) 1-methyl 2-[1-(4-chloro-3-trifluoromethyl-phenyl)-meth-(E)-ylidene]-succinate in 20 mL MeOH and the reaction mixture was hydrogenated at RT and 3 bar $H_2$ for 3 h. The catalyst was filtered off and the solvent was evaporated down i.vac. The crude product was further reacted without purification.

Yield: 1.85 g (92% of theory) $R_f$=0.38 (silica gel, PE/EtOAc/AcOH 75:25:5)

24c methyl 2-(4-chloro-3-trifluoromethyl-benzyl)-4-oxo-4-[4-(2-oxo-1,4-dihydro-2H-quinazolin-3-yl)-piperidin-1-yl]-butanoate A solution of 1.5 g (4.6 mmol) 1-methyl 2-(4-chloro-3-trifluoromethyl-benzyl)-succinate, 1.64 g (5.1 mmol) TBTU, 0.69 g (5.0 mmol) HOBt and 1.32 mL (7.5 mmol) ethyldiisopropylamine in 100 mL of a THF/water mixture (9:1) was stirred for 10 min at RT and then combined with 1.2 g (5.0 mmol) of 3-piperidin-4-yl-3,4-dihydro-1H-quinazolin-2-one. The reaction mixture was stirred for 2 h at RT, evaporated down i. vac., the residue was combined with saturated $NaHCO_3$ solution, exhaustively extracted with EtOAc and the combined organic extracts were dried over $MgSO_4$. After the desiccant and solvent had been eliminated the desired product was obtained, which was further reacted without purification.

Yield: 2.2 g (89% of theory) $R_f$=0.6 (silica gel, DCM/MeOH/cyc/$NH_3$ 70:15:15:2)

24d 2-(4-chloro-3-trifluoromethyl-benzyl)-4-oxo-4-[4-(2-oxo-1,4-dihydro-2H-quinazolin-3-yl)-piperidin-1-yl]-butanoic acid 16 mL 1 M NaOH solution were added to a solution of 2.2 g (4.1 mmol) methyl 2-(4-chloro-3-trifluoromethyl-benzyl)-4-oxo-4-[4-(2-oxo-1,4-dihydro-2H-quinazolin-3-yl)-piperidin-1-yl]-butanoate in 20 mL MeOH and the reaction mixture was stirred for 5 h at 50° C. It was diluted with 170 mL water, extracted twice with 30 mL tert-butylmethylether, the aqueous phase was combined with 16 mL 1 M HCl, extracted three times with 70 mL EtOAc and the combined organic phases were dried over $Na_2SO_4$. After the desiccant and solvent had been eliminated the residue was triturated with diisopropylether, suction filtered and dried in the air.

Yield: 1.1 g (51% of theory) $R_f$=0.25 (silica gel, DCM/MeOH/cyc/$NH_3$ 70:15:15:2)

24e 2-(4-chloro-3-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione Prepared analogously to 24c from 790 mg (1.5 mmol) 2-(4-chloro-3-trifluoromethyl-benzyl)-4-oxo-4-[4-(2-oxo-1,4-dihydro-2H-quinazolin-3-yl)-piperidin-1-yl]-butanoic acid and 370 mg (1.6 mmol) 1-methyl-[4,4']bipiperidinyl.

Yield: 530 mg (51% of theory)

EI: $(M)^+$=687/689 (Cl) $R_f$=0.6 (silica gel, DCM/MeOH/cyc/$NH_3$ 70:15:15:2)

Example 24.1

2-(4-chloro-3-trifluoromethyl-benzyl)-1-[4-(4-methyl-piperazin-1-yl)-piperidin-1-yl]-4-[4-(2-oxo-1,4-dihydro-2H-quinazolin-3-yl)-piperidin-1-yl]-butan-1,4-dione

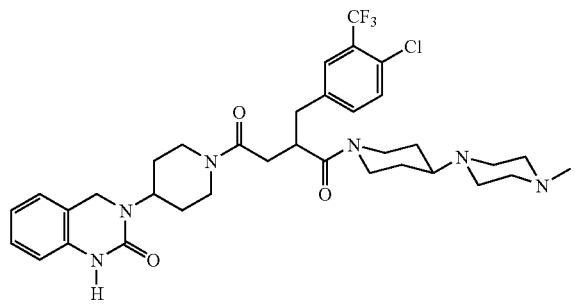

280 mg (1.53 mmol) 1-methyl-4-piperidin-4-yl-piperazine were added to a solution of 800 mg (1.53 mmol) 2-(4-chloro-3-trifluoromethyl-benzyl)-4-oxo-4-[4-(2-oxo-1,4-dihydro-2H-quinazolin-3-yl)-piperidin-1-yl]-butanoic acid, 544 mg (1.7 mmol) TBTU, 206 mg (1.53 mmol) HOBt and 0.69 mL (4.94 mmol) triethylamine in 100 mL THF and the reaction mixture was stirred for 2.5 h at RT. It was evaporated down i. vac., the residue was taken up in DCM, the organic phase was washed twice with saturated $NaHCO_3$ solution and dried over $MgSO_4$. After the desiccant and solvent had been eliminated the residue was purified by chromatography (silica gel, MeOH).

Yield: 400 mg (38% of theory) EI: $(M)^+$=688/690 (Cl) $R_f$=0.25 (silica gel, MeOH)

Example 24.2

1-[1,4']bipiperidinyl-1'-yl-2-(4-chloro-3-trifluoromethyl-benzyl)-4-[4-(2-oxo-1,4-dihydro-2H-quinazolin-3-yl)-piperidin-1-yl]-butan-1,4-dione

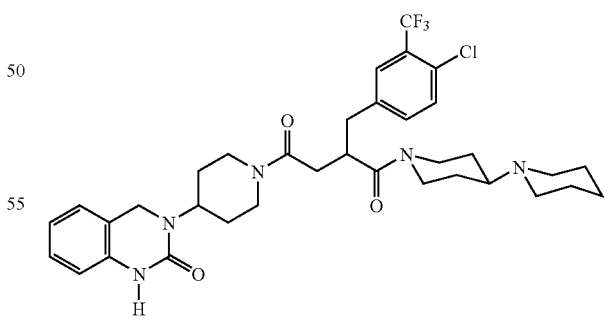

Prepared analogously to Example 24.1 from 800 mg (1.53 mmol) 2-(4-chloro-3-trifluoromethyl-benzyl)-4-oxo-4-[4-(2-oxo-1,4-dihydro-2H-quinazolin-3-yl)-piperidin-1-yl]-butanoic acid and 271 mg (1.61 mmol) [1,4']bipiperidinyl.

Yield: 470 mg (46% of theory) EI: $(M)^+$=673/675 (Cl) $R_f$=0.28 (silica gel, MeOH)

Example 24.3

[4-(1-{2-(4-chloro-3-trifluoromethyl-benzyl)-4-oxo-4-[4-(2-oxo-1,4-dihydro-2H-quinazolin-3-yl)-piperidin-1-yl]-butyryl}-piperidin-4-yl)-piperazin-1-yl]-acetic acid

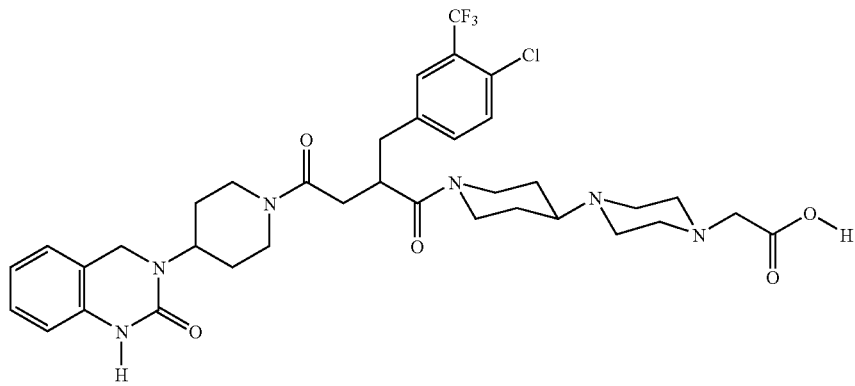

Prepared analogously to Example 16.4 from 105 mg (0.2 mmol) 2-(4-chloro-3-trifluoromethyl-benzyl)-4-oxo-4-[4-(2-oxo-1,4-dihydro-2H-quinazolin-3-yl)-piperidin-1-yl]-butanoic acid and 51 mg (0.2 mmol) ethyl(4-piperidin-4-yl-piperazin-1-yl)-acetate.

Yield: 13 mg (8% of theory) ESI-MS: $(M+H)^+=733/735$ (Cl) Retention time (HPLC): 6.3 min (method A)

Example 24.4 methyl(1'-{2-(4-chloro-3-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate

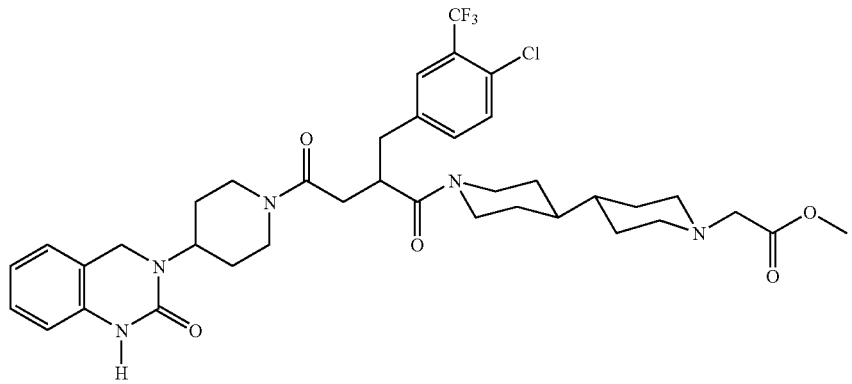

Prepared analogously to Example 16.5 from 209 mg (0.4 mmol) 2-(4-chloro-3-trifluoromethyl-benzyl)-4-oxo-4-[4-(2-oxo-1,4-dihydro-2H-quinazolin-3-yl)-piperidin 1-yl]-butanoic acid and 102 mg (0.4 mmol) ethyl[4,4']bipiperidinyl-1-yl-acetate.

Yield: 17 mg (17% of theory) ESI-MS: $(M+H)^+=746/748$ (Cl) $R_f=0.44$ (silica gel, DCM/MeOH 9:1)

Example 24.5

(1'-{2-(4-chloro-3-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetic acid

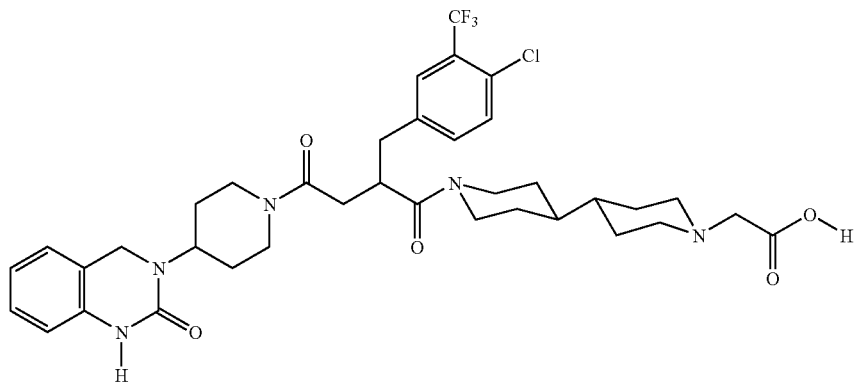

Prepared analogously to Example 16.6 from 198 mg (0.26 mmol) methyl(1'-{2-(4-chloro-3-trifluoromethyl-benzyl)-4-oxo-4-[4-(2-oxo-1,4-dihydro-2H-quinazolin-3-yl)-piperidin-1-yl]-butyryl}-[4,4']bipiperidinyl-1-yl)-acetate.

Yield: 19 mg (9% of theory) ESI-MS: $(M+H)^+=732/734$ (Cl) $R_f=0.22$ (silica gel, DCM/MeOH 9:1)

Example 24.6

2-(4-chloro-3-trifluoromethyl-benzyl)-1-(1'-methyl-[4,4']bipiperidinyl-1-yl)-4-[4-(2-oxo-1,4-dihydro-2H-quinazolin-3-yl)-piperidin-1-yl]-butan-1,4-dione

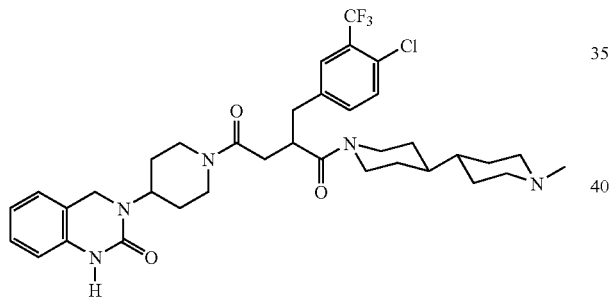

Prepared analogously to Example 24.1 from 800 mg (1.53 mmol) 2-(4-chloro-3-trifluoromethyl-benzyl)-4-oxo-4-[4-(2-oxo-1,4-dihydro-2H-quinazolin-3-yl)-piperidin-1-yl]-butanoic acid and 279 mg (1.53 mmol) 1-methyl-[4,4']bipiperidinyl.

Yield: 320 mg (30% of theory) EI: $(M)^+=687/689$ (Cl) $R_f=0.20$ (silica gel, MeOH)

The following compounds may also be prepared by the processes described hereinbefore:

| Example | Structure |
|---|---|
| 25.1 | 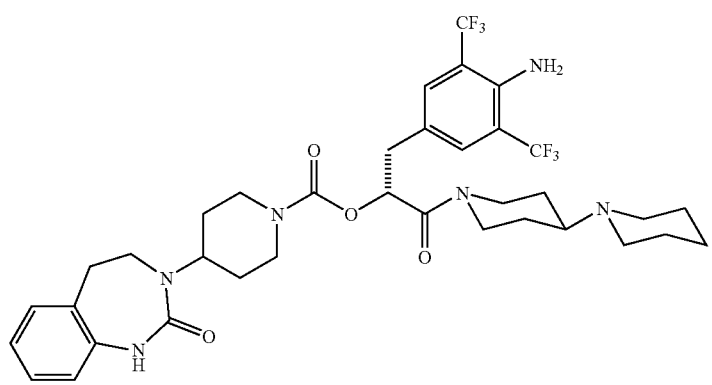 |

-continued
| Example | Structure |
|---------|-----------|
| 25.2 | 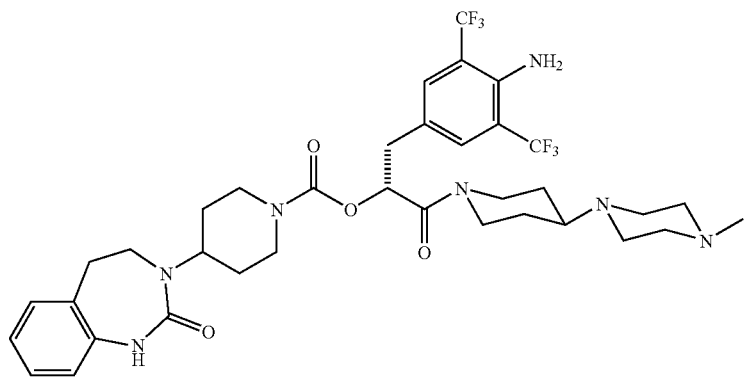 |
| 25.3 | 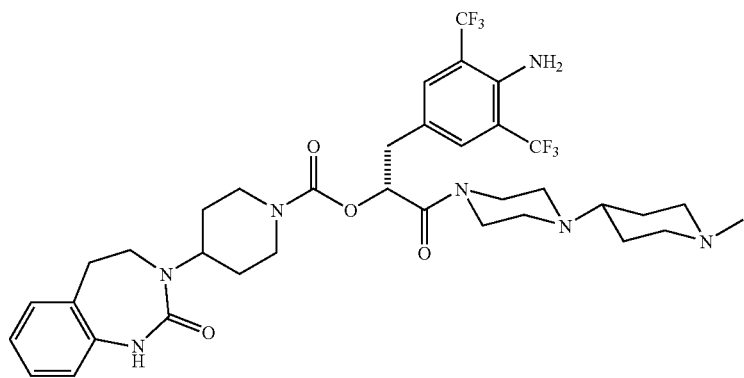 |
| 25.4 | 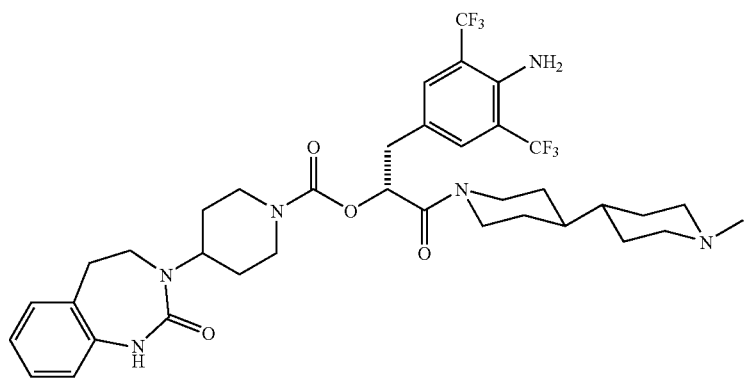 |
| 25.5 | 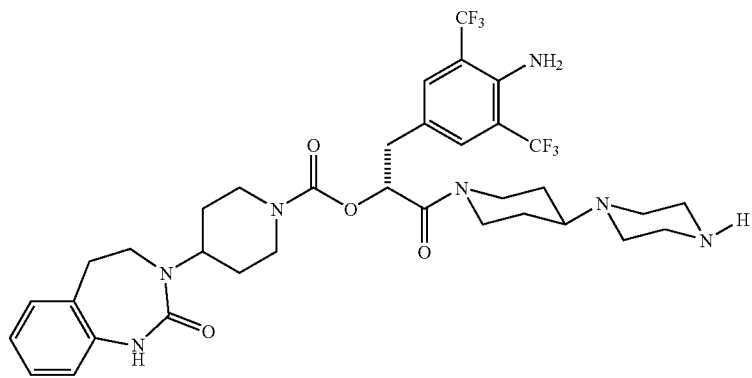 |

-continued
| Example | Structure |
|---|---|
| 25.6 | 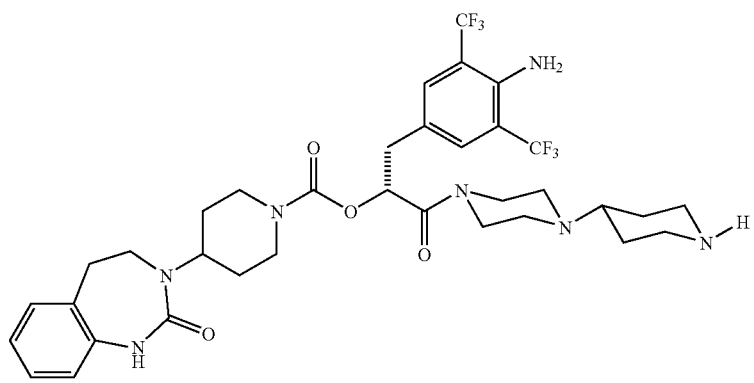 |
| 25.7 | 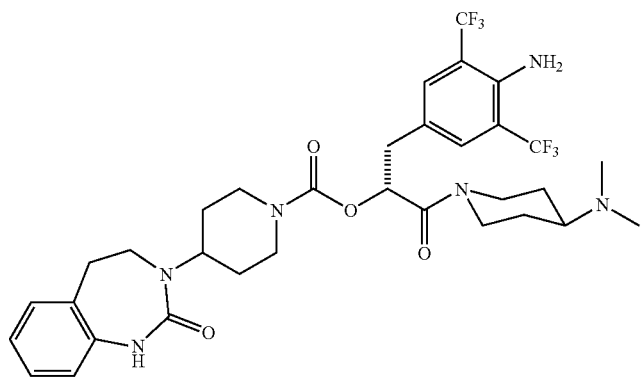 |
| 25.8 | 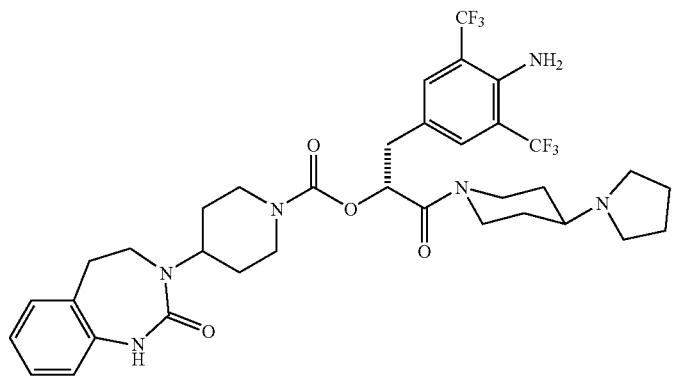 |
| 25.9 | 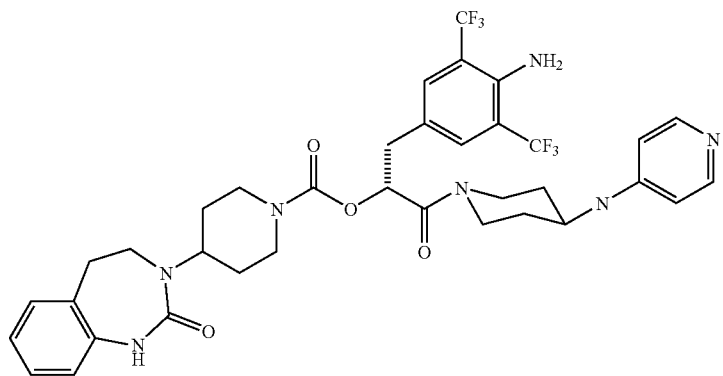 |

| Example | Structure |
|---------|-----------|
| 25.10 | 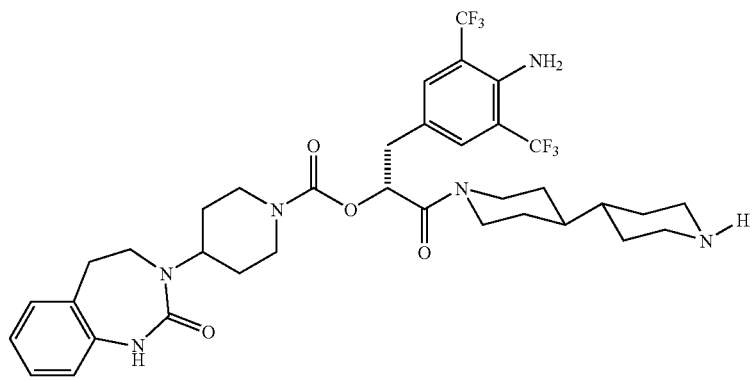 |
| 26.1 | 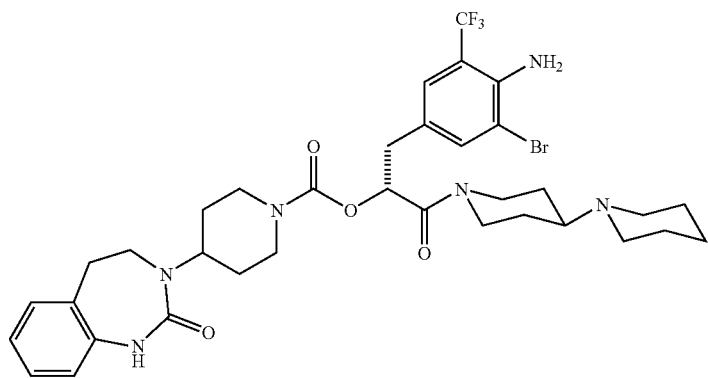 |
| 26.2 | 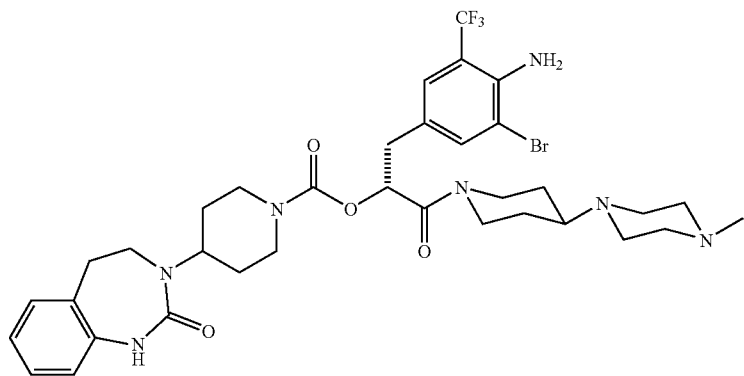 |
| 26.3 | 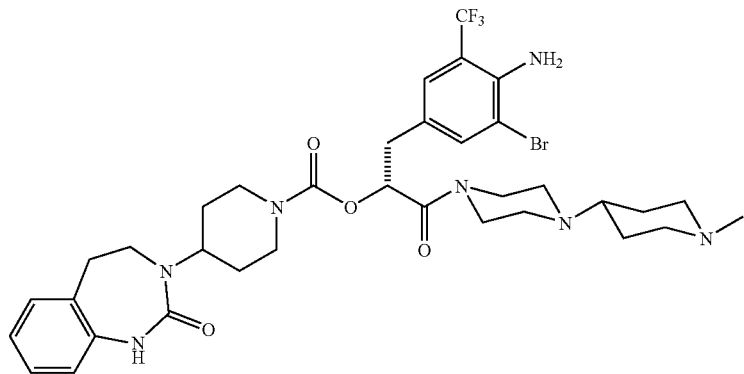 |

-continued
| Example | Structure |
|---------|-----------|
| 26.4 | 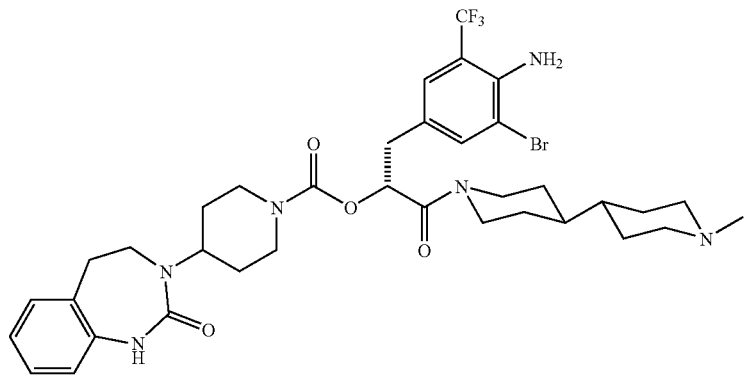 |
| 26.5 | 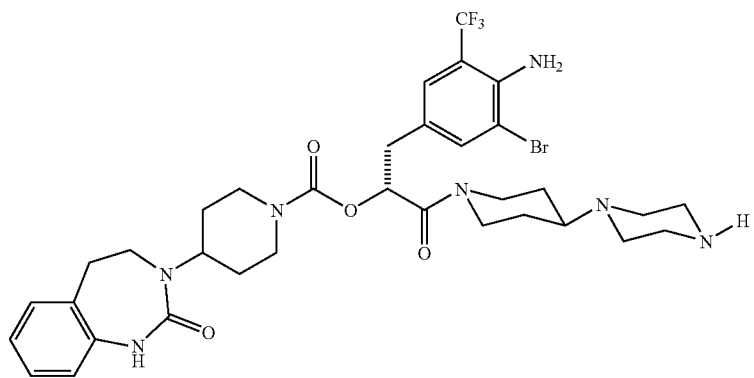 |
| 26.6 | 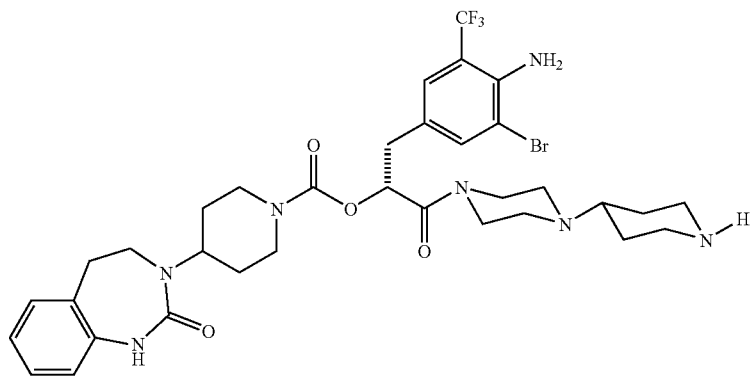 |
| 26.7 | 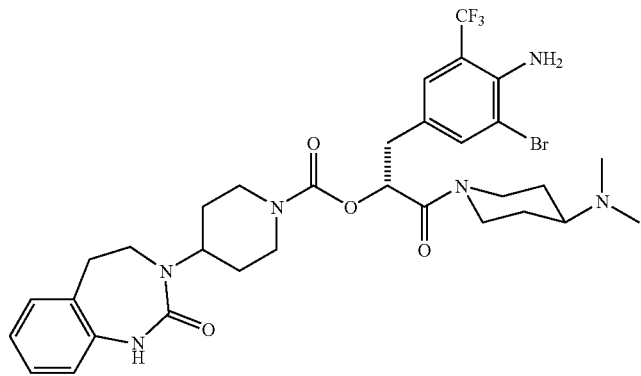 |

-continued
| Example | Structure |
|---|---|
| 26.8 | 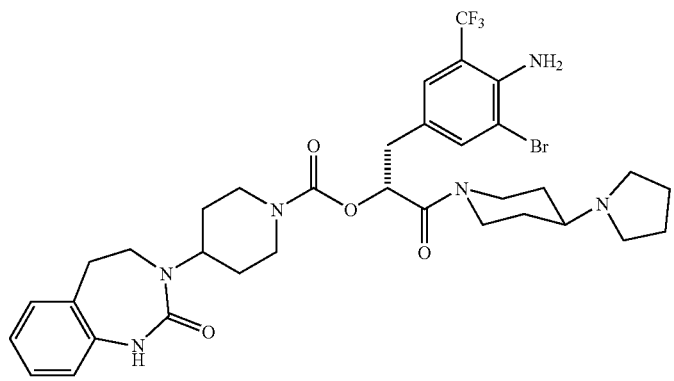 |
| 26.9 | 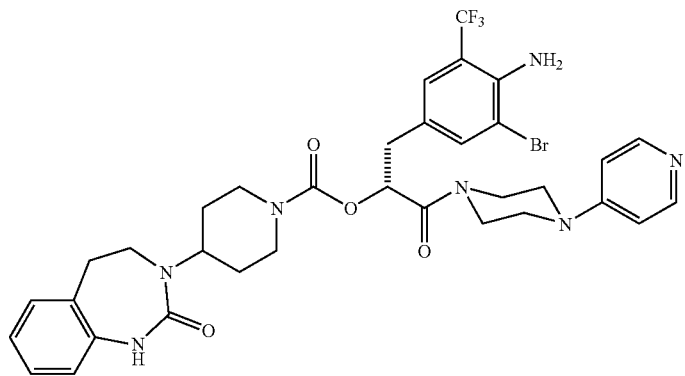 |
| 26.10 | 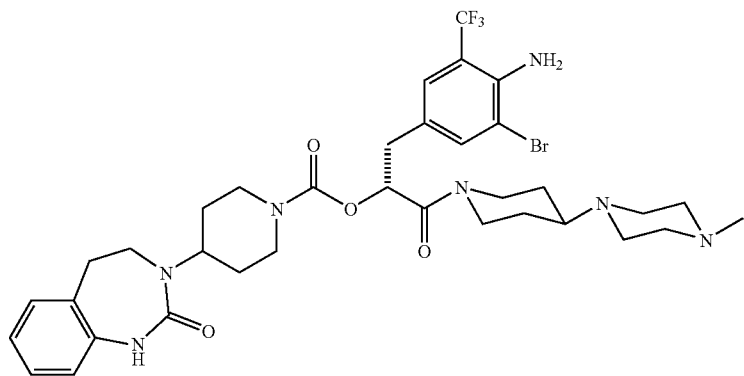 |
| 27.1 | 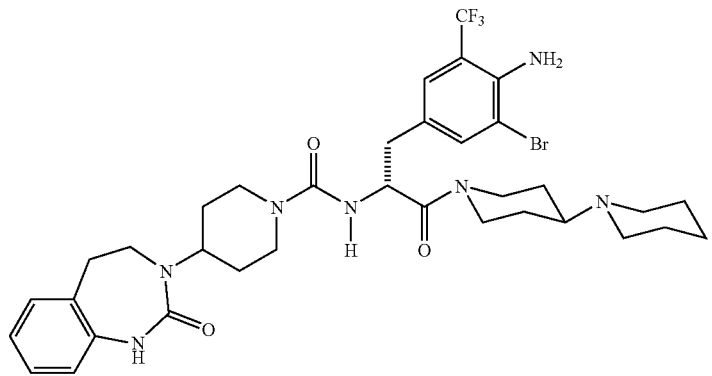 |

-continued
| Example | Structure |
|---------|-----------|
| 27.2 | 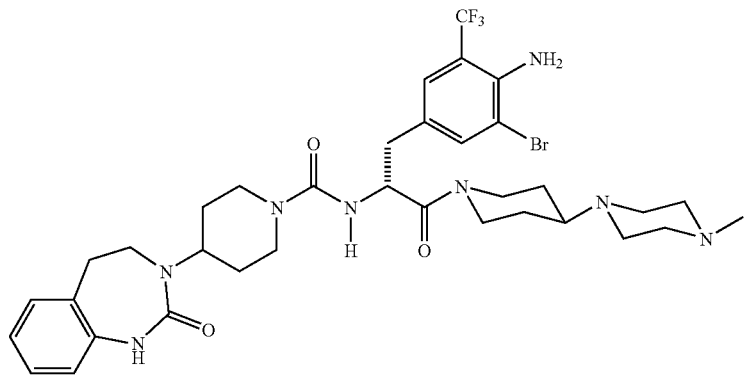 |
| 27.3 | 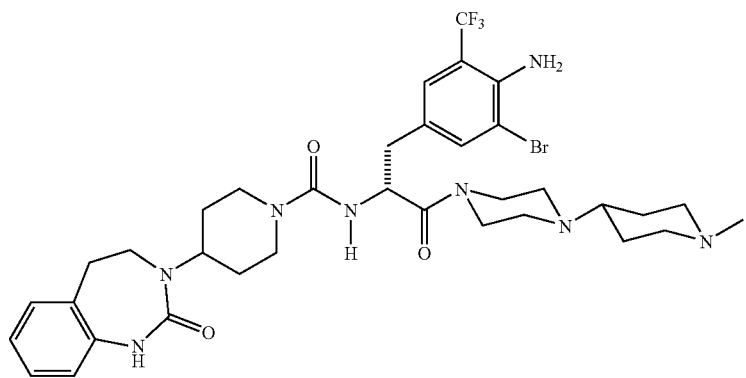 |
| 27.4 | 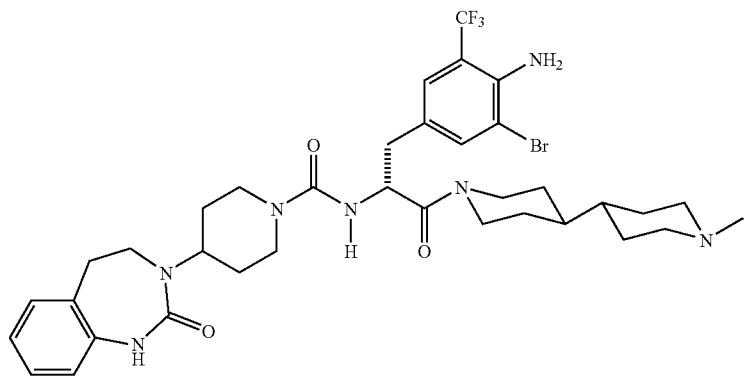 |
| 27.5 | 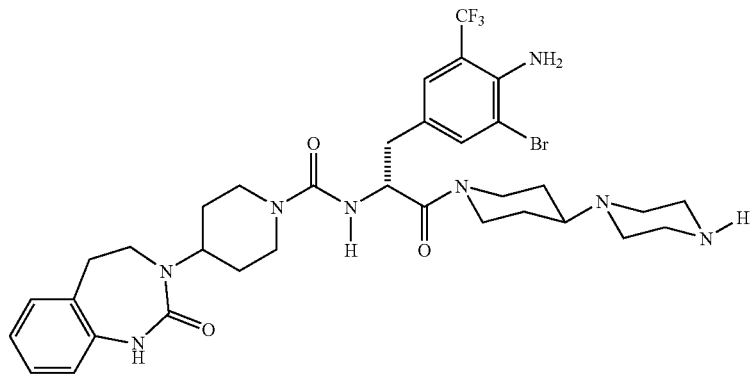 |

| Example | Structure |
|---|---|
| 27.6 | 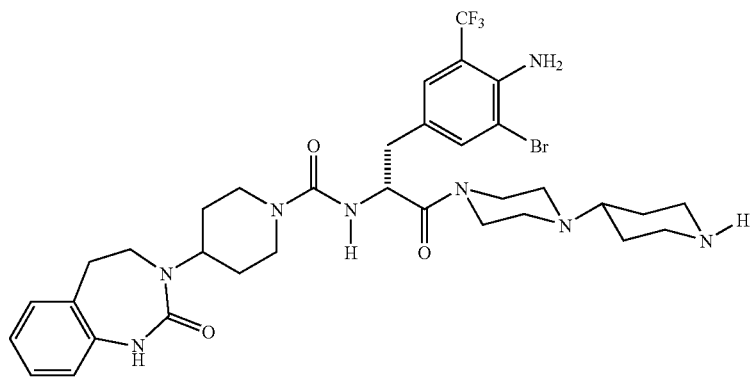 |
| 27.7 | 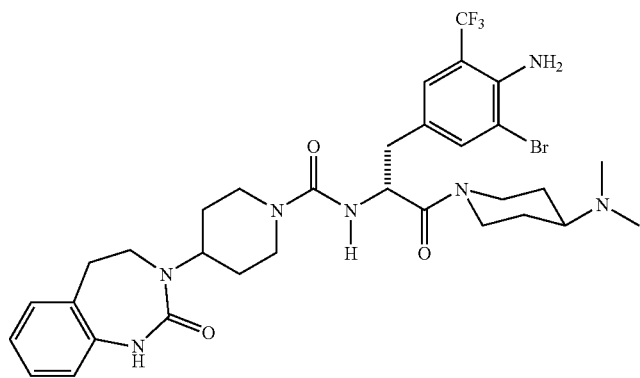 |
| 27.8 | 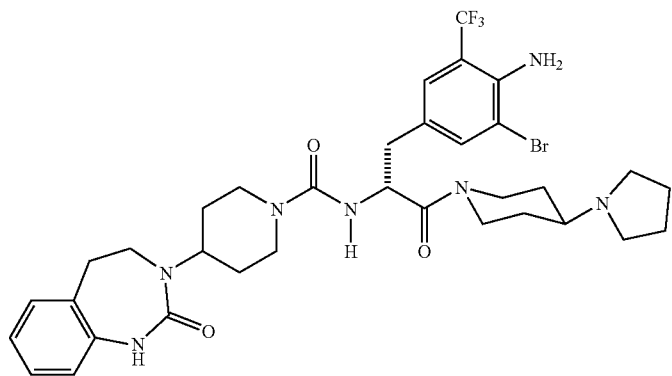 |
| 27.9 | 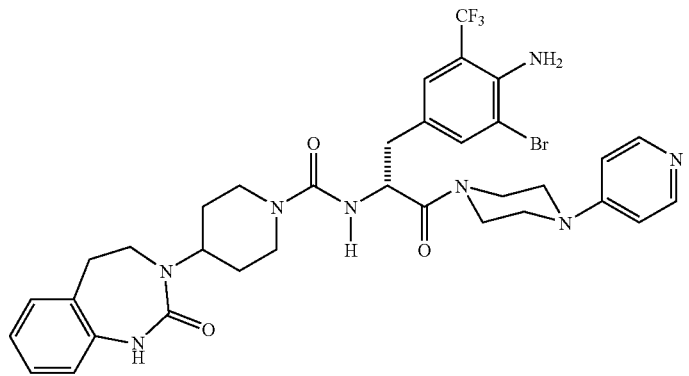 |

| Example | Structure |
|---|---|
| 27.10 | 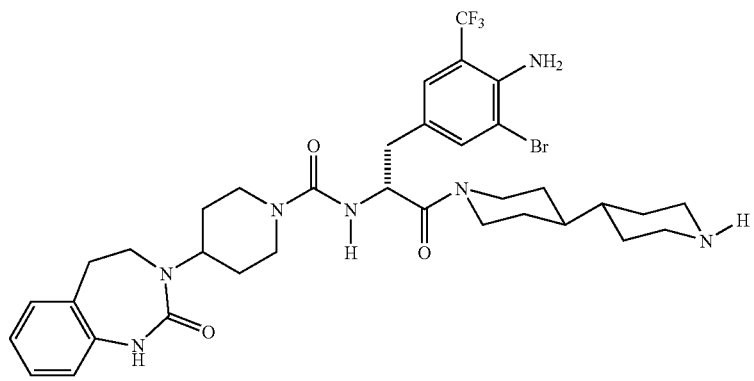 |
| 28.1 | 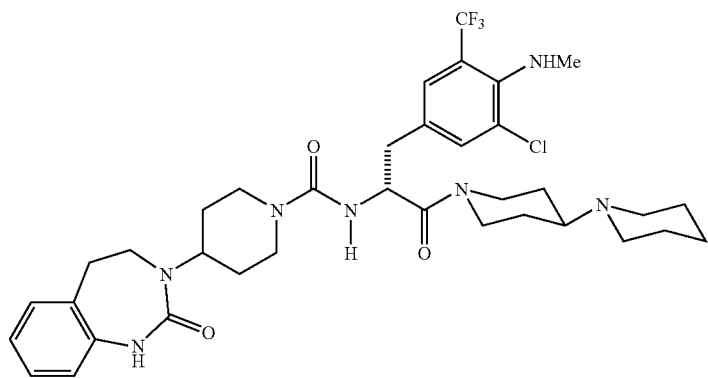 |
| 28.2 | 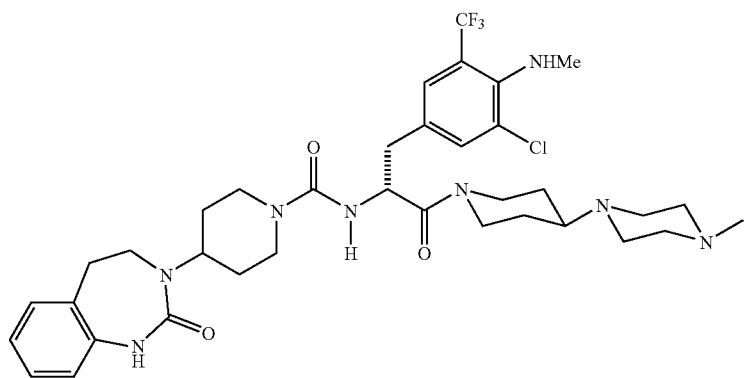 |
| 28.3 | 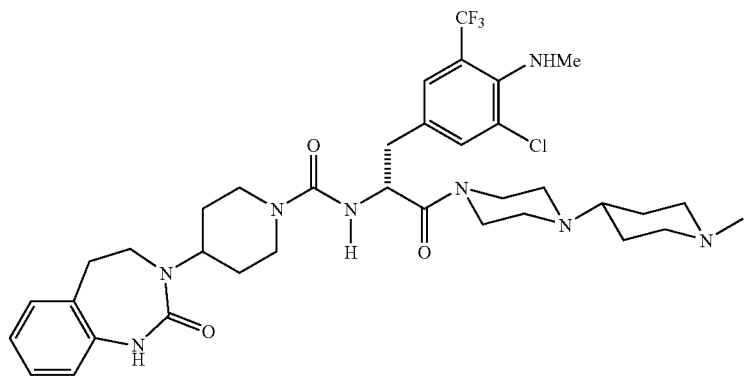 |

-continued
| Example | Structure |
|---------|-----------|
| 28.4 | 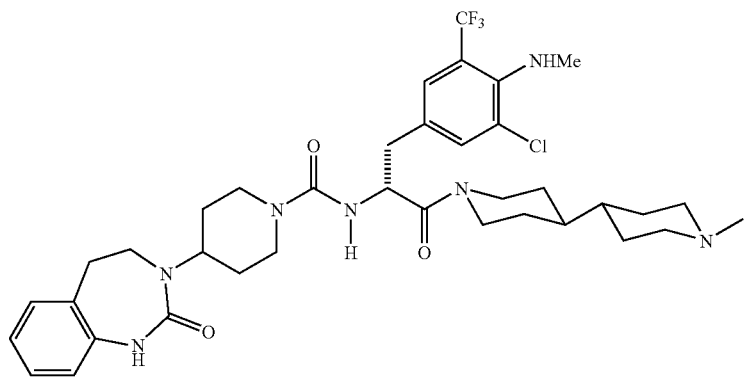 |
| 28.5 | 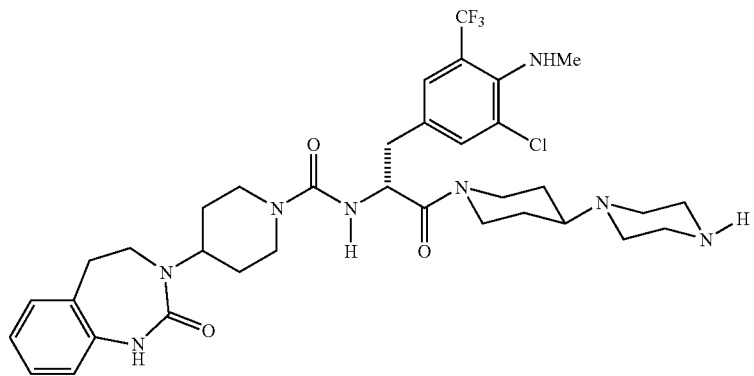 |
| 28.6 | 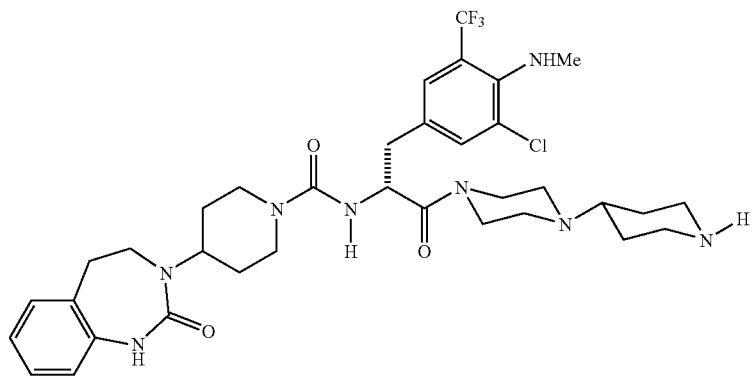 |
| 28.7 | 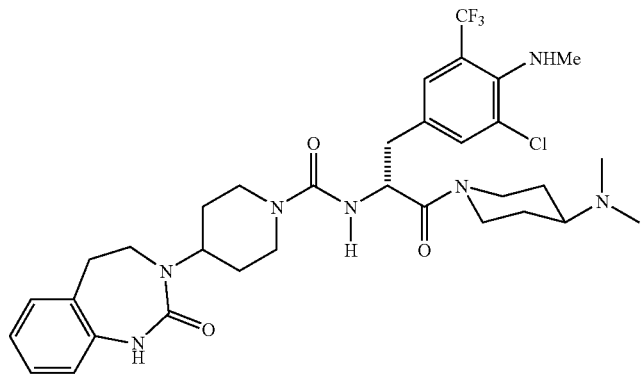 |

-continued
| Example | Structure |
|---|---|
| 28.8 | 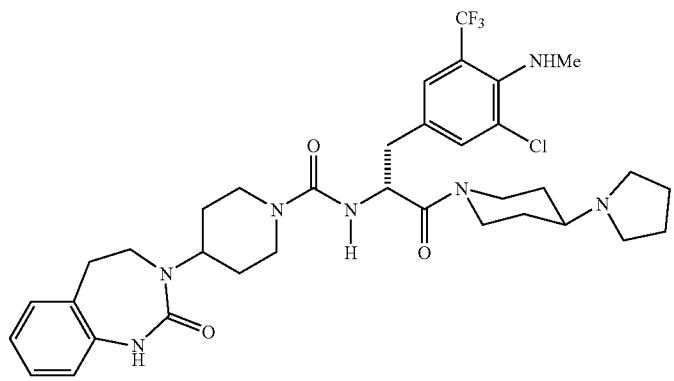 |
| 28.9 | 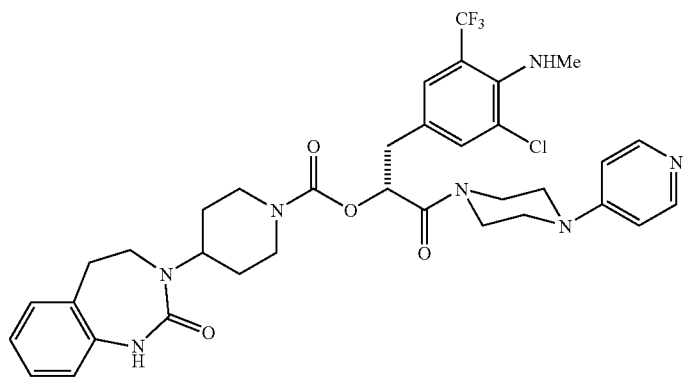 |
| 28.10 | 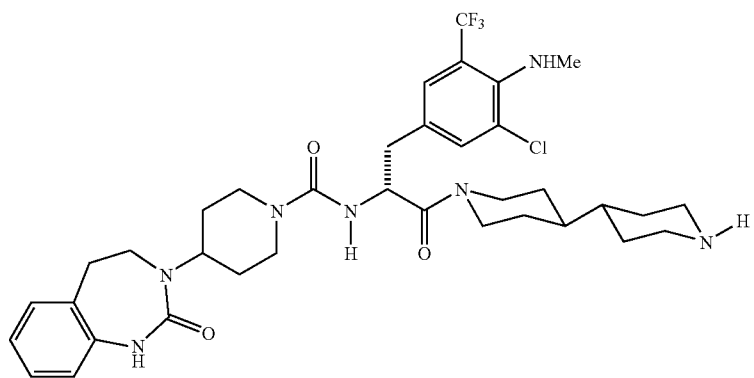 |
| 29.1 | 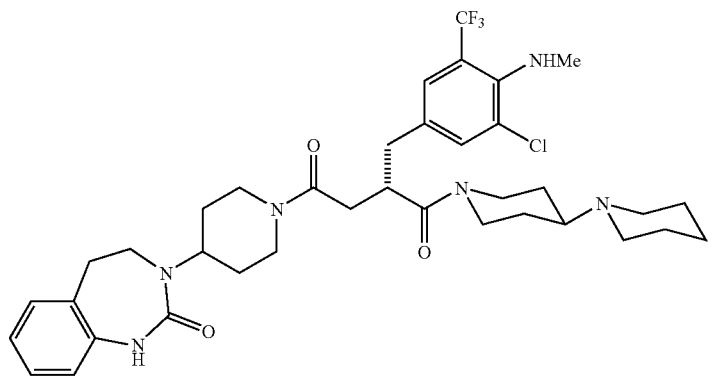 |

| Example | Structure |
|---------|-----------|
| 29.2 | 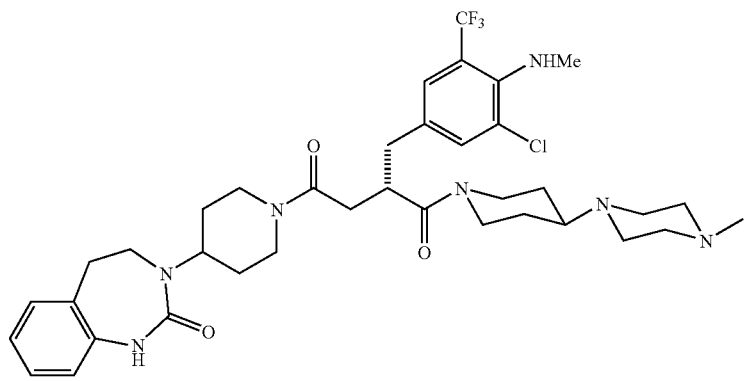 |
| 29.3 | 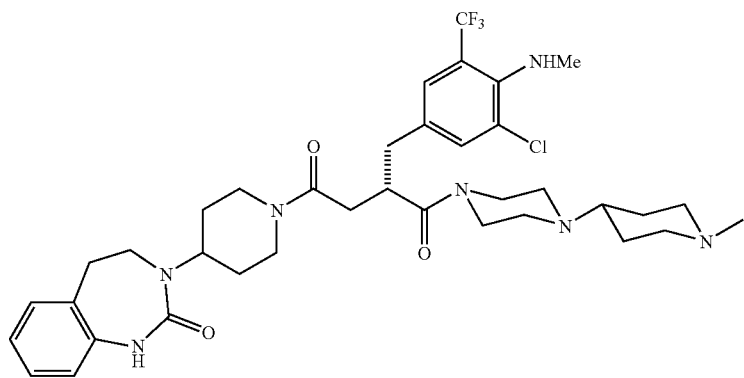 |
| 29.4 | 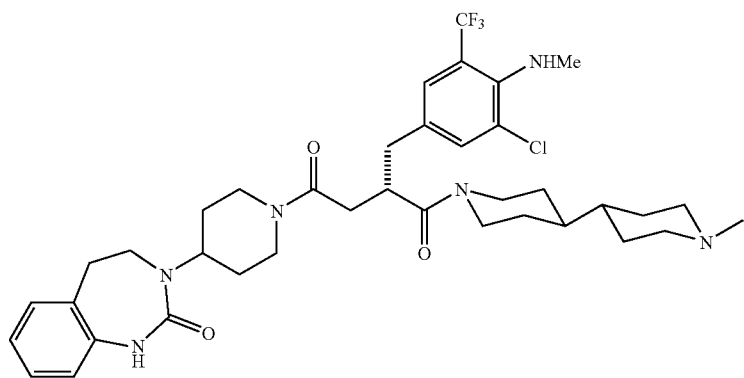 |
| 29.5 | 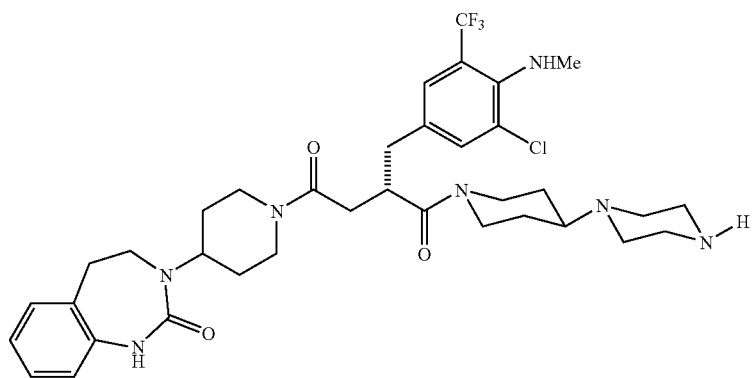 |

| Example | Structure |
|---|---|
| 29.6 | 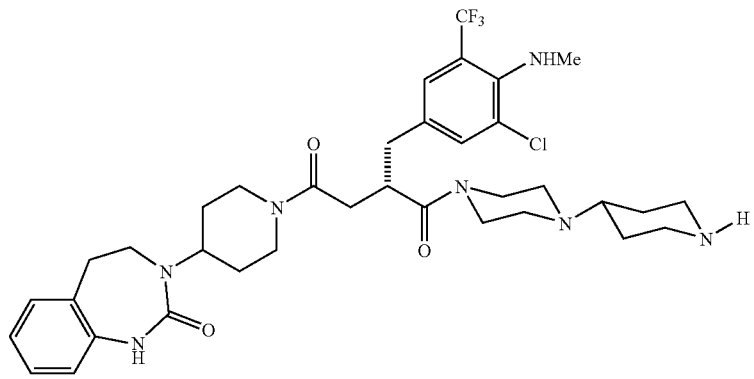 |
| 29.7 | 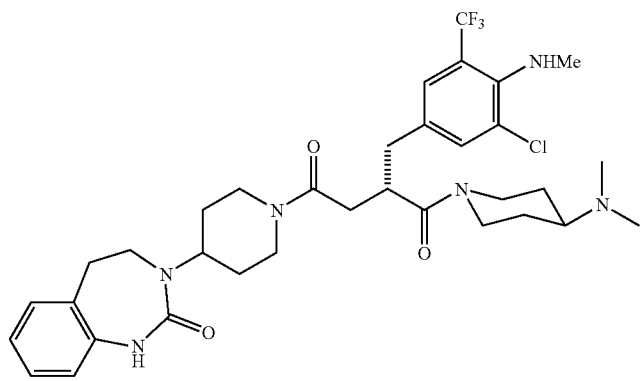 |
| 29.8 | 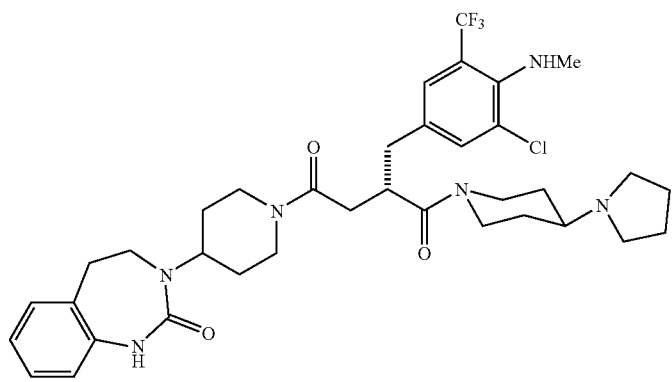 |
| 29.9 | 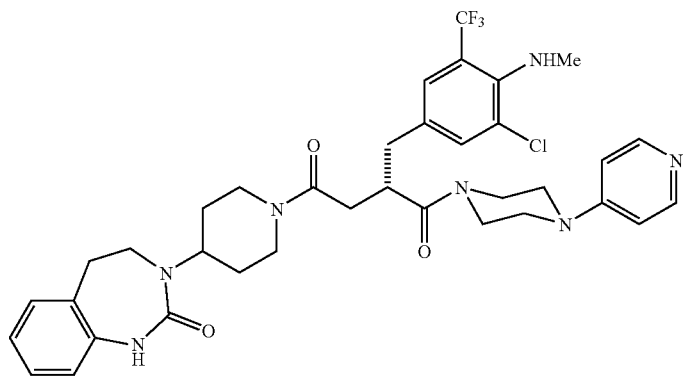 |

| Example | Structure |
|---|---|
| 29.10 | 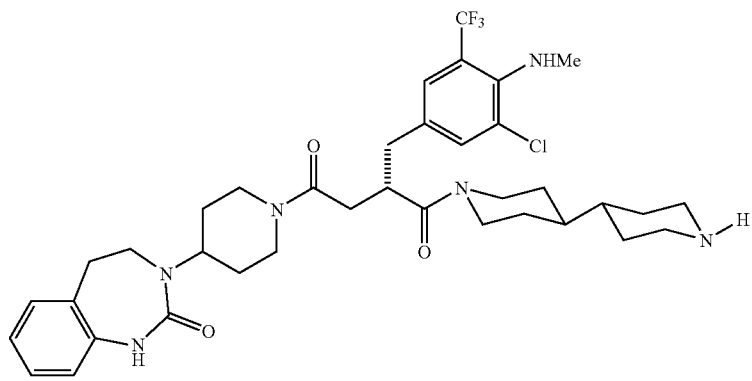 |
| 30.1 | 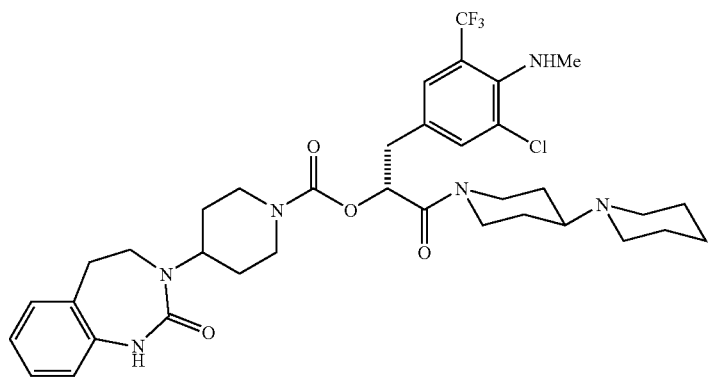 |
| 30.2 | 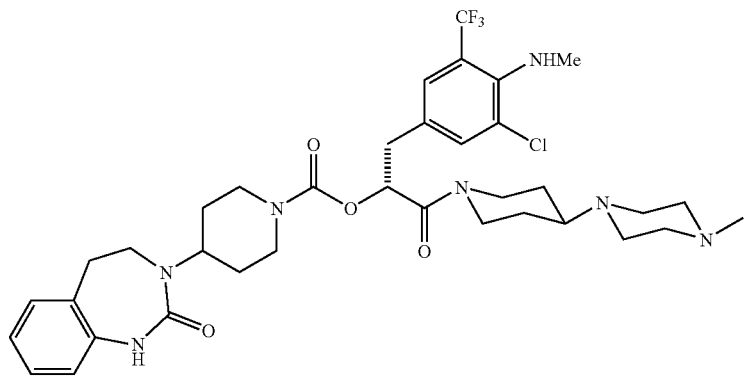 |
| 30.3 | 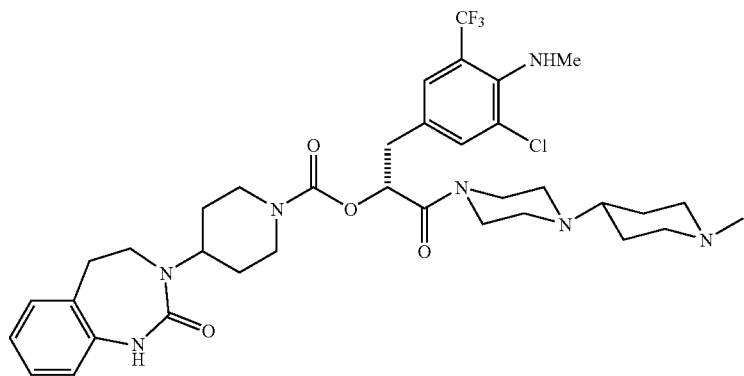 |

-continued
| Example | Structure |
|---------|-----------|
| 30.4 | 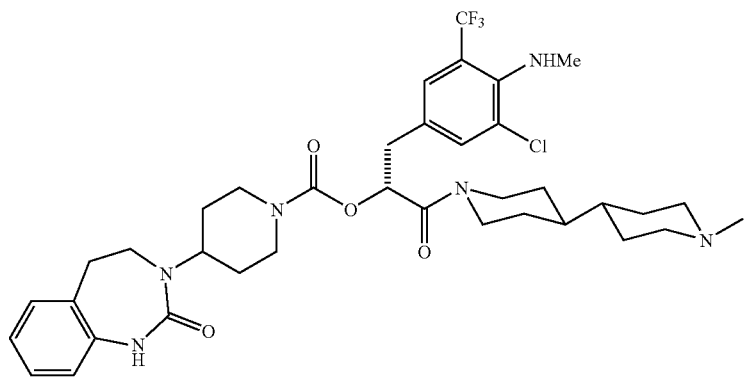 |
| 30.5 | 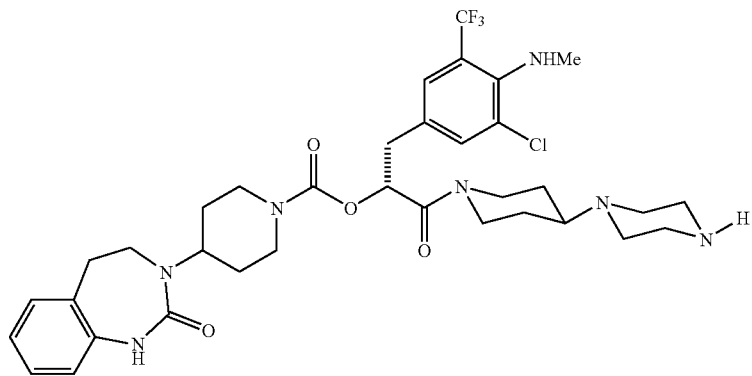 |
| 30.6 | 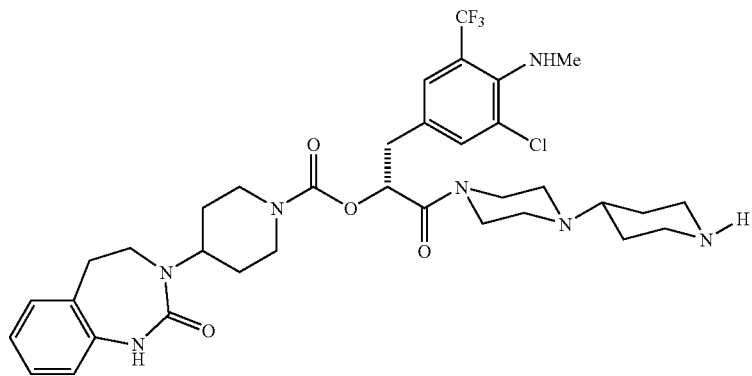 |
| 30.7 | 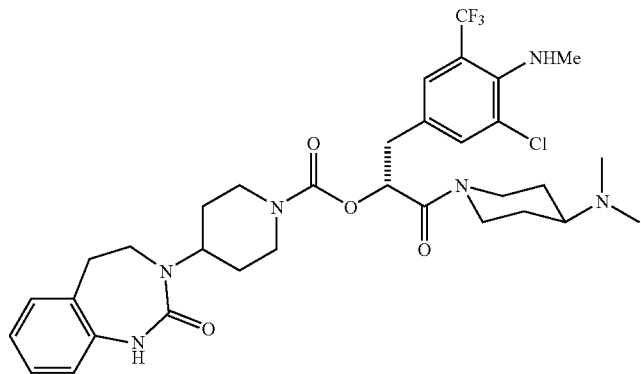 |

-continued
| Example | Structure |
|---------|-----------|
| 30.8 | 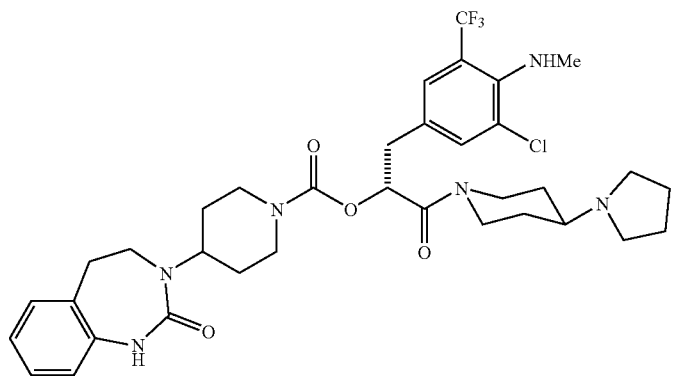 |
| 30.9 | 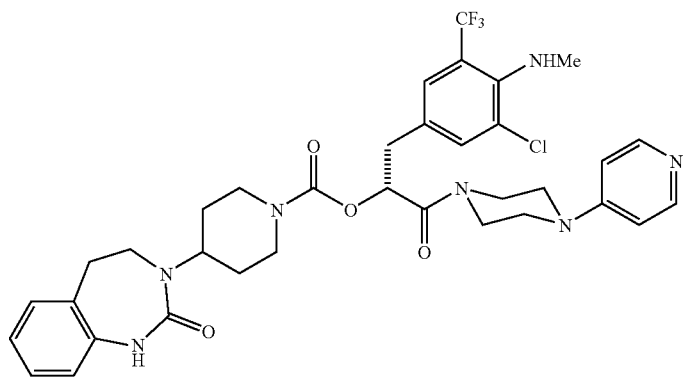 |
| 30.10 | 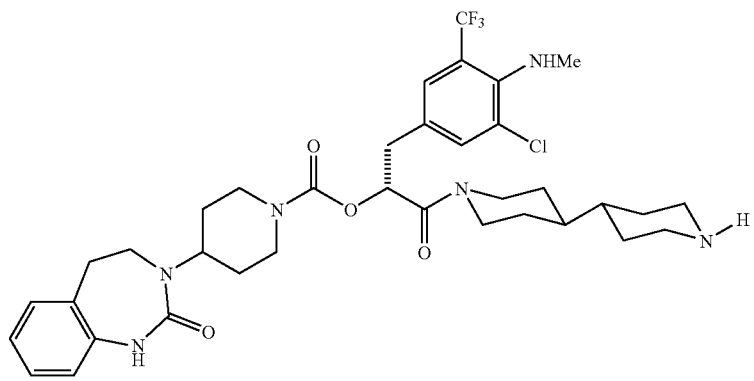 |

The following compounds may be obtained using 4-amino-3-chloro-5-methyl-benzoic acid as starting material:
| Example | Structure |
|---|---|
| 31.1 | 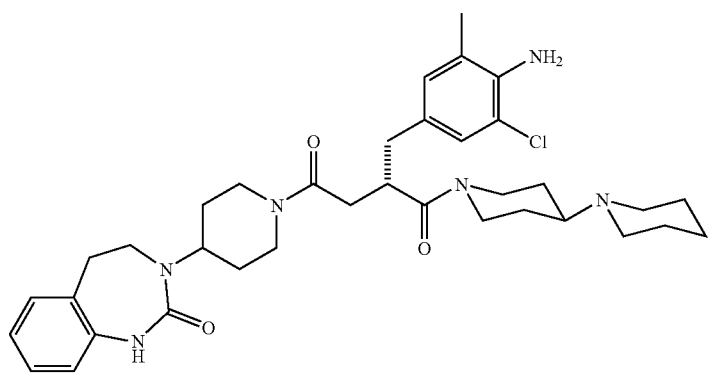 |
| 31.2 | 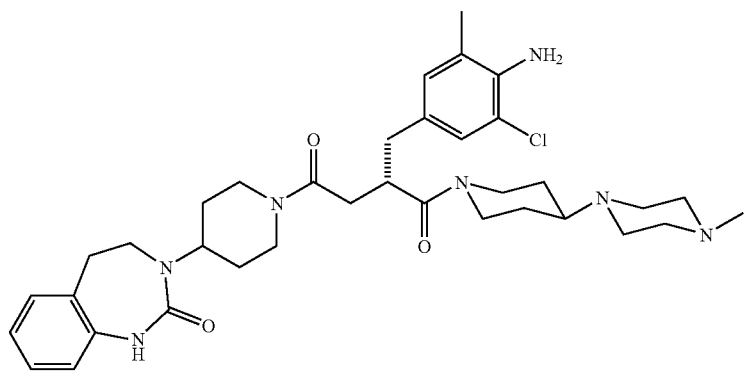 |
| 31.3 | 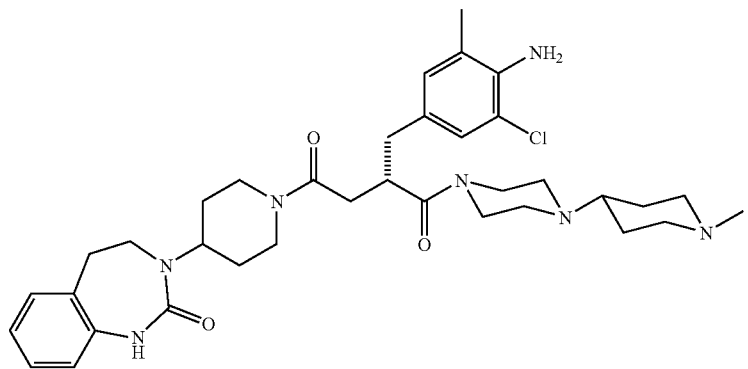 |
| 31.4 | 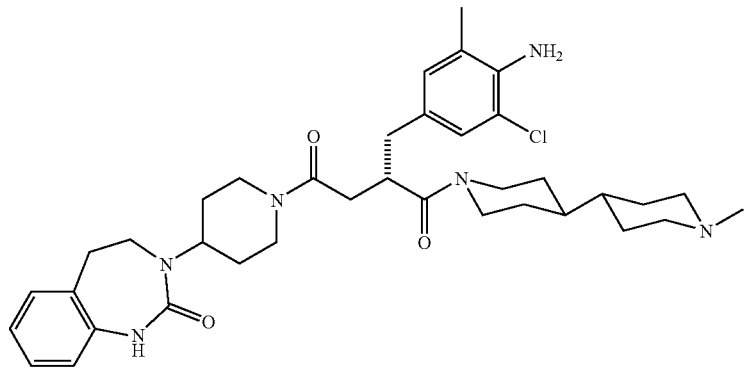 |

-continued
| Example | Structure |
|---------|-----------|
| 31.5 | 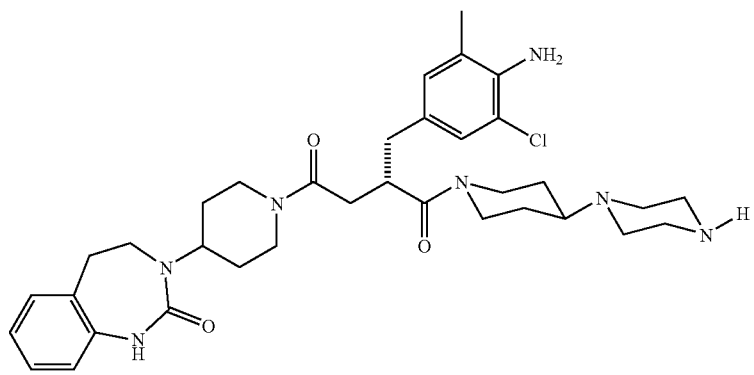 |
| 31.6 | 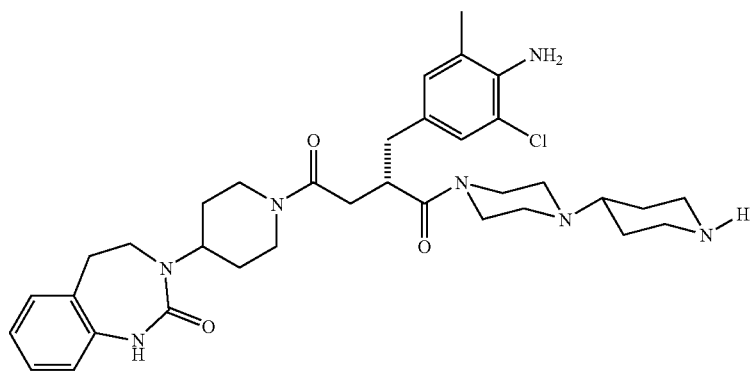 |
| 31.7 | 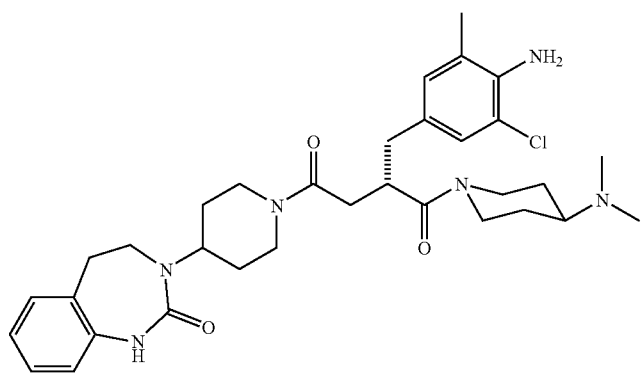 |
| 31.8 | 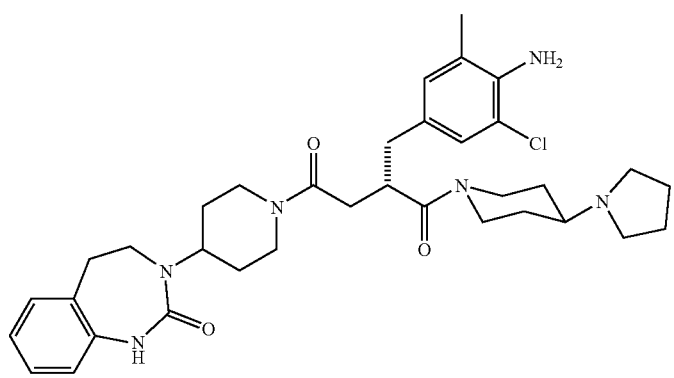 |

-continued
| Example | Structure |
|---------|-----------|
| 31.9 | 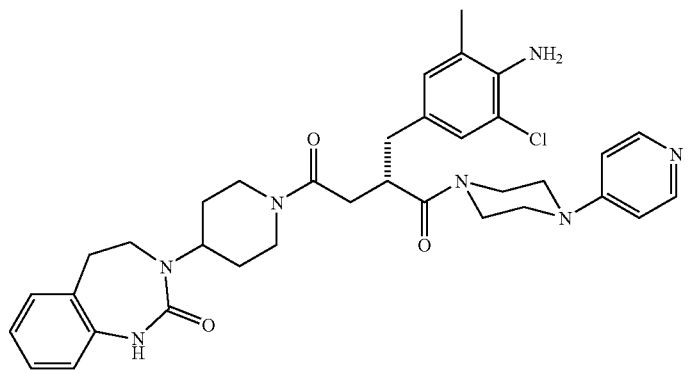 |
| 31.10 | 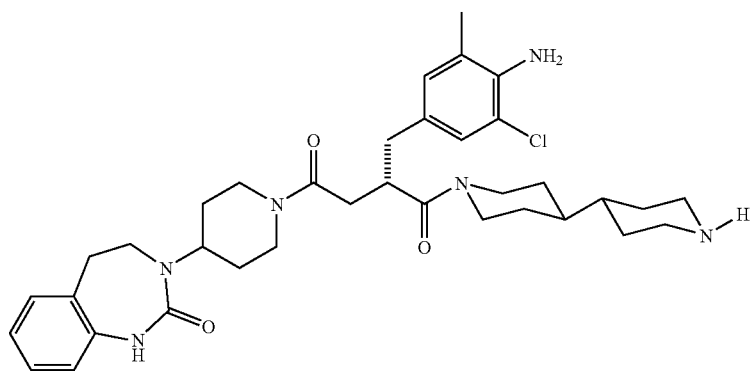 |
| 32.1 | 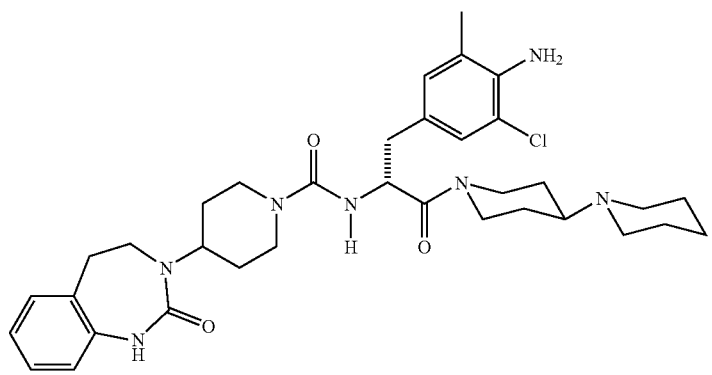 |
| 32.2 | 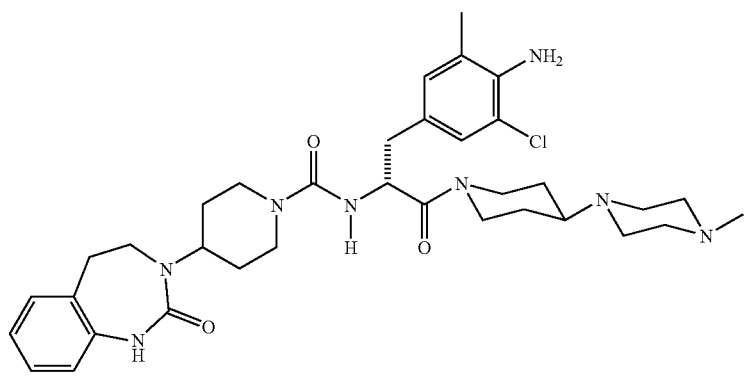 |

-continued
| Example | Structure |
|---|---|
| 32.3 | 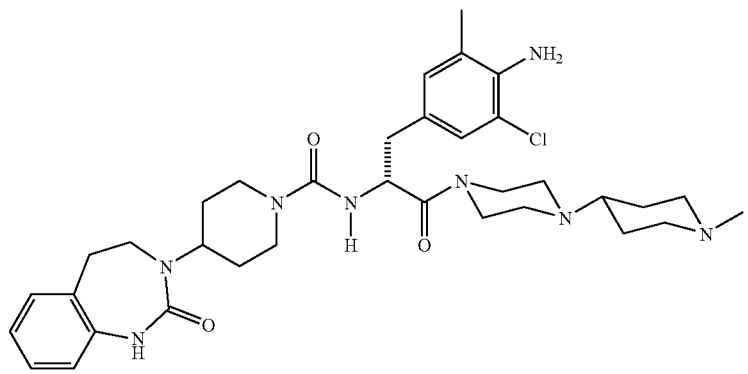 |
| 32.4 | 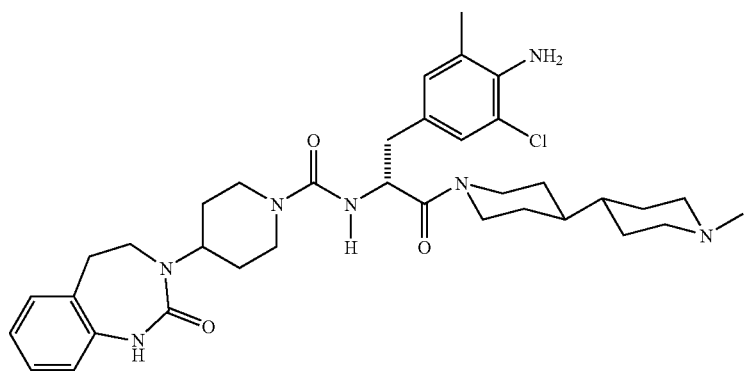 |
| 32.5 | 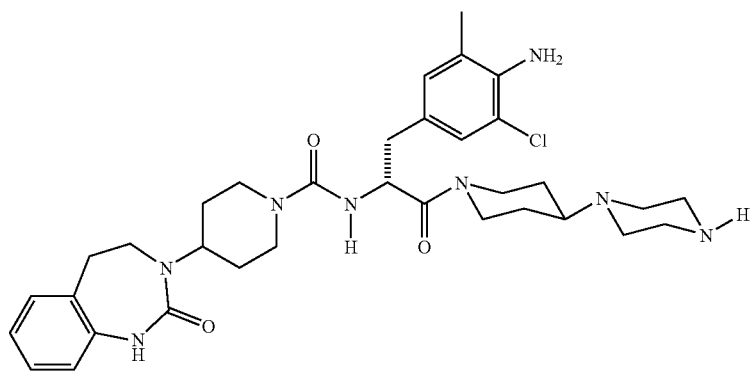 |
| 32.6 | 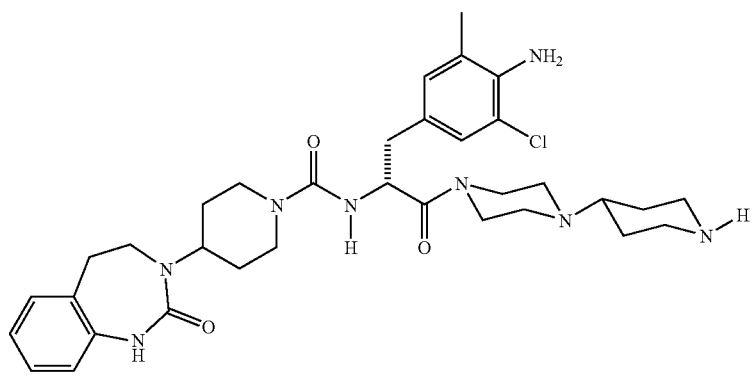 |

-continued
| Example | Structure |
|---|---|
| 32.7 | 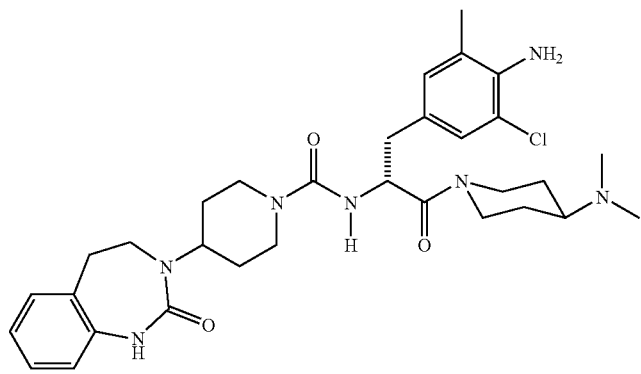 |
| 32.8 | 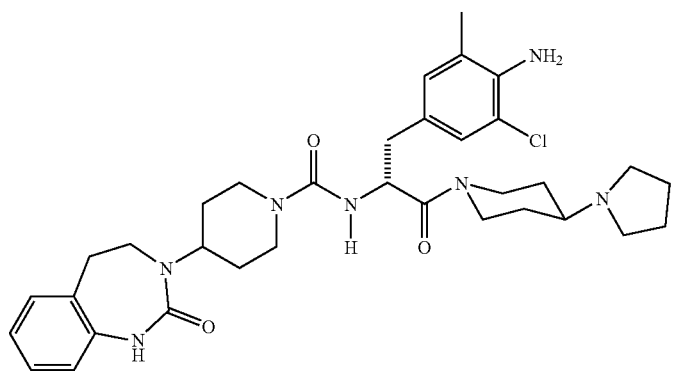 |
| 32.9 | 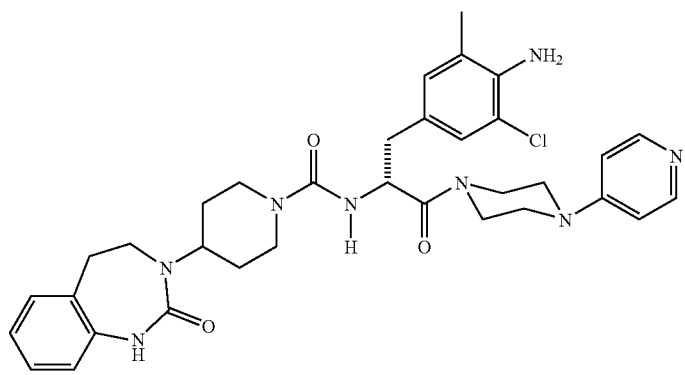 |
| 32.10 | 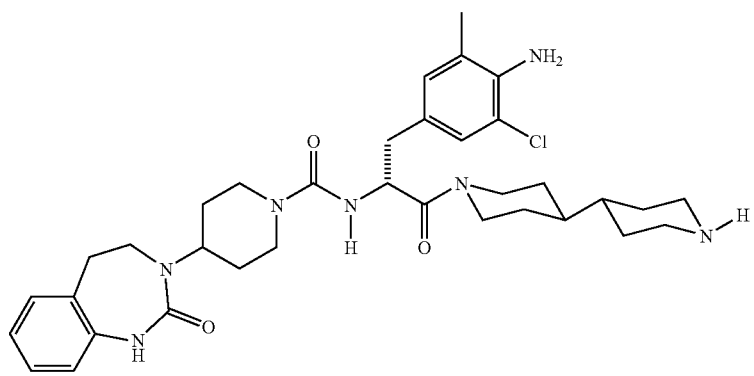 |

-continued
| Example | Structure |
|---------|-----------|
| 33.1 | 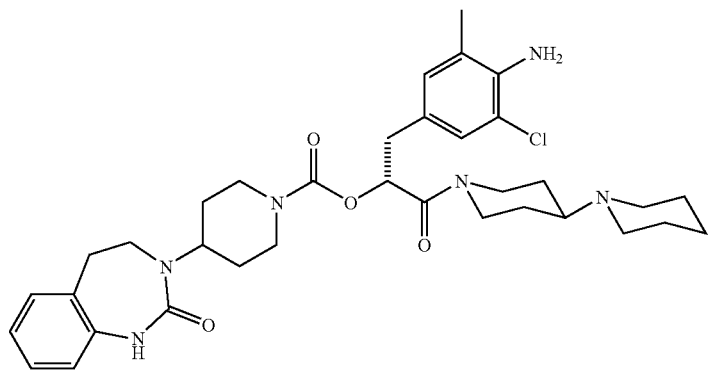 |
| 33.2 | 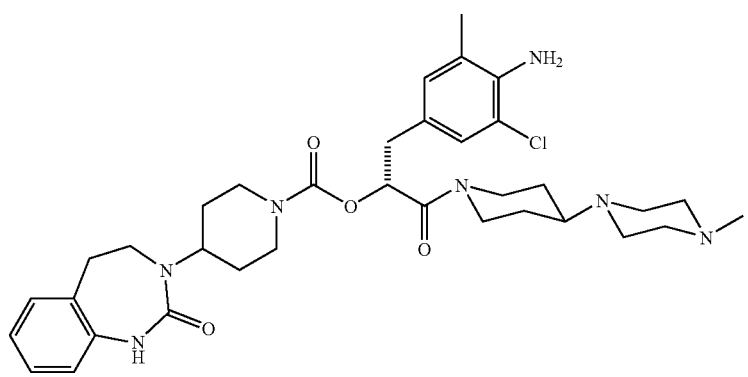 |
| 33.3 | 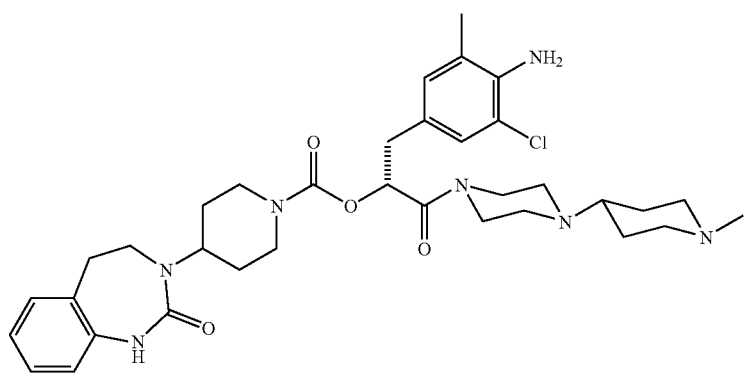 |
| 33.4 | 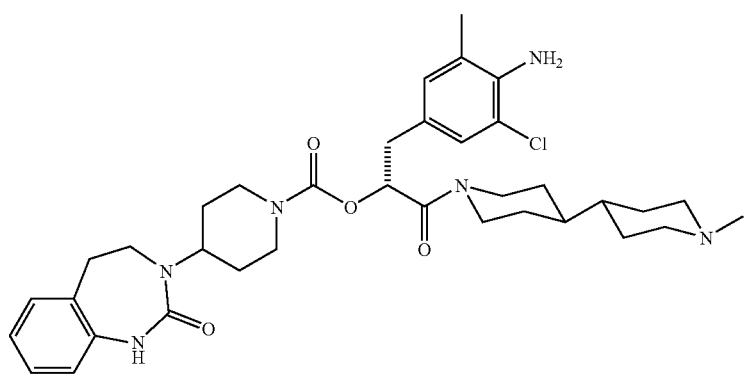 |

-continued
| Example | Structure |
|---|---|
| 33.5 | 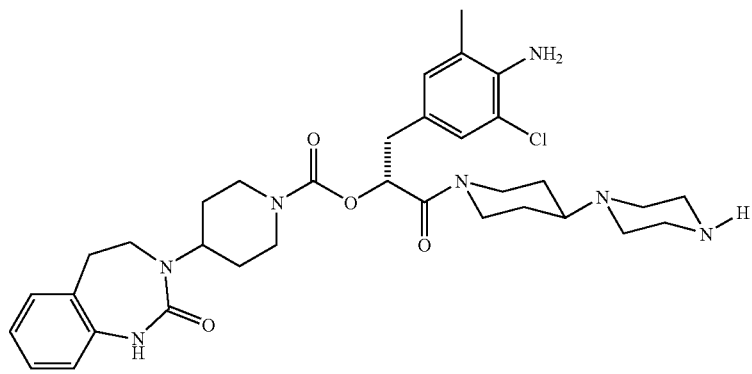 |
| 33.6 | 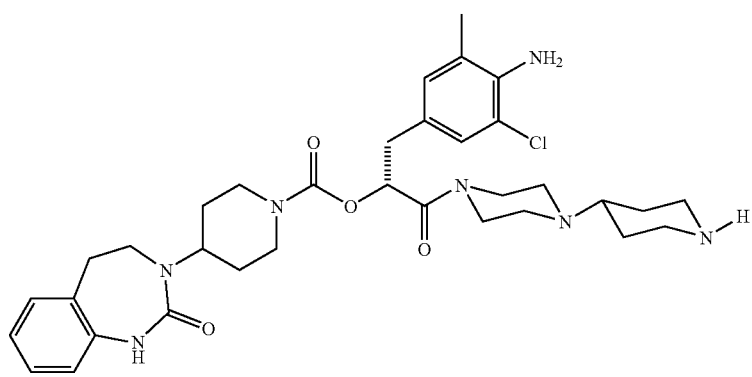 |
| 33.7 | 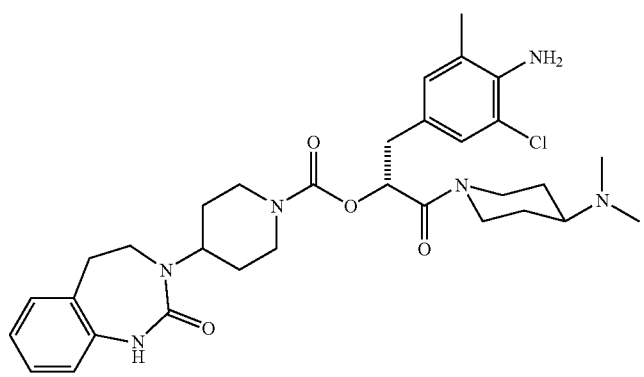 |
| 33.8 | 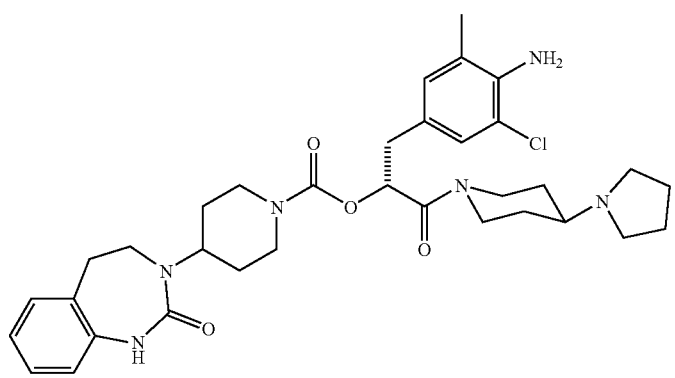 |

-continued
| Example | Structure |
|---|---|
| 33.9 | 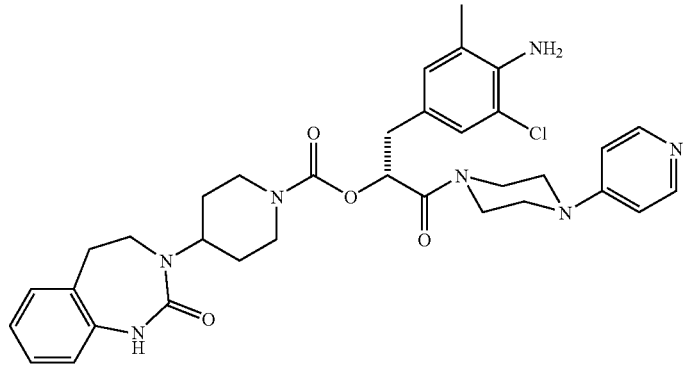 |
| 33.10 | 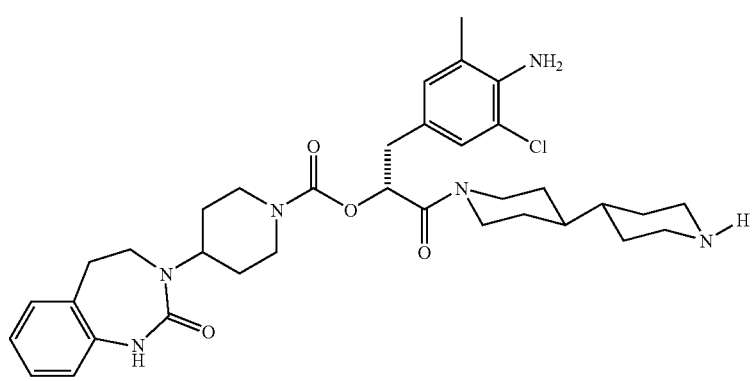 |
The following compounds may be obtained using 2-chloro-6-trifluoromethyl-phenol as starting material, if necessary blocking the phenolic hydroxy function using a suitable protective group:
| Example | Structure |
|---|---|
| 34.1 | 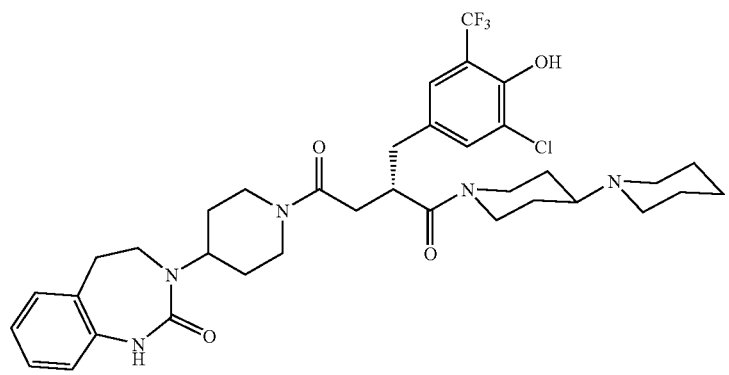 |

-continued
| Example | Structure |
|---|---|
| 34.2 | 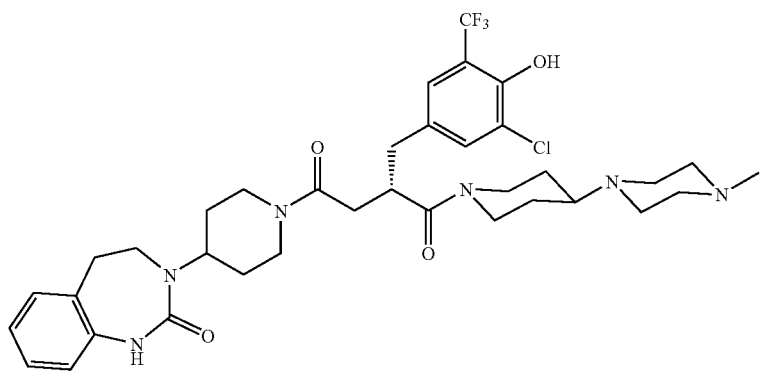 |
| 34.3 | 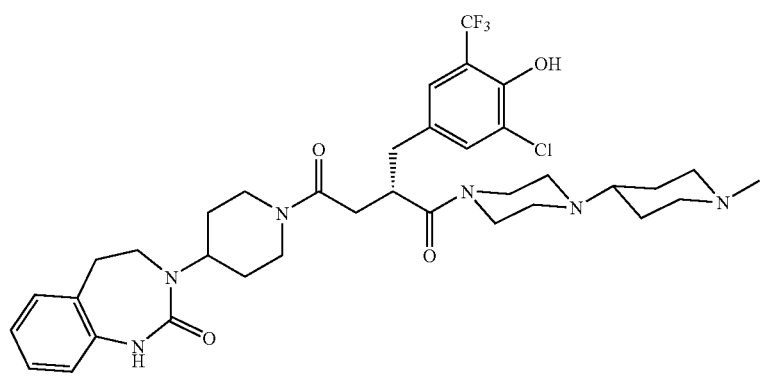 |
| 34.4 | 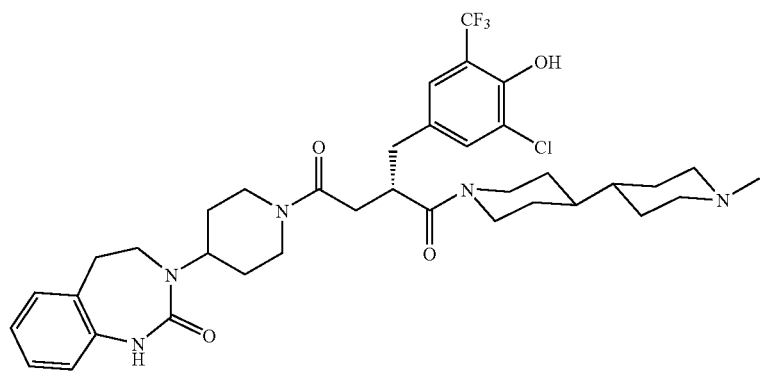 |
| 34.5 | 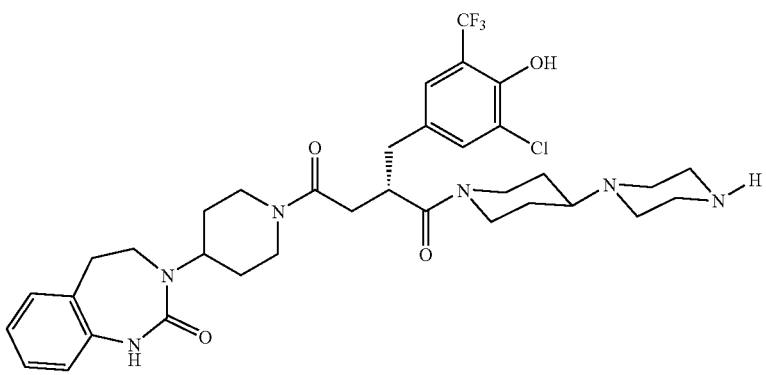 |

-continued
| Example | Structure |
|---|---|
| 34.6 | 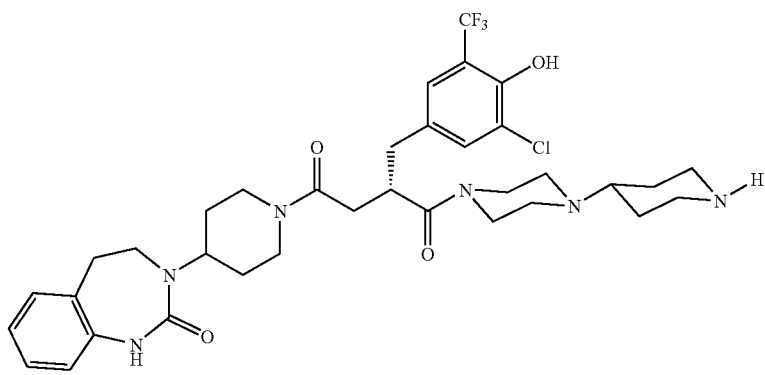 |
| 34.7 | 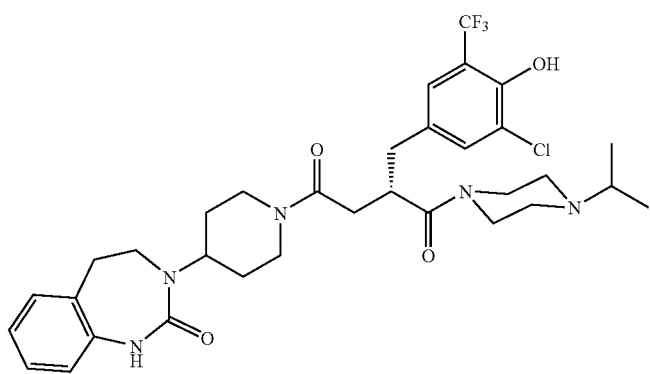 |
| 34.8 | 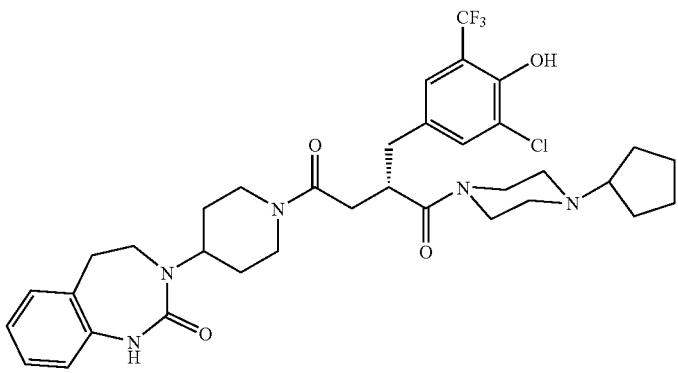 |
| 34.9 | 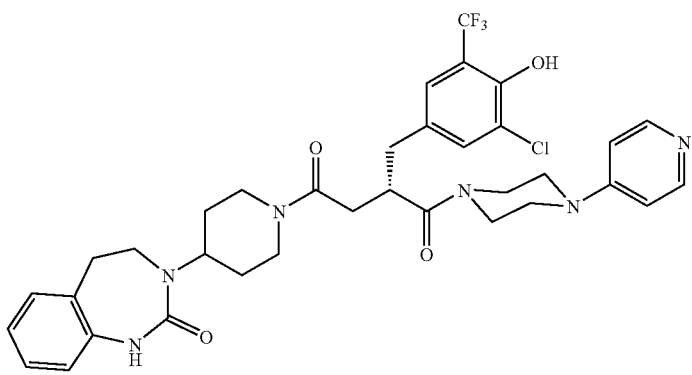 |

-continued
| Example | Structure |
|---------|-----------|
| 34.10 | 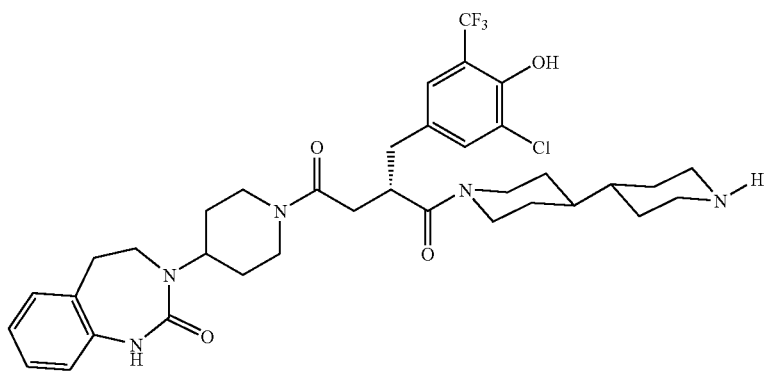 |
| 35.1 | 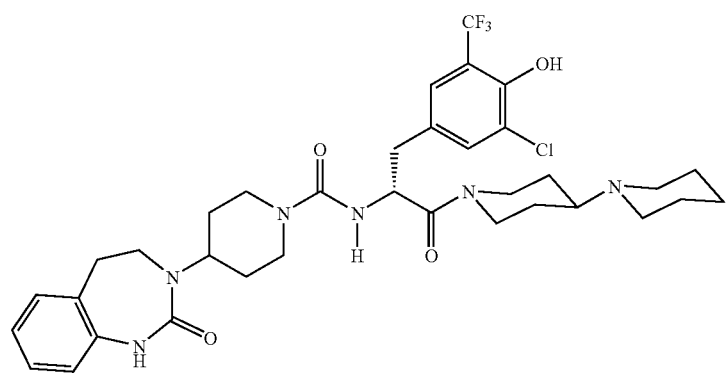 |
| 35.2 | 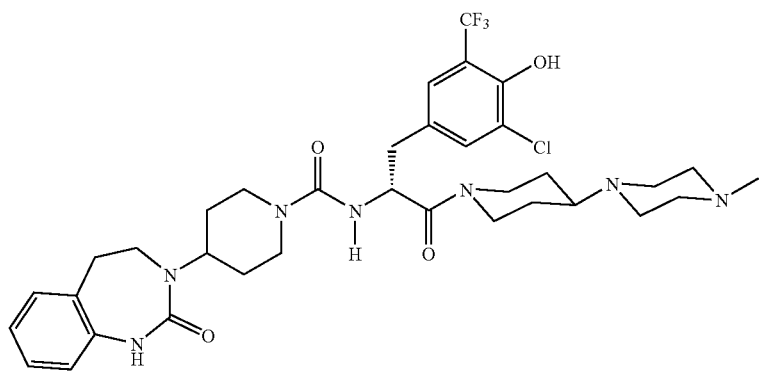 |
| 35.3 | 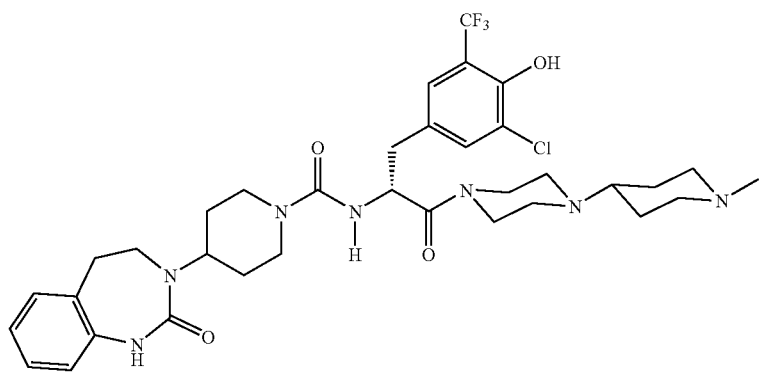 |

| Example | Structure |
|---|---|
| 35.4 | 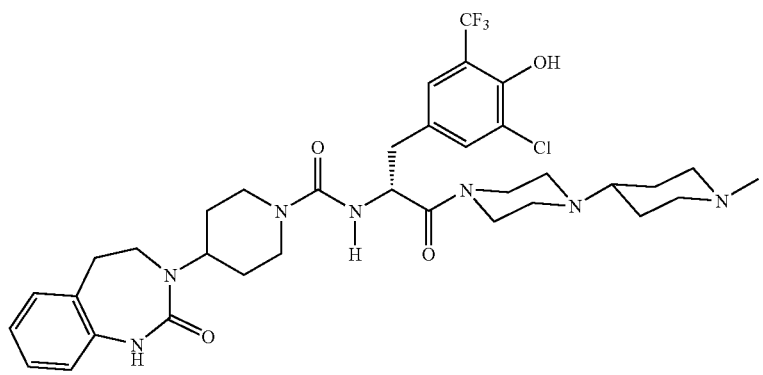 |
| 35.5 | 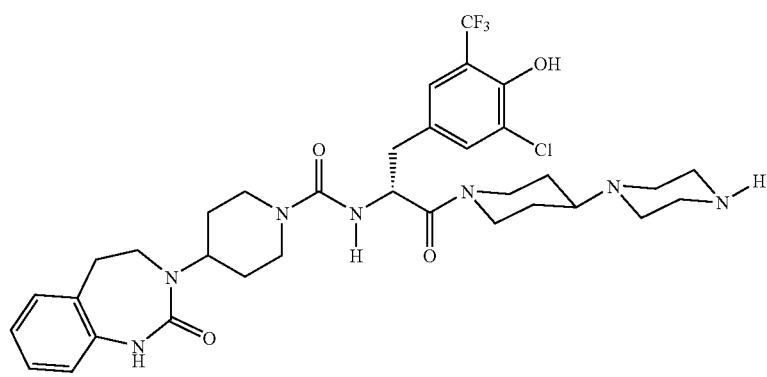 |
| 35.6 | 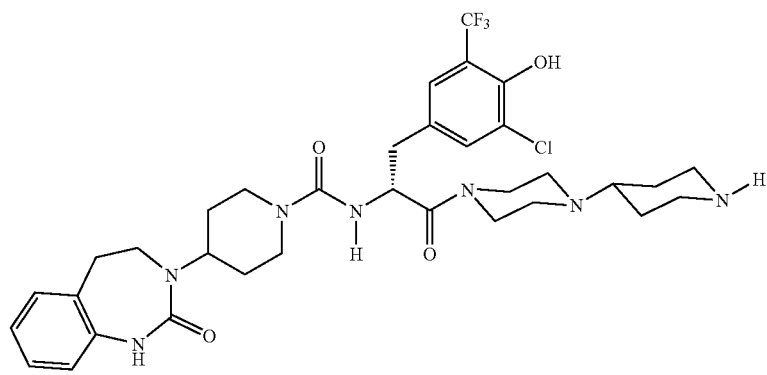 |
| 35.7 | 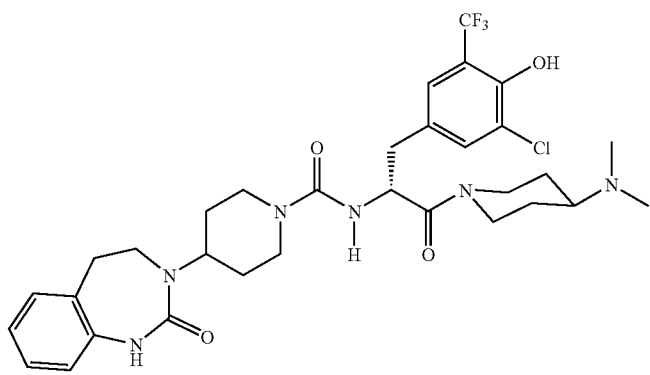 |

-continued
| Example | Structure |
|---------|-----------|
| 35.8 | 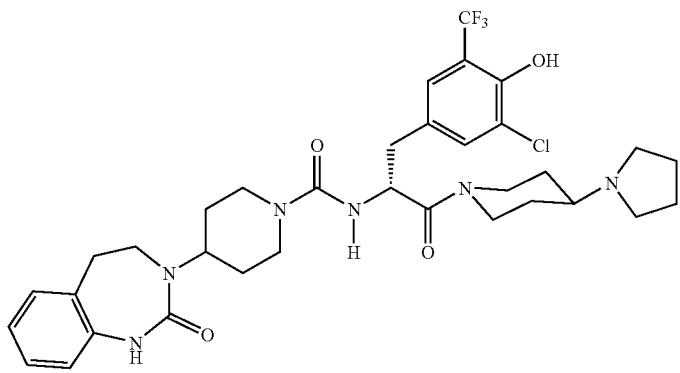 |
| 35.9 | 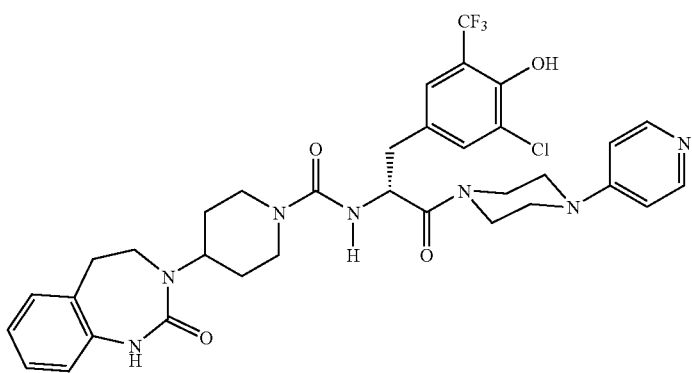 |
| 35.10 | 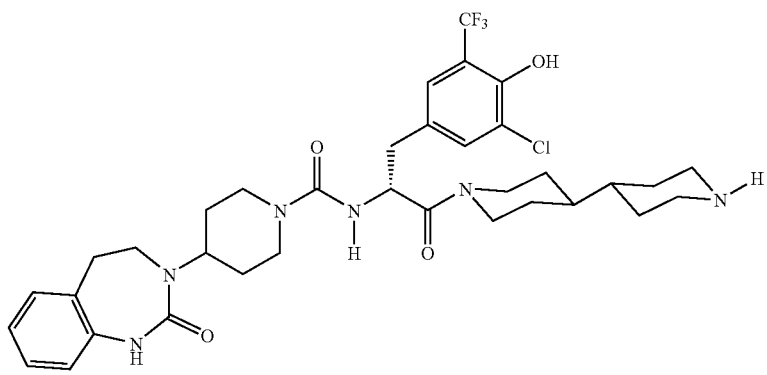 |
| 36.1 | 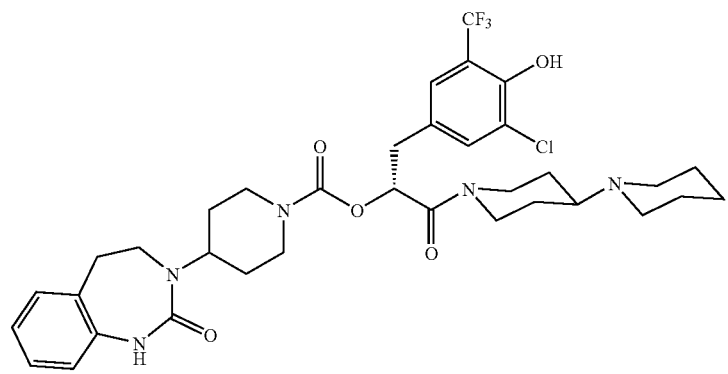 |

-continued
| Example | Structure |
|---|---|
| 36.2 | 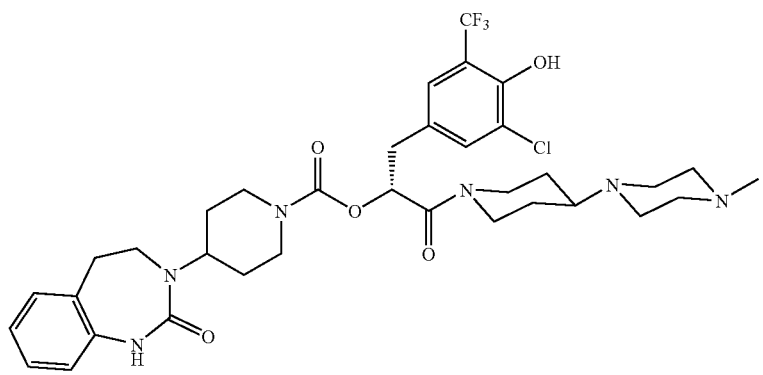 |
| 36.3 | 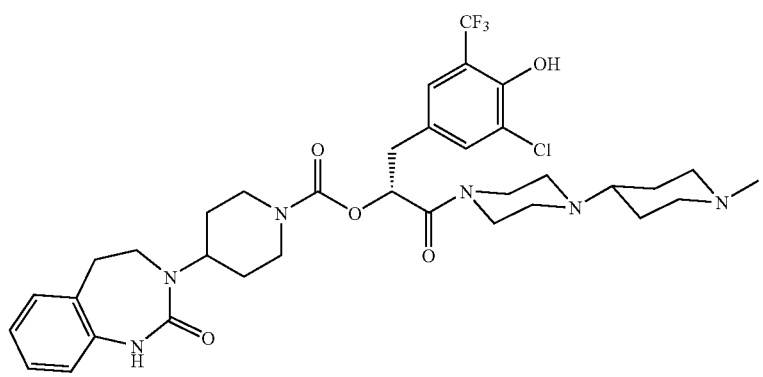 |
| 36.4 | 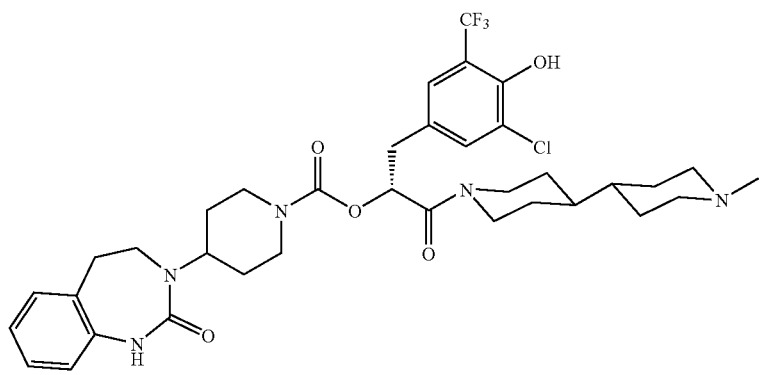 |
| 36.5 | 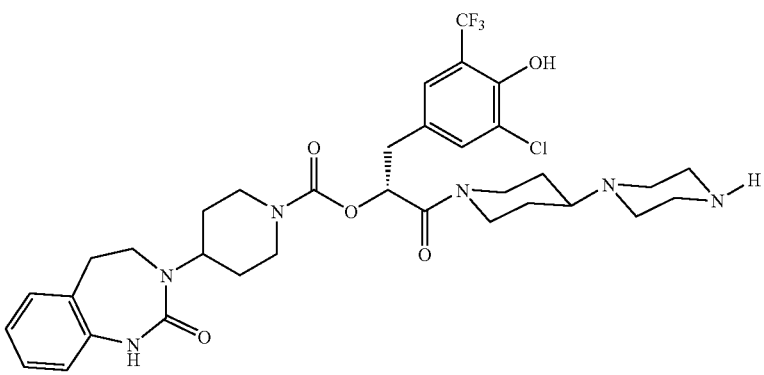 |

| Example | Structure |
|---|---|
| 36.6 | 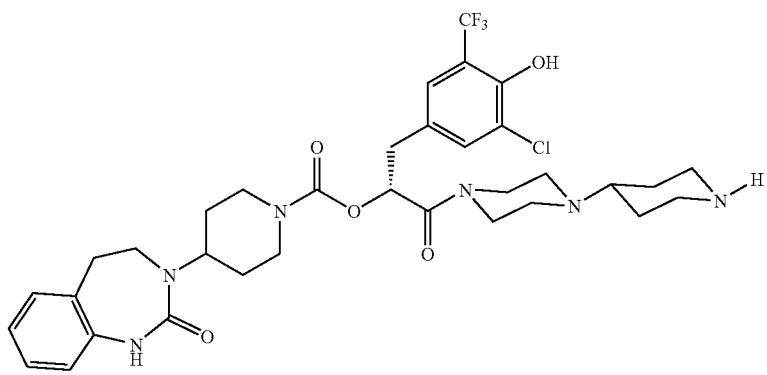 |
| 36.7 | 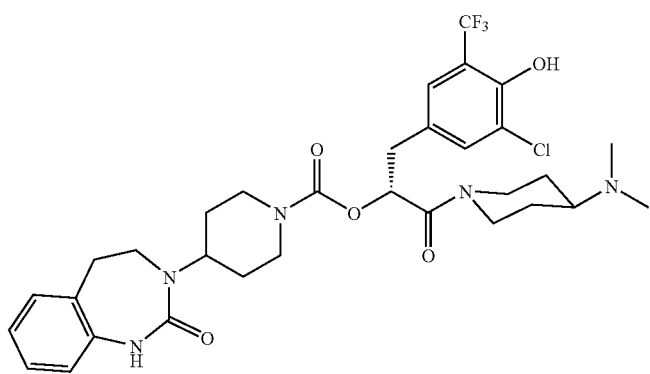 |
| 36.8 | 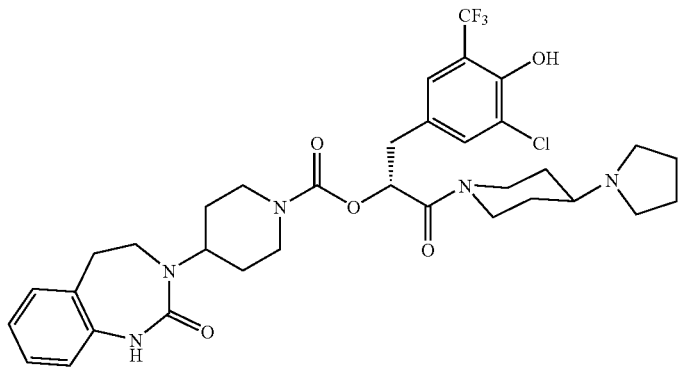 |
| 36.9 | 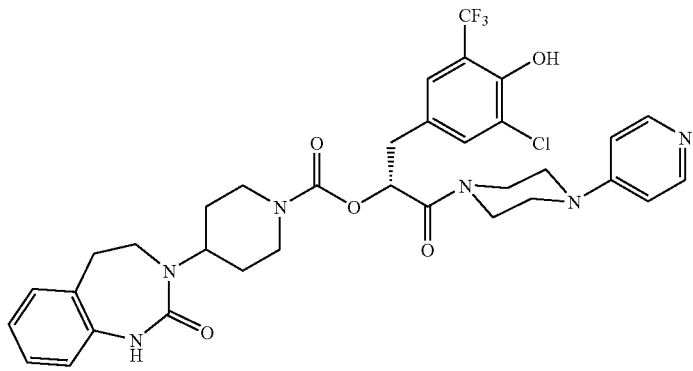 |

| Example | Structure |
|---|---|
| 36.10 | 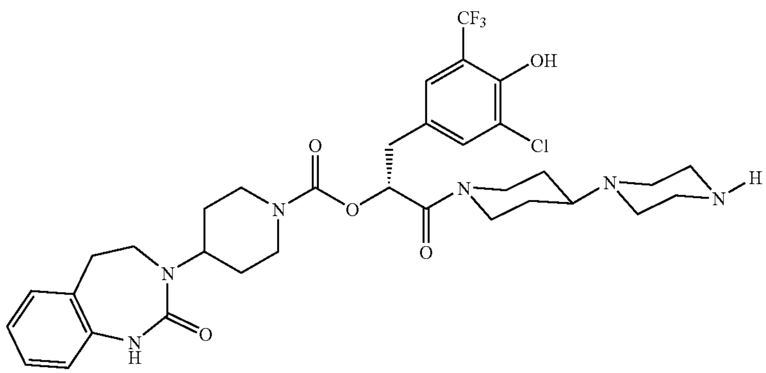 |

Example 37

(S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-thieno[3,2-d]pyrimidin-3-yl)-piperidin-1-yl]-butan-1,4-dione

Example 37.1

(S)-2-(4-amino-3-chloro-5-trifluoromethyl-benzyl)-1-[4-(4-methyl-piperazin-1-yl)-piperidin-1-yl]-4-[4-(5-oxo-4,5,7,8-tetrahydro-2-thia-4,6-diaza-azulen-6-yl)-piperidin-1-yl]-butan-1,4-dione

Example 37.2

(S)-2-(4-amino-3-chloro-5-trifluoromethyl-benzyl)—[4-(4-methyl-piperazin-1-yl)-piperidin-1-yl]-4-[4-(2-oxo-1,2,4,5-tetrahydro-thieno[3,2-d]-1,3-diazepin-3-yl)-piperidin-1-yl]-butan-1,4-dione

Example 37.3

(S)-2-(4-amino-3-chloro-5-trifluoromethyl-benzyl)-1-[4-(4-methyl-piperazin-1-yl)—piperidin-1-yl]-4-[4-(2-oxo-1,2,4,5-tetrahydro-thieno[2,3-d]-1,3-diazepin-3-yl)-piperidin-1-yl]-butan-1,4-dione

Example 37.4

(S)-2-(4-amino-3-chloro-5-trifluoromethyl-benzyl)-1-[4-(4-methyl-piperazin-1-yl)-piperidin-1-yl]-4-[4-(2-oxo-1,4-dihydro-2H-thieno[2,3-d]pyrimidin-3-yl)-piperidin-1-yl]-butan-1,4-dione

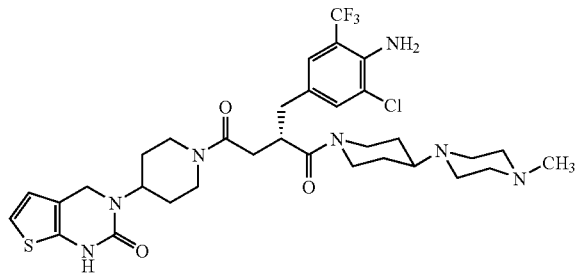

Example 37.5

(S)-2-(4-amino-3-chloro-5-trifluoromethyl-benzyl)-1-(4,4-difluoro-1,4'-bipiperidinyl-1'-yl)-4-[4-(2-oxo-1,2,4,5-tetrahydro-1,3-benzodiazepin-3-yl)-piperidin-1-yl]-butan-1,4-dione

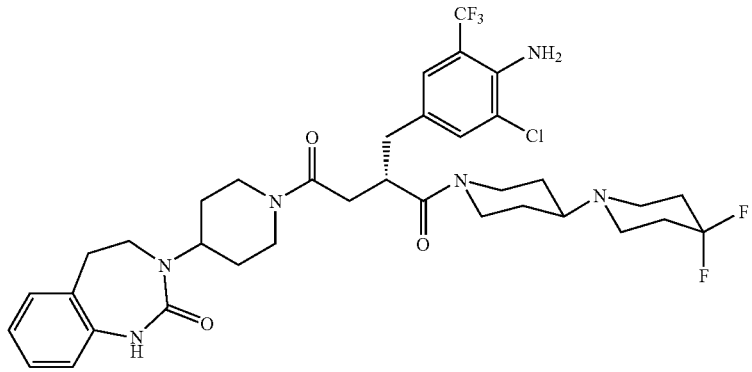

The following Examples describe the preparation of pharmaceutical formulations which contain as active substance any desired compound of general formula (I):

Example I

Capsules for Powder Inhalation Containing 1 mg of Active Ingredient

Composition:

| 1 capsule for powder inhalation contains: | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:

| 1 puff contains: | |
|---|---|
| active ingredient | 1.0 mg |
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:

| 1 vial contains: | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metering Aerosol Containing 1 mg of Active Ingredient

Composition:

| 1 puff contains: | |
|---|---|
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| active ingredient | 1.0 mg |
|---|---|
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI Injectable Solution Containing 5 mg of Active Substance Per 5 ml

Composition:

| active substance | 5 mg |
|---|---|
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with Wfi; transferred into ampoules under nitrogen gas.

Example VII injectable Solution Containing 100 mg of Active Substance Per 20 ml Composition:

| active substance | 100 mg |
|---|---|
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 10 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII

Lyophilisate Containing 10 mg of Active Substance

Composition:

| Active substance | 10 mg |
|---|---|
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| Polysorbate 80 = Tween 80 | 20 mg |
|---|---|
| mannitol | 200 mg |
| water for injections ad | 10 ml |

Preparation:

Polysorbate 80 and mannitol are dissolved in water for injections (WfI); transferred into ampoules.

Example IX

Tablets Containing 20 mg of Active Substance

Composition:

| active substance | 20 mg |
|---|---|
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| active substance | 20 mg |
|---|---|
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size 3 hard gelatine capsules in a capsule filling machine.

Example XI

Suppositories Containing 50 mg of Active Substance

Composition:

| active substance | 50 mg |
|---|---|
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

Example XII injectable Solution Containing 10 mg of Active Substance Per 1 ml

Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

The invention claimed is:

1. A compound selected from the group consisting of:

(1) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(23) (S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(25) (S)-2-(4-amino-3-bromo-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(27) (S)-2-(4-amino-3-bromo-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(28) (S)-2-(4-amino-3-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(29) (S)-2-(4-amino-3-chloro-5-trifluoromethyl-benzyl)-1-(4-dimethylamino-piperidin-1-yl)-4-[4-(2-oxo-1,2,4,5-tetrahydro-1,3-benzodiazepin-3-yl)-piperidin-1-yl]-butan-1,4-dione,

(30) (S)-2-(4-amino-3-chloro-5-trifluoromethyl-benzyl)-1-(3-dimethylamino-piperidin-1-yl)-4-[4-(2-oxo-1,2,4,5-tetrahydro-1,3-benzodiazepin-3-yl)-piperidin-1-yl]-butan-1,4-dione,

(31) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyrrolidin-1-yl-piperidin-1-yl)-butan-1,4-dione,

(32) (S)-2-(4-amino-3-chloro-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(33) (S)-2-(4-amino-3-chloro-5-trifluoromethyl-benzyl)-1-[4-(4-cyclopropylmethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(34) (S)-2-(4-amino-3-chloro-5-trifluoromethyl-benzyl)-1-(4-morpholine-4-yl-piperidin-1-yl)-4-[4-(2-oxo-1,2,4,5-tetrahydro-1,3-benzodiazepin-3-yl)-piperidin-1-yl]-butan-1,4-dione,

(35) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione,

(36) (S)-2-(4-amino-3-chloro-5-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione,

(37) (S)-2-(4-amino-3-chloro-5-trifluoromethyl-benzyl)-1-[4-(4-isopropyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(38) (S)-2-(4-amino-3-chloro-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione,

(44) (S)-2-(4-amino-3-chloro-5-trifluoromethyl-benzyl)-1-(4-azetidin-1-yl-piperidin-1-yl)-4-[4-(2-oxo-1,2,4,5-tetrahydro-1,3-benzodiazepin-3-yl)-piperidin-1-yl]-butan-1,4-dione,

(45) (S)-1-[4-(4-acetyl-piperazin-1-yl)-piperidin-1-yl]-2-(4-amino-3-chloro-5-trifluoromethyl-benzyl)-4-[4-(2-oxo-1,2,4,5-tetrahydro-1,3-benzodiazepin-3-yl)-piperidin-1-yl]-butan-1,4-dione,

(46) (S)-2-(4-amino-3-chloro-5-trifluoromethyl-benzyl)-1-(4-diethylaminomethyl-piperidin-1-yl)-4-[4-(2-oxo-1,2,4,5-tetrahydro-1,3-benzodiazepin-3-yl)-piperidin-1-yl]-butan-1,4-dione,

(47) (S)-2-(4-amino-3-chloro-5-trifluoromethyl-benzyl)-1-[4-(4-ethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(49) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3,4,5,6-tetrahydro-2H-4,4'-bipyridinyl-1-yl)-butan-1,4-dione,

(53) (S)-2-(4-amino-3-chloro-5-trifluoromethyl-benzyl)-1-[4-(4-benzyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione,

(55) (S)-2-(4-amino-3-chloro-5-trifluoromethyl-benzyl)-1-[4-(4-dimethylaminomethyl-phenyl)-piperidin-1-yl]-4-[4-(2-oxo-1,2,4,5-tetrahydro-1,3-benzodiazepin-3-yl)-piperidin-1-yl]-butan-1,4-dione,

(56) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-ethyl)-piperazin-1-yl]-piperidin-1-yl}-butan-1,4-dione,

(57) (S)-2-(4-amino-3-chloro-5-trifluoromethyl-benzyl)-1-(1'-methanesulphonyl-4,4'-bipiperidinyl-1-yl)-4-[4-(2-oxo-1,2,4,5-tetrahydro-1,3-benzodiazepin-3-yl)-piperidin-1-yl]-butan-1,4-dione,

(59) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperidin-1-yl-methyl-piperidin-1-yl)-butan-1,4-dione,

(60) (S)-2-(4-amino-3-chloro-5-trifluoromethyl-benzyl)-1-[4-(2-dimethylamino-ethyl)-piperidin-1-yl]-4-[4-(2-oxo-1,2,4,5-tetrahydro-1,3-benzodiazepin-3-yl)-piperidin-1-yl]-butan-1,4-dione,

(63) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-piperidin-1-yl-butan-1,4-dione,

(64) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-propyl-piperidin-1-yl)-butan-1,4-dione,

(65) (S)-2-(4-amino-3-chloro-5-trifluoromethyl-benzyl)-1-(4-benzyl-piperidin-1-yl)-4-[4-(2-oxo-1,2,4,5-tetrahydro-1,3-benzodiazepin-3-yl)-piperidin-1-yl]-butan-1,4-dione,

(66) (S)-2-(4-amino-3-chloro-5-trifluoromethyl-benzyl)-1-[4-(2-diethylamino-ethyl)-piperidin-1-yl]-4-[4-(2-oxo-1,2,4,5-tetrahydro-1,3-benzodiazepin-3-yl)-piperidin-1-yl]-butan-1,4-dione,

(68) N-(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-N-methyl-methanesuiphonamide,

(69) N-(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-methanesulphonamide,

(70) (S)-2-(4-amino-3-chloro-5-trifluoromethyl-benzyl)-1-[4-(cyclopentyl-methyl-amino)-piperidin-1-yl]-4-[4-(2-oxo-1,2,4,5-tetrahydro-1,3-benzodiazepin-3-yl)-piperidin-1-yl]-butan-1,4-dione,

(71) (S)-2-(4-amino-3-chloro-5-trifluoromethyl-benzyl)-1-(4-methyl-piperidin-1-yl)-4-[4-(2-oxo-1,2,4,5-tetrahydro-1,3-benzodiazepin-3-yl)-piperidin-1-yl]-butan-1,4-dione,

(72) methyl (1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-acetate,

(73) (S)-2-(4-amino-3-chloro-5-trifluoromethyl-benzyl)-1-(4-hydroxy-piperidin-1-yl)-4-[4-(2-oxo-1,2,4,5-tetrahydro-1,3-benzodiazepin-3-yl)-piperidin-1-yl]-butan-1,4-dione,

(74) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-trifluoromethyl-piperidin-1-yl)-butan-1,4-dione,

(75) (S)-2-(4-amino-3-chloro-5-trifluoromethyl-benzyl)-1-[4-(1,1-dioxo-1,6-isothiazolidin-2-yl)-piperidin-1-yl]-4-[4-(2-oxo-1,2,4,5-tetrahydro-1,3-benzodiazepin-3-yl)-piperidin-1-yl]-butan-1,4-dione,

(76) (S)-2-(4-amino-3-chloro-5-trifluoromethyl-benzyl)-1-[4-(2-oxo-perhydro-1,3-oxazin-3-yl)-piperidin-1-yl]-4-[4-(2-oxo-1,2,4,5-tetrahydro-1,3-benzodiazepin-3-yl)-piperidin-1-yl]-butan-1,4-dione,

(77) methyl 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidine-4-carboxylate,

(78) (S)-2-(4-amino-3-chloro-5-trifluoromethyl-benzyl)-1-(4-cyclohexyl-piperidin-1-yl)-4-[4-(2-oxo-1,2,4,5-tetrahydro-1,3-benzodiazepin-3-yl)-piperidin-1-yl]-butan-1,4-dione,

(79) (S)-2-(4-amino-3-chloro-5-trifluoromethyl-benzyl)-1-(4-tert-butylamino-piperidin-1-yl)-4-[4-(2-oxo-1,2,4,5-tetrahydro-1,3-benzodiazepin-3-yl)-piperidin-1-yl]-butan-1,4-dione,

(80) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-phenyl-piperidin-1-yl)-butan-1,4-dione,

(81) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-p-tolyl-piperidin-1-yl)-butan-1,4-dione,

(83) (S)-2-(4-amino-3-chloro-5-trifluoromethyl-benzyl)-1-[4-(2-oxo-imidazolidin-1-yl)-piperidin-1-yl]-4-[4-(2-oxo-1,2,4,5-tetrahydro-1,3-benzodiazepin-3-yl)-piperidin-1-yl]-butan-1,4-dione,

(84) (S)-2-(4-amino-3-chloro-5-trifluoromethyl-benzyl)-1-(4-amino-4-methyl-piperidin-1-yl)-4-[4-(2-oxo-1,2,4,5-tetrahydro-1,3-benzodiazepin-3-yl)-piperidin-1-yl]-butan-1,4-dione,

(87) (S)-2-(4-amino-3-chloro-5-trifluoromethyl-benzyl)-1-[4-(2-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(88) (S)-2-(4-amino-3-chloro-5-trifluoromethyl-benzyl)-1-[4-(4-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(90) (S)-2-(4-amino-3-chloro-5-trifluoromethyl-benzyl)-1-[4-(2,4-dimethyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione,

(91) (S)-2-(4-amino-3-chloro-5-trifluoromethyl-benzyl)-1-(4-imidazol-1-yl-piperidin-1-yl)-4-[4-(2-oxo-1,2,4,5-tetrahydro-1,3-benzodiazepin-3-yl)-piperidin-1-yl]-butan-1,4-dione,

(92) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-1,2,4-triazol-1-yl-piperidin-1-yl)-butan-1,4-dione,

(98) 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-carboxylic acid,

(99) (1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-acetic acid, (101) (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione, (102) (S)-2-(4-amino-3-chloro-5-trifluoromethyl-benzyl)-1-[4-(1H-imidazol-4-yl)-piperidin-1-yl]-4-[4-(2-oxo-1,2,4,5-tetrahydro-1,3-benzodiazepin-3-yl)-piperidin-1-yl]-butan-1,4-dione, (108) (S)-2-(4-amino-3-chloro-5-trifluoromethyl-benzyl)-1-[4-(5-methyl-2,5-diaza-bicyclo[2.2.1]hept-2-yl)-piperidin-1-yl]-4-[4-(2-oxo-1,2,4,5-tetrahydro-1,3-benzodiazepin-3-yl)-piperidin-1-yl]-butan-1,4-dione, (109) (S)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro- 1,3-benzodiazepin-3-yl)-piperidin-1-yl]-butan-1,4-dione, (113) (S)-2-(4-amino-3,5-bis-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, (114) (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione, (115) (S)-2-(4-amino-3,5-bis-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione, (116) (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1 -yl)-butan-1,4-dione, and (121) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl) -piperidin-1-carboxylate, or an enantiomer, diastereomer or salt thereof.

2. A physiologically acceptable salt of a compound according to claim 1.

3. A pharmaceutical composition containing a compound according to claim 1 or a physiologically acceptable salt thereof together with an inert carrier or diluent.

4. A method for treating headache, migraine headache or cluster headache which comprises the administration of a therapeutically effective amount of a compound according to claim 1 or a physiologically acceptable salt thereof.

5. In accordance with claim 1, (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

6. In accordance with claim 1, (S)-2-(4-amino-3-bromo-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

7. In accordance with claim 1, (S)-2-(4-amino-3-bromo-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione, or a salt thereof.

8. In accordance with claim 1, (S)-2-(4-amino-3-bromo-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione, or a salt thereof.

9. In accordance with claim 1, (S)-2-(4-amino-3-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

10. In accordance with claim 1, (S)-2-(4-amino-3-chloro-5-trifluoromethyl-benzyl)-1-(4-dimethylamino-piperidin-1-yl)-4-[4-(2-oxo-1,2,4,5-tetrahydro-1,3-benzodiazepin-3-yl)-piperidin-1-yl]-butan-1,4-dione, or a salt thereof.

11. In accordance with claim 1, (S)-2-(4-amino-3-chloro-5-trifluoromethyl-benzyl)-1-(3-dimethylamino-piperidin-1-yl)-4-[4-(2-oxo-1,2,4,5-tetrahydro-1,3-benzodiazepin-3-yl)-piperidin-1-yl]-butan-1,4-dione, or a salt thereof.

12. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-pyrrolidin-1-yl-piperidin-1-yl)-butan- 1,4-dione, or a salt thereof.

13. In accordance with claim 1, (S)-2-(4-amino-3-chloro-5-trifluoromethyl-benzyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butan-1,4-dione, or a salt thereof.

14. In accordance with claim 1, (S)-2-(4-amino-3-chloro-5-trifluoromethyl-benzyl)-1-[4-(4-cyclopropylmethyl-piperazin-1-yl)-piperidin--yl]-4-[4-(2-oxo-1,2,4,5-tetrahydro-1,3-benzodiazepin-3-yl)-piperidin-1-yl]-butan-1,4-dione, or a salt thereof.

15. In accordance with claim 1, (S)-2-(4-amino-3-chloro-5-trifluoromethyl-benzyl)-1-(4-morpholine-4-yl-piperidin-1-yl)-4-[4-(2-oxo-1,2,4,5-tetrahydro-1,3-benzodiazepin-3-yl)-piperidin-1-yl]-butan-1,4-dione, or a salt thereof.

16. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione, or a salt thereof.

17. In accordance with claim 1, (S)-2-(4-amino-3-chloro-5-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

18. In accordance with claim 1, (S)-2-(4-amino-3-chloro-5-trifluoromethyl-benzyl)-1-[4-(4-isopropyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

19. In accordance with claim 1, (S)-2-(4-amino-3-chloro-5-trifluoromethyl-benzyl)-1-1,4'-bipiperidinyl-1'-yl-4-[4-(2-oxo-1,2,4,5-tetrahydro-1,3-benzodiazepin-3-yl)-piperidin-1-yl]-butan-1,4-dione, or a salt thereof.

20. In accordance with claim 1, (S)-2-(4-amino-3-chloro-5-trifluoromethyl-benzyl)-1-(4-azetidin-1-yl-piperidin-1-yl)-4-[4-(2-oxo-1,2,4,5-tetrahydro-1,3-benzodiazepin -3-yl)-piperidin-1-yl]-butan-1,4-dione, or a salt thereof.

21. In accordance with claim 1, (S)-1-[4-(4-acetyl-piperazin-1-yl)-piperidin-1-yl]-2-(4-amino-3-chloro-5-trifluoromethyl-benzyl)-4-[4-(2-oxo-1,2,4,5-tetrahydro-1,3-benzodiazepin-3-yl)-piperidin-1-yl]-butan-1,4-dione, or a salt thereof.

22. In accordance with claim 1, (S)-2-(4-amino-3-chloro-5-trifluoromethyl-benzyl)-1-(4-diethylaminomethyl-piperidin-1-yl)-4-[4-(2-oxo-1,2,4,5-tetrahydro-1,3-benzodiazepin-3-yl)-piperidin-1-yl]-butan-1,4-dione, or a salt thereof.

23. In accordance with claim 1, (S)-2-(4-amino-3-chloro-5-trifluoromethyl-benzyl)-1-[4-(4-ethyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

24. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(3,4,5,6-tetrahydro-2H-4,4'-bipyridinyl-1-yl)-butan-1,4-dione, or a salt thereof.

25. In accordance with claim 1, (S)-2-(4-amino-3-chloro-5-trifluoromethyl-benzyl)-1-[4-(4-benzyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

26. In accordance with claim 1, (S)-2-(4-amino-3-chloro-5-trifluoromethyl-benzyl)-1-[4-(4-dimethylaminomethyl-phenyl)-piperidin-1-yl]-4-[4-(2-oxo-1,2,4,5-tetrahydro-1,3-benzodiazepin-3-yl)-piperidin-1-yl]-butan-1,4-dione, or a salt thereof.

27. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-{4-[4-(2,2,2-trifluoro-ethyl)-piperazin-1-yl]-piperidin-1-yl}-butan-1,4-dione, or a salt thereof.

28. In accordance with claim 1, (S)-2-(4-amino-3-chloro-5-trifluoromethyl-benzyl)-1-(1'-methanesulphonyl-4,4'-bipiperidinyl-1-yl)-4-[4-(2-oxo-1,2,4,5-tetrahydro-1,3-benzodiazepin-3-yl)-piperidin-1-yl]-butan-1,4-dione, or a salt thereof.

29. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperidin-1-yl-methyl-piperidin-1-yl)-butan-1,4-dione, or a salt thereof.

30. In accordance with claim 1, (S)-2-(4-amino-3-chloro-5-trifluoromethyl-benzyl)-1-[4-(2-dimethylamino-ethyl)-piperidin-1-yl]-4-[4-(2-oxo-1,2,4,5-tetrahydro-1,3-benzodiazepin-3-yl)-piperidin-1-yl]-butan-1,4-dione, or a salt thereof.

31. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-piperidin-1-yl-butan-1,4-dione, or a salt thereof.

32. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-propyl-piperidin-1-yl)-butan-1,4-dione, or a salt thereof.

33. In accordance with claim 1, (S)-2-(4-amino-3-chloro-5-trifluoromethyl-benzyl)-1-(4-benzyl-piperidin-1-yl)-4-[4-(2-oxo-1,2,4,5-tetrahydro-1,3-benzodiazepin-3-yl)-piperidin-1-yl]-butan-1,4-dione, or a salt thereof.

34. In accordance with claim 1, (S)-2-(4-amino-3-chloro-5-trifluoromethyl-benzyl)-1-[4-(2-diethylamino-ethyl)-piperidin-1-yl]-4-[4-(2-oxo-1,2,4,5-tetrahydro-1,3-benzodiazepin-3-yl)-piperidin-1-yl]-butan-1,4-dione, or a salt thereof.

35. In accordance with claim 1, N-(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-N-methyl-methanesulphonamide, or a salt thereof.

36. In accordance with claim 1, N-(1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-methanesulphonamide, or a salt thereof.

37. In accordance with claim 1, (S)-2-(4-amino-3-chloro-5-trifluoromethyl-benzyl)-1-[4-(cyclopentyl-methyl-amino)-piperidin-1-yl]-4-[4-(2-oxo-1,2,4,5-tetrahydro-1,3-benzodiazepin-3-yl)-piperidin-1-yl]-butan-1,4-dione, or a salt thereof.

38. In accordance with claim 1, (S)-2-(4-amino-3-chloro-5-trifluoromethyl-benzyl)-1-(4-methyl-piperidin-1-yl)-4-[4-(2-oxo-1,2,4,5-tetrahydro-1,3-benzodiazepin-3-yl)-piperidin-1-yl]-butan-1,4-dione, or a salt thereof.

39. In accordance with claim 1, methyl (1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-acetate, or a salt thereof.

40. In accordance with claim 1, (S)-2-(4-amino-3-chloro-5-trifluoromethyl-benzyl)-1-(4-hydroxy-piperidin-1-yl)-4-[4-(2-oxo-1,2,4,5-tetrahydro-1,3-benzodiazepin-3-yl)-piperidin-1-yl]-butan-1,4-dione, or a salt thereof.

41. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-trifluoromethyl-piperidin-1-yl)-butan-1,4-dione, or a salt thereof.

42. In accordance with claim 1, (S)-2-(4-amino-3-chloro-5-trifluoromethyl-benzyl)-1-[4-(1,1-dioxo-1,6-isothiazolidin-2-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

43. In accordance with claim 1, (S)-2-(4-amino-3-chloro-5-trifluoromethyl-benzyl)-1-[4-(2-oxo-perhydro-1,3-oxazin-3-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

44. In accordance with claim 1, methyl 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidine-4-carboxylate, or a salt thereof.

45. In accordance with claim 1, (S)-2-(4-amino-3-chloro-5-trifluoromethyl-benzyl)-1-(4-cyclohexyl-piperidin-1-yl)-4-[4-(2-oxo-1,2,4,5-tetrahydro-1,3-benzodiazepin-3-yl)-piperidin-1-yl]-butan-1,4-dione, or a salt thereof.

46. In accordance with claim 1, (S)-2-(4-amino-3-chloro-5-trifluoromethyl-benzyl)-1-(4-tert-butylamino-piperidin-1-yl)-4-[4-(2-oxo-1,2,4,5-tetrahydro-1,3-benzodiazepin-3-yl)-piperidin-1-yl]-butan-1,4-dione, or a salt thereof.

47. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-phenyl-piperidin-1-yl)-butan-1,4-dione, or a salt thereof.

48. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-p-tolyl-piperidin-1-yl)-butan-1,4-dione, or a salt thereof.

49. In accordance with claim 1, (S)-2-(4-amino-3-chloro-5-trifluoromethyl-benzyl)-1-[4-(2-oxo-imidazolidin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

50. In accordance with claim 1, (S)-2-(4-amino-3-chloro-5-trifluoromethyl-benzyl)-1-(4-amino-4-methyl-piperidin-1-yl)-4-[4-(2-oxo-1,2,4,5-tetrahydro-1,3-benzodiazepin-3-yl)-piperidin-1-yl]-butan-1,4-dione, or a salt thereof.

51. In accordance with claim 1, (S)-2-(4-amino-3-chloro-5-trifluoromethyl-benzyl)-1-[4-(2-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

52. In accordance with claim 1, (S)-2-(4-amino-3-chloro-5-trifluoromethyl-benzyl)-1-[4-(4-methyl-imidazol-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

53. In accordance with claim 1, (S)-2-(4-amino-3-chloro-5-trifluoromethyl-benzyl)-1-[4-(2,4-dimethyl-imidazol-1-

54. In accordance with claim 1, (S)-2-(4-amino-3-chloro-5-trifluoromethyl-benzyl)-1-(4-imidazol-1-yl-piperidin-1-yl)-4-[4-(2-oxo-1,2,4,5-tetrahydro-1,3-benzodiazepin-3-yl)-piperidin-1-yl]-butan-1,4-dione, or a salt thereof.

55. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-1,2,4-triazol-1-yl-piperidin-1-yl)-butan-1,4-dione, or a salt thereof.

56. In accordance with claim 1, 1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-carboxylic acid, or a salt thereof.

57. In accordance with claim 1, (1-{(S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyryl}-piperidin-4-yl)-acetic acid, or a salt thereof.

58. In accordance with claim 1, (S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione, or a salt thereof.

59. In accordance with claim 1, (S)-2-(4-amino-3-chloro-5-trifluoromethyl-benzyl)-1-[4-( 1H-imidazol-4-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

60. In accordance with claim 1, (S)-2-(4-amino-3-chloro-5-trifluoromethyl-benzyl)-1-[4-(5-methyl-2,5-diaza-bicyclo[2.2.1]hept-2-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

61. In accordance with claim 1, (S)-2-(4-amino-3,5-bis-trifluoromethyl-benzyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

62. In accordance with claim 1, (S)-2-(4-amino-3,5-bis-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butan-1,4-dione, or a salt thereof.

63. In accordance with claim 1, (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-perhydro-azepin-1-yl-piperidin-1-yl)-butan-1,4-dione, or a salt thereof.

64. In accordance with claim 1, (S)-2-(4-amino-3,5-bis-trifluoromethyl-benzyl)-1-1,4'-bipiperidinyl-1'-yl-4-[4-(2-oxo-1,2,4,5-tetrahydro-1,3-benzodiazepin-3 -yl)-piperidin-1-yl]-butan-1,4-dione, or a salt thereof.

65. In accordance with claim 1, (S)-2-(4-amino-3,5-bis-trifluoromethyl-benzyl)-4-[4-(2-oxo-1,2,4,5-tetrahydro-1,3-benzodiazepin-3-yl)-piperidin-1-yl]-1-(4-piperazin-1-yl-piperidin-1-yl)-butan-1,4-dione, or a salt thereof.

66. In accordance with claim 1, (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidin-1-carboxylate, or a salt thereof.

* * * * *

UNITED STATES PATENT AND TRADEMARK OFFICE
CERTIFICATE OF CORRECTION

| | | |
|---|---|---|
| PATENT NO. | : 7,595,312 B2 | Page 1 of 1 |
| APPLICATION NO. | : 10/687262 | |
| DATED | : September 29, 2009 | |
| INVENTOR(S) | : Rudolf et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 203 days.

Delete the phrase "by 203 days" and insert -- by 634 days --

Signed and Sealed this

Eighth Day of June, 2010

David J. Kappos
*Director of the United States Patent and Trademark Office*